US008183012B2

(12) United States Patent
Schultz et al.

(10) Patent No.: US 8,183,012 B2
(45) Date of Patent: *May 22, 2012

(54) METHODS AND COMPOSITION FOR THE PRODUCTION OF ORTHOGONAL TRNA-AMINOACYLTRNA SYNTHETASE PAIRS

(75) Inventors: Peter G. Schultz, La Jolla, CA (US); Lei Wang, San Diego, CA (US); John Christopher Anderson, San Diego, CA (US); Jason Chin, Cambridge (GB); David R. Liu, Lexington, MA (US); Thomas J. Magliery, North Haven, CT (US); Eric L. Meggers, Philadelphia, PA (US); Ryan Aaron Mehl, Lancaster, PA (US); Miro Pastrnak, San Diego, CA (US); Steven William Santoro, Cambridge, MA (US); Zhiwen Zhang, San Diego, CA (US)

(73) Assignees: The Scripps Research Institute, LaJolla, CA (US); The Regents of the University of California, Oakland, CA (US)

( * ) Notice: Subject to any disclaimer, the term of this patent is extended or adjusted under 35 U.S.C. 154(b) by 505 days.

This patent is subject to a terminal disclaimer.

(21) Appl. No.: 11/009,635

(22) Filed: Dec. 10, 2004

(65) Prior Publication Data

US 2005/0208536 A1    Sep. 22, 2005

Related U.S. Application Data

(62) Division of application No. 10/126,931, filed on Apr. 19, 2002, now Pat. No. 7,083,970.

(60) Provisional application No. 60/285,030, filed on Apr. 19, 2001, provisional application No. 60/355,514, filed on Feb. 6, 2002.

(51) Int. Cl.
*C12Q 1/68* (2006.01)
*C12N 9/22* (2006.01)
*C12N 1/21* (2006.01)
*C12N 15/74* (2006.01)

(52) U.S. Cl. ............... 435/69.1; 435/6.1; 435/252.3; 435/320.1; 435/199

(58) Field of Classification Search ............ None
See application file for complete search history.

(56) References Cited

U.S. PATENT DOCUMENTS

| 5,370,995 | A | 12/1994 | Hennecke et al. | |
| 6,706,504 | B1 | 3/2004 | Madison | |
| 6,927,042 | B2 | 8/2005 | Schultz et al. | |
| 7,045,337 | B2* | 5/2006 | Schultz et al. | 435/252.3 |
| 7,083,970 | B2* | 8/2006 | Schultz et al. | 435/252.3 |
| 7,129,333 | B2 | 10/2006 | Schultz et al. | |
| 7,183,082 | B2 | 2/2007 | Schultz et al. | |
| 7,199,222 | B2 | 4/2007 | Shultz et al. | |
| 7,217,809 | B2 | 5/2007 | Schultz et al. | |
| 7,238,510 | B2 | 7/2007 | Schultz et al. | |
| 7,262,040 | B2 | 8/2007 | Schultz et al. | |
| 7,354,761 | B2 | 4/2008 | Schultz et al. | |
| 7,368,275 | B2 | 5/2008 | Schultz et al. | |
| 7,378,263 | B2 | 5/2008 | Schultz et al. | |
| 7,399,619 | B2 | 7/2008 | Xie et al. | |
| 7,432,092 | B2* | 10/2008 | Schultz et al. | 435/183 |
| 7,494,796 | B2 | 2/2009 | Alfonta et al. | |
| 7,524,647 | B2 | 4/2009 | Schultz et al. | |
| 7,527,943 | B2 | 5/2009 | Anderson et al. | |
| 7,560,535 | B2 | 7/2009 | Schultz et al. | |
| 7,575,895 | B2 | 8/2009 | Anderson et al. | |
| 7,608,423 | B2 | 10/2009 | Chin et al. | |
| 7,618,775 | B2 | 11/2009 | Chin et al. | |
| 7,625,717 | B2 | 12/2009 | Chin et al. | |
| 7,638,297 | B2 | 12/2009 | Anderson et al. | |
| 7,638,300 | B2* | 12/2009 | Schultz et al. | 435/69.1 |
| 7,642,085 | B2 | 1/2010 | Schultz et al. | |
| 7,709,604 | B2 | 5/2010 | Zhang et al. | |
| 7,713,721 | B2 | 5/2010 | Schultx et al. | |
| 7,718,410 | B2 | 5/2010 | Deiters et al. | |
| 7,741,071 | B2 | 6/2010 | Zhang et al. | |
| 7,790,847 | B2 | 9/2010 | Wang et al. | |
| 7,794,978 | B2 | 9/2010 | Chin et al. | |
| 7,807,411 | B2 | 10/2010 | Wang et al. | |
| 7,824,893 | B2 | 11/2010 | Deiters et al. | |
| 7,825,226 | B2 | 11/2010 | Schultz et al. | |
| 7,834,159 | B2 | 11/2010 | Schultz et al. | |
| 2004/0198637 | A1 | 10/2004 | Schultz et al. | |
| 2004/0265952 | A1 | 12/2004 | Deiters et al. | |
| 2005/0009049 | A1 | 1/2005 | Chin et al. | |

(Continued)

FOREIGN PATENT DOCUMENTS

WO    WO 2009/059056    5/2009

(Continued)

OTHER PUBLICATIONS

Hong et al. (1996) "Transfer RNA-dependent cognate amino acid recognition by an aminoacyl-tRNA synthetase." *The EMBO Journal*, 15(8): 1983-1991.

Coleman et al. (1986) "Enzyme-linked immunosorbent assay (ELISA) for detection of antibodies to protein-reactive drugs and metabolites: criteria for identification of antibody activity," *J. Immunol. Meth.*, 88(1):37-44.

Ohno et al. (2001) "Changing the amino acid specificity of yeast tyrosyl-tRNA synthetase by genetic engineering," *J. Biochem.*, 130:417-423.

Novagen Protocol from online catalog, 5 pages, 1995.

Anderson et al., Exploring the Limits of Codon and Anticodon Size, *Chemistry and Biology*, vol. 9, 237-244 (2002).

(Continued)

*Primary Examiner* — Kagnew H Gebreyesus
(74) *Attorney, Agent, or Firm* — Quine Intellectual Property Law Group, P.C.; Paul Littlepage

(57) ABSTRACT

This invention provides compositions and methods for generating components of protein biosynthetic machinery including orthogonal tRNAs, orthogonal aminoacyl-tRNA synthetases, and orthogonal pairs of tRNAs/synthetases. Methods for identifying orthogonal pairs are also provided. These components can be used to incorporate unnatural amino acids into proteins in vivo.

31 Claims, 35 Drawing Sheets

U.S. PATENT DOCUMENTS

| | | | |
|---|---|---|---|
| 2005/0136513 A1 | 6/2005 | Zhang et al. |
| 2005/0208536 A1 | 9/2005 | Schultz et al. |
| 2005/0227318 A1 | 10/2005 | Alfonta et al. |
| 2005/0250183 A1 | 11/2005 | Schultz et al. |
| 2005/0272121 A1 | 12/2005 | Xie et al. |
| 2006/0063244 A1 | 3/2006 | Schultz et al. |
| 2006/0073507 A1 | 4/2006 | Deiters et al. |
| 2006/0110784 A1 | 5/2006 | Deiters et al. |
| 2006/0110796 A1 | 5/2006 | Schultz et al. |
| 2006/0134746 A1 | 6/2006 | Deiters et al. |
| 2006/0160175 A1 | 7/2006 | Anderson et al. |
| 2006/0177900 A1 | 8/2006 | Anderson et al. |
| 2006/0246509 A1 | 11/2006 | Deiters et al. |
| 2007/0009990 A1 | 1/2007 | Alfonta et al. |
| 2007/0020634 A1 | 1/2007 | Anderson et al. |
| 2007/0042461 A1 | 2/2007 | Anderson et al. |
| 2007/0111193 A1 | 5/2007 | Zhang et al. |
| 2007/0117184 A1 | 5/2007 | Schultz et al. |
| 2007/0154952 A1 | 7/2007 | Chin et al. |
| 2007/0166791 A1 | 7/2007 | Chin et al. |
| 2007/0172915 A1 | 7/2007 | Schultz et al. |
| 2007/0178448 A1 | 8/2007 | Tsao et al. |
| 2007/0184517 A1 | 8/2007 | Schultz et al. |
| 2007/0238152 A1 | 10/2007 | Wang et al. |
| 2007/0281335 A1 | 12/2007 | Ryu et al. |
| 2008/0044886 A1 | 2/2008 | Wang et al. |
| 2008/0064059 A1 | 3/2008 | Schultz et al. |
| 2008/0113407 A1 | 5/2008 | Liu et al. |
| 2008/0166766 A1 | 7/2008 | Liu et al. |
| 2008/0166783 A1 | 7/2008 | Schultz et al. |
| 2008/0167243 A1 | 7/2008 | Schultz et al. |
| 2008/0171317 A1 | 7/2008 | Deiters et al. |
| 2008/0176277 A1 | 7/2008 | Chin et al. |
| 2008/0176284 A1 | 7/2008 | Schultz et al. |
| 2008/0213828 A1 | 9/2008 | Schultz et al. |
| 2008/0220472 A1 | 9/2008 | Deiters et al. |
| 2008/0227152 A1 | 9/2008 | Schultz et al. |
| 2008/0227153 A1 | 9/2008 | Schultz et al. |
| 2008/0227195 A1 | 9/2008 | Chin et al. |
| 2008/0233611 A1 | 9/2008 | Schultz et al. |
| 2008/0241903 A1 | 10/2008 | Schultz et al. |
| 2008/0261311 A1 | 10/2008 | Schultz et al. |
| 2009/0053791 A1 | 2/2009 | Schultz et al. |
| 2009/0068717 A1 | 3/2009 | Schultz et al. |
| 2009/0081690 A1 | 3/2009 | Deiters et al. |
| 2009/0137424 A1 | 5/2009 | Tsao et al. |
| 2009/0148887 A1 | 6/2009 | Brustad et al. |
| 2009/0163368 A1 | 6/2009 | Liu et al. |
| 2009/0181429 A1 | 7/2009 | Ryu et al. |
| 2009/0181858 A1 | 7/2009 | Deiters et al. |
| 2009/0197339 A1 | 8/2009 | Young et al. |
| 2009/0208994 A1 | 8/2009 | Seyedsayamodost et al. |
| 2009/0209000 A1 | 8/2009 | Wang et al. |
| 2009/0215117 A1 | 8/2009 | Schultz et al. |
| 2009/0227002 A1 | 9/2009 | Schultz et al. |
| 2009/0263376 A1 | 10/2009 | Grunewald et al. |
| 2009/0298119 A1 | 12/2009 | Wang et al. |
| 2009/0298124 A1 | 12/2009 | Alfonta et al. |
| 2010/0009425 A1 | 1/2010 | Schultz et al. |
| 2010/0021963 A1 | 1/2010 | Liu et al. |
| 2010/0160618 A1 | 6/2010 | Chin et al. |
| 2010/0291559 A1 | 11/2010 | Anderson et al. |
| 2010/0297693 A1 | 11/2010 | Young et al. |

FOREIGN PATENT DOCUMENTS

| | | |
|---|---|---|
| WO | WO 2009/064416 | 5/2009 |
| WO | WO 2009/151491 | 12/2009 |
| WO | WO 2010/114615 | 10/2010 |

OTHER PUBLICATIONS

Azoulay et al., Glutamine analogues as Potential Antimalarials,. *Eur. J. Med. Chem.* 26, 201-5 (1991).

Bain et al., Biosynthetic site-specific Incorporation of a non-natural amino acid into a polypeptide, *J. Am. Chem. Soc.*, 111:8013-8014 (1989).

Barton et al., Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. *Tetrahedron Lett.* 43, 4297-4308 (1987).

Boles et al., *Nat. Struct. Biol.*, 1:283 (1994).

Bradley et al., tRNA2Gln Su+2 mutants that increase amber suppression, *J. Bacteriol.* 145:704-712 (1981).

Brick et al., *J. Mol. Biol.*, 208:83-98 (1988).

Brunner, New Photolabeling and crosslinking methods, *Annu. Rev. Biochem.*, 62:483-514 (1993).

Budisa et al., *Eur. J. Biochem.*, 230:788 (1995).

Budisa et al., *FASEB J.* 13:41-51 (1999).

Budisa et al., *J. Mol. Biol.*, 270:616 (1997).

Budisa et al., *Proc. Natl. Acad. Sci. U S A*, 95:455 (1998).

Christie & Rapoport, Synthesis of Optically Pure Pipecolates from L-Asparagine. Application to the Total Synthesis of (+)-Apovincamine through Amino Acid Decarbonylation and Iminium Ion Cyclization. *J. Org. Chem.* 50:1239-1246 (1985).

Cornish et al., *Angew. Chem. Int. Ed. Engl.*, 34:621 (1995).

Cornish et al., *J. Am. Chem. Soc.*, 118:8150-8151 (1996).

Craig et al., Absolute Configuration of the Enantiomers of 7-Chloro-4 [[4-(diethylamino)-1-methylbutyl]amino]quinoline (Chloroquine). *J. Org. Chem.* 53, 1167-1170 (1988).

Database NCBI, GenBank Accession No. E64348, Bult et al. 'Complete genome sequence of the methanogenic archaeon, *Methanococcus jannaschii*,' Gene Sequence, Jun. 3, 1996.

Doctor & Mudd, *J. Biol. Chem.*, 238:3677 (1963).

Doring et al., *Science*, 292:501 (2001).

Dougherty, *Curr. Opin. Chem. Biol.*, 4:645 (2000).

Duewel et al., *Biochemistry*, 36:3404 (1997).

Dunten & Mowbray, Crystal structure of the dipeptide binding protein from *Escherichia coli* involved in active transport and chemotaxis. *Protein Science* 4, 2327-34 (1995).

Ellman et al., Biosynthetic method for introducing unnatural amino acids site-specifically into proteins, *Methods in Enz.*, 202:301-336 (1992).

Ellman et al., Site-specific incorporation of novel backbone structures into proteins, *Science*, 255:197-200 (1992).

England et al., *Cell*, 96:89 (1999).

Fechter et al., Major tyrosine identity determinants in *Methanococcus jannaschii* and *Saccharomyces cerevisiae* tRNATyr are conserved but expressed differently, *Eur. J. Biochem.* 268:761-767 (2001).

Francisco et al., Production and fluorescence-activated cell sorting of *Escherichia coli* expressing a functional antibody fragment on the external surface. *Proc Natl Acad Sci U S A.* 90:10444-8 (1993).

Francklyn et al. (2002) "Aminoacyl-tRNA synthetases: Versatile players in the changing theater of translation." *RNA*, 8:1363-1372.

Friedman & Chatterrji, Synthesis of Derivatives of Glutamine as Model Substrates for Anti-Tumor Agents. *J. Am. Chem. Soc.* 81, 3750-3752 (1959).

Furter, *Protein Sci.*, 7:419 (1998).

Gabriel & McClain, A set of plasmids constitutively producing different RNA levels in *Escherichia coli*, *J. Mol. Biol.* 290 (1999) 385-389.

Gallivan et al., *Chem. Biol.*, 4:739 (1997).

GenBank Accession No. Q57834, Nov. 1, 1997.

Giegé et al., *Biochimie*, 78:605 (1996).

Giegé et al., Universal rules and idiosyncratic features in tRNA identity, *Nucleic Acids Res.* 26:5017-5035 (1998).

Gay et al., *FEBS Lett.* 318:167 (1993).

Guckian et al., *Angew. Chem. Int. Ed. Engl.*, 36, 2825 (1997).

Hamano-Takaku et al., *J. Biol. Chem.*, 275:40324 (2000).

Hartley et al., Expression of its cloned inhibitor permits expression of a cloned ribonuclease, *J. Mol. Biol.* 202:913-915 (1988).

He, et al., *Microbiology*, 147:2817-2829 (2001).

Hendrickson et al., *EMBO J.*, 9:1665 (1990).

Hirao, et al., An unnatural base pair for incorporating amino acid analogues into protein, *Nature Biotechnology*, 20:177-182 (2002).

Hohsaka et al., *J. Am. Chem. Soc.*, 121:34 (1999).

Ibba & Hennecke, *FEBS Lett.*, 364:272 (1995).

Ibba et al., *Biochemistry*, 33:7107 (1994).

Ibba (1996) "Strategies for in vitro and in vivo incorporation translation with non-natural amino acids" *Biotechnol. Genet. Eng. Rev.* 13:197-216.
Jakubowski & Goldman, *Microbiol. Rev.*, 56:412 (1992).
Jeruzalmi & Steitz, *EMBO J.*, 17, 4101-4113 (1998).
Jucovic & Hartley, Protein-protein interaction: a genetic selection for compensating mutations at the barnase-barstar interface. *Proceedings of the National Academy of Sciences of the United States of America*, 93: 2343-2347 (1996).
Kiga et al. (2002) "An engineered *Escherichia coli* tyrosyl-tRNA synthetase for site-specific incorporation of an unnatural amino acid into proteins in eukaryotic translation and its application in a wheat germ cell-free system." *PNAS*, vol. 99, No. 15, pp. 9715-9723.
Kiick & Tirrell, *Tetrahedron*, 56:9487 (2000).
King et al., A New Synthesis of Glutamine and of γ-Dipeptides of Glutamic Acid from Phthylated Intermediates. *J. Chem. Soc.*, 4:3315-3319 (1949).
Kleeman et al., *J. Biol. Chem.*, 272:14420 (1997).
Kleina et al., Construction of *Escherichia coli* amber suppressor tRNA genes. II. Synthesis of additional tRNA genes and improvement of suppressor efficiency, *J. Mol. Biol.* 213:705-717 (1990).
Kool, *Curr. Opin. Chem. Biol.*, 4:602 (2000).
Koskinen & Rapoport, Synthesis of 4-Substituted Prolines as Conformationally Constrained Amino Acid Analogues. *J. Org. Chem.* 54, 1859-1866. (1989).
Kowal & Oliver, *Nucl. Acid. Res.*, 25:4685 (1997).
Kowal et al., *Proc. Natl. Acad. Sci. U S A*, 98:2268 (2001).
Krieg et al., Photocrosslinking of the signal sequence of nascent preprolactin of the 54-kilodalton polypeptide of the signal recognition particle, *Proc. Natl. Acad. Sci*, 83(22):8604-8608 (1986).
Kwok & Wong, *Can. J. Biochem.*, 58:213 (1980).
Lee et al., *Biotechnology Letters*, 20:479-482, (1998).
Liu & Schultz, Progress toward the evolution of an organism with an expanded genetic code, *Proc. Natl. Acad. Sci. USA* 96:4780-4785 (1999).
Liu et al., *Chem. Biol.*, 4:685 (1997).
Liu et al., Engineering a tRNA and aminoacyl-tRNA synthetase for the site-specific incorporation of unnatural amino acids into proteins in vivo, *Proc. Natl. Acad. Sci. USA* 94:10091-10097 (1997).
Lorincz et al., *Cytometry*, 24, 321-329 (1996).
Lu et al., *Nat. Neurosci.*, 4:239 (2001).
Ma et al., *Biochemistry*, 32:7939 (1993).
Magliery, Expanding the Genetic Code: Selection of Efficient Suppressors of Four-base Codons and Identification of "Shifty" Four-base Codons with a Library Approach in *Escherichia coli, J. Mol. Biol.* 307: 755-769 (2001).
Matsoukas et al., *J. Med. Chem.*, 38: 4660-4669 (1995).
McMinn et al., *J. Am. Chem. Soc.*, 121:11586 (1999).
Meggers et al., *J. Am. Chem. Soc.*, 122:10714 (2000).
Mendel et al., Site-Directed Mutagenesis with an Expanded Genetic Code, *Annu. Rev. Biophys. Biomol. Struct.* 24, 435-62 (1995).
Miller et al., *Neuron*, 20:619 (1998).
Minks et al., *Anal. Biochem.*, 284:29 (2000).
Moore et al., *J. Mol. Biol.*, 298:195 (2000).
Nagagawa et al. (2000) "Mutational Analysis of Invariant Valine B12 in Insulin: Implications for Receptor Binding." *Biochemistry*, 39:15826-15835.
Nickitenko et al., A structure of DppA, a periplasmic depeptide transport/chemosensory receptor. *Biochemistry* 34, 16585-16595 (1995).
Nilsson, et al. *Protein Eng.* 1:107-113 (1987).
Noren et al., A general method for site-specific incorporation of unnatural amino acids into proteins, *Science* 244 182-188 (1989).
Nowak et al., *Science*, 268:439-42 (1995).
Ogawa et al., *J. Am. Chem. Soc.*, 122:3274 (2000).
Ogawa et al., *J. Am. Chem. Soc.*, 122:8803 (2000).
Ohno et al. (1998) "Co-expression of yeast amber suppressor tRNATyr and tyrosyl-tRNA synthetase in *Escherichia coli*: possibility to expand the genetic code." *J. Biochem* 124(6):23169-23175.
O'Mahony et al., Glycine tRNA mutants with normal anticodon loop size cause 1 frameshifting, *Proc. Natl. Acad. Sci. USA* 86:7979-7983 (1989).
Pastrnak & Schultz, *Bioorg. Med. Chem.*, 9:2373 (2001).

Pastrnak et al., A new orthogonal suppressor tRNA/aminoacyl-tRNA synthetase pair for evolving an organism with an expanded genetic code, *Helv. Chim. Acta* 83:2277-2286 (2000).
Piccirilli et al., *Nature*, 1990, 343:33 (1990).
Saks et al. (1996) "An engineered Tetrahymena tRNAGln for in Vivo Incorporation of Unnatural Amino Acids into Proteins by Nonsense Suppression" *J. Biol. Chem* 271(38): 23169-23175.
Santoro & Schultz, *Proc. Natl. Acad Sci USA*, Apr. 2; 99(7):4185-90 (2002).
Santoro et al., *Nature Biotech*, 20:1044-1048, 2002.
Sayers et al., 5', 3' Exonuclease in phosphorothioate-based oligonucleotide-directed mutagenesis, *Nucleic Acids Res.*, 16(3):791-802 (1988).
Shao & Tam, *J. Am. Chem. Soc.*, 117:3893-3899 (1995).
Sharma et al., *FEBS Lett.*, 467:37 (2000).
Sieber et al., *Nature Biotechnology*, 19:456-460 (2001).
Sprinzl et al., Compilation of tRNA sequences and sequences of tRNA genes, *Nucleic Acids Res.* 26:148-153 (1998).
Steer & Schimmel, Major anticodon-binding region missing from an archaebacterial tRNA synthetase, *J. Biol. Chem.* 274:35601-35606 (1999).
Subasinghe et al., Quisqualic acid analogues: synthesis of beta-heterocyclic 2-aminopropanoic acid derivatives and their activity at a novel quisqualate-sensitized site. *J. Med. Chem.* 35 4602-7 (1992).
Sussman et al., Crystal structure of yeast phenylalanine transfer RNA. I. Crystallographic refinement, *J. Mol. Biol.* 123:607-630 (1978).
Switzer et al., *J. Am. Chem. Soc.*, 111:8322 (1989).
Tae et al., *J. Am. Chem. Soc.*, 123:7439 (2001).
Tang et al., *Angew. Chem. Int. Ed. Engl.*, 40:1494 (2001).
Turcatti et al., *J. Biol. Chem.*, 271:19991 (1996).
van Hest & Tirrell, *FEBS Lett.*, 428:68 (1998).
van Hest et al., *J. Am. Chem. Soc.*, 122:1282 (2000).
Wakasugi et al., *EMBO J.* 17:297-305 (1998).
Wang & Schultz, *Chem. and Biol.* 8:883-890 (2001).
Wang & Schultz, Expanding the genetic code, *Chem. Commun.*, 1:1-11 (2002).
Wang et al., A new functional suppressor tRNA/aminoacyl-tRNA synthetase pair for the in vivo incorporation of unnatural amino acids into proteins, *J. Am. Chem. Soc.* 122:5010-5011 (2000).
Wang et al., Expanding the genetic code of *Escherichia coli, Science*, 292:498-500 (2001).
Wang et al., *J. Am. Chem. Soc.* 124, 1836-1837(2002).
Weiner et al., A binding protein for L-glutamine and its relation to active transport in *E. coli*. *Archives of Biochemistry and Biophysics*, 142:715-717 (1971).
Whelihan & Schimmel, *EMBO J.*, 16:2968 (1997).
Yarus, Translational efficiency of transfer RNA's: Use of an expanded anticodon, *Science* 218:646-652 (1982).
Zlokarnik et al., *Science*, 279, 84-88 (1998).
GenBank Accession No. 030250; Klenk et al. (May 30, 2000) The complete genome sequence of the hyperthermophilic, sulphate-reducing archaeon *Archaroglobus fulgidus*, Retrieved from NCBI Nucleotide [online]; National Center for Biotechnology Information U.S. National Library of Medicine, Bethesda, Md., USA.
Eriani et. al. (1990) "Partition of tRNA synthetases into two classes based on mutually exclusive sets of sequence motifs." *Nature*, 347: 203-206.
Ames et al. (1973) "Illicit transport: the oligopeptide permease," *PNAS*, 70(2):456-458.
Labarre et al.(1987) "Genetic analysis of amino acid transport in the facultatively heterotrophic cyanobacterium *synechocystis* sp. strain," *J. Bacteriol.*, 169(10):4668-4673.
Payne et al. (1984) "Transport and hydrolysis of antibacterial peptide analogues in *Escherichia coli*: backbone-modified aminoxy peptides," *J. Gen. Microbiol.*, 130:2253-2265.
Borman (2003) Reinventing Biology: Bacteria make protein with nonnatural amino acid they synthesize themselves, CENEAR, 81(3):7.
Hendrickson et al. (2004) "Incorporation of Nonnatural Amino Acids into Proteins," Ann. Rev. Biochem., 73:147-176.

Kang et al. (2002) "A cell-free protein synthesis system as an investigational tool for the translation stop processes," FEBS Letters, 517(1-3):211-214.

Rinaldi (2004) "A New Code for Life," EMBO Reports, 5(4):336-339.

Shi et al. (1994) "Region of a conserved sequence motif in a class II tRNA synthetase needed for transfer of an activated amino acid to an RNA substrate," *Biochem*, 33:5312-5318.

* cited by examiner

|  | 32 | | 67 | 70 | | 107 | 155 | | 160 | | 167 |
|---|---|---|---|---|---|---|---|---|---|---|---|
| Wild Type | Tyr | -- | Ala Asp Leu | His | -- | Glu | -- Gln Val Asn Asp | Ile | His Tyr Leu Gly | Val | Asp Val Ala |
| Library 1 | NNN | -- | Ala Asp Leu | His | -- | NNN | -- Gln Val Asn NNN | NNN | His Tyr NNN Gly | Val | Asp Val Ala |
| Library 2 | NNN | -- | Ala Asp Leu | His | -- | Glu | -- Gln Val Asn NNN | NNN | His Tyr NNN Gly | Val | Asp Val NNN |
| Library 3 | NNN | -- | NNN Asp Leu | NNN | -- | Glu | -- NNN Val Asn NNN | Ile | His Tyr Leu Gly | Val | Asp Val NNN |

Consensus sequence

Ile -- Gln Asp Leu Tyr -- Glu -- Ala Val Asn Ala Ile His Tyr Leu Gly Val Asp Val Leu

Fig. 4

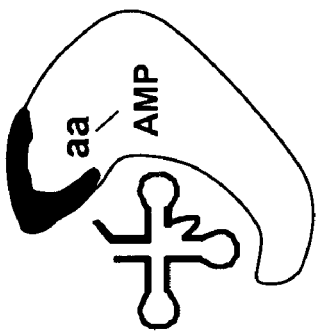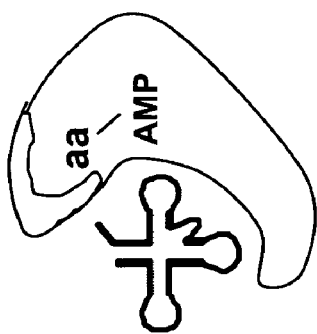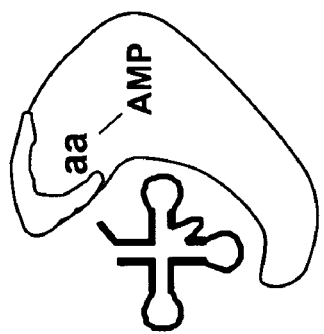
Fig. 5

```
EcTyrRS  1 WFGNMNVLTFLRDIGKHFSVNQMINKEAVKQRLNREDQGISFTE
HsTyrRS  1 -LSKEYTLDVYRLS---SVVTQHDSKKAGAEVVKQVEHPLLSG-
MjTyrRS  1 LDKDYTLNVYRLALKTTLKRARRSMELIAREDENPKVAE
HsTyrRS  1 LSKEYTLDVYRLSSVVTQHDSKKAGAEVVKQVEHPLLSG
```
*M. jannaschii* 
*E. coli* 
*Chimera #1* 
*Chimera #2* 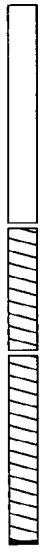
*Chimera #3* 
Fig. 6

Mutant tRNAs selected from anticodon-loop library

```
ATL LIB  ------------------------------------NN---NN-----------------------------------------
JY       CCGGCGGTAGTTCAGCCTGGTAGAACGGCGGACTCTAGATCCGCATGTCGCTGGTTCAAATCCGCCCGCCGACCA
AA2      CCGGCGGTAGTTCAGCCTGGTAGAACGGCGGACACTAAATCCGCATGTCGCTGGTTCAAATCCGCCCGCCGACCA
AA3      CCGGCGGTAGTTCAGCCTGGTAGAACGGCGGACACTAAATCCGCATGTCGCTGGTTCAAATCCGCCTGCCGACCA
AA4      CCGGCGGTAGTTCAGCCTGGTAGAACGGCGGAATCTAAATCCGCATGTCGTTGGTTCAAATCCGCCCGCCGACCA
```

Mutant tRNAs selected from all-loop library

Mutant tRNAs surviving both selections

```
AL LIB   -------------NNN--N--------N---NN-----N-N----NN------N-N------NN---------------
JY       CCGGCGGTAGTTCAGCCTGGTAGAACGGCGGACTCTAGATCCGCATGTCGCTGGTTCAAATCCGCCCGCCGACCA
J15      CCGGCGGTAGTTCAGTGAGAAGAAGAACGGCGGACTCTAAATCCGCATGTCGCTGGTTCAAGTCCGCCCGCCGACCA
J17      CCGGCGGTAGTTCAGCAGGGCAGAAGAACGGCGGACTCTAAATCCGCATGGCGCTGGTTCAAATCCGCCCGCCGACCA
J18      CCGGCGGTAGTTCAGATAGGGAGAACGGCGGACTCTAACTCCGCATGGCGCTGGTTCAATTCCGCCCGCCGACCA
J22      CCGGCGGTAGTTCAGGTAGGGAGAACGGCGGACTCTAACTCCGCATGTCGCTGGTTCAAGTCCGCCCGCCGACCA
```

Mutant tRNAs surviving negative selection only

```
AL LIB   -------------NNN--N--------N---NN-----N-N----NN------N-N------NN---------------
JY       CCGGCGGTAGTTCAGCCTGGTAGAACGGCGGACTCTAGATCCGCATGTCGCTGGTTCAAATCCGCCCGCCGACCA
N11      CCGGCGGTAGTTCAGTTCAGTTCAGGGAGAACGGCGGACTCTAAATCCGCACGTCGCTGGTTCAAGTCCGCCCGCCGACCA
N12      CCGGCGGTAGTTCAGGGTGGGAGAACGGCGGAGTCTAGGTCCGCATGCCGCTGGTTCAATACCGCCCGCCGACCA
N13      CCGGCGGTAGTTCAGTTCGGCAGAACGGCGGAGTCTATATCCGCACGCCGCTGGTTCAACCCCGCCCGCCGACCA
N16      CCGGCGGTAGTTCAGTGTGAAGAACGGCGGATTCTATCTCCGCACGCGCGCTGGTTCAAGGCCGCCCGCCGACCA
```

Fig. 13

| Construct Number | Mutations | Fluorescence Enhancement (fold) |
|---|---|---|
| 1 | M1 (−7 to 884) | 12 |
| 2 | M1 | - |
| 3 | M1 | - |
| 4 | D10 | 4 |
| 5 | R96 | - |
| 6 | Q107 | 32 |
| 7 | A159 | 6 |
| 8 | Q169 | - |
| 9 | Q232 | 20 |
| 10 | M1, Q107 | 220 |
| 11 | M1, A159 | 48 |
| 12 | M1, Q232 | 82 |

Figure 17B

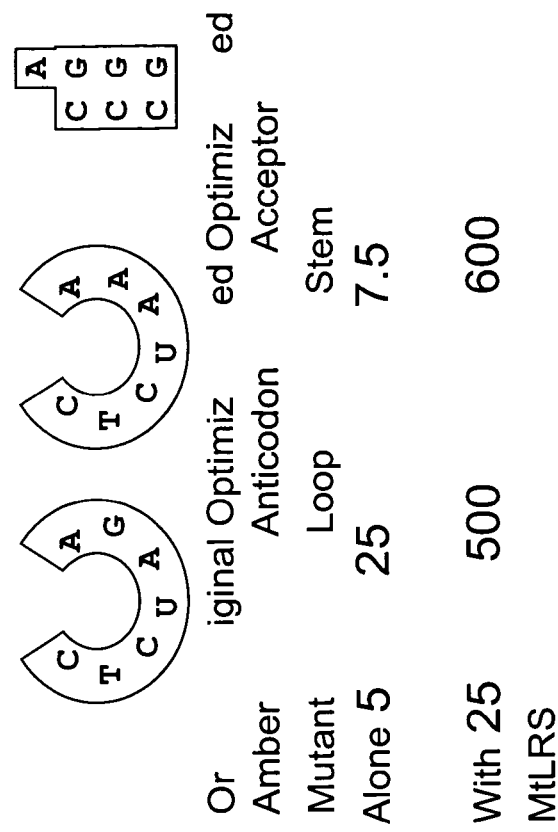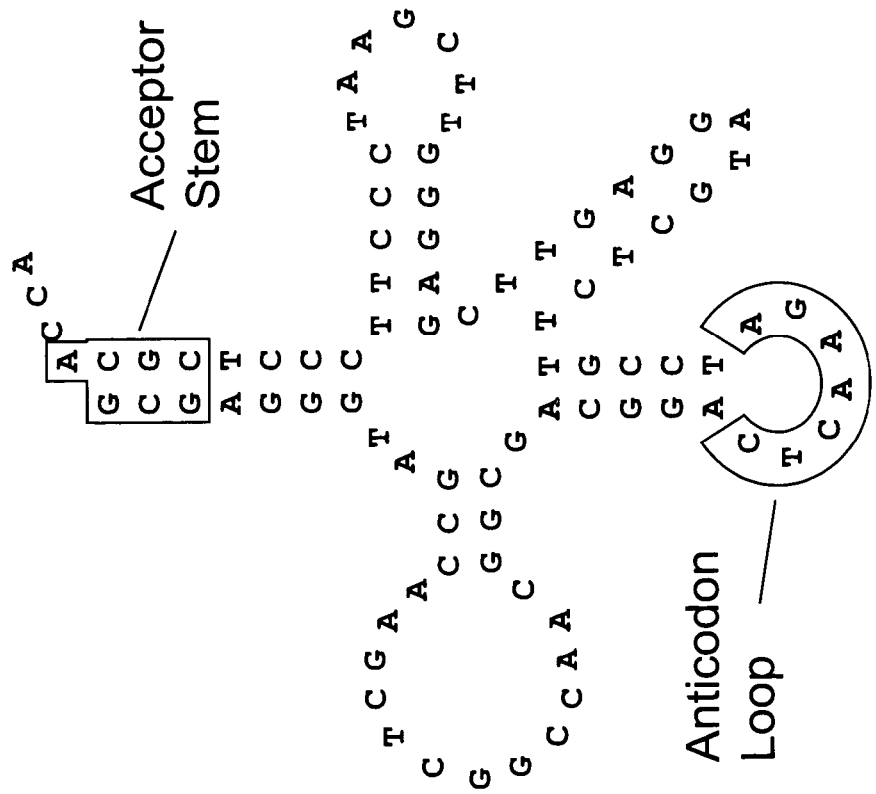

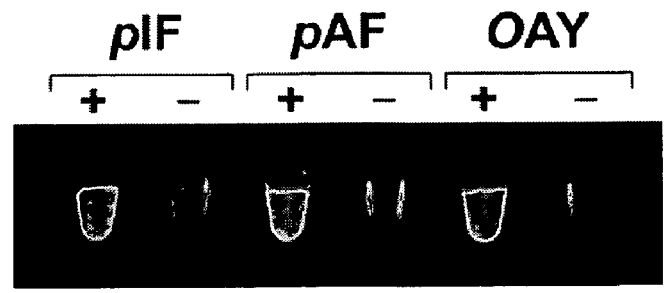
Fig. 23A
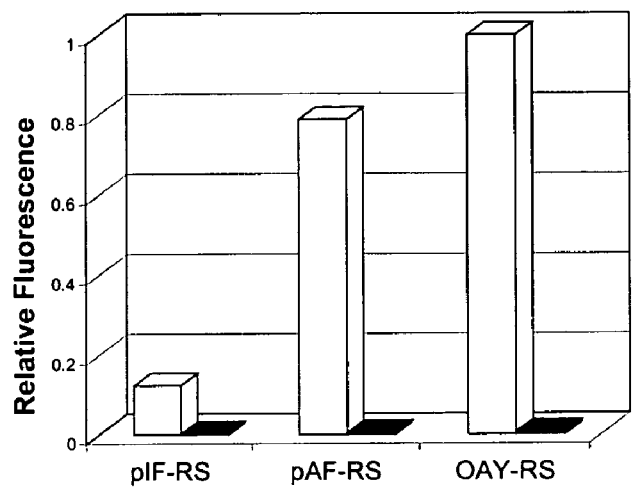
Fig. 23B
Fig. 23C
| Cm IC$_{50}$ (µg/mL) | pIF-RS | pAF-RS | OAY-RS(1) |
|---|---|---|---|
| − Unnatural | < 5 | < 5 | < 5 |
| + Unnatural | 75 | 100 | 120 |
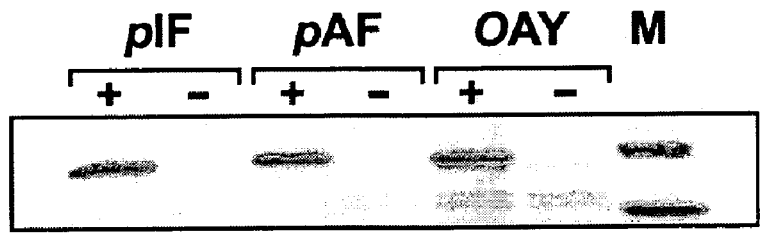
Fig. 23D

SEQUENCE LISTING

```
<160> NUMBER OF SEQ ID NOS: 108

<210> SEQ ID NO 1
<211> LENGTH: 77
<212> TYPE: DNA
<213> ORGANISM: Methanococcus jannaschii

<400> SEQUENCE: 1
ccggcggtag ttcagcaggg cagaacggcg gactctaaat ccgcatggcg ctggttcaaa      60
tccggcccgc cggacca                                                    77

<210> SEQ ID NO 2
<211> LENGTH: 88
<212> TYPE: DNA
<213> ORGANISM: Halobacterium sp. NRC-1

<400> SEQUENCE: 2
cccagggtag ccaagctcgg ccaacggcga cggactctaa atccgttctc gtaggagttc      60
gagggttcga atcccttccc tgggacca                                        88
```

<210> SEQ ID NO 3
<211> LENGTH: 89
<212> TYPE: DNA
<213> ORGANISM: Halobacterium sp. NRC-1

<400> SEQUENCE: 3

```
gcgagggtag ccaagctcgg ccaacggcga cggacttcct aatccgttct cgtaggagtt    60
cgagggttcg aatccctccc ctcgcacca                                      89
```

<210> SEQ ID NO 4
<211> LENGTH: 921
<212> TYPE: DNA
<213> ORGANISM: Methanococcus jannaschii

<400> SEQUENCE: 4

```
atggacgaat tgaaatgat aaagagaaac acatctgaaa ttatcagcga ggaagagtta     60
agagaggttt taaaaaaga tgaaaaatct gctcagatag gttttgaacc aagtggtaaa    120
atacatttag gcattatct ccaaataaaa aagatgattg atttacaaaa tgctggattt    180 gataataatta tattgttggc tgatttacac gcctatttaa accagaaagg agagttggat   240
gagattagaa aaataggaga ttataacaaa aaagttttg aagcaatggg gttaaaggca    300
aaatatgttt atggaagtac tttccagctt gataaggatt atacactgaa tgtctataga   360
ttggctttaa aaactacctt aaaaagagca agaaggagta tggaacttat agcaagagag   420
gatgaaaatc caaggttgc tgaagttatc atccaataa tgcaggttaa tgcaattcat    480
tatcctggcg ttgatgttgc agttggaggg atggagcaga aaaaatata catgttagca   540 agggagcttt taccaaaaaa ggttgtttgt attcacaacc ctgtcttaac gggtttggat   600
ggagaaggga agatgagttc ttcaaaaggg aatttttatag ctgttgatga ctctccagaa   660
gagattaggg ctaagataaa gaagcatac tgcccagctg gagttgttga aggaaatcca   720
ataatggaga tagctaaata cttccttgaa tatccttaa ccataaaaaag gccagaaaaa   780 tttggtggag atttgacagt tagtagctat gaggagttag agagtttatt taaaaataag   840
gaattgcatc caatggattt aaaaaatgct gtagctgaag aacttataaa gattttagag   900
ccaattagaa agagattata a                                             921
```

<210> SEQ ID NO 5
<211> LENGTH: 917
<212> TYPE: DNA
<213> ORGANISM: Methanococcus jannaschii

<400> SEQUENCE: 5

```
atggacgaat tgaaatgat aaagagaaac acatctgaaa ttatcagcga ggaagagtta     60
agagaggttt taaaaaaga tgaaaaatct gctgggatag gttttgaacc aagtggtaaa    120
atacatttag gcattatct ccaaataaaa aagatgattg atttacaaaa tgctggattt    180 gataataatta tattgttggc tgatttacac gcctatttaa accagaaagg agagttggat   240
gagattagaa aaataggaga ttataacaaa aaagttttg aagcaatggg gttaaaggca    300
aaatgtgctt atggaagtcc tttccagctt gataaggatt atacactgaa tgtctataga   360
ttggctttaa aaactacctt aaaaagagca agaaggagta tggaacttat agaagagagg   420
atgaaaatcc aaaggttgct gaagttatct atccaataat gcaggttaat ggttatcatt   480
atcttggcgt tgatgttgca gttggaggga tggagcagaa aaaatacac atgttagcaa   540 gggagcttt accaaaaaag gttgtttgta ttcacaaccc tgtcttaacg ggtttggatg   600
```

```
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
caattagaaa gagatta                                                  917

<210> SEQ ID NO 6
<211> LENGTH: 917
<212> TYPE: DNA
<213> ORGANISM: Methanococcus jannaschii

<400> SEQUENCE: 6
atggacgaat tgaaatgat aaagagaaac acatctgaaa ttatcagcga ggaagagtta     60
agagaggttt taaaaaaga tgaaaaatct gctcagatag gttttgaacc aagtggtaaa    120
atacatttag gcattatct ccaaataaaa aagatgattg atttacaaaa tgctggattt    180
gatataatta tattgttggc tgatttacac gcctatttaa accagaaagg agagttggat    240
gagattagaa aataggaga ttataacaaa aaagttttg aagcaatggg gttaaaggca    300
aaatatgttt atggaagtcc tttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat tgttctcatt    480
attatggcgt tgatgttgca gttggaggga tggagcagag aaaaatacac atgttagcaa    540
gggagctttt accaaaaaag gttgtttgta ttcacaaccc tgtcttaacg ggtttggatg    600
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
caattagaaa gagatta                                                  917

<210> SEQ ID NO 7
<211> LENGTH: 917
<212> TYPE: DNA
<213> ORGANISM: Methanococcus jannaschii

<400> SEQUENCE: 7
atggacgaat tgaaatgat aaagagaaac acatctgaaa ttatcagcga ggaagagtta     60
agagaggttt taaaaaaga tgaaaaatct gctactatag gttttgaacc aagtggtaaa    120
atacatttag gcattatct ccaaataaaa aagatgattg atttacaaaa tgctggattt    180
gatataatta tattgttggc tgatttacac gcctatttaa accagaaagg agagttggat    240
gagattagaa aataggaga ttataacaaa aaagttttg aagcaatggg gttaaaggca    300
aaatatgttt atggaagtac gttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat ccgttgcatt    480
atgctggcgt tgatgttgca gttggaggga tggagcagag aaaaatacac atgttagcaa    540
gggagctttt accaaaaaag gttgtttgta ttcacaaccc tgtcttaacg ggtttggatg    600
```

```
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
caattagaaa gagatta                                                  917

<210> SEQ ID NO 8
<211> LENGTH: 917
<212> TYPE: DNA
<213> ORGANISM: Methanococcus jannaschii

<400> SEQUENCE: 8
atggacgaat tgaaatgat aaagagaaac acatctgaaa ttatcagcga ggaagagtta     60
agagaggttt taaaaaaga tgaaaatct gctcatatag gttttgaacc aagtggtaaa     120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagttttg aagcaatggg gttaaaggca    300
aaatatgttt atggaagtga gttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat cggccgcatt    480
atcctggcgt tgatgttgca gttggaggga tggagcagag aaaaatacac atgttagcaa    540
gggagctttt accaaaaaag gttgtttgta ttcacaaccc tgtcttaacg ggtttggatg    600
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
caattagaaa gagatta                                                  917

<210> SEQ ID NO 9
<211> LENGTH: 917
<212> TYPE: DNA
<213> ORGANISM: Methanococcus jannaschii

<400> SEQUENCE: 9
atggacgaat tgaaatgat aaagagaaac acatctgaaa ttatcagcga ggaagagtta     60
agagaggttt taaaaaaga tgaaaatct gcttatatag gttttgaacc aagtggtaaa     120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagttttg aagcaatggg gttaaaggca    300
aaatatgttt atggaagtcc tttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat cagagtcatt    480
atgatggcgt tgatgttgca gttggaggga tggagcagag aaaaatacac atgttagcaa    540
gggagctttt accaaaaaag gttgtttgta ttcacaaccc tgtcttaacg ggtttggatg    600
```

| | |
|---|---|
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttatttt aaaaataagg | 840 |
| aattgcatcc aatggattta aaaaatgctg tagctgaaga acttataaag attttagagc | 900 |
| caattagaaa gagatta | 917 |

<210> SEQ ID NO 10
<211> LENGTH: 917
<212> TYPE: DNA
<213> ORGANISM: Methanococcus jannaschii

<400> SEQUENCE: 10

| | |
|---|---|
| atggacgaat ttgaaatgat aaagagaaac acatctgaaa ttatcagcga ggaagagtta | 60 |
| agagaggttt taaaaaaaga tgaaaaatct gcttcgatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtac gttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat acgtatcatt | 480 |
| atgctggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttatttt aaaaataagg | 840 |
| aattgcatcc aatggattta aaaaatgctg tagctgaaga acttataaag attttagagc | 900 |
| caattagaaa gagatta | 917 |

<210> SEQ ID NO 11
<211> LENGTH: 917
<212> TYPE: DNA
<213> ORGANISM: Methanococcus jannaschii

<400> SEQUENCE: 11

| | |
|---|---|
| atggacgaat ttgaaatgat aaagagaaac acatctgaaa ttatcagcga ggaagagtta | 60 |
| agagaggttt taaaaaaaga tgaaaaatct gctcctatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtat gttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat aatacgcatt | 480 |
| atgggggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |

| gagaaggaaa gatgagttct tcaaaaggga atttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 12
<211> LENGTH: 917
<212> TYPE: DNA
<213> ORGANISM: Methanococcus jannaschii

<400> SEQUENCE: 12

| atggacgaat ttgaaatgat aaagagaaac acatctgaaa ttatcagcga ggaagagtta | 60 |
| agagaggttt taaaaaaaga tgaaaaatct gctacgatag gttttgaacc aagtggtaaa | 120 |
| atacatttag ggcattatct ccaaataaaa aagatgattg atttacaaaa tgctggattt | 180 |
| gataataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atgaagtca tttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat cagactcatt | 480 |
| atgagggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 13
<211> LENGTH: 917
<212> TYPE: DNA
<213> ORGANISM: Methanococcus jannaschii

<400> SEQUENCE: 13

| atggacgaat ttgaaatgat aaagagaaac acatctgaaa ttatcagcga ggaagagtta | 60 |
| agagaggttt taaaaaaaga tgaaaaatct gctcatatag gttttgaacc aagtggtaaa | 120 |
| atacatttag ggcattatct ccaaataaaa aagatgattg atttacaaaa tgctggattt | 180 |
| gataataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atgaagtaa gttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat ccgtgtcatt | 480 |
| atcatggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |

| | |
|---|---|
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttatt aaaaataagg | 840 |
| aattgcatcc aatggattta aaaaatgctg tagctgaaga acttataaag attttagagc | 900 |
| caattagaaa gagatta | 917 |

<210> SEQ ID NO 14
<211> LENGTH: 917
<212> TYPE: DNA
<213> ORGANISM: Methanococcus jannaschii

<400> SEQUENCE: 14

| | |
|---|---|
| atggacgaat tgaaatgat aaagagaaac acatctgaaa ttatcagcga ggaagagtta | 60 |
| agagaggttt taaaaaaga tgaaaatct gctgctatag gttttgaacc aagtggtaaa | 120 |
| atacatttag ggcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtcg gttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat gtgattcatt | 480 |
| atgatggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttatt aaaaataagg | 840 |
| aattgcatcc aatggattta aaaaatgctg tagctgaaga acttataaag attttagagc | 900 |
| caattagaaa gagatta | 917 |

<210> SEQ ID NO 15
<211> LENGTH: 917
<212> TYPE: DNA
<213> ORGANISM: Methanococcus jannaschii

<400> SEQUENCE: 15

| | |
|---|---|
| atggacgaat tgaaatgat aaagagaaac acatctgaaa ttatcagcga ggaagagtta | 60 |
| agagaggttt taaaaaaga tgaaaatct gctgggatag gttttgaacc aagtggtaaa | 120 |
| atacatttag ggcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtac tttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat acgtattatt | 480 |
| atgctggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |

| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 16
<211> LENGTH: 917
<212> TYPE: DNA
<213> ORGANISM: Methanococcus jannaschii

<400> SEQUENCE: 16

| atggacgaat ttgaaatgat aaagagaaac acatctgaaa ttatcagcga ggaagagtta | 60 |
| agagaggttt taaaaaaaga tgaaaaatct gctctgatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtcc gttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat cagattcatt | 480 |
| ctagtggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 17
<211> LENGTH: 921
<212> TYPE: DNA
<213> ORGANISM: Methanococcus jannaschii

<400> SEQUENCE: 17

| atggacgaat ttgaaatgat aaagagaaac acatctgaaa ttatcagcga ggaagagtta | 60 |
| agagaggttt taaaaaaaga tgaaaaatct gctgacatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtga attccagctt gataaggatt atacactgaa tgtctataga | 360 |
| ttggctttaa aaactacctt aaaaagagca agaaggagta tggaacttat agcaagagag | 420 |
| gatgaaaatc caaaggttgc tgaagttatc tatccaataa tgcaggttaa tggaatgcat | 480 |
| tatcaaggcg ttgatgttgc agttggaggg atggagcaga gaaaaataca catgttagca | 540 |
| agggagcttt taccaaaaaa ggttgtttgt attcacaacc ctgtcttaac gggtttggat | 600 |

| ggagaaggaa agatgagttc ttcaaaaggg aattttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 18
<211> LENGTH: 921
<212> TYPE: DNA
<213> ORGANISM: Methanococcus jannaschii

<400> SEQUENCE: 18

| atggacgaat ttgaaatgat aaagagaaac acatctgaaa ttatcagcga ggaagagtta | 60 |
| agagaggttt taaaaaaga tgaaaatct gcttacatag gttttgaacc aagtggtaaa | 120 |
| atacatttag gcattatct ccaaataaaa aagatgattg atttacaaaa tgctggattt | 180 |
| gataataatta tattgttggc tgatttacac gcctatttaa accagaaagg agagttggat | 240 |
| gagattagaa aataggaga ttataacaaa aagttttg aagcaatggg gttaaaggca | 300 |
| aaatatgttt atggaagtct attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa tgatattcat | 480 |
| tatacaggcg ttgatgttgc agttggaggg atggagcaga gaaaaataca catgttagca | 540 |
| agggagcttt taccaaaaaa ggttgtttgt attcacaacc ctgtcttaac gggtttggat | 600 |
| ggagaaggaa agatgagttc ttcaaaaggg aattttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 19
<211> LENGTH: 921
<212> TYPE: DNA
<213> ORGANISM: Methanococcus jannaschii

<400> SEQUENCE: 19

| atggacgaat ttgaaatgat aaagagaaac acatctgaaa ttatcagcga ggaagagtta | 60 |
| agagaggttt taaaaaaga tgaaaatct gctctaatag gttttgaacc aagtggtaaa | 120 |
| atacatttag gcattatct ccaaataaaa aagatgattg atttacaaaa tgctggattt | 180 |
| gataataatta tattgttgac agatttaaac gcctatttaa accagaaagg agagttggat | 240 |
| gagattagaa aataggaga ttataacaaa aagttttg aagcaatggg gttaaaggca | 300 |
| aaatatgttt atggaagtga attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa tgatattcat | 480 |
| tatttaggcg ttgatgttgc agttggaggg atggagcaga gaaaaataca catgttagca | 540 |
| agggagcttt taccaaaaaa ggttgtttgt attcacaacc ctgtcttaac gggtttggat | 600 |

| | |
|---|---|
| ggagaaggaa agatgagttc ttcaaaaggg aatttttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 20
<211> LENGTH: 921
<212> TYPE: DNA
<213> ORGANISM: Methanococcus jannaschii

<400> SEQUENCE: 20

| | |
|---|---|
| atggacgaat ttgaaatgat aaagagaaac acatctgaaa ttatcagcga ggaagagtta | 60 |
| agagaggttt taaaaaaaga tgaaaatct gctctaatag gttttgaacc aagtggtaaa | 120 |
| atacatttag gcattatct ccaaataaaa aagatgattg atttacaaaa tgctggattt | 180 |
| gatataatta tattgttgac agatttaaaa gcctatttaa accagaaagg agagttggat | 240 |
| gagattagaa aataggaga ttataacaaa aaagttttg aagcaatggg gttaaaggca | 300 |
| aaatatgttt atggaagtga attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgtcagttaa tgtaattcat | 480 |
| tatttaggcg ttgatgttgt agttggaggg atggagcaga aaaaataca catgttagca | 540 |
| agggagcttt taccaaaaaa ggttgtttgt attcacaacc ctgtcttaac gggtttggat | 600 |
| ggagaaggaa agatgagttc ttcaaaaggg aatttttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 21
<211> LENGTH: 921
<212> TYPE: DNA
<213> ORGANISM: Methanococcus jannaschii

<400> SEQUENCE: 21

| | |
|---|---|
| atggacgaat ttgaaatgat aaagagaaac acatctgaaa ttatcagcga ggaagagtta | 60 |
| agagaggttt taaaaaaaga tgaaaatct gctctaatag gttttgaacc aagtggtaaa | 120 |
| atacatttag gcattatct ccaaataaaa aagatgattg atttacaaaa tgctggattt | 180 |
| gatataatta tattgttgcc agatttatca gcctatttaa accagaaagg agagttggat | 240 |
| gagattagaa aataggaga ttataacaaa aaagttttg aagcaatggg gttaaaggca | 300 |
| aaatatgttt atggaagtga attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa tgatattcat | 480 |
| tatttaggcg ttgatgttgc agttggaggg atggagcaga aaaaataca catgttagca | 540 |
| agggagcttt taccaaaaaa ggttgtttgt attcacaacc ctgtcttaac gggtttggat | 600 |

| | |
|---|---|
| ggagaaggaa agatgagttc ttcaaaaggg aatttttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 22
<211> LENGTH: 921
<212> TYPE: DNA
<213> ORGANISM: Methanococcus jannaschii

<400> SEQUENCE: 22

| | |
|---|---|
| atggacgaat ttgaaatgat aaagagaaac acatctgaaa ttatcagcga ggaagagtta | 60 |
| agagaggttt taaaaaaaga tgaaaaatct gctacaatag gttttgaacc aagtggtaaa | 120 |
| atacatttag gcattatct ccaaataaaa aagatgattg atttacaaaa tgctggattt | 180 |
| gataataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atgaagtga attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa tgatattcat | 480 |
| tatgcaggcg ttgatgttgc agttggaggg atggagcaga gaaaaataca catgttagca | 540 |
| agggagcttt taccaaaaaa ggttgttttgt attcacaacc ctgtcttaac gggtttggat | 600 |
| ggagaaggaa agatgagttc ttcaaaaggg aatttttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 23
<211> LENGTH: 921
<212> TYPE: DNA
<213> ORGANISM: Methanococcus jannaschii

<400> SEQUENCE: 23

| | |
|---|---|
| atggacgaat ttgaaatgat aaagagaaac acatctgaaa ttatcagcga ggaagagtta | 60 |
| agagaggttt taaaaaaaga tgaaaaatct gctacaatag gttttgaacc aagtggtaaa | 120 |
| atacatttag gcattatct ccaaataaaa aagatgattg atttacaaaa tgctggattt | 180 |
| gataataatta tattgttgtc cgatttacca gcctatttaa accagaaagg agagttggat | 240 |
| gagattagaa aataggaga ttataacaaa aaagttttg aagcaatggg gttaaaggca | 300 |
| aaatatgttt atgaagtga attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa tgatattcat | 480 |
| tatttaggcg ttgatgttgc agttggaggg atggagcaga gaaaaataca catgttagca | 540 |
| agggagcttt taccaaaaaa ggttgttttgt attcacaacc ctgtcttaac gggtttggat | 600 |

| ggagaaggaa agatgagttc ttcaaaaggg aattttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 24
<211> LENGTH: 921
<212> TYPE: DNA
<213> ORGANISM: Methanococcus jannaschii

<400> SEQUENCE: 24

| atggacgaat ttgaaatgat aaagagaaac acatctgaaa ttatcagcga ggaagagtta | 60 |
| agagaggttt taaaaaaaga tgaaaaatct gctacaatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atgaagtat gttccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa ttcatcacat | 480 |
| tatgacggcg ttgatgttgc agttggaggg atggagcaga gaaaaataca catgttagca | 540 |
| agggagcttt taccaaaaaa ggttgtttgt attcacaacc ctgtcttaac gggtttggat | 600 |
| ggagaaggaa agatgagttc ttcaaaaggg aattttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 25
<211> LENGTH: 921
<212> TYPE: DNA
<213> ORGANISM: Methanococcus jannaschii

<400> SEQUENCE: 25

| atggacgaat ttgaaatgat aaagagaaac acatctgaaa ttatcagcga ggaagagtta | 60 |
| agagaggttt taaaaaaaga tgaaaaatct gctcaaatag gttttgaacc aagtggtaaa | 120 |
| atacatttag gcattatct ccaaataaaa aagatgattg atttacaaaa tgctggattt | 180 |
| gatataatta tattgttgcc agatttacac gcctatttaa accagaaagg agagttggat | 240 |
| gagattagaa aataggaga ttataacaaa aaagttttg aagcaatggg gttaaaggca | 300 |
| aaatatgttt atgaagtga attccagctt gataaggatt atacactgaa tgtctataga | 360 |
| ttggctttaa aaactacctt aaaaagagca agaaggagta tggaacttat agcaagagag | 420 |
| gatgaaaatc caaggttgc tgaagttatc tatccaataa tgcaggttaa tgatattcat | 480 |
| tatttaggcg ttgatgttga cgttggaggg atggagcaga gaaaaataca catgttagca | 540 |
| agggagcttt taccaaaaaa ggttgtttgt attcacaacc ctgtcttaac gggtttggat | 600 |

```
ggagaaggaa agatgagttc ttcaaaaggg aatttttatag ctgttgatga ctctccagaa      660
gagattaggg ctaagataaa gaaagcatac tgcccagctg gagttgttga aggaaatcca      720
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagattata a                                                921

<210> SEQ ID NO 26
<211> LENGTH: 921
<212> TYPE: DNA
<213> ORGANISM: Methanococcus jannaschii

<400> SEQUENCE: 26
atggacgaat tgaaatgat  aaagagaaac acatctgaaa ttatcagcga ggaagagtta       60
agagaggttt taaaaaaga  tgaaaaatct gctcacatag gttttgaacc aagtggtaaa      120
atacatttag ggcattatct ccaaataaaa aagatgattg atttacaaaa tgctggattt      180
gatataatta tattgttggc tgatttacac gcctatttaa accagaaagg agagttggat      240
gagattagaa aaataggaga ttataacaaa aaagtttttg aagcaatggg gttaaaggca      300
aaatatgttt atgaagtgc  attccagctt gataaggatt atacactgaa tgtctataga      360
ttggctttaa aaactacctt aaaaagagca agaaggagta tggaacttat agcaagagag      420
gatgaaaatc caaggttgc  tgaagttatc tatccaataa tgcaggttaa tggacaccat      480
tatataggcg ttgatgttgc agttggaggg atggagcaga gaaaaataca catgttagca      540
agggagcttt taccaaaaaa ggttgtttgt attcacaacc ctgtcttaac gggtttggat      600
ggagaaggaa agatgagttc ttcaaaaggg aatttttatag ctgttgatga ctctccagaa      660
gagattaggg ctaagataaa gaaagcatac tgcccagctg gagttgttga aggaaatcca      720
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagattata a                                                921

<210> SEQ ID NO 27
<211> LENGTH: 921
<212> TYPE: DNA
<213> ORGANISM: Methanococcus jannaschii

<400> SEQUENCE: 27
atggacgaat tgaaatgat  aaagagaaac acatctgaaa ttatcagcga ggaagagtta       60
agagaggttt taaaaaaga  tgaaaaatct gcttacatag gttttgaacc aagtggtaaa      120
atacatttag ggcattatct ccaaataaaa aagatgattg atttacaaaa tgctggattt      180
gatataatta tattgttggc tgatttacac gcctatttaa accagaaagg agagttggat      240
gagattagaa aaataggaga ttataacaaa aaagtttttg aagcaatggg gttaaaggca      300
aaatatgttt atgaagtgc  attccagctt gataaggatt atacactgaa tgtctataga      360
ttggctttaa aaactacctt aaaaagagca agaaggagta tggaacttat agcaagagag      420
gatgaaaatc caaggttgc  tgaagttatc tatccaataa tgcaggttaa ttgcgcacat      480
tatttaggcg ttgatgttgc agttggaggg atggagcaga gaaaaataca catgttagca      540
agggagcttt taccaaaaaa ggttgtttgt attcacaacc ctgtcttaac gggtttggat      600
```

| | |
|---|---|
| ggagaaggaa agatgagttc ttcaaaaggg aatttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagattata a | 921 |

<210> SEQ ID NO 28
<211> LENGTH: 917
<212> TYPE: DNA
<213> ORGANISM: Methanococcus jannaschii

<400> SEQUENCE: 28

| | |
|---|---|
| atggacgaat tgaaatgat aaagagaaac acatctgaaa ttatcagcga ggaagagtta | 60 |
| agagaggttt taaaaaaga tgaaaatct gctggtatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagttc cttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat acgagtcatt | 480 |
| atctgggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 29
<211> LENGTH: 917
<212> TYPE: DNA
<213> ORGANISM: Methanococcus jannaschii

<400> SEQUENCE: 29

| | |
|---|---|
| atggacgaat tgaaatgat aaagagaaac acatctgaaa ttatcagcga ggaagagtta | 60 |
| agagaggttt taaaaaaga tgaaaatct gctacgatag gttttgaacc aagtggtaaa | 120 |
| atacatttag gcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atggaagtaa tttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat ccgcttcatt | 480 |
| atcagggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |

| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 30
<211> LENGTH: 917
<212> TYPE: DNA
<213> ORGANISM: Methanococcus jannaschii

<400> SEQUENCE: 30

| atggacgaat ttgaaatgat aaagagaaac acatctgaaa ttatcagcga ggaagagtta | 60 |
| agagaggttt taaaaaaaga tgaaaatct gctacgatag gttttgaacc aagtggtaaa | 120 |
| atacatttag ggcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atgaagtct gttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat cctcttcatt | 480 |
| atgagggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |
| gagaaggaaa gatgagttct tcaaaaggga attttatagc tgttgatgac tctccagaag | 660 |
| agattagggc taagataaag aaagcatact gcccagctgg agttgttgaa ggaaatccaa | 720 |
| taatggagat agctaaatac ttccttgaat atcctttaac cataaaaagg ccagaaaaat | 780 |
| ttggtggaga tttgacagtt aatagctatg aggagttaga gagtttattt aaaaataagg | 840 |
| aattgcatcc aatggattta aaaaatgctg tagctgaaga acttataaag attttagagc | 900 |
| caattagaaa gagatta | 917 |

<210> SEQ ID NO 31
<211> LENGTH: 917
<212> TYPE: DNA
<213> ORGANISM: Methanococcus jannaschii

<400> SEQUENCE: 31

| atggacgaat ttgaaatgat aaagagaaac acatctgaaa ttatcagcga ggaagagtta | 60 |
| agagaggttt taaaaaaaga tgaaaatct gctcttatag gttttgaacc aagtggtaaa | 120 |
| atacatttag ggcattatct ccaaataaaa aagatgattg atttacaaaa tgctggattt | 180 |
| gatataatta tattgttggc tgatttacac gcctatttaa accagaaagg agagttggat | 240 |
| gagattagaa aataggaga ttataacaaa aaagttttg aagcaatggg gttaaaggca | 300 |
| aaatatgttt atgaagtac tttccagctt gataaggatt atacactgaa tgtctataga | 360 |
| ttggctttaa aaactacctt aaaaagagca agaaggagta tggaacttat agaagagagg | 420 |
| atgaaaatcc aaaggttgct gaagttatct atccaataat gcaggttaat ccggttcatt | 480 |
| atcagggcgt tgatgttgca gttggaggga tggagcagag aaaaatacac atgttagcaa | 540 |
| gggagctttt accaaaaaag gttgtttgta ttcacaaccc tgtcttaacg ggtttggatg | 600 |

```
gagaaggaaa gatgagttct tcaaaaggga attttatagc tgttgatgac tctccagaag      660
agattagggc taagataaag aaagcatact gcccagctgg agttgttgaa ggaaatccaa      720
taatggagat agctaaatac ttccttgaat atcctttaac cataaaaagg ccagaaaaat      780
ttggtggaga tttgacagtt aatagctatg aggagttaga gagtttatttt aaaaataagg    840 aattgcatcc aatggattta aaaaatgctg tagctgaaga acttataaag attttagagc      900
caattagaaa gagatta                                                    917

<210> SEQ ID NO 32
<211> LENGTH: 917
<212> TYPE: DNA
<213> ORGANISM: Methanococcus jannaschii

<400> SEQUENCE: 32
atggacgaat ttgaaatgat aaagagaaac acatctgaaa ttatcagcga ggaagagtta      60
agagaggttt taaaaaaaga tgaaaaatct gctactatag gttttgaacc aagtggtaaa     120
atacatttag gcattatctt ccaaataaaa aagatgattg atttacaaaa tgctggatt     180 gatataatta tattgttggc tgatttacac gcctatttaa accagaaagg agagttggat    240
gagattagaa aataggaga ttataacaaa aaagttttgg aagcaatggg gttaaaggca    300
aaatatgttt atggaagttc gttccagctt gataaggatt atacactgaa tgtctataga   360
ttggctttaa aaactacctt aaaaagagca agaaggagta tggaacttat agaagagagg    420
atgaaaatcc aaaggttgct gaagttatct atccaataat gcaggttaat ccactgcatt    480
atcagggcgt tgatgttgca gttggaggga tggagcagag aaaaatacac atgttagcaa    540
gggagctttt accaaaaaag gttgtttgta ttcacaaccc tgtcttaacg ggtttggatg    600
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat   780
ttggtggaga tttgacagtt aatagctatg aggagttaga gagtttatttt aaaaataagg  840 aattgcatcc aatggattta aaaaatgctg tagctgaaga acttataaag attttagagc    900
caattagaaa gagatta                                                  917

<210> SEQ ID NO 33
<211> LENGTH: 2799
<212> TYPE: DNA
<213> ORGANISM: Archaeoglobus fulgidus

<400> SEQUENCE: 33
atgagcgatt tcaggataat tgaggagaag tggcagaagg cgtgggagaa ggacagaatt      60
tttgagtccg atcctaatga aaggagaag ttttttctca caattccccta tccttacctt    120 aatgaaaatc ttcacgcagg tcacacgaga accttcacaa ttggcgatgc cttcgccaga    180
tacatgagaa tgaagggcta caacgttctc tttcccctcg gctttcatgt tacgggcacc    240
ccaatcattg gccttgcgga gctcatagcc aagagggacg agaggacgat agaggtttac    300
accaaatacc atgacgttcc gctgaggac ttgcttcagc tcacaactcc agagaaaatc    360
gttgagtact tctcaaggga ggcgctgcag gctttgaaga gcataggcta ctccattgac    420
tggaggaggg ttttcaccac aaccgatgaa gagtatcaga gattcatcga gtggcagtac   480
tggaagctca aggagcttgg cctgattgtg aagggcaccc accccgtcag atactgcccc    540
cacgaccaga atcctgttga agaccacgac cttctcgctg gggaggaggc aactattgtt    600
```

```
gaatttaccg ttataaagtt caggcttgaa gatggagacc tcattttccc ctgtgcaact    660
ctccgtcccg aaaccgtgtt tggcgtcacg aacatctggg taaagccgac aacctacgta    720
attgccgagg tggatgggga aaagtggttt gtgagcaaag aggcttacga gaagctcacc    780
tacacggaga aaaagtcag gctgctggag gaggttgatg cgtcgcagtt cttcggcaag    840
tacgtcatag tcccgctggt aaacagaaaa gtgccaattc tgcctgcaga gtttgttgac    900
accgacaacg caacaggagt tgtgatgagc gttcccgcac acgctccttt tgacctggct    960
gccattgagg acttgaagag agacgaggaa acgctggcga agtacggaat tgacaaaagc   1020
gttgtagaga gcataaagcc aatagttctg attaagacgg acattgaagg tgttcctgct   1080
gagaagctaa taagagagct tggagtgaag agccagaagg acaaggagct gctggataag   1140
gcaaccaaga ccctctacaa gaaggagtac cacacgggaa tcatgctgga caacacgatg   1200
aactatgctg gaatgaaagt ttctgaggcg aaggagagag ttcatgagga tttggttaag   1260
cttggcttgg gggatgtttt ctacgagttc agcgagaagc ccgtaatctg caggtgcgga   1320
acgaagtgcg ttgttaaggt tgttagggac cagtggttcc tgaactactc caacagagag   1380
tggaaggaga aggttctgaa tcaccttgaa aagatgcgaa tcatccccga ctactacaag   1440
gaggagttca ggaacaagat tgagtggctc agggacaagg cttgtgccag aaggaagggg   1500 cttgaacga gaattccgtg ggataaggag tggctcatcg agagcctttc agactcaaca   1560
atctacatgg cctactacat ccttgccaag tacatcaacg caggattgct caaggccgag   1620
aacatgactc ccgagttcct cgactacgtg ctgctgggca aggtgaggt tgggaaagtt   1680 gcggaagctt caaaactcag cgtggagtta atccagcaga tcagggacga cttcgagtac   1740
tggtatcccg ttgacctaag aagcagtggc aaggacttgg ttgcaaacca cctgctcttc   1800
tacctcttcc accacgtcgc cattttcccg ccagataagt ggccgagggc aattgccgta   1860
aacggatacg tcagccttga gggcaagaag atgagcaaga gcaaagggcc cttgctaacg   1920
atgaagaggg cggtgcagca gtatggtgcg gatgtgacga ggctctacat cctccacgct   1980
gcagagtacg cacgcgatgc ggactggaag agcagagagg ttgaagggct tgcaaaccac   2040
ctcaggaggt tctacaacct cgtgaaggag aactacctga agaggtggg agagctaaca   2100 accctcgacc gctggcttgt gagcaggatg cagagggcaa taaggaagt gagggaggct   2160 atggacaacc tgcagacgag gagggccgtg aatgccgcct tcttcgagct catgaacgac   2220
gtgagatggt atctgaggag aggaggtgag aacctcgcta taatactgga cgactggatc   2280
aagctcctcg ccccctttgc tccgcacatt tgcgaggagc tgtggcactt gaagcatgac   2340
agctacgtca gcctcgaaag ctacccagaa tacgacgaaa ccagggttga cgaggaggcg   2400
gagagaattg aggaatacct ccgaaacctt gttgaggaca ttcaggaaat caagaagttt   2460
gttagcgatg cgaaggaggt ttacattgct cccgccgaag actggaaggt taaggcagca   2520
aaggtcgttg ctgaaagcgg ggatgttggg gaggcgatga agcagcttat gcaggacgag   2580
gagcttagga agctcggcaa agaagtgtca aatttcgtca agaagatttt caaagacaga   2640
aagaagctga tgctagttaa ggagtgggaa gttctgcagc agaacctgaa atttattgag   2700
aatgagaccg gactgaaggt tattcttgat actcagagag ttcctgagga gaagaggagg   2760
caggcagttc cgggcaagcc cgcgatttat gttgcttaa                          2799
```

<210> SEQ ID NO 34
<211> LENGTH: 2814
<212> TYPE: DNA
<213> ORGANISM: Methanobacterium thermoautotrophicum

<400> SEQUENCE: 34

```
gtggatattg aaagaaaatg gcgtgataga tggagagatg ctggcatatt tcaggctgac      60
cctgatgaca gagaaaagat attcctcaca gtcgcttacc cctacccag tggtgcgatg     120
cacataggac acgggaggac ctacactgtc cctgatgtct atgcacggtt caagaggat     180
cagggctaca acgtcctgtt tcccatggcc tggcatgtca cagggg cccc tgtcataggg    240
atagcgcgga ggattcagag aaggatccc  tggaccctca aaatctacag ggaggtccac    300
agggtccccg aggatgagct tgaacgtttc agtgaccctg agtacatagt tgaatacttc    360
agcagggaat accggtctgt tatggaggat atgggctact ccatcgactg gaggcgtgaa    420
ttcaaaacca cggatcccac ctacagcagg ttcatacagt ggcagataag gaagctgagg    480
gaccttggcc tcgtaaggaa gggcgcccat cctgttaagt actgccctga atgtgaaaac    540
cctgtgggtg accatgacct ccttgagggt gaggggttg ccataaacca gctcacactc     600
ctcaaattca acttggaga ctcatacctg gtcgcagcca ccttcaggcc cgagacaatc     660
tatgggcca ccaacctctg gctgaaccct gatgaggatt atgtgagggt tgaaacaggt      720
ggtgaggagt ggataataag cagggctgcc gtggataatc tttcacacca gaaactggac    780
ctcaaggttt ccggtgacgt caaccccggg gacctgatag gatgtgcgt ggagaatcct     840
gtgacgggcc aggaacaccc catactcccg gcttccttcg ttgaccctga atatgccaca    900
ggtgttgtgt tctctgtccc tgcacatgcc cctgcagact tcatagccct tgaggacctc    960
aggacagacc atgaactcct tgaaaggtac ggtcttgagg atgtggttgc tgatattgag   1020
cccgtgaatg tcatagcagt ggatggctac ggtgagttcc cggcggccga ggttatagag   1080
aaatttggtg tcagaaacca ggaggacccc cgccttgagg atgccaccgg ggagctatac   1140
aagatcgagc atgcgagggg tgttatgagc agccacatcc ctgtctatgg tggtatgaag   1200
gtctctgagg cccgtgaggt catcgctgat gaactgaagg accagggcct tgcagatgag   1260
atgtatgaat tcgctgagcg acctgttata tgccgctgcg gtggcaggtg cgttgtgagg   1320
gtcatgagg accagtggtt catgaagtac tctgatgacg cctggaagga cctcgcccac   1380
aggtgcctcg atggcatgaa gataataccc gaggaggtcc gggccaactt tgaatactac   1440
atcgactggc tcaatgactg gcatgttca aggaggatag gccttggaac aaggctgccc    1500
tgggatgaga ggtggatcat cgaacccctc acagactcaa caatctacat ggcatattac   1560
accatcgcac accgcctcag ggagatggat gccggggaga tggacgatga gttctttgat   1620
gccatattcc tagatgattc aggaaccttt gaggatctca gggaggaatt ccggtactgg   1680
tacccccttg actggaggct ctctgcaaag gacctcatag gcaatcacct gacattccat   1740
atattccacc actcagccat attccctgag tcagggtggc cccgggggc tgtggtcttt   1800
ggtatgggcc ttcttgaggg caacaagatg tcatcctcca agg caacgt catactcctg   1860
agggatgcca tcgagaagca cggtgcagac gtggtgcggc tcttcctcat gtcctcagca   1920
gagccatggc aggactttga ctggaggag agtgaggtca tcgggacccg caggaggatt   1980
gaatggttca gggaattcgg agagagggtc tcaggtatcc tggatggtag gccagtcctc   2040
agtgaggtta ctccagctga acctgaaagc ttcattggaa ggtggatgat gggtcagctg   2100
aaccagagga tacgtgaagc cacaagggcc cttgaatcat tccagacaag aaaggcagtt   2160
caggaggcac tctatctcct taaaaaggat gttgaccact accttaagcg tgttgagggt   2220
agagttgatg atgaggttaa atctgtcctt gcaaacgttc tgcacgcctg gataaggctc   2280
atggctccat tcatacccta cactgctgag gagatgtggg agaggtatgg tggtgagggt   2340
```

-continued

```
tttgtagcag aagctccatg gcctgacttc tcagatgatg cagagagcag ggatgtgcag    2400
gttgcagagg agatggtcca gaataccgtt agagacattc aggaaatcat gaagatcctt    2460
ggatccaccc cggagagggt ccacatatac acctcaccaa aatggaaatg ggatgtgcta    2520
agggtcgcag cagaggtagg aaaactagat atgggctcca taatgggaag ggtttcagct    2580
gagggcatcc atgataacat gaaggaggtt gctgaatttg taaggaggat catcagggac    2640
cttggtaaat cagaggttac ggtgatagac gagtacagcg tactcatgga tgcatctgat    2700
tacattgaat cagaggttgg agccagggtt gtgatacaca gcaaaccaga ctatgaccct    2760
gaaaacaagg ctgtgaatgc cgttcccctg aagccagcca tataccttga atga          2814
```

<210> SEQ ID NO 35
<211> LENGTH: 306
<212> TYPE: PRT
<213> ORGANISM: Methanococcus jannaschii

<400> SEQUENCE: 35

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Ser Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
```

Arg Leu
305

<210> SEQ ID NO 36
<211> LENGTH: 255
<212> TYPE: PRT
<213> ORGANISM: Methanococcus jannaschii

<400> SEQUENCE: 36

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ala His
145                 150                 155                 160

Tyr Gln Gly Val Asp Val Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile
                245                 250                 255

<210> SEQ ID NO 37
<211> LENGTH: 306
<212> TYPE: PRT
<213> ORGANISM: Methanococcus jannaschii

<400> SEQUENCE: 37

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

```
Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Cys Ala Tyr Gly Ser Pro Phe Gln Leu Asp Lys
        100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Tyr His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 38
<211> LENGTH: 306
<212> TYPE: PRT
<213> ORGANISM: Methanococcus jannaschii

<400> SEQUENCE: 38

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Tyr Val Tyr Gly Ser Pro Phe Gln Leu Asp Lys
        100                 105                 110

Asp Tyr Thr Leu Asn Val Tyr Arg Leu Ala Leu Lys Thr Thr Leu Lys
        115                 120                 125
```

```
Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Cys Ser His
145                 150                 155                 160

Tyr Tyr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 39
<211> LENGTH: 306
<212> TYPE: PRT
<213> ORGANISM: Methanococcus jannaschii

<400> SEQUENCE: 39

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Leu Ile Lys Ile Leu Glu Pro Ile Arg Lys
    290                 295                 300

Arg Leu
305

<210> SEQ ID NO 40
<211> LENGTH: 306
<212> TYPE: PRT
<213> ORGANISM: Methanococcus jannaschii

<400> SEQUENCE: 40

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Arg Pro His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255
```

```
Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 41
<211> LENGTH: 306
<212> TYPE: PRT
<213> ORGANISM: Methanococcus jannaschii

<400> SEQUENCE: 41

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
                20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Ser His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 42
<211> LENGTH: 306
<212> TYPE: PRT
<213> ORGANISM: Methanococcus jannaschii

<400> SEQUENCE: 42

| Met | Asp | Glu | Phe | Glu | Met | Ile | Lys | Arg | Asn | Thr | Ser | Glu | Ile | Ile | Ser |
|---|---|---|---|---|---|---|---|---|---|---|---|---|---|---|---|
| 1 | | | | 5 | | | | | 10 | | | | | 15 | |

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 43
<211> LENGTH: 306
<212> TYPE: PRT
<213> ORGANISM: Methanococcus jannaschii

<400> SEQUENCE: 43

Met Asp Glu Phe Glu Met Ile Lys Arg Asn Thr Ser Glu Ile Ile Ser
1               5                   10                  15

-continued

```
Glu Glu Glu Leu Arg Glu Val Leu Lys Lys Asp Glu Lys Ser Ala Pro
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Met Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Asn Thr His
145                 150                 155                 160

Tyr Gly Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 44
<211> LENGTH: 306
<212> TYPE: PRT
<213> ORGANISM: Methanococcus jannaschii

<400> SEQUENCE: 44

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
 65                  70                  75                  80
```

```
Glu Ile Arg Lys Ile Gly Asp Tyr Asn Lys Lys Val Phe Glu Ala Met
                85                  90                  95

Gly Leu Lys Ala Lys Tyr Val Tyr Gly Ser His Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Thr His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 45
<211> LENGTH: 306
<212> TYPE: PRT
<213> ORGANISM: Methanococcus jannaschii

<400> SEQUENCE: 45

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140
```

```
Lys Val Ala Glu Val Ile Tyr Pro Ile Met Gln Val Asn Pro Cys His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Leu Ile Lys Ile Leu Glu Pro Ile Arg Lys
290                 295                 300

Arg Leu
305

<210> SEQ ID NO 46
<211> LENGTH: 306
<212> TYPE: PRT
<213> ORGANISM: Methanococcus jannaschii

<400> SEQUENCE: 46

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Tyr His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205
```

```
Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Gly Leu Ile Lys Ile Leu Glu Pro Ile Arg Lys
        290                 295                 300

Arg Leu
305

<210> SEQ ID NO 47
<211> LENGTH: 306
<212> TYPE: PRT
<213> ORGANISM: Methanococcus jannaschii

<400> SEQUENCE: 47

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270
```

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 48
<211> LENGTH: 306
<212> TYPE: PRT
<213> ORGANISM: Methanococcus jannaschii

<400> SEQUENCE: 48

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Ile His
145                 150                 155                 160

Ser Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 49
<211> LENGTH: 306

```
<212> TYPE: PRT
<213> ORGANISM: Methanococcus jannaschii

<400> SEQUENCE: 49

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Asp
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Met His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 50
<211> LENGTH: 306
<212> TYPE: PRT
<213> ORGANISM: Methanococcus jannaschii

<400> SEQUENCE: 50

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
```

```
              35                  40                  45
Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Leu Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Asp Ile His
145                 150                 155                 160

Tyr Thr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 51
<211> LENGTH: 306
<212> TYPE: PRT
<213> ORGANISM: Methanococcus jannaschii

<400> SEQUENCE: 51

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Thr Asp Leu Asn Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
```

```
                    100                 105                 110
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 52
<211> LENGTH: 306
<212> TYPE: PRT
<213> ORGANISM: Methanococcus jannaschii

<400> SEQUENCE: 52

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Thr Asp Leu Lys Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Ser Val Asn Val Ile His
145                 150                 155                 160

Tyr Leu Gly Val Asp Val Val Val Gly Gly Met Glu Gln Arg Lys Ile
```

```
                    165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
            195                 200                 205
Lys Gly Asn Phe Ile Ala Val Asp Asp Ser Pro Glu Glu Ile Arg Ala
        210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
        290                 295                 300
Arg Leu
305

<210> SEQ ID NO 53
<211> LENGTH: 306
<212> TYPE: PRT
<213> ORGANISM: Methanococcus jannaschii

<400> SEQUENCE: 53

Met Asp Glu Phe Glu Met Ile Lys Arg Asn Thr Ser Glu Ile Ile Ser
1               5                  10                  15
Glu Glu Glu Leu Arg Glu Val Leu Lys Lys Asp Glu Lys Ser Ala Leu
                20                  25                  30
Ile Gly Phe Glu Pro Ser Gly Lys Ile His Leu Gly His Tyr Leu Gln
            35                  40                  45
Ile Lys Lys Met Ile Asp Leu Gln Asn Ala Gly Phe Asp Ile Ile Ile
        50                  55                  60
Leu Leu Pro Asp Leu Ser Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Asp Ile His
145                 150                 155                 160
Tyr Leu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
            195                 200                 205
Lys Gly Asn Phe Ile Ala Val Asp Asp Ser Pro Glu Glu Ile Arg Ala
        210                 215                 220
Lys Ile Lys Lys Ala Tyr Cys Pro Ala Gly Val Val Glu Gly Asn Pro
```

```
                225                 230                 235                 240
Ile Met Glu Ile Ala Lys Tyr Phe Leu Glu Tyr Pro Leu Thr Ile Lys
                    245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 54
<211> LENGTH: 306
<212> TYPE: PRT
<213> ORGANISM: Methanococcus jannaschii

<400> SEQUENCE: 54

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
```

```
                   290                 295                 300

Arg Leu
305

<210> SEQ ID NO 55
<211> LENGTH: 306
<212> TYPE: PRT
<213> ORGANISM: Methanococcus jannaschii

<400> SEQUENCE: 55

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ser Asp Leu Pro Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 56
<211> LENGTH: 306
<212> TYPE: PRT
<213> ORGANISM: Methanococcus jannaschii

<400> SEQUENCE: 56
```

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Met Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ser Ser His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 57
<211> LENGTH: 306
<212> TYPE: PRT
<213> ORGANISM: Methanococcus jannaschii

<400> SEQUENCE: 57

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60
```

```
Leu Leu Pro Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                   90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Asp Ile His
145                 150                 155                 160

Tyr Leu Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 58
<211> LENGTH: 306
<212> TYPE: PRT
<213> ORGANISM: Methanococcus jannaschii

<400> SEQUENCE: 58

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala His
             20                  25                  30

Ile Gly Phe Glu Pro Ser Gly Lys Ile His Leu Gly His Tyr Leu Gln
         35                  40                  45

Ile Lys Lys Met Ile Asp Leu Gln Asn Ala Gly Phe Asp Ile Ile Ile
     50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Tyr Val Tyr Gly Ser Ala Phe Gln Leu Asp Lys
            100                 105                 110

Asp Tyr Thr Leu Asn Val Tyr Arg Leu Ala Leu Lys Thr Thr Leu Lys
        115                 120                 125
```

```
Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly His His
145                 150                 155                 160

Tyr Ile Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 59
<211> LENGTH: 306
<212> TYPE: PRT
<213> ORGANISM: Methanococcus jannaschii

<400> SEQUENCE: 59

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ala Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Cys Ala His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
            210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                    245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Leu Ile Lys Ile Leu Glu Pro Ile Arg Lys
            290                 295                 300

Arg Leu
305

<210> SEQ ID NO 60
<211> LENGTH: 306
<212> TYPE: PRT
<213> ORGANISM: Methanococcus jannaschii

<400> SEQUENCE: 60

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255
```

```
Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 61
<211> LENGTH: 306
<212> TYPE: PRT
<213> ORGANISM: Methanococcus jannaschii

<400> SEQUENCE: 61

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 62
<211> LENGTH: 306
<212> TYPE: PRT
<213> ORGANISM: Methanococcus jannaschii

<400> SEQUENCE: 62

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 63
<211> LENGTH: 306
<212> TYPE: PRT
<213> ORGANISM: Methanococcus jannaschii

<400> SEQUENCE: 63

Met Asp Glu Phe Glu Met Ile Lys Arg Asn Thr Ser Glu Ile Ile Ser
1               5                   10                  15

```
Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 64
<211> LENGTH: 306
<212> TYPE: PRT
<213> ORGANISM: Methanococcus jannaschii

<400> SEQUENCE: 64

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80
```

```
Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 65
<211> LENGTH: 932
<212> TYPE: PRT
<213> ORGANISM: Archaeoglobus fulgidus

<400> SEQUENCE: 65

Met Ser Asp Phe Arg Ile Ile Glu Glu Lys Trp Gln Lys Ala Trp Glu
1               5                   10                  15

Lys Asp Arg Ile Phe Glu Ser Asp Pro Asn Gly Lys Glu Lys Phe Phe
            20                  25                  30

Leu Thr Ile Pro Tyr Pro Tyr Leu Asn Gly Asn Leu His Ala Gly His
        35                  40                  45

Thr Arg Thr Phe Thr Ile Gly Asp Ala Phe Ala Arg Tyr Met Arg Met
    50                  55                  60

Lys Gly Tyr Asn Val Leu Phe Pro Leu Gly Phe His Val Thr Gly Thr
65                  70                  75                  80

Pro Ile Ile Gly Leu Ala Glu Leu Ile Ala Lys Arg Asp Glu Arg Thr
                85                  90                  95

Ile Glu Val Tyr Thr Lys Tyr His Asp Val Pro Leu Glu Asp Leu Leu
            100                 105                 110

Gln Leu Thr Thr Pro Glu Lys Ile Val Glu Tyr Phe Ser Arg Glu Ala
        115                 120                 125

Leu Gln Ala Leu Lys Ser Ile Gly Tyr Ser Ile Asp Trp Arg Arg Val
    130                 135                 140
```

```
Phe Thr Thr Thr Asp Glu Glu Tyr Gln Arg Phe Ile Glu Trp Gln Tyr
145                 150                 155                 160

Trp Lys Leu Lys Glu Leu Gly Leu Ile Val Lys Gly Thr His Pro Val
            165                 170                 175

Arg Tyr Cys Pro His Asp Gln Asn Pro Val Glu Asp His Asp Leu Leu
        180                 185                 190

Ala Gly Glu Glu Ala Thr Ile Val Glu Phe Thr Val Ile Lys Phe Arg
    195                 200                 205

Leu Glu Asp Gly Asp Leu Ile Phe Pro Cys Ala Thr Leu Arg Pro Glu
210                 215                 220

Thr Val Phe Gly Val Thr Asn Ile Trp Val Lys Pro Thr Thr Tyr Val
225                 230                 235                 240

Ile Ala Glu Val Asp Gly Glu Lys Trp Phe Val Ser Lys Glu Ala Tyr
                245                 250                 255

Glu Lys Leu Thr Tyr Thr Glu Lys Lys Val Arg Leu Leu Glu Glu Val
            260                 265                 270

Asp Ala Ser Gln Phe Phe Gly Lys Tyr Val Ile Val Pro Leu Val Asn
        275                 280                 285

Arg Lys Val Pro Ile Leu Pro Ala Glu Phe Val Asp Thr Asp Asn Ala
290                 295                 300

Thr Gly Val Val Met Ser Val Pro Ala His Ala Pro Phe Asp Leu Ala
305                 310                 315                 320

Ala Ile Glu Asp Leu Lys Arg Asp Glu Glu Thr Leu Ala Lys Tyr Gly
                325                 330                 335

Ile Asp Lys Ser Val Val Glu Ser Ile Lys Pro Ile Val Leu Ile Lys
            340                 345                 350

Thr Asp Ile Glu Gly Val Pro Ala Glu Lys Leu Ile Arg Glu Leu Gly
        355                 360                 365

Val Lys Ser Gln Lys Asp Lys Glu Leu Leu Asp Lys Ala Thr Lys Thr
370                 375                 380

Leu Tyr Lys Lys Glu Tyr His Thr Gly Ile Met Leu Asp Asn Thr Met
385                 390                 395                 400

Asn Tyr Ala Gly Met Lys Val Ser Glu Ala Lys Glu Arg Val His Glu
                405                 410                 415

Asp Leu Val Lys Leu Gly Leu Gly Asp Val Phe Tyr Glu Phe Ser Glu
            420                 425                 430

Lys Pro Val Ile Cys Arg Cys Gly Thr Lys Cys Val Val Lys Val Val
        435                 440                 445

Arg Asp Gln Trp Phe Leu Asn Tyr Ser Asn Arg Glu Trp Lys Glu Lys
450                 455                 460

Val Leu Asn His Leu Glu Lys Met Arg Ile Ile Pro Asp Tyr Tyr Lys
465                 470                 475                 480

Glu Glu Phe Arg Asn Lys Ile Glu Trp Leu Arg Asp Lys Ala Cys Ala
                485                 490                 495

Arg Arg Lys Gly Leu Gly Thr Arg Ile Pro Trp Asp Lys Glu Trp Leu
            500                 505                 510

Ile Glu Ser Leu Ser Asp Ser Thr Ile Tyr Met Ala Tyr Tyr Ile Leu
        515                 520                 525

Ala Lys Tyr Ile Asn Ala Gly Leu Leu Lys Ala Glu Asn Met Thr Pro
530                 535                 540

Glu Phe Leu Asp Tyr Val Leu Leu Gly Lys Gly Glu Val Gly Lys Val
545                 550                 555                 560

Ala Glu Ala Ser Lys Leu Ser Val Glu Leu Ile Gln Gln Ile Arg Asp
                565                 570                 575
```

```
Asp Phe Glu Tyr Trp Tyr Pro Val Asp Leu Arg Ser Ser Gly Lys Asp
            580                 585                 590

Leu Val Ala Asn His Leu Leu Phe Tyr Leu Phe His His Val Ala Ile
            595                 600                 605

Phe Pro Pro Asp Lys Trp Pro Arg Ala Ile Ala Val Asn Gly Tyr Val
610                 615                 620

Ser Leu Glu Gly Lys Lys Met Ser Lys Ser Lys Gly Pro Leu Leu Thr
625                 630                 635                 640

Met Lys Arg Ala Val Gln Gln Tyr Gly Ala Asp Val Thr Arg Leu Tyr
            645                 650                 655

Ile Leu His Ala Ala Glu Tyr Asp Ser Asp Ala Asp Trp Lys Ser Arg
            660                 665                 670

Glu Val Glu Gly Leu Ala Asn His Leu Arg Arg Phe Tyr Asn Leu Val
            675                 680                 685

Lys Glu Asn Tyr Leu Lys Glu Val Gly Glu Leu Thr Thr Leu Asp Arg
            690                 695                 700

Trp Leu Val Ser Arg Met Gln Arg Ala Ile Lys Glu Val Arg Glu Ala
705                 710                 715                 720

Met Asp Asn Leu Gln Thr Arg Arg Ala Val Asn Ala Ala Phe Phe Glu
            725                 730                 735

Leu Met Asn Asp Val Arg Trp Tyr Leu Arg Arg Gly Gly Glu Asn Leu
            740                 745                 750

Ala Ile Ile Leu Asp Asp Trp Ile Lys Leu Leu Ala Pro Phe Ala Pro
            755                 760                 765

His Ile Cys Glu Glu Leu Trp His Leu Lys His Asp Ser Tyr Val Ser
            770                 775                 780

Leu Glu Ser Tyr Pro Glu Tyr Asp Glu Thr Arg Val Asp Glu Glu Ala
785                 790                 795                 800

Glu Arg Ile Glu Glu Tyr Leu Arg Asn Leu Val Glu Asp Ile Gln Glu
            805                 810                 815

Ile Lys Lys Phe Val Ser Asp Ala Lys Glu Val Tyr Ile Ala Pro Ala
            820                 825                 830

Glu Asp Trp Lys Val Lys Ala Ala Lys Val Val Ala Glu Ser Gly Asp
            835                 840                 845

Val Gly Glu Ala Met Lys Gln Leu Met Gln Asp Glu Glu Leu Arg Lys
850                 855                 860

Leu Gly Lys Glu Val Ser Asn Phe Val Lys Lys Ile Phe Lys Asp Arg
865                 870                 875                 880

Lys Lys Leu Met Leu Val Lys Glu Trp Glu Val Leu Gln Gln Asn Leu
            885                 890                 895

Lys Phe Ile Glu Asn Glu Thr Gly Leu Lys Val Ile Leu Asp Thr Gln
            900                 905                 910

Arg Val Pro Glu Glu Lys Arg Arg Gln Ala Val Pro Gly Lys Pro Ala
            915                 920                 925

Ile Tyr Val Ala
            930

<210> SEQ ID NO 66
<211> LENGTH: 937
<212> TYPE: PRT
<213> ORGANISM: Methanobacterium thermoautotrophicum

<400> SEQUENCE: 66

Val Asp Ile Glu Arg Lys Trp Asp Arg Trp Arg Asp Ala Gly Ile
1               5                   10                  15
```

```
Phe Gln Ala Asp Pro Asp Arg Glu Lys Ile Phe Leu Thr Val Ala
            20                  25                  30

Tyr Pro Tyr Pro Ser Gly Ala Met His Ile Gly His Gly Arg Thr Tyr
            35                  40                  45

Thr Val Pro Asp Val Tyr Ala Arg Phe Lys Arg Met Gln Gly Tyr Asn
        50                  55                  60

Val Leu Phe Pro Met Ala Trp His Val Thr Gly Ala Pro Val Ile Gly
65                  70                  75                  80

Ile Ala Arg Arg Ile Gln Arg Lys Asp Pro Trp Thr Leu Lys Ile Tyr
                85                  90                  95

Arg Glu Val His Arg Val Pro Glu Asp Glu Leu Glu Arg Phe Ser Asp
            100                 105                 110

Pro Glu Tyr Ile Val Glu Tyr Phe Ser Arg Glu Tyr Arg Ser Val Met
            115                 120                 125

Glu Asp Met Gly Tyr Ser Ile Asp Trp Arg Arg Glu Phe Lys Thr Thr
130                 135                 140

Asp Pro Thr Tyr Ser Arg Phe Ile Gln Trp Gln Ile Arg Lys Leu Arg
145                 150                 155                 160

Asp Leu Gly Leu Val Arg Lys Gly Ala His Pro Val Lys Tyr Cys Pro
                165                 170                 175

Glu Cys Glu Asn Pro Val Gly Asp His Asp Leu Leu Glu Gly Glu Gly
            180                 185                 190

Val Ala Ile Asn Gln Leu Thr Leu Leu Lys Phe Lys Leu Gly Asp Ser
            195                 200                 205

Tyr Leu Val Ala Ala Thr Phe Arg Pro Glu Thr Ile Tyr Gly Ala Thr
210                 215                 220

Asn Leu Trp Leu Asn Pro Asp Glu Asp Tyr Val Arg Val Glu Thr Gly
225                 230                 235                 240

Gly Glu Glu Trp Ile Ile Ser Arg Ala Ala Val Asp Asn Leu Ser His
                245                 250                 255

Gln Lys Leu Asp Leu Lys Val Ser Gly Asp Val Asn Pro Gly Asp Leu
            260                 265                 270

Ile Gly Met Cys Val Glu Asn Pro Val Thr Gly Gln Glu His Pro Ile
            275                 280                 285

Leu Pro Ala Ser Phe Val Asp Pro Glu Tyr Ala Thr Gly Val Val Phe
290                 295                 300

Ser Val Pro Ala His Ala Pro Ala Asp Phe Ile Ala Leu Glu Asp Leu
305                 310                 315                 320

Arg Thr Asp His Glu Leu Leu Glu Arg Tyr Gly Leu Glu Asp Val Val
                325                 330                 335

Ala Asp Ile Glu Pro Val Asn Val Ile Ala Val Asp Tyr Gly Glu
            340                 345                 350

Phe Pro Ala Ala Glu Val Ile Glu Lys Phe Gly Val Arg Asn Gln Glu
            355                 360                 365

Asp Pro Arg Leu Glu Asp Ala Thr Gly Glu Leu Tyr Lys Ile Glu His
            370                 375                 380

Ala Arg Gly Val Met Ser Ser His Ile Pro Val Tyr Gly Gly Met Lys
385                 390                 395                 400

Val Ser Glu Ala Arg Glu Val Ile Ala Asp Leu Lys Asp Gln Gly
                405                 410                 415

Leu Ala Asp Glu Met Tyr Glu Phe Ala Glu Arg Pro Val Ile Cys Arg
            420                 425                 430

Cys Gly Gly Arg Cys Val Val Arg Val Met Glu Asp Gln Trp Phe Met
```

```
                435                 440                 445
Lys Tyr Ser Asp Asp Ala Trp Lys Asp Leu Ala His Arg Cys Leu Asp
450                 455                 460
Gly Met Lys Ile Ile Pro Glu Glu Val Arg Ala Asn Phe Glu Tyr Tyr
465                 470                 475                 480
Ile Asp Trp Leu Asn Asp Trp Ala Cys Ser Arg Arg Ile Gly Leu Gly
                485                 490                 495
Thr Arg Leu Pro Trp Asp Glu Arg Trp Ile Ile Glu Pro Leu Thr Asp
                500                 505                 510
Ser Thr Ile Tyr Met Ala Tyr Tyr Thr Ile Ala His Arg Leu Arg Glu
                515                 520                 525
Met Asp Ala Gly Glu Met Asp Asp Glu Phe Phe Asp Ala Ile Phe Leu
530                 535                 540
Asp Asp Ser Gly Thr Phe Glu Asp Leu Arg Glu Glu Phe Arg Tyr Trp
545                 550                 555                 560
Tyr Pro Leu Asp Trp Arg Leu Ser Ala Lys Asp Leu Ile Gly Asn His
                565                 570                 575
Leu Thr Phe His Ile Phe His His Ser Ala Ile Phe Pro Glu Ser Gly
                580                 585                 590
Trp Pro Arg Gly Ala Val Val Phe Gly Met Gly Leu Leu Glu Gly Asn
                595                 600                 605
Lys Met Ser Ser Ser Lys Gly Asn Val Ile Leu Leu Arg Asp Ala Ile
610                 615                 620
Glu Lys His Gly Ala Asp Val Val Arg Leu Phe Leu Met Ser Ser Ala
625                 630                 635                 640
Glu Pro Trp Gln Asp Phe Asp Trp Arg Glu Ser Glu Val Ile Gly Thr
                645                 650                 655
Arg Arg Arg Ile Glu Trp Phe Arg Glu Phe Gly Glu Arg Val Ser Gly
                660                 665                 670
Ile Leu Asp Gly Arg Pro Val Leu Ser Glu Val Thr Pro Ala Glu Pro
                675                 680                 685
Glu Ser Phe Ile Gly Arg Trp Met Met Gly Gln Leu Asn Gln Arg Ile
690                 695                 700
Arg Glu Ala Thr Arg Ala Leu Glu Ser Phe Gln Thr Arg Lys Ala Val
705                 710                 715                 720
Gln Glu Ala Leu Tyr Leu Leu Lys Lys Asp Val Asp His Tyr Leu Lys
                725                 730                 735
Arg Val Glu Gly Arg Val Asp Asp Glu Val Lys Ser Val Leu Ala Asn
                740                 745                 750
Val Leu His Ala Trp Ile Arg Leu Met Ala Pro Phe Ile Pro Tyr Thr
                755                 760                 765
Ala Glu Glu Met Trp Glu Arg Tyr Gly Gly Glu Gly Phe Val Ala Glu
770                 775                 780
Ala Pro Trp Pro Asp Phe Ser Asp Asp Ala Glu Ser Arg Asp Val Gln
785                 790                 795                 800
Val Ala Glu Glu Met Val Gln Asn Thr Val Arg Asp Ile Gln Glu Ile
                805                 810                 815
Met Lys Ile Leu Gly Ser Thr Pro Glu Arg Val His Ile Tyr Thr Ser
                820                 825                 830
Pro Lys Trp Lys Trp Asp Val Leu Arg Val Ala Ala Glu Val Gly Lys
                835                 840                 845
Leu Asp Met Gly Ser Ile Met Gly Arg Val Ser Ala Glu Gly Ile His
850                 855                 860
```

```
Asp Asn Met Lys Glu Val Ala Glu Phe Val Arg Arg Ile Ile Arg Asp
865                 870                 875                 880

Leu Gly Lys Ser Glu Val Thr Val Ile Asp Glu Tyr Ser Val Leu Met
            885                 890                 895

Asp Ala Ser Asp Tyr Ile Glu Ser Glu Val Gly Ala Arg Val Val Ile
        900                 905                 910

His Ser Lys Pro Asp Tyr Asp Pro Glu Asn Lys Ala Val Asn Ala Val
    915                 920                 925

Pro Leu Lys Pro Ala Ile Tyr Leu Glu
    930                 935

<210> SEQ ID NO 67
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 67
atgcatgctg cattaatgaa tcggccaacg                                    30

<210> SEQ ID NO 68
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 68
tccccgcgga ggtggcactt ttcgggg                                       27

<210> SEQ ID NO 69
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 69
ggaattccat taggacgaat ttgaaatg                                      28

<210> SEQ ID NO 70
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 70
aaactgcagt tataatctct ttctaattgg ctc                                33

<210> SEQ ID NO 71
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 71
aaaactgcag                                                          10

<210> SEQ ID NO 72
<211> LENGTH: 10
<212> TYPE: DNA
<213> ORGANISM: Artificial Sequence
```

```
<220> FEATURE:
<223> OTHER INFORMATION: synthetic oligonucleotide

<400> SEQUENCE: 72
aaaactgcag                                                                 10

<210> SEQ ID NO 73
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 73
ggaattccat atggacgaat ttgaaatg                                             28

<210> SEQ ID NO 74
<211> LENGTH: 69
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (30)..(31)
<223> OTHER INFORMATION: N=A+T+G+C

<400> SEQUENCE: 74 gtatttacc acttggttca aaacctatmn nagcagattt ttcatctttt tttcatcttt            60
ttttaaaac                                                                  69

<210> SEQ ID NO 75
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 75
taggttttga accaagtggt aaaatac                                              27

<210> SEQ ID NO 76
<211> LENGTH: 62
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (33)..(34)
<223> OTHER INFORMATION: N=A+T+G+C

<400> SEQUENCE: 76
cattcagtgt ataatcctta tcaagctgga amnnacttcc ataaacatat tttgccttta          60
ac                                                                         62

<210> SEQ ID NO 77
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 77
tccagcttga taaggattat acactgaatg                                           30
```

```
<210> SEQ ID NO 78
<211> LENGTH: 69
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (29)..(30)
<223> OTHER INFORMATION: N=A+T+G+C
<220> FEATURE:
<221> NAME/KEY: misc_feature
<222> LOCATION: (38)..(39)
<223> OTHER INFORMATION: N=A+T+G+C
<220> FEATURE:
<221> NAME/KEY: misc_feature
<222> LOCATION: (41)..(42)
<223> OTHER INFORMATION: N=A+T+G+C

<400> SEQUENCE: 78
catccctcca actgcaacat caacgccmnn ataatgmnnm nnattaacct gcattattgg      60
atagataac                                                             69

<210> SEQ ID NO 79
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 79
gcgttgatgt tgcagttgga gggatg                                          26

<210> SEQ ID NO 80
<211> LENGTH: 4
<212> TYPE: PRT
<213> ORGANISM: Methanococcus jannaschii

<400> SEQUENCE: 80

Ala Asp Leu His
1

<210> SEQ ID NO 81
<211> LENGTH: 13
<212> TYPE: PRT
<213> ORGANISM: Methanococcus jannaschii

<400> SEQUENCE: 81

Gln Val Asn Asp Ile His Tyr Leu Gly Val Asp Val Ala
1               5                   10

<210> SEQ ID NO 82
<211> LENGTH: 13
<212> TYPE: PRT
<213> ORGANISM: Methanococcus jannaschii
<220> FEATURE:
<221> NAME/KEY: MISC_FEATURE
<222> LOCATION: (4)..(5)
<223> OTHER INFORMATION: any
<220> FEATURE:
<221> NAME/KEY: MISC_FEATURE
<222> LOCATION: (8)..(8)
<223> OTHER INFORMATION: any

<400> SEQUENCE: 82

Gln Val Asn Xaa Xaa His Tyr Xaa Gly Val Asp Val Ala
1               5                   10

<210> SEQ ID NO 83
```

```
<211> LENGTH: 13
<212> TYPE: PRT
<213> ORGANISM: Methanococcus jannaschii
<220> FEATURE:
<221> NAME/KEY: MISC_FEATURE
<222> LOCATION: (4)..(5)
<223> OTHER INFORMATION: any
<220> FEATURE:
<221> NAME/KEY: MISC_FEATURE
<222> LOCATION: (8)..(8)
<223> OTHER INFORMATION: any
<220> FEATURE:
<221> NAME/KEY: MISC_FEATURE
<222> LOCATION: (13)..(13)
<223> OTHER INFORMATION: any

<400> SEQUENCE: 83

Gln Val Asn Xaa Xaa His Tyr Xaa Gly Val Asp Val Xaa
1               5                   10

<210> SEQ ID NO 84
<211> LENGTH: 13
<212> TYPE: PRT
<213> ORGANISM: Methanococcus jannaschii
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (4)..(4)
<223> OTHER INFORMATION: any
<220> FEATURE:
<221> NAME/KEY: MISC_FEATURE
<222> LOCATION: (13)..(13)
<223> OTHER INFORMATION: any

<400> SEQUENCE: 84

Xaa Val Asn Xaa Ile His Tyr Leu Gly Val Asp Val Xaa
1               5                   10

<210> SEQ ID NO 85
<211> LENGTH: 4
<212> TYPE: PRT
<213> ORGANISM: Artificial Sequence
<220> FEATURE:
<223> OTHER INFORMATION: consensus sequence from
      pentafluorophenylalanine selection

<400> SEQUENCE: 85

Gln Asp Leu Tyr
1

<210> SEQ ID NO 86
<211> LENGTH: 13
<212> TYPE: PRT
<213> ORGANISM: Artificial Sequence
<220> FEATURE:
<223> OTHER INFORMATION: consensus sequence from
      pentafluorophenylalanine selection

<400> SEQUENCE: 86

Ala Val Asn Ala Ile His Tyr Leu Gly Val Asp Val Leu
1               5                   10

<210> SEQ ID NO 87
<211> LENGTH: 44
<212> TYPE: PRT
<213> ORGANISM: Escherichia coli

<400> SEQUENCE: 87
```

```
Trp Phe Gly Asn Met Asn Val Leu Thr Phe Leu Arg Asp Ile Gly Lys
1               5                   10                  15

His Phe Ser Val Asn Gln Met Ile Asn Lys Glu Ala Val Lys Gln Arg
            20                  25                  30

Leu Asn Arg Glu Asp Gln Gly Ile Ser Phe Thr Glu
        35                  40

<210> SEQ ID NO 88
<211> LENGTH: 39
<212> TYPE: PRT
<213> ORGANISM: Homo sapiens

<400> SEQUENCE: 88

Leu Ser Lys Glu Tyr Thr Leu Asp Val Tyr Arg Leu Ser Ser Val Val
1               5                   10                  15

Thr Gln His Asp Ser Lys Lys Ala Gly Ala Glu Val Val Lys Gln Val
            20                  25                  30

Glu His Pro Leu Leu Ser Gly
        35

<210> SEQ ID NO 89
<211> LENGTH: 39
<212> TYPE: PRT
<213> ORGANISM: Methanococcus jannaschii

<400> SEQUENCE: 89

Leu Asp Lys Asp Tyr Thr Leu Asn Val Tyr Arg Leu Ala Leu Lys Thr
1               5                   10                  15

Thr Leu Lys Arg Ala Arg Arg Ser Met Glu Leu Ile Ala Arg Glu Asp
            20                  25                  30

Glu Asn Pro Lys Val Ala Glu
        35

<210> SEQ ID NO 90
<211> LENGTH: 77
<212> TYPE: RNA
<213> ORGANISM: Methanococcus jannaschii
<220> FEATURE:
<221> NAME/KEY: misc_feature
<222> LOCATION: (33)..(34)
<223> OTHER INFORMATION: any
<220> FEATURE:
<221> NAME/KEY: misc_feature
<222> LOCATION: (38)..(39)
<223> OTHER INFORMATION: any

<400> SEQUENCE: 90
ccggcgguag uucagccugg uagaacggcg ganncuannu ccgcaugucg cugguucaaa    60
uccggcccgc cggacca                                                  77

<210> SEQ ID NO 91
<211> LENGTH: 77
<212> TYPE: RNA
<213> ORGANISM: Methanococcus jannaschii
<220> FEATURE:
<221> NAME/KEY: misc_feature
<222> LOCATION: (16)..(18)
<223> OTHER INFORMATION: any
<220> FEATURE:
<221> NAME/KEY: misc_feature
<222> LOCATION: (21)..(21)
<223> OTHER INFORMATION: any
<220> FEATURE:
<221> NAME/KEY: misc_feature
<222> LOCATION: (33)..(33)
<223> OTHER INFORMATION: any
```

```
<220> FEATURE:
<221> NAME/KEY: misc_feature
<222> LOCATION: (38)..(39)
<223> OTHER INFORMATION: any
<220> FEATURE:
<221> NAME/KEY: misc_feature
<222> LOCATION: (46)..(46)
<223> OTHER INFORMATION: any
<220> FEATURE:
<221> NAME/KEY: misc_feature
<222> LOCATION: (48)..(48)
<223> OTHER INFORMATION: any
<220> FEATURE:
<221> NAME/KEY: misc_feature
<222> LOCATION: (60)..(61)
<223> OTHER INFORMATION: any

<400> SEQUENCE: 91
ccggcgguag uucagnnngg nagaacggcg ganucuannu ccgcangncg cugguucaan    60
nccggcccgc cggacca                                                  77

<210> SEQ ID NO 92
<211> LENGTH: 77
<212> TYPE: DNA
<213> ORGANISM: Methanococcus jannaschii

<400> SEQUENCE: 92
ccggcggtag ttcagcctgg tagaacggcg gactctagat ccgcatgtcg ctggttcaaa    60
tccggcccgc cggacca                                                  77

<210> SEQ ID NO 93
<211> LENGTH: 77
<212> TYPE: DNA
<213> ORGANISM: Methanococcus jannaschii

<400> SEQUENCE: 93
ccggcggtag ttcagcctgg tagaacggcg gacactaaat ccgcatgtcg ctggttcaaa    60
tccggcccgc cggacca                                                  77

<210> SEQ ID NO 94
<211> LENGTH: 77
<212> TYPE: DNA
<213> ORGANISM: Methanococcus jannaschii

<400> SEQUENCE: 94
ccggcggtag ttcagcctgg tagaacggcg gacactaaat ccgcatgtcg ctggttcaaa    60
tccggcctgc cggacca                                                  77

<210> SEQ ID NO 95
<211> LENGTH: 77
<212> TYPE: DNA
<213> ORGANISM: Methanococcus jannaschii

<400> SEQUENCE: 95
ccggcggtag ttcagcctgg tagaacggcg gaatctaaat ccgcatgtcg ttggttcaaa    60
tccggcccgc cggacca                                                  77

<210> SEQ ID NO 96
<211> LENGTH: 77
<212> TYPE: DNA
<213> ORGANISM: Methanococcus jannaschii

<400> SEQUENCE: 96
ccggcggtag ttcagtgagg aagaacggcg gactctaaat ccgcaaggcg ctggttcaag    60
```

```
tccggcccgc cggacca                                               77

<210> SEQ ID NO 97
<211> LENGTH: 77
<212> TYPE: DNA
<213> ORGANISM: Methanococcus jannaschii

<400> SEQUENCE: 97
ccggcggtag ttcagcaggg cagaacggcg gactctaaat ccgcatggcg ctggttcaaa    60
tccggcccgc cggacca                                               77

<210> SEQ ID NO 98
<211> LENGTH: 77
<212> TYPE: DNA
<213> ORGANISM: Methanococcus jannaschii

<400> SEQUENCE: 98
ccggcggtag ttcagatagg gagaacggcg gactctaact ccgcatggcg ctggttcaat    60
tccggcccgc cggacca                                               77

<210> SEQ ID NO 99
<211> LENGTH: 77
<212> TYPE: DNA
<213> ORGANISM: Methanococcus jannaschii

<400> SEQUENCE: 99
ccggcggtag ttcaggtagg gagaacggcg gactctaact ccgcatgtcg ctggttcaag    60
tccggcccgc cggacca                                               77

<210> SEQ ID NO 100
<211> LENGTH: 77
<212> TYPE: DNA
<213> ORGANISM: Methanococcus jannaschii

<400> SEQUENCE: 100
ccggcggtag ttcagtaggg aagaacggcg gactctaaat ccgcacgtcg ctggttcaag    60
tccggcccgc cggacca                                               77

<210> SEQ ID NO 101
<211> LENGTH: 77
<212> TYPE: DNA
<213> ORGANISM: Methanococcus jannaschii

<400> SEQUENCE: 101
ccggcggtag ttcagggtgg gagaacggcg gagtctaggt ccgcatgccg ctggttcaat    60
accggcccgc cggacca                                               77

<210> SEQ ID NO 102
<211> LENGTH: 77
<212> TYPE: DNA
<213> ORGANISM: Methanococcus jannaschii

<400> SEQUENCE: 102
ccggcggtag ttcagttcgg cagaacggcg gagtctatat ccgcacgccg ctggttcaac    60
cccggcccgc cggacca                                               77

<210> SEQ ID NO 103
<211> LENGTH: 77
<212> TYPE: DNA
<213> ORGANISM: Methanococcus jannaschii
```

-continued

```
<400> SEQUENCE: 103
ccggcggtag ttcagtgtgg aagaacggcg gattctatct ccgcacggcg ctggttcaag    60
gccggcccgc cggacca                                                   77

<210> SEQ ID NO 104
<211> LENGTH: 88
<212> TYPE: DNA
<213> ORGANISM: Halobacterium sp. NRC-1

<400> SEQUENCE: 104
gcgagggtag ccaagctcgg ccaacggcga cggactcaag atccgttctc gtaggagttc    60
gagggttcga atcccttccc tcgcacca                                       88

<210> SEQ ID NO 105
<211> LENGTH: 89
<212> TYPE: DNA
<213> ORGANISM: Halobacterium sp. NRC-1

<400> SEQUENCE: 105
gcgagggtag ccaagctcgg ccaacggcga cggacttcct aatccgttct cgtaggagtt    60
cgagggttcg aatcccttcc ctcgcacca                                      89

<210> SEQ ID NO 106
<211> LENGTH: 76
<212> TYPE: RNA
<213> ORGANISM: Thermus thermophilus

<400> SEQUENCE: 106
gcucgcguag cucagcaggu agagcacacc cuugguaagg gugaggucgc cgguucgagc    60
ccggccgcga gcucca                                                    76

<210> SEQ ID NO 107
<211> LENGTH: 76
<212> TYPE: RNA
<213> ORGANISM: Thermus thermophilus

<400> SEQUENCE: 107
gaucgcguag cucagcaggu agagcacacc cuugguaagg gugaggucgc cgguucgagc    60
ccggccgcga ucucca                                                    76

<210> SEQ ID NO 108
<211> LENGTH: 76
<212> TYPE: RNA
<213> ORGANISM: Thermus thermophilus

<400> SEQUENCE: 108
gaucgcguag cucagcaggu agagcacacc cuucuaaagg gugaggucgc cgguucgagc    60
ccggccgcga ucucca                                                    76
```

METHODS AND COMPOSITION FOR THE PRODUCTION OF ORTHOGONAL TRNA-AMINOACYLTRNA SYNTHETASE PAIRS

CROSS-REFERENCE TO RELATED APPLICATIONS

This application is a divisional of U.S. patent application Ser. No. 10/126,931 filed Apr. 19, 2002 and claims priority to U.S. provisional patent application Ser. No. 60/285,030, filed Apr. 19, 2001, and U.S. patent application Ser. No. 60/355,514, filed Feb. 6, 2002, the specifications of which are incorporated herein in their entirety.

STATEMENT AS TO RIGHTS TO INVENTIONS MADE UNDER FEDERALLY SPONSORED RESEARCH AND DEVELOPMENT

The invention was made with United States Government support under Grant No. N0001498F0402 from the Office of Naval Research, Contract No. NIH GM62159 from the National Institutes of Health, and Contract Nos. DE -FG03-00ER45812, DE-AC03-76SF00098 from the Department of Energy. The United States Government has certain rights in the invention.

FIELD OF THE INVENTION

The invention relates to the field of translation biochemistry. In particular, the invention relates to methods for producing mutated orthogonal tRNAs, mutated orthogonal aminoacyl-tRNA synthetases, and pairs thereof. The invention also provides methods for identifying orthogonal pairs, which are used for the incorporation of unnatural amino acids into proteins in vivo, and related compositions.

BACKGROUND OF THE INVENTION

Proteins carry out virtually all of the complex processes of life, from photosynthesis to signal transduction and the immune response. To understand and control these intricate activities, a better understanding of the relationship between the structure and function of proteins is needed.

Unlike small organic molecule synthesis wherein almost any structural change can be made to influence functional properties of a compound, the synthesis of proteins is limited to changes encoded by the twenty natural amino acids. The genetic code of every known organism, from bacteria to human, encodes the same twenty common amino acids. These amino acids can be modified by post-translational modification of proteins, e.g., glycosylation, phosphorylation or oxidation, or in rarer instances, by the enzymatic modification of aminoacylated suppressor tRNAs, e.g., in the case of selenocysteine. Nonetheless, polypeptides, which are synthesized from only these 20 simple building blocks, carry out all of the complex processes of life.

Both site-directed and random mutagenesis, in which specific amino acids in a protein can be replaced with any of the other nineteen common amino acids, have become important tools for understanding the relationship between the structure and function of proteins. These methodologies have made possible the generation of proteins with enhanced properties, including stability, catalytic activity and binding specificity. Nevertheless, changes in proteins are limited to the 20 common amino acids, most of which have simple functional groups. See Knowles, J. R. Tinkering with enzymes: what are we learning? Science, 236:1252-1258 (1987); and, Zoller, M. J., Smith, M. Oligonucleotide-directed mutagenesis of DNA fragments cloned into M13 vectors, Methods Enzymol, 100: 468-500 (1983). By expanding the genetic code to include additional amino acids with novel biological, chemical or physical properties, the properties of proteins, e.g., the size, acidity, nucleophilicity, hydrogen-bonding, hydrophobic properties, etc., can be modified as compared to a protein composed of only amino acids from the 20 common amino acids, e.g., as in a naturally occurring protein.

Several strategies have been employed to introduce unnatural amino acids into proteins. The first experiments involved the derivatization of amino acids with reactive sidechains such as Lys, Cys and Tyr, for example, the conversion of lysine to $N^\epsilon$-acetyl-lysine. Chemical synthesis also provides a straightforward method to incorporate unnatural amino acids, but routine solid-phase peptide synthesis is generally limited to small peptides or proteins with less than 100 residues. With the recent development of enzymatic ligation and native chemical ligation of peptide fragments, it is possible to make larger proteins, but such methods are not easily scaled. See, e.g., P. E. Dawson and S. B. H. Kent, Annu. Rev. Biochem., 69:923 (2000). A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, Angew. Chem. Int. Ed. Engl., 1995, 34:621 (1995); C. J. Noren, S. J. Anthony-Cahill, M. C. Griffith, P. G. Schultz, A general method for site-specific incorporation of unnatural amino acids into proteins, Science 244 182-188 (1989); and, J. D. Bain, C. G. Glabe, T. A. Dix, A. R. Chamberlin, E. S. Diala, Biosynthetic site-specific incorporation of a non-natural amino acid into a polypeptide, J. Am. Chem. Soc. 111 8013-8014 (1989). A broad range of functional groups has been introduced into proteins for studies of protein stability, protein folding, enzyme mechanism, and signal transduction. Although these studies demonstrate that the protein biosynthetic machinery tolerates a wide variety of amino acid side chains, the method is technically demanding, and yields of mutant proteins are low.

Over 50 years ago, it was found that many analogs of natural amino acids inhibit the growth of bacteria. Analysis of the proteins produced in the presence of these amino acid analogs revealed that they had been substituted for their natural counterparts to various extents. See, e.g., M. H. Richmond, Bacteriol. Rev., 26:398 (1962). This occurs because the aminoacyl-tRNA synthetase, the enzyme responsible for the attachment of the correct amino acid to its cognate tRNA, cannot rigorously distinguish the analog from the corresponding natural amino acid. For instance, norleucine is charged by methionyl-tRNA synthetase, and p-fluorophenylalanine is charged by phenylalanine-tRNA synthetase. See, D. B. Cowie, G. N. Cohen, E. T. Bolton and H. de Robichon-Szulmajster, Biochim. Biophys. Acta, 1959, 34:39 (1959); and, R. Munier and G. N. Cohen, Biochim. Biophys. Acta. 1959, 31:378 (1959).

An in vivo method, termed selective pressure incorporation, was later developed to exploit the promiscuity of wild-type synthetases. See, e.g., N. Budisa, C. Minks, S. Alefelder, W. Wenger, F. M. Dong, L. Moroder and R. Huber, FASEB J., 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage λ lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been inserted in place of leucine, resulting in increased thermal and chemical stability of a leucine-zipper protein. See, e.g. Y. Tang, G. Ghirlanda, W. A. Petka, T. Nakajima, W. F. DeGrado and D. A. Tirrell, *Angew. Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.* 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Karnbrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been inserted efficiently, allowing for additional modification of proteins by chemical means. See, e.g., J. C. M. van Hest and D. A. Tirrell, *FEBS Lett.*, 428:68 (1998); J. C. M. van Hest, K. L. Kiick and D. A. Tirrell, *J. Am. Chem. Soc.*, 122:1282 (2000); and, K. L. Kiick and D. A. Tirrell, *Tetrahedron*, 56:9487 (2000).

The success of this method depends on the recognition of the unnatural amino acid analogs by aminoacyl-tRNA synthetases, which, in general, requires high selectivity to insure the fidelity of protein translation. Therefore, the range of chemical functionality accessible via this route is limited. For instance, although thiaproline can be incorporated quantitatively into proteins, oxaproline and selenoproline cannot. See, N. Budisa, C. Minks, F. J. Medrano, J. Lutz, R. Huber and L. Moroder, *Proc. Natl. Acad. Sci. USA*, 95:455 (1998). One way to expand the scope of this method is to relax the substrate specificity of aminoacyl-tRNA synthetases, which has been achieved in a limited number of cases. For example, it was found that replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.*, 275:40324 (2000).

The fidelity of aminoacylation is maintained both at the level of substrate discrimination and proofreading of non-cognate intermediates and products. Therefore, an alternative strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

At least one major limitation of the methods described above is that all sites corresponding to a particular natural amino acid throughout the protein are replaced. The extent of incorporation of the natural and unnatural amino acid may also vary—only in rare cases can quantitative substitution be achieved since it is difficult to completely deplete the cognate natural amino acid inside the cell. Another limitation is that these strategies make it difficult to study the mutant protein in living cells, because the multi-site incorporation of analogs often results in toxicity. Finally, this method is applicable in general only to close structural analogs of the common amino acids, again because substitutions must be tolerated at all sites in the genome.

Solid-phase synthesis and semi-synthetic methods have also allowed for the synthesis of a number of small proteins containing novel amino acids. For example, see the following publications and references cited within: Crick, F. J. C., Barrett; L. Brenner, S. Watts-Tobin, R. General nature of the genetic code for proteins. *Nature*, 192:1227-1232 (1961); Hofmann, K., Bohn, H. Studies on polypeptides. XXXVI. The effect of pyrazole-imidazole replacements on the S-protein activating potency of an S-peptide fragment, *J. Am. Chem.*, 5914-5919 (1966); Kaiser, E. T. Synthetic approaches to biologically active peptides and proteins including enzymes, Acc. Chem. Res., 47-54 (1989); Nakatsuka, T., Sasaki, T., Kaiser, E. T. Peptide segment coupling catalyzed by the semisynthetic enzyme thiosubtilisin, *J. Am. Chem. Soc.*, 109:3808-3810 (1987); Schnolzer, M., Kent, S B H. Constructing proteins by dovetailing unprotected synthetic peptides: backbone-engineered HIV protease, *Science*, 256 (5054):221-225 (1992); Chaiken, I. M. Semisynthetic peptides and proteins, *CRC Crit. Rev. Biochem.*, 11(3):255-301 (1981); Offord, R. E. Protein engineering by chemical means? *Protein Eng.*, 1(3):151-157 (1987); and, Jackson, D. Y., Burnier, J., Quan, C., Stanley, M., Tom, J., Wells, J. A. A Designed Peptide Ligase for Total Synthesis of Ribonuclease A with Unnatural Catalytic Residues, *Science*, 266(5183): 243-247 (1994).

Chemical modification has been used to introduce a variety of unnatural side chains, including cofactors, spin labels and oligonucleotides into proteins in vitro. See, e.g., Corey, D. R., Schultz, P. G. Generation of a hybrid sequence-specific single-stranded deoxyribonuclease, *Science,* 283(4832): 1401-1403 (1987); Kaiser, E. T., Lawrence D. S., Rokita, S. E. The chemical modification of enzymatic specificity, *Rev. Biochem.,* 54:565-595 (1985); Kaiser, E. T., Lawrence, D. S. Chemical mutation of enzyme active sites, *Science,* 226(4674):505-511 (1984); Neet, K. E., Nanci A, Koshland, D. E. Properties of thiol-subtilisin, *J. Biol. Chem.,* 243(24): 6392-6401 (1968); Polgar, L. B., M. L. A new enzyme containing a synthetically formed active site. Thiol-subtilisin. *J. Am. Chem. Soc.,* 88:3153-3154 (1966); and, Pollack, S. J., Nakayama, G. Schultz, P. G. Introduction of nucleophiles and spectroscopic probes into antibody combining sites, *Science,* 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. New Photolabeling and crosslinking methods, *Annu. Rev. Biochem.,* 62:483-514 (1993); and, Krieg, U. C., Walter, P., Hohnson, A. E. Photocrosslinking of the signal sequence of nascent preprolactin of the 54-kilodalton polypeptide of the signal recognition particle, *Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotrophic for a particular amino acid. See, e.g., Noren, C. J., Anthony-Cahill, Griffith, M. C., Schultz, P. G. A general method for site-specific incorporation of unnatural amino acids into proteins, *Science,* 244:182-188 (1989); M. W. Nowak, et al., *Science* 268:439-42 (1995); Bain, J. D., Glabe, C. G., Dix, T. A., Chamberlin, A. R., Diala, E. S. Biosynthetic site-specific Incorporation of a non-natural amino acid into a polypeptide, *J. Am. Chem. Soc.,* 111:8013-8014 (1989); N. Budisa et al., *FASEB J.* 13:41-51 (1999); Ellman, J. A., Mendel, D., Anthony-Cahill, S., Noren, C. J., Schultz, P. G. Biosynthetic method for introducing unnatural amino acids site-specifically into proteins, *Methods in Enz.,* 301-336 (1992); and, Mendel, D., Cornish, V. W. & Schultz, P. G. Site-Directed Mutagenesis with an Expanded Genetic Code, *Annu. Rev. Biophys. Biomol. Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5', 3' Exonuclease in phosphorothioate-based oligonucleotide-directed mutagenesis, *Nucleic Acids Res.,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; and, Ellman, J. A., Mendel, D., Schultz, P. G. Site-specific incorporation of novel backbone structures into proteins, *Science,* 197-200 (1992).

In general, these in vitro approaches are limited by difficulties in achieving site-specific incorporation of the amino acids, by the requirement that the amino acids be simple derivatives of the common twenty amino acids or problems inherent in the synthesis of large proteins or peptide fragments.

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science,* 268:439 (1995); and, D. A. Dougherty, *Curr. Opin. Chem. Biol.,* 4:645 (2000). A *Xenopus oocyte* was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserted the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.,* 271:19991 (1996); the incorporation of biotinylated amino acids to identify surface-exposed residues in ion channels, see, e.g., J. P. Gallivan, H. A. Lester and D. A. Dougherty, *Chem. Biol.,* 4:739 (1997); the use of caged tyrosine analogs to monitor conformational changes in an ion channel in real time, see, e.g., J. C. Miller, S. K. Silverman, P. M. England, D. A. Dougherty and H. A. Lester, *Neuron,* 20:619 (1998); and, the use of α-hydroxy amino acids to change ion channel backbones for probing their gating mechanisms, see, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.,* 4:239 (2001).

However, there are limitations microinjection method, e.g., the suppressor tRNA has to be chemically aminoacylated with the unnatural amino acid in vitro, and the acylated tRNA is consumed as a stoichiometric reagent during translation and cannot be regenerated. This limitation results in poor suppression efficiency and low protein yields, necessitating highly sensitive techniques to assay the mutant protein, such as electrophysiological measurements. Moreover, this method is only applicable to cells that can be microinjected.

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation. Therefore, improvements to the process are needed to provide more efficient and effective methods to alter the biosynthetic machinery of the cell. The present invention addresses these and other needs, as will be apparent upon review of the following disclosure.

SUMMARY OF THE INVENTION

The present invention provides compositions of components used in protein biosynthetic machinery, which include orthogonal tRNA-aminoacyl-tRNA synthetase pairs and the individual components of the pairs. Methods for generating and selecting orthogonal tRNAs, orthogonal aminoacyl-tRNA synthetases, and pairs thereof that can use an unnatural amino acid are also provided. Compositions of the invention include novel orthogonal tRNA-aminoacyl-tRNA synthetase pairs, e.g., mutRNATyr-mutTyrRS pairs, mutRNALeu-mutLeuRS pairs, mutRNAThr-mutThrRS pairs, mutRNAGlu-mutGluRS pairs, and the like. The novel orthogonal pairs can be use to incorporate an unnatural amino acid in a polypeptide in vivo. Other embodiments of the invention include selecting orthogonal pairs.

Compositions of the present invention include an orthogonal aminoacyl-tRNA synthetase (O-RS), where the O-RS preferentially aminoacylates an orthogonal tRNA (O-tRNA) with an unnatural amino acid, optionally, in vivo. In one embodiment, the O-RS comprises a nucleic acid comprising a polynucleotide sequence selected from the group consisting of: SEQ ID NO: 4-34 (see, Table 5) and a complementary polynucleotide sequence thereof. In another embodiment, the O-RS has improved or enhanced enzymatic properties, e.g., the $K_m$ is higer or lower, the $k_{cat}$ is higher or lower, the value of $k_{cat}/K_m$ is higher or lower or the like, for the unnatural amino acid compared to a naturally occurring amino acid, e.g., one of the 20 known amino acids.

The unnatural amino acids of the present invention encompass a variety of substances. For example, they optionally include (but are not limited to) such molecules as: an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine. Additionally, other examples optionally include (but are not limited to) an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

The present invention also includes a polypeptide comprising an amino acid sequence encoded by a coding polynucleotide sequence which is selected from: a coding polynucleotide sequence selected from SEQ ID NO: 4-34 (see, Table 5 for sequences); a coding polynucleotide sequence encoding a polypeptide selected from SEQ ID NO: 35-66 a polynucleotyide sequence which hybridizes under highly stringent conditions over substantially the entire length of such polynucleotide sequences; and complementary sequences of any of such sequences. Additionally, such polypeptide optionally encodes an orthogonal aminoacyl tRNA sythetase and/or an amino acid sequence selected from SEQ ID NO:35 to SEQ ID NO:66.

The present invention also includes a nucleic acid comprising a polynucleotide sequence selected from the group consisting of: a polynucleotide sequence selected from SEQ ID NO:1 to SEQ ID NO:3 (or a complementary polynucleotide sequence thereof) and a polynucleotide sequence which hybridizes under highly stringent conditions over substantially the entire length of such polynucleotide sequences. Such nucleic acids also include wherein the polynucleotide sequence comprises an orthogonal tRNA and/or wherein the polynucleotide sequence forms a complementary pair with an orthogonal aminoacyl-tRNA synthetase (which optionally is selected from the those whose sequence is listed in SEQ ID NO:35 to SEQ ID NO:66.

Compositions of an orthogonal tRNA (O-tRNA) are also included, where the O-tRNA recognizes a selector codon and wherein the O-tRNA is preferentially aminoacylated with an unnatural amino acid by an orthogonal aminoacyl-tRNA synthetase. In one embodiment, the O-tRNA comprises a nucleic acid comprising a polynucleotide sequence selected from the group consisting of: SEQ ID NO:1-3 (see, Table 5) and a complementary polynucleotide sequence thereof.

Selector codons of the present invention expand the genetic codon framework of protein biosynthetic machinery. For example, a selector codon includes, e.g., a unique three base codon (composed of natural or unnatural bases), a nonsense codon (such as a stop codon, e.g., an amber codon, or an opal codon), an unnatural codon, a rare codon, a codon comprising at least four bases, a codon comprising at least five bases, a codon comprising at least six bases, or the like.

In one embodiment, the O-tRNA (optionally comprising within compositions) can include an orthogonal aminoacyl-tRNA synthetase (O-RS), e.g., where the O-tRNA and the O-RS are complementary, e.g., an O-tRNA/O-RS pair. In one embodiment, a pair comprises e.g., a mutRNATyr-mutTyrRS pair, such as mutRNATyr-SS12TyrRS pair, a mutRNALeu-mutLeuRS pair, a mutRNAThr-mutThrRS pair, a mutRNA-Glu-mutGluRS pair, or the like. In another embodiment, the pair is other than a mutRNAGln-mutGlnRS derived from *Escherichia coli*, a mutRNAAsp-mutAspRS derived from yeast or a mutRNAPheCUA-mutphenlalanineRS from yeast, where these pairs do not possess the properties of the pairs of the present invention.

The O-tRNA and the O-RS can be derived by mutation of a naturally occurring tRNA and RS from a variety of organisms. In one embodiment, the O-tRNA and O-RS are derived from at least one organism, where the organism is a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. ther-*

*mophilus*, or the like. Optionally, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the O-tRNA is derived by mutation of a naturally occurring tRNA from a first organism and the O-RS is derived by mutation of a naturally occurring RS from a second organism. In one embodiment, the O-tRNA and O-RS can be derived from a mutated tRNA and mutated RS.

The O-tRNA and the O-RS also can optionally be isolated from a variety of organisms. In one embodiment, the O-tRNA and O-RS are isolated from at least one organism, where the organism is a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. thermophilus*, or the like. Optionally, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the O-tRNA is isolated from a naturally occurring tRNA from a first organism and the O-RS is isolated from a naturally occurring RS from a second organism. In one embodiment, the O-tRNA and O-RS can be isolated from one or more library (which optionally comprises one or more O-tRNA and/or O-RS from one or more organism (including those comprising prokaryotes and/or eukaryotes).

In another aspect, the compositions of the present invention can be in a cell. Optionally, the compositions of the present invention can be in an in vitro translation system.

Methods for generating components of the protein biosynthetic machinery, such as O-RSs, O-tRNAs, and orthogonal O-tRNA/O-RS pairs that can be used to incorporate an unnatural amino acid are provided in the present invention. Methods for selecting an orthogonal tRNA-tRNA synthetase pair for use in in vivo translation system of an organism are also provided. The unnatural amino acids and selectors codons used in the methods are described above and below.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, e.g., a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like; (b) selecting (and/or screening) the library of RSs (optionally mutant RSs) for members that aminoacylate an orthogonal tRNA (O-tRNA) in the presence of an unnatural amino acid and a natural amino acid, thereby providing a pool of active (optionally mutant) RSs; and/or, (c) selecting (optionally through negative selection) the pool for active RSs (e.g., mutant RSs) that preferentially aminoacylate the O-tRNA in the absence of the unnatural amino acid, thereby providing the at least one recombinant O-RS; wherein the at least one recombinant O-RS preferentially aminoacylates the O-tRNA with the unnatural amino acid. Recombinant O-RSs produced by the methods are also included in the present invention.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, e.g., alanine.

Libraries of mutant RSs can be generated using various mutagenesis techniques known in the art. For example, the mutant RSs can be generated by site-specific mutations, random mutations, diversity generating recombination mutations, chimeric constructs, and by other methods described herein or known in the art.

In one embodiment, selecting (and/or screening) the library of RSs (optionaly mutant RSs) for members that are active, e.g., that aminoacylate an orthogonal tRNA (O-tRNA) in the presence of an unnatural amino acid and a natural amino acid, includes: introducing a positive selection or screening marker, e.g., an antibiotic resistance gene, or the like, and the library of (optionally mutant) RSs into a plurality of cells, wherein the positive selection and/or screening marker comprises at least one selector codon, e.g., an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (e.g., a cell surface marker).

In one embodiment, negatively selecting or screening the pool for active RSs (optionally mutants) that preferentially aminoacylate the O-tRNA in the absence of the unnatural amino acid includes: introducing a negative selection or screening marker with the pool of active (optionally mutant) RSs from the positive selection or screening into a plurality of cells of a second organism, wherein the negative selection or screening marker comprises at least one selector codon (e.g., an antibiotic resistance gene, e.g., a chloramphenicol acetyltransferase (CAT) gene); and, identifying cells that survive or show a specific screening response in a 1st media supplemented with the unnatural amino acid and a screening or selection agent, but fail to survive or to show the specific response in a 2nd media not supplemented with the unnatural amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selctor codon) either with or without one or more unnatural amino acid. Colonies growing exclusively on the plates containing unnatural amino acids are thus regarded as containing recombinant O-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (e.g., negatively selecting) the pool for active (optionally mutant) RSs includes: isolating the pool of active mutant RSs from the positive selection step (b); introducing a negative selection or screening marker, wherein the negative selection or screening marker comprises at least one selector codon (e.g., a toxic marker gene, e.g., a ribonuclease barnase gene, comprising at least one selector codon), and the pool of active (optionally mutant) RSs into a plurality of cells of a second organism; and identifying cells that survive or show a specific screening response in a 1st media not supplemented with the unnatural amino acid, but fail to survive or show a specific screening response in a 2nd media supplemented with the unnatural amino acid, thereby providing surviving or screened cells with the at least one recombinant O-RS, wherein the at least one recombinant O-RS is specific for the unnatural amino acid. In one aspect, the at least one selector codon comprises about two or more selector codons. Such embodiments optionally can include wherein the at least one selector codon comprises two or more selector codons, and wherein the first and second organism are different (e.g., each organism is optionally, e.g., a prokaryote, a eukaryote, a mammal, an *Escherichia coli*, a fungi, a yeast, an archaebacteria, a eubacteria, a plant, an insect, a protist, etc.). Also, some aspects include wherein the negative selction marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, e.g., at least about two times. In one aspect, the second set of mutated O-RS derived from at least one recombinant O-RS can be generated by mutagenesis, e.g., random mutagenesis, site-specific mutagenesis, recombination or a combination thereof.

The stringency of the selection/screening steps, e.g., the positive selection/screening step (b), the negative selection/screening step (c), or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the unnatural amino acid or an analogue. In one embodiment, the mutated synthetase is displayed on a cell surface, on a phage display or the like.

The methods embodied herein optionally comprise wherein the unnatural amino acid is selected from, e.g.: an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine. A recombinant O-RS produced by the methods herein is also included in the current invention.

Methods for producing a recombinant orthogonal tRNA (O-tRNA) include: (a) generating a library of mutant tRNAs derived from at least one tRNA, e.g., a suppressor tRNA, from a first organism; (b) selecting (e.g., negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS(O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, e.g., prokaryotes (e.g., *Methanococcus jannaschii*, *Methanobacteium thermoautotrophicum*, *Escherichia coli*, *Halobacterium*, etc.), eukaryotes, mammals, fungi, yeasts, archaebacteria, eubacteria, plants, insects, protists, etc. Additionally, the recombinant tRNA is optionally aminoacylated by an unnatrual amino acid, wherein the unnatural amino acid is biosynthesized in vivo either naturally or through genetic manipulation. The unnatural amino acid is optionally added to a growth medium for at least the first or second organism.

In one aspect, selecting (e.g., negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS(O-RS) can include: introducing a positive selection or screening marker gene, wherein the positive marker gene comprises a drug resistance gene (e.g., β-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, e.g., an antibiotic, thereby providing a pool of cells possessing the at least one recombinant tRNA, where the at least recombinant tRNA is aminoacylated by the O-RS and inserts an amino acid into a translation product encoded by the positive marker gene, in response to the at least one selector codons. In another embodiment, the concentration of the selection and/or screening agent is varied. Recombinant O-tRNAs produced by the methods of the present invention are also included.

Methods for generating specific O-tRNA/O-RS pairs are provided. Methods include: (a) generating a library of mutant tRNAs derived from at least one tRNA from a first organism; (b) negatively selecting or screening the library for (optionally mutan) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS(O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of an unnatural amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the unnatural amino acid, thereby providing the at least one specific O-tRNA/O-RS pair, wherein the at least one specific O-tRNA/O-RS pair comprises at least one recombinant O-RS that is specific for the unnatural amino acid and the at least one recombinant O-tRNA. Specific O-tRNA/O-RS pairs produced by the methods are included. For example, the specific O-tRNA/O-RS pair can include, e.g., a mutRNATyr-mutTyrRS pair, such as a mutRNATyr-SS 12TyrRS pair, a mutRNALeu-mutLeuRS pair, a mutRNAThr-mutThrRS pair, a mutRNAGlu-mutGluRS pair, or the like. Additionally, such methods include wherein the first and thrid organism are the same (e.g., *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, e.g., *Methanococcus jannaschii, Methanobacterium thermoautotrophicum, Halobacterium, Escherichia coli, A. fulgidus, P. furiosus, P. horikoshii, A. pernix, T thermophilus*, or the like. Alternatively, the organisms optionally comprise a eukaryotic organism, e.g., plants (e.g., complex plants such as monocots, or dicots), algae, protists, fungi (e.g., yeast, etc), animals (e.g., mammals, insects, arthropods, etc.), or the like. In another embodiment, the second organism is a prokaryotic organism, e.g., *Methanococcus jannaschii, Methanobacterium thermoautotrophicum, Halobacterium, Escherichia coli, A. fulgidus, Halobacterium, P. furiosus, P. horikoshii, A. pemix, T. thermophilus*, or the like. Alternatively, the second organism can be a eukaryotic organism, e.g., a yeast, a animal cell, a plant cell, a fungus, a mammalian cell, or the like. In various embodiments the first and second organisms are different.

The various methods of the invention (above) optionally comprise wherein selecting or screening comprises one or more positive or negative selection or screening, e.g., a change in amino acid permeability, a change in translation efficiency, and a change in translational fidelity. Additionally, the one or more change is optionally based upon a mutation in one or more gene in an organism in which an orthogonal tRNA-tRNA synthetase pair are used to produce such protein. Selecting and/or screening herein optionally comprises wherein at least 2 selector codons within one or more selection gene or within one or more screening gene are use. Such multiple selector codons are optionally within the same gene or within different screening/selection genes. Additionally, the optional multiple selector codons are optionally different selector codons or comprise the same type of selector codons.

Kits are an additional feature of the invention. For example, the kits can include one or more translation system as noted above (e.g., a cell), one or more unnatural amino acid, e.g., with appropriate packaging material, containers for holding the components of the kit, instructional materials for practicing the methods herein and/or the like. Similarly, products of the translation systems (e.g., proteins such as EPO analogues comprising unnatural amino acids) can be provided in kit form, e.g., with containers for holding the components of the kit, instructional materials for practicing the methods herein and/or the like.

BRIEF DESCRIPTION OF THE DRAWINGS

FIG. 4 illustrates a consensus sequence (SEQ ID NO:85 and SEQ ID NO:86) for pentafluorophenylalanine selection to generate directed libraries for these analogues. Four regions of the protein are illustrated: residue 32, residues 67-70 (SEQ ID NO:80 for wild type, library 1, and library 2), residue 107, and residues 155-167 (SEQ ID NO:81 for wild type, SEQ ID NO:82 for library 1, SEQ ID NO:83 for library 2, and SEQ ID NO:84 for library 3).

FIG. 5 schematically illustrates the transplantation of one domain, e.g., the CPI domain, from one organism, e.g., *Escherichia coli*, to the synthetase of other organism, e.g., *Methanococcus jannaschii* TyrRS.

FIG. 6 schematically illustrates the construction of chimeric *Methanococcus jannaschii/Escherichia coli* synthetases. The *E. coli* TyrRS is SEQ ID NO:87, the *H.sapiens* TyrRS is SEQ ID NO:88, and the *M. jannaschii* TyrRS is SEQ ID NO:89.

FIG. 13 illustrates DNA sequences of mutant suppressor tRNAs selected from anticodon-loop (AA2 (SEQ ID NO. 93), AA3 (SEQ ID NO. 94), and AA4 (SEQ ID NO 95)) and all-loop library (J15 (SEQ ID NO. 96), J17 (SEQ ID NO. 97), J18 (SEQ ID NO. 98), J22 (SEQ ID NO. 99), N11 (SEQ ID NO. 100), N12 (SEQ ID NO. 101), N13 (SEQ ID NO. 102), and N16 (SEQ ID NO. 103)). JY stands for the wild-type *Methanococcus jannaschii* tRNACUATyrCUA (SEQ ID NO:92).

FIG. 21, Panel A and Panel B, illustrates mutated amber suppressor tRNAs from a Halobacterium NRC-1, which are generated by mutating, e.g., randomizing, the anticodon loop of the leucyl tRNA (SEQ ID NO:104) and selecting (Panel B) for more efficient suppression of a selector codon, e.g., an amber codon in a reporter gene(s), e.g., using a combination of selection steps, such as selection based on β-lactamase and selection based on barnase. Panel B illustrates IC50 values in μg/ml of ampicillin for a β-lactamase amber suppression system with three mutant tRNA constructs, original amber mutant, optimized anticodon loop, and optimized acceptor stem, alone or with an RS, e.g., MtLRS. The optimized anticodon and optimized acceptor stem gave the highest values in the β-lactamase selection step.

FIG. 23 Panels A-D, illustrates the activity of the dominant synthetase variant from each successful evolution experiment. FIG. 23A is a photograph illustrating long-wavelength ultraviolet illumination of cells containing pREP/YC-JY-CUA and the indicated synthetase variant, grown in either the presence (+) or absence (−) of the corresponding unnatural amino acid. FIG. 23B illustrates a fluorimetric analysis of cells containing pREP/YC-JYCUA and the indicated synthetase variant, grown in either the presence (left) or absence (right) of the corresponding unnatural amino acid. FIG. 23C is a table that illustrates a Cm $IC_{50}$ analysis of cells containing pREP/YC-JYCUA and the indicated synthetase variant, grown in either the presence or absence of the corresponding unnatural amino acid. FIG. 23D illustrates a protein expression analysis from cells containing pBAD/JYAMB4TAG and the indicated synthetase variant, grown in either the presence (+) or absence (−) of the corresponding unnatural amino acid.

FIG. 25, Panels A-B, illustrate components of the multipurpose reporter plasmid system for directing the evolution of *M. jannaschii* TyrRS.

DETAILED DESCRIPTION

Introduction

Figure 1:
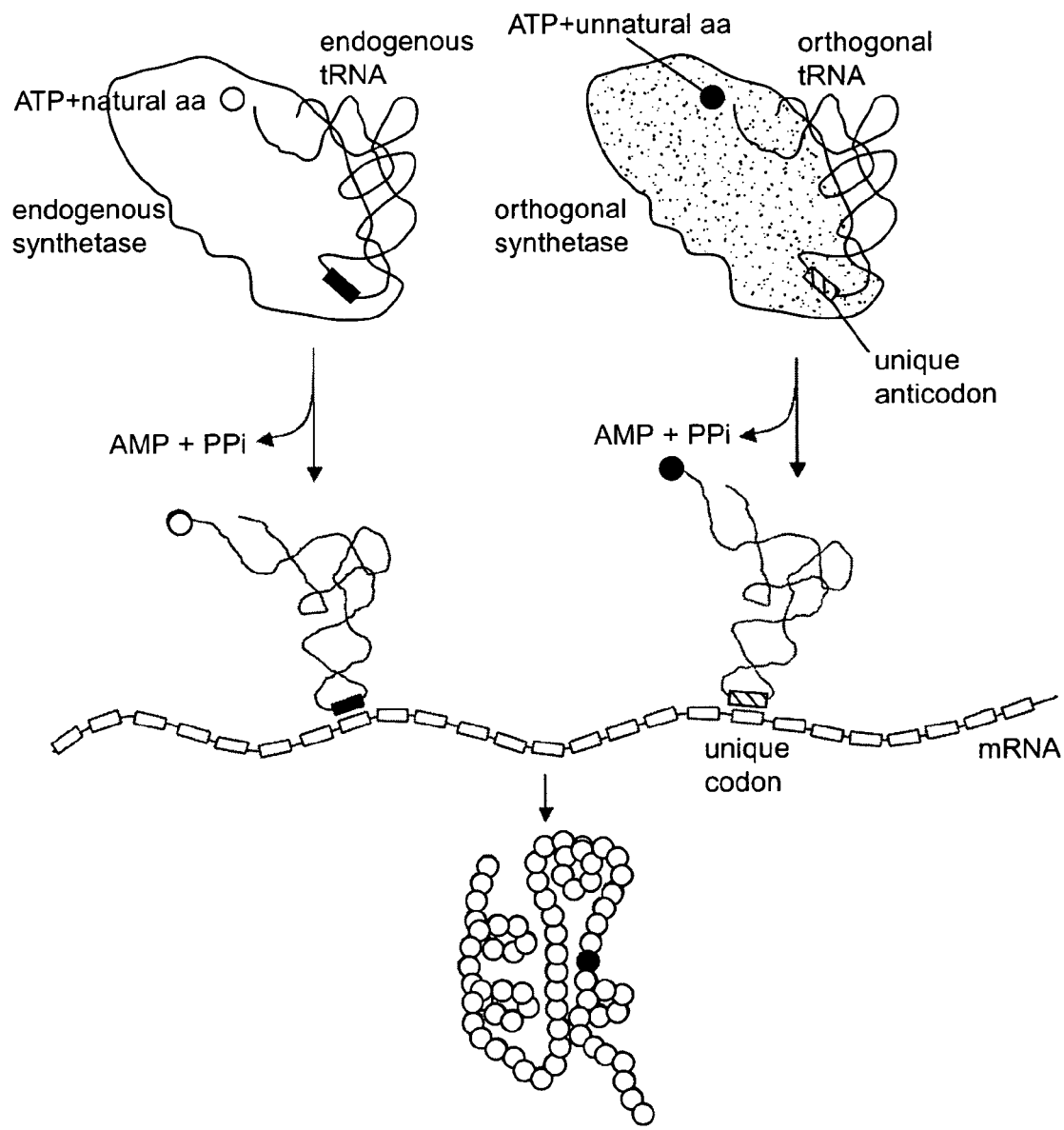
FIG. 1 schematically illustrates site-specific incorporation of unnatural amino acids into proteins in vivo. An orthogonal aminoacyl-tRNA synthetase aminoacylates an orthogonal tRNA with an unnatural amino acid. The acylated orthogonal tRNA inserts the unnatural amino acid at the position specified by a selector codon, e.g., a unique codon, which is introduced into the gene encoding a protein of interest.

Proteins are at the crossroads of virtually every biological process, from photosynthesis and vision to signal transduction and the immune response. These complex functions result from a polyamide based polymer consisting of twenty relatively simple building blocks arranged in a defined primary sequence.

The present invention includes methods and composition for use in the site-specific incorporation of unnatural amino acids directly into proteins in vivo. Importantly, the unnatural amino acid is added to the genetic repertoire, rather than substituting for one of the common 20 amino acids. The present invention provides methods for generating, methods for identifying and compositions comprising the components used by the biosynthetic machinery to incorporate an unnatural amino acid into a protein. The present invention, e.g., (i) allows the site-selective insertion of one or more unnatural amino acids at any desired position of any protein, (ii) is applicable to both prokaryotic and eukaryotic cells, (iii) enables in vivo studies of mutant proteins in addition to the generation of large quantities of purified mutant proteins, and (iv) is adaptable to incorporate any of a large variety of non-natural amino acids, into proteins in vivo. Thus, in a specific polypeptide sequence a number of different site-selective insertions of unnatural amino acids is possible. Such insertions are optionally all of the same type (e.g., multiple examples of one type of unnatural amino acid inserted at multiple points in a polypeptide) or are optionally of diverse types (e.g., different unnatural amino acid types are inserted at multiple points in a polypeptide).

Definitions

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes acombination of two or more such molecules, and the like.

Unless defined otherwise, all scientific and technical terms are understood to have the same meaning as commonly used in the art to which they pertain. For the purpose of the present invention, the following terms are defined below.

As used herein, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

The term "preferentially aminoacylates" refers to an efficiency, e.g., about 70% efficient, about 75% efficient, about 85% efficient, about 90%, about 95%, about 99% or more efficient, at which an O-RS aminoacylates an O-tRNA with an unnatural amino acid compared to a naturally occurring tRNA or starting material used to generate the O-tRNA. The unnatural amino acid is then incorporated into a growing polypeptide chain with high fidelity, e.g., at greater than about 75% efficiency for a given selector codon, at greater than about 80% efficiency for a given selector codon, at greater than about 90% efficiency for a given selector codon, greater than about 95% efficiency for a given selector codon, or greater than about 99% efficiency for a given selector codon.

The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; codons derived from natural or unnatural base pairs and the like. For a given system, a selector codon can also include one of the natural three base codons, wherein the endogenous system does not use said natural three base codon, e.g., a system that is lacking a tRNA that recognizes the natural three base codon or a system wherein the natural three base codon is a rare codon.

As used herein, the term "orthogonal" refers to a molecule (e.g., an orthogonal tRNA (O-tRNA) and/or an orthogonal aminoacyl tRNA synthetase (O-RS)) that is used with reduced efficiency by a system of interest (e.g., a translational system, e.g., a cell). Orthogonal refers to the inability or reduced efficiency, e.g., less than 20% efficient, less than 10% efficient, less than 5% efficient, or e.g., less than 1% efficient, of an orthogonal tRNA and/or orthogonal RS to function in the translation system of interest. For example, an orthogonal tRNA in a translation system of interest aminoacylates any endogenous RS of a translation system of interest with reduced or even zero efficiency, when compared to aminoacylation of an endogenous tRNA by the endogenous RS. In another example, an orthogonal RS aminoacylates any endogenous tRNA in the translation system of interest with reduced or even zero efficiency, as compared to aminoacylation of the endogenous tRNA by an endogenous RS. "Improvement in orthogonality" refers to enhanced orthogonality compared to a starting material or a naturally occurring tRNA or RS.

The term "complementary" refers to components of an orthogonal pair, O-tRNA and O-RS that can function together, e.g., the O-RS aminoacylates the O-tRNA.

The term "derived from" refers to a component that is isolated from an organism or isolated and modified, or generated, e.g., chemically synthesized, using information of the component from the organism.

The term "translation system" refers to the components necessary to incorporate a naturally occurring amino acid into a growing polypeptide chain (protein). For example, components can include ribosomes, tRNAs, synthetases, mRNA and the like. The components of the present invention can be added to a translation system, in vivo or in vitro.

The term "inactive RS" refers to a synthetase that have been mutated so that it no longer can aminoacylate its cognate tRNA with an amino acid.

The term "selection agent" refers to an agent that when present allows for a selection of certain components from a population, e.g., an antibiotic, wavelength of light, an antibody, a nutrient or the like. The selection agent can be varied, e.g., such as concentration, intensity, etc.

The term "positive selection marker" refers to a marker than when present, e.g., expressed, activated or the like, results in identification of an organism with the positive selection marker from those without the positive selection marker.

The term "negative selection marker" refers to a marker than when present, e.g., expressed, activated or the like, allows identification of an organism that does not possess the desired property (e.g., as compared to an organism which does possess the desired property).

The term "reporter" refers to a component that can be used to select components described in the present invention. For example, a reporter can include a green fluorescent protein, a firefly luciferase protein, or genes such as β-gal/lacZ (β-galactosidase), Adh (alcohol dehydrogenase) or the like.

The term "not efficiently recognized" refers to an efficiency, e.g., less than about 10%, less than about 5%, or less than about 1%, at which a RS from one organism aminoacylates O-tRNA.

The term "eukaryote" refers to organisms belonging to the phylogenetic domain Eucarya such as animals (e.g., mammals, insects, reptiles, birds, etc.), ciliates, plants, fungi (e.g., yeasts, etc.), flagellates, microsporidia, protists, etc. Additionally, the term "prokaryote" refers to non-eukaryotic organisms belonging to the Eubacteria (e.g., *Escherichia coli, Thermus thermophilus*, etc.) and Archaea (e.g., *Methanococcus jannaschii, Methanobacterium thermoautotrophicum, Halobacterium* such as *Haloferax volcanii* and *Halobacterium* species NRC-1, *A. fulgidus, P. furiosus, P. horikoshii, A. pernix*, etc.) phylogenetic domains A "suppressor tRNA" is a tRNA that alters the reading of a messenger RNA (mRNA) in a given translation system. A suppressor tRNA can read through, e.g., a stop codon, a four base codon, or a rare codon.

Discussion

The present invention relates to methods and compositions for new components of biosynthetic translational machinery that allows for the incorporation of unnatural amino acids into proteins in vivo. Specifically, compositions comprising and methods for generating orthogonal tRNAs and orthogonal-RS and orthogonal tRNAs/orthogonal-RS pairs are provided. These components, when introduced into a host cell, can be used in the translation system of the cell to incorporate an unnatural amino acid in vivo into a polypeptide (protein) of interest. For example, this can provide site-specific unnatural amino acid mutagenesis; or, optionally, random unnatural amino acid mutagenesis. The orthogonal tRNA delivers the unnatural amino acid in response to a selector codon and the orthogonal synthetase preferentially aminoacylates an orthogonal tRNA with the unnatural amino acid. The O-RS does not efficiently aminoacylate the orthogonal tRNA with any of the common twenty amino acids. Methods for making and identifying orthogonal pairs are also provided.

The site-specific incorporation of unnatural amino acids into proteins in vivo is schematically illustrated in FIG. 1. A selector codon, e.g., a unique codon, is introduced into a gene of interest. The gene is transcribed into mRNA and conventional translation begins on the ribosome. Endogenous synthetases aminoacylate endogenous tRNAs with natural amino acids (aa) in the presence of ATP. An orthogonal tRNA is enzymatically aminoacylated by an orthogonal synthetase with an unnatural amino acid in the presence of ATP. When the ribosome encounters a selector codon, an orthogonal tRNA, which is modified to contain a selector anticodon, e.g., a unique anticodon, it is able to decode the mutation as an unnatural amino acid, and translation proceeds to the full-length product with the incorporated unnatural amino acid.

Orthogonal Aminoacyl tRNA Synthetase, O-RS

In order to specifically incorporate an unnatural amino acid in vivo, the substrate specificity of the synthetase is altered so that only the desired unnatural amino acid, but not any common 20 amino acids are charged to the tRNA. If the orthogonal synthetase is promiscuous, it will result in mutant proteins with a mixture of natural and unnatural amino acids at the target position. For instance, in an attempt to site-specifically, incorporate p-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.*, 7:419 (1998). Because yeast PheRS does not have high substrate specificity for p-F-Phe, the mutagenesis site was translated with 64-75% p-F-Phe and the remainder as Phe and Lys even in the excess of p-F-Phe added to the growth media. In addition, at the Phe codon positions, 7% p-F-Phe was found, indicating that the endogenous *Escherichia coli* PheRS incorporates p-F-Phe in addition to Phe. Because of its translational infidelity, this approach is not generally applicable to other unnatural amino acids. Modification of the substrate specificity of a synthetase was expected to be difficult due to the high intrinsic fidelity of the natural synthetases and the fact that unnatural amino acids are not required for any cellular function. The present invention solves this problem and provides composition of, and methods for, generating synthetases that have modified substrate specificity, such as an unnatural amino acid. Using the components of the present invention, the efficiency of incorporation of an unnatural amino acid into is, e.g., greater than about 75%, greater than about 85%, greater than about 95%, greater than about 99% or more.

Compositions of the present invention include an orthogonal aminoacyl-tRNA synthetase (O-RS), where the O-RS preferentially aminoacylates an orthogonal tRNA (O-tRNA) with an unnatural amino acid, optionally, in vivo. In one embodiment, the O-RS comprises a nucleic acid comprising a polynucleotide sequence selected from the group consisting of: SEQ ID NO: 4-34 (see, Table 5) and a complementary polynucleotide sequence thereof. In another embodiment, the O-RS has improved or enhanced enzymatic properties, e.g., the $K_m$ is lower, the $k_{cat}$ is higher, the value of $k_{cat}/K_m$ is higher or the like, for the unnatural amino acid compared to a naturally occurring amino acid, e.g., one of the 20 known amino acids. Sequences of exemplary O-tRNA and O-RS molecules can be found in Example 10.

Methods for producing an O-RS are based on generating a pool of mutant synthetases from the framework of a wild-type synthetase, and then selecting for mutated RSs based on their specificity for an unnatural amino acid relative to the common twenty. To isolate such a synthetase, the selection methods of the present invention are: (i) sensitive, as the activity of desired synthetases from the initial rounds can be low and the population small; (ii) "tunable", since it is desirable to vary the selection stringency at different selection rounds; and, (iii) general, so that it can be used for different unnatural amino acids.

Figure 2A:
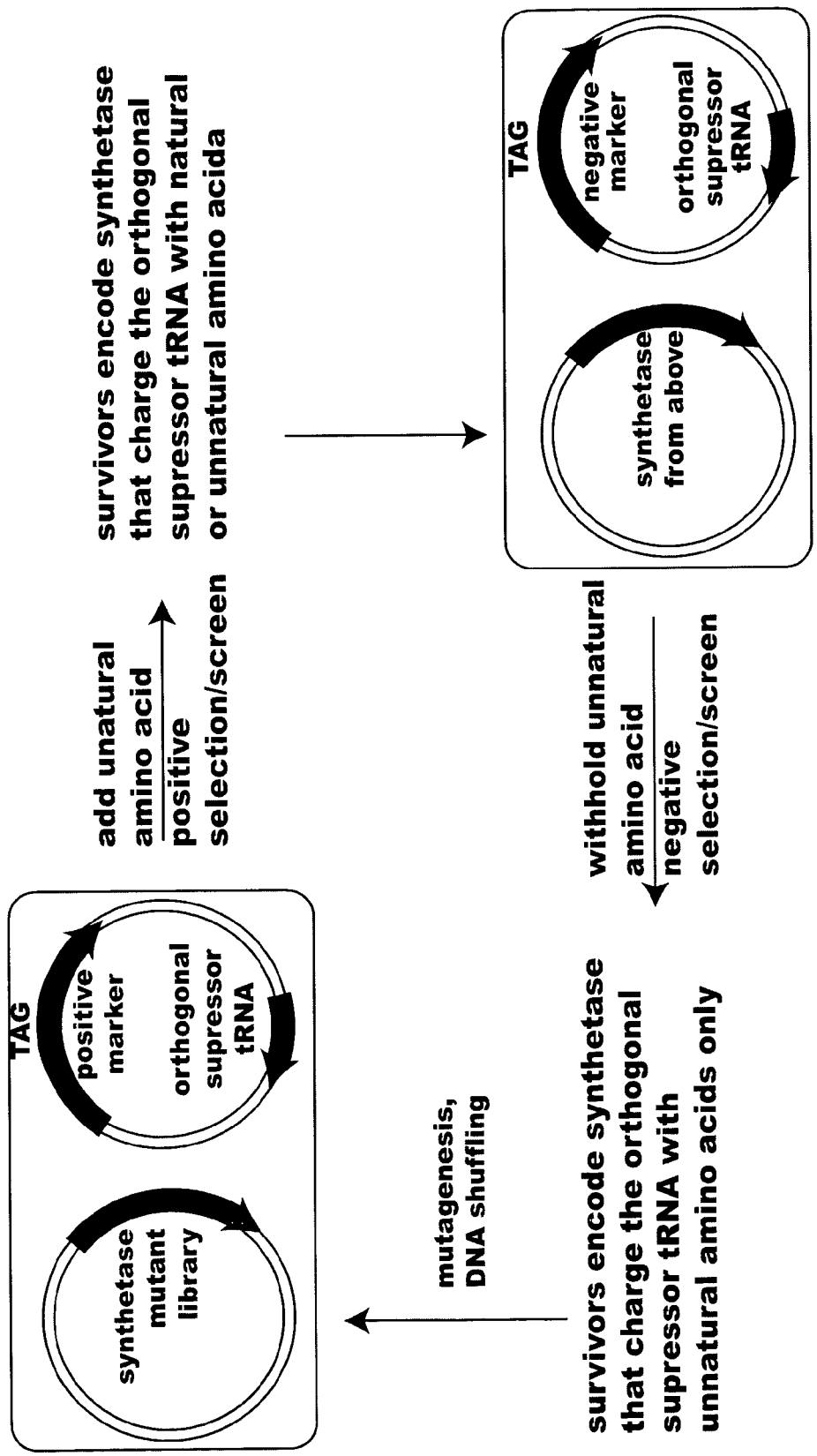
FIG. 2, Panel A and Panel B, schematically illustrates examples of selection methods for active synthetases that aminoacylate with unnatural amino acids. Panel A illustrates the general selection/screen for aminoacyl-tRNA synthetases with unnatural amino acids specificities. In the positive selection, active synthetases with either natural or unnatural amino acid specificities are identified; in the negative selection, synthetases with natural amino acid specificities are eliminated. Only synthetases charging the orthogonal tRNA with the unnatural amino acid can survive both selections/screens. Panel B schematically illustrates one embodiment of the selection/screen for synthetases preferentially aminoacylating an O-tRNA with an unnatural amino acid. For example, expression vectors containing an orthogonal suppressor tRNA and a member of a library of mutated RS with a positive selection marker, e.g., β-lactamase, with a selector codon, e.g., an amber codon, are introduced into an organism and grown in the presence a selector agent, e.g., ampicillin. The expression of the positive selection marker allows the cell to survive in the selection agent. Survivors encode synthetases capable of charging any natural or unnatural amino acid (aa) onto the O-tRNA. The active synthetases are transformed into a second strain in the expression vector, and an expression vector with a negative selection marker, e.g., a toxic gene, such as barnase, that when expressed kills the cells, with one or more selector codons, e.g., TAG. The cells are grown without the unnatural amino acid. If the synthetase provided aminoacylates the O-tRNA with a natural amino acid, the negative selection marker is expressed and the cell dies. If the synthetase preferentially aminoacylates the O-tRNA, no negative selection marker is expressed, because there is no unnatural amino acid and the cell lives. This provides at least one orthogonal synthetase that preferentially aminoacylates the O-tRNA with the desired unnatural codon.
Figure 2B:
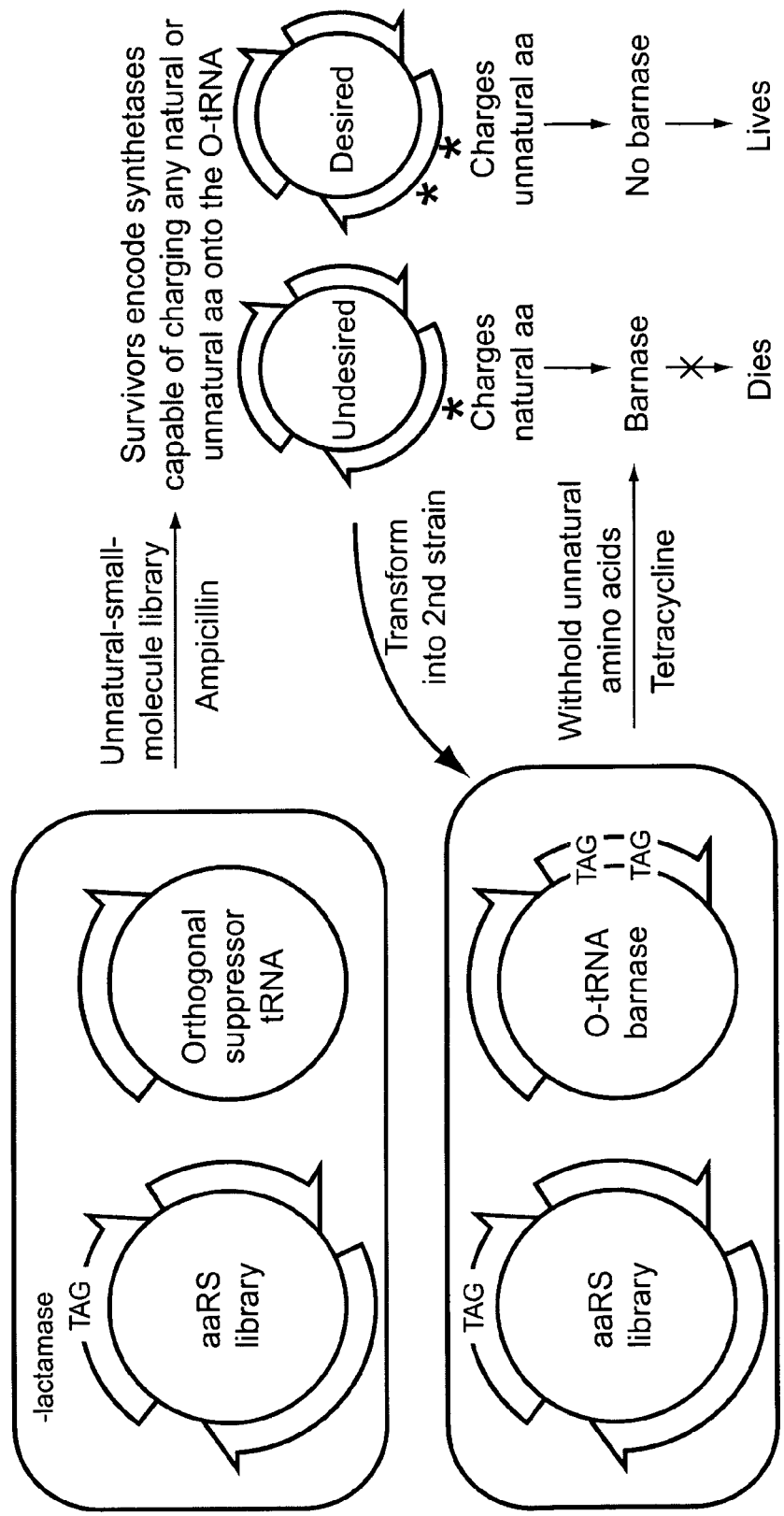

The present invention provides methods to generate an orthogonal aminoacyl tRNA synthetase by mutating the synthetase, e.g., at the active site in the synthetase, at the editing mechanism site in the synthetase, at different sites by combining different domains of synthetases, or the like, and applying a selection process. FIG. 2, Panel A schematically illustrates an in vivo selection/screen strategy, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods. Of course, in other embodiments, the invention optionall cn utilize different orders of steps to identify (e.g., O-RS, O-tRNA, pairs, etc.), e.t., negative selection/screening followed by positive selection/screening or vice verse or any such combinations thereof.

For example, see, FIG. 2, Panel B. In FIG. 2, Panel B, a selector codon, e.g., an amber codon, is placed in a reporter gene, e.g., an antibiotic resistance gene, such as β-lactamase, with a selector codon, e.g., TAG. This is placed in an expression vector with members of the mutated RS library. This expression vector along with an expression vector with an orthogonal tRNA, e.g., a orthogonal suppressor tRNA, are introduced into a cell, which is grown in the presence of a selection agent, e.g., antibiotic media, such as ampicillin. Only if the synthetase is capable of aminoacylating (charging) the suppressor tRNA with some amino acid does the selector codon get decoded allowing survival of the cell on antibiotic media.

Applying this selection in the presence of the unnatural amino acid, the synthetase genes that encode synthetases that have some ability to aminoacylate are selected away from those synthetases that have no activity. The resulting pool of synthetases can be charging any of the 20 naturally occurring amino acids or the unnatural amino acid. To further select for those synthetases that exclusively charge the unnatural amino acid, a second selection, e.g., a negative selection, is applied. In this case, an expression vector containing a negative selection marker and an O-tRNA is used, along with an expression vector containing a member of the mutated RS library. This negative selection marker contains at least one selector codon, e.g., TAG. These expression vectors are introduced into another cell and grown without unnatural amino acids and, optionally, a selection agent, e.g., tetracycline. In the negative selection, those synthetases with specificities for natural amino acids charge the orthogonal tRNA, resulting in suppression of a selector codon in the negative marker and cell death. Since no unnatural amino acid is added, synthetases with specificities for the unnatural amino acid survive. For example, a selector codon, e.g., a stop codon, is introduced into the reporter gene, e.g., a gene that encodes a toxic protein, such as barnase. If the synthetase is able to charge the suppressor tRNA in the absence of unnatural amino acid, the cell will be killed by translating the toxic gene product. Survivors passing both selection/screens encode synthetases specifically charging the orthogonal tRNA with an unnatural amino acid.

In one embodiment, methods for producing at least one recombinant orthogonal aminoacyl-tRNA synthetase (O-RS) include: (a) generating a library of mutant RSs derived from at least one aminoacyl-tRNA synthetase (RS) from a first organism; (b) selecting the library of mutant RSs for members that aminoacylate an orthogonal tRNA (O-tRNA) in the presence of an unnatural amino acid and a natural amino acid, thereby providing a pool of active mutant RSs; and, (c) negatively selecting the pool for active mutant RSs that preferentially aminoacylate the O-tRNA in the absence of the unnatural amino acid, thereby providing the at least one recombinant O-RS; wherein the at least one recombinant O-RS preferentially aminoacylates the O-tRNA with the unnatural amino acid. Optionally, more mutations are introduced by mutagenesis, e.g., random mutagenesis, recombination or the like, into the selected synthetase genes to generate a second-generation synthetase library, which is used for further rounds of selection until a mutant synthetase with desired activity is evolved. Recombinant O-RSs produced by the methods are included in the present invention. As explained below, orthogonal tRNA/synthetase pairs or the invention are also optionally generated by importing such from a first organism into a second organism.

In one embodiment, the RS is an inactive RS. The inactive RS can be generated by mutating an active RS. For example, the inactive RS can be generated by mutating at least about 5 amino acids to different amino acids, e.g., alanine.

Figure 3:
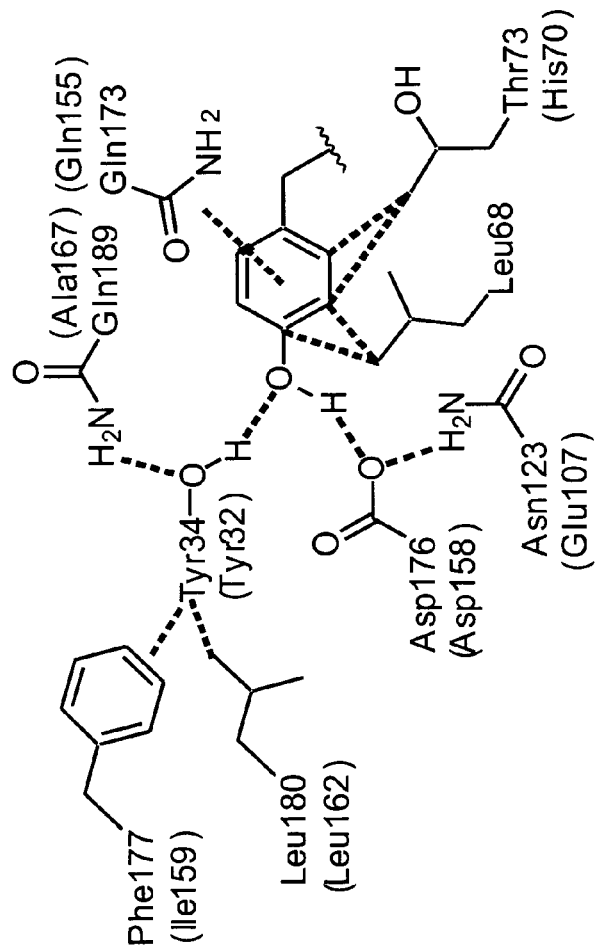
FIG. 3 illustrates site-specific mutations to generate directed libraries for tyrosine analogues. Four regions of the protein are illustrated: residue 32, residues 67-70 (SEQ ID NO:80 for wild type, library 1, and library 2), residue 107, and residues 155-167 (SEQ ID NO:81 for wild type, SEQ ID NO:82 for library 1, SEQ ID NO:83 for library 2, and SEQ ID NO:84 for library 3).
Figure 7:
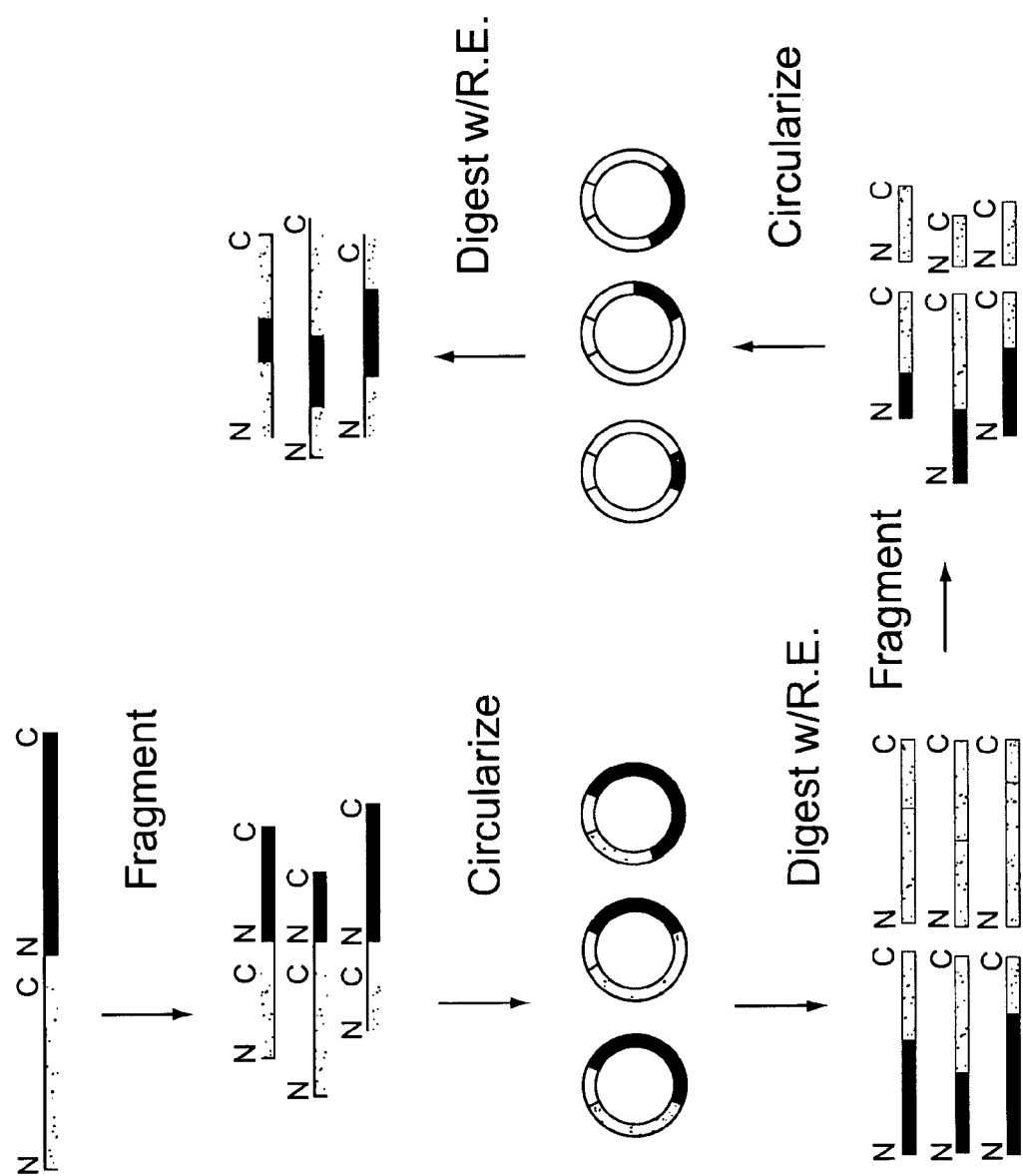
FIG. 7 schematically illustrates the generation of a library of chimeric synthetases, e.g., *Methanococcus jannaschii/Escherichia coli* synthetases.

The library of mutant RSs can be generated using various mutagenesis techniques known in the art. For example, the mutant RSs can be generated by site-specific mutations, random point mutations, in vitro homologous recombinant, chimeric constructs or the like. In one embodiment, mutations are introduced into the editing site of the synthetase to hamper the editing mechanism and/or to alter substrate specificity. See, e.g., FIG. 3 and FIG. 4. FIG. 3 illustrates site-specific mutations to generate directed libraries for tyrosine analogues. FIG. 4 illustrates a consensus sequence for pentafluorophenylalanine selection to generate directed libraries for these analogues. Libraries of mutant RSs also include chimeric synthetase libraries, e.g., libraries of chimeric *Methanococcus jannaschii/Escherichia coli* synthetases. The domain of one synthetase can be added or exchanged with a domain from another synthetase. FIG. 5 schematically illustrates the transplantation of one domain, e.g., the CP1 domain, from one organism, e.g., *Escherichia coli*, to the synthetase of other organism, e.g., *Methanococcus jannaschii* TyrRS. CP1 can be transplanted from *Escherichia coli* TyrRS to *H. sapiens* TyrRS. See, e.g., Wakasugi, K., et al., *EMBO J.* 17:297-305 (1998). FIG. 6 schematically illustrates the construction of chimeric *Methanococcus jannaschii/Escherichia coli* synthetases and FIG. 7 schematically illustrates the generation of a library of chimeric synthetases, e.g., *Methanococcus jannaschii/Escherichia coli* synthetases. See, e.g., Sieber, et al., *Nature Biotechnology*, 19:456-460 (2001). The chimeric library is screened for a variety of properties, e.g., for members that are expressed and in frame, for members that lack activity with a desired synthetase, and/or for members that show activity with a desired synthetase.

In one embodiment, the positive selection step includes: introducing a positive selection marker, e.g., an antibiotic resistance gene, or the like, and the library of mutant RSs into a plurality of cells, wherein the positive selection marker comprises at least one selector codon, e.g., an amber codon; growing the plurality of cells in the presence of a selection agent; selecting cells that survive in the presence of the selection agent by suppressing the at least one selector codon in the positive selection marker, thereby providing a subset of positively selected cells that contains the pool of active mutant RSs. Optionally, the selection agent concentration can be varied.

In one embodiment, negative selection includes: introducing a negative selection marker with the pool of active mutant RSs from the positive selection into a plurality of cells of a second organism, wherein the negative selection marker is an antibiotic resistance gene, e.g., a chloramphenicol acetyltransferase (CAT) gene, comprising at least one selector codon; and, selecting cells that survive in a 1st media supplemented with the unnatural amino acid and a selection agent, but fail to survive in a 2nd media not supplemented with the unnatural amino acid and the selection agent, thereby providing surviving cells with the at least one recombinant O-RS. Optionally, the concentration of the selection agent is varied.

The $1^{st}$ and $2^{nd}$ media described above can include, e.g., a direct replica plate method. For example, after passing the positive selection, cells are grown in the presence of either ampicillin or chloramphenicol and the absence of the unnatural amino acid. Those cells that do not survive are isolated from a replica plate supplemented with the unnatural amino acid. No transformation into a second negative selection strain is needed, and the phenotype is known. Compared to other potential selection markers, a positive selection based on antibiotic resistance offers the ability to tune selection stringency by varying the concentration of the antibiotic, and to compare the suppression efficiency by monitoring the highest antibiotic concentration cells can survive. In addition, the growth process is also an enrichment procedure. This can lead to a quick accumulation of the desired phenotype.

In another embodiment, negatively selecting the pool for active mutant RSs includes: isolating the pool of active mutant RSs from the positive selection step (b); introducing a negative selection marker, wherein the negative selection marker is a toxic marker gene, e.g., a ribonuclease barnase gene, comprising at least one selector codon, and the pool of active mutant RSs into a plurality of cells of a second organism; and selecting cells that survive in a 1st media not supplemented with the unnatural amino acid, but fail to survive in a 2nd media supplemented with the unnatural amino acid, thereby providing surviving cells with the at least one recombinant O-RS, wherein the at least one recombinant O-RS is specific for the unnatural amino acid. Optionally, the negative selection marker comprises two or more selector codons.

In one aspect, positive selection is based on suppression of a selector codon in a positive selection marker, e.g., a chloramphenicol acetyltransferase (CAT) gene comprising a selector codon, e.g., an amber stop codon, in the CAT gene, so that chloramphenicol can be applied as the positive selection pressure. In addition, the CAT gene can be used as both a positive marker and negative marker as describe herein in the presence and absence of unnatural amino acid. Optionally, the CAT gene comprising a selector codon is used for the positive selection and a negative selection marker, e.g., a toxic marker, such as a barnase gene comprising at least one or more selector codons, is used for the negative selection.

In another aspect, positive selection is based on suppression of a selector codon at nonessential position in the β-lactamase gene, rendering cells ampicillin resistant; and a negative selection using the ribonuclease barnase as the negative marker is used. In contrast to β-lactamase, which is secreted into the periplasm, CAT localizes in the cytoplasm; moreover, ampicillin is bacteriocidal, while chloramphenicol is bacteriostatic.

The recombinant O-RS can be further mutated and selected. In one embodiment, the methods for producing at least one recombinant orthogonal aminoacyl-tRNA synthetase (O-RS) can further comprise: (d) isolating the at least one recombinant O-RS; (e) generating a second set of mutated O-RS derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, e.g., at least about two times. In one aspect, the second set of mutated O-RS can be generated by mutagenesis, e.g., random mutagenesis, site-specific mutagenesis, recombination or a combination thereof.

The stringency of the selection steps, e.g., the positive selection step (b), the negative selection step (c) or both the positive and negative selection steps (b) and (c), in the above described-methods, optionally include varying the selection stringency. For example, because barnase is an extremely toxic protein, the stringency of the negative selection can be controlled by introducing different numbers of selector codons into the barnase gene. In one aspect of the present invention, the stringency is varied because the desired activity can be low during early rounds. Thus, less stringent selection criteria are applied in early rounds and more stringent criteria are applied in later rounds of selection.

Other types of selections can be used in the present invention for, e.g., O-RS, O-tRNA, and O-tRNA/O-RS pair. For example, the positive selection step (b), the negative selection step (c) or both the positive and negative selection steps (b) and (c) can include using a reporter, wherein the reporter is detected by fluorescence-activated cell sorting (FACS). For example, a positive selection can be done first with a positive selection marker, e.g., chloramphenicol acetyltransferase (CAT) gene, where the CAT gene comprises a selector codon, e.g., an amber stop codon, in the CAT gene, which followed by a negative selection screen, that is based on the inability to suppress a selector codon(s), e.g., two or more, at positions within a negative marker, e.g., T7 RNA polymerase gene. In one embodiment, the positive selection marker and the negative selection marker can be found on the same vector, e.g., plasmid. Expression of the negative marker drives expression of the reporter, e.g., green fluorescent protein (GFP). The stringency of the selection and screen can be varied, e.g., the intensity of the light need to fluorescence the reporter can be varied. In another embodiment, a positive selection can be done with a reporter as a positive selection marker, which is screened by FACs, followed by a negative selection screen, that is based on the inability to suppress a selector codon(s), e.g., two or more, at positions within a negative marker, e.g., barnase gene.

Optionally, the reporter is displayed on a cell surface, e.g., on a phage display or the like. Cell-surface display, e.g., the OmpA-based cell-surface display system, relies on the expression of a particular epitope, e.g., a poliovirus C3 peptide fused to an outer membrane porin OmpA, on the surface of the *Escherichia coli* cell. The epitope is displayed on the cell surface only when a selector codon in the protein message is suppressed during translation. The displayed peptide then contains the amino acid recognized by one of the mutant aminoacyl-tRNA synthetases in the library, and the cell containing the corresponding synthetase gene can be isolated with antibodies raised against peptides containing specific unnatural amino acids. The OmpA-based cell-surface display system was developed and optimized by Georgiou et al. as an alternative to phage display. See, Francisco, J. A., Campbell, R., Iverson, B. L. & Georgoiu, G. Production and fluorescence-activated cell sorting of *Escherichia coli* expressing a functional antibody fragment on the external surface. *Proc. Natl. Acad. Sci. USA* 90:10444-8 (1993).

Other embodiments of the present invention include carrying one or more of the selection steps in vitro. The selected component, e.g., synthetase and/or tRNA, can then be introduced into a cell for use in in vivo incorporation of an unnatural amino acid.

Orthogonal tRNA

Compositions of an orthogonal tRNA (O-tRNA) are also a feature of the invention, e.g., where the O-tRNA recognizes a selector codon and the O-tRNA is preferentially aminoacylated with an unnatural amino acid by an orthogonal aminoacyl-tRNA synthetase. In one embodiment, the O-tRNA comprises a nucleic acid comprising a polynucleotide sequence selected from the group consisting of: SEQ ID NO: 4-34 (see, Table 5) and a complementary polynucleotide sequence thereof.

Figure 8:
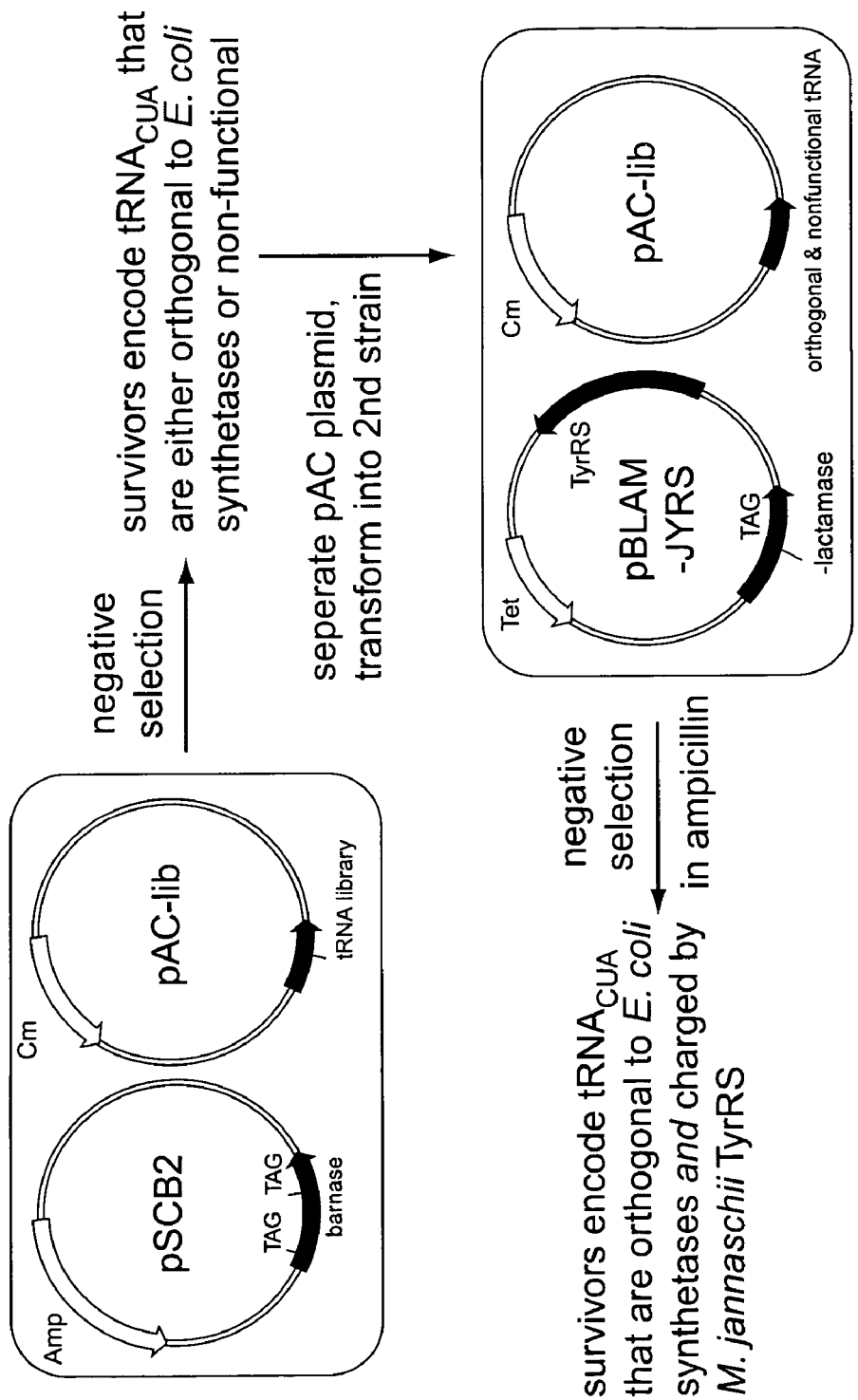
FIG. 8 schematically illustrates an example for selection of suppressor tRNAs that are poor substrates for an endogenous synthetases, e.g., an *Escherichia coli* synthetase, and that are charged efficiently by a cognate synthetase of interest. Expression vectors that contain a member of a mutated tRNA library and another vector with a negative selection marker, e.g., a toxic gene, such as barnase, with one or more selector codons are introduced into a cell of an organism. Survivors of the negative selection encode mutated tRNAs that are either orthogonal to the organism or non-functional. The vectors from the survivors are isolated and transformed into other cells along with a positive selection marker, e.g., β-lactamase gene, with a selector codon. The cells are grown in the presence of a selection agent, e.g., ampicillin, and an RS from an organism from the same source, e.g., *Methanococcus jannaschii*, as the tRNA. Survivors of this selection encode mutant tRNA that are orthogonal to the cell's synthetases, e.g., *Escherichia coli*'s synthetases, and aminoacylated by RS from the same source as the tRNA.

Methods for producing a recombinant orthogonal tRNA (O-tRNA) are provided herein. For example, to improve the orthogonality of a tRNA while preserving its affinity toward a desired RS, the methods include a combination of negative and positive selections with a mutant suppressor tRNA library in the absence and presence of the cognate synthetase, respectively. See, FIG. 8. In the negative selection, a selector codon(s) is introduced in a marker gene, e.g., a toxic gene, such as barnase, at a nonessential position. When a member of the mutated tRNA library, e.g., derived from *Methanococcus jannaschii*, is aminoacylated by endogenous host, e.g., *Escherichia coli* synthetases (i.e., it is not orthogonal to the host, e.g., *Escherichia coli* synthetases), the selector codon, e.g., an amber codon, is suppressed and the toxic gene product produced leads to cell death. Cells harboring orthogonal tRNAs or non-functional tRNAs survive. Survivors are then subjected to a positive selection in which a selector codon, e.g., an amber codon, is placed in a positive marker gene, e.g., a drug resistance gene, such as a lactamase gene. These cells also contain an expression vector with a cognate RS. These cells are grown in the presence of a selection agent, e.g., ampicillin. tRNAs are then selected for their ability to be aminoacylated by the coexpressed cognate synthetase and to insert an amino acid in response to this selector codon. Cells harboring non-functional tRNAs, or tRNAs that cannot be recognized by the synthetase of interest are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation survive both selections.

Methods of producing a recombinant O-tRNA include: (a) generating a library of mutant tRNAs derived from at least one tRNA, e.g., a suppressor tRNA, from a first organism; (b) negatively selecting the library for mutant tRNAs that are aminoacylated by an aminoacyl-tRNA synthetase (RS) from a second organism in the absence of a RS from the first organism, thereby providing a pool of mutant tRNAs; and, (c) selecting the pool of mutant tRNAs for members that are aminoacylated by an introduced orthogonal RS(O-RS), thereby providing at least one recombinant O-tRNA; wherein the at least one recombinant O-tRNA recognizes a selector codon and is not efficiency recognized by the RS from the second organism and is preferentially aminoacylated by the O-RS. In one embodiment, the recombinant O-tRNA possesses an improvement of orthogonality.

Figure 9A:
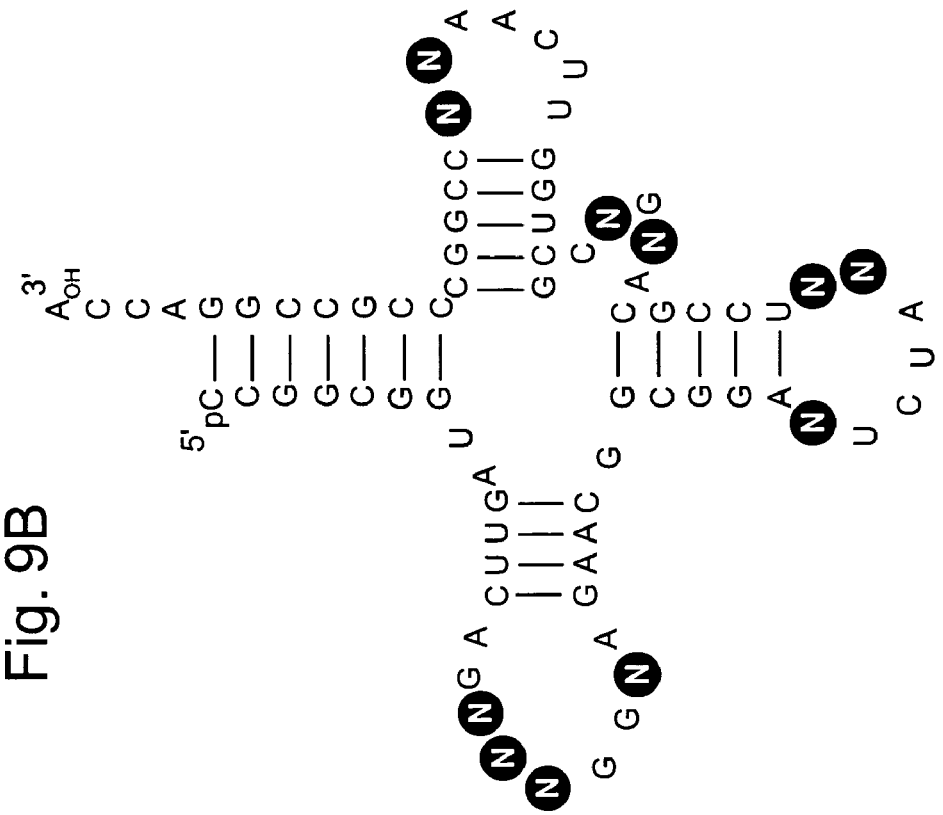
FIG. 9, Panel A and B, schematically illustrates a mutated anticodon-loop tRNA library, Panel A (SEQ ID NO:90), and a mutated all-loop library, Panel B (SEQ ID NO:91), from *Methanococcus jannaschii* tRNA$_{TyrCUA}$. Randomly mutated nucleotides (N) are shaded in black.
Figure 9B:
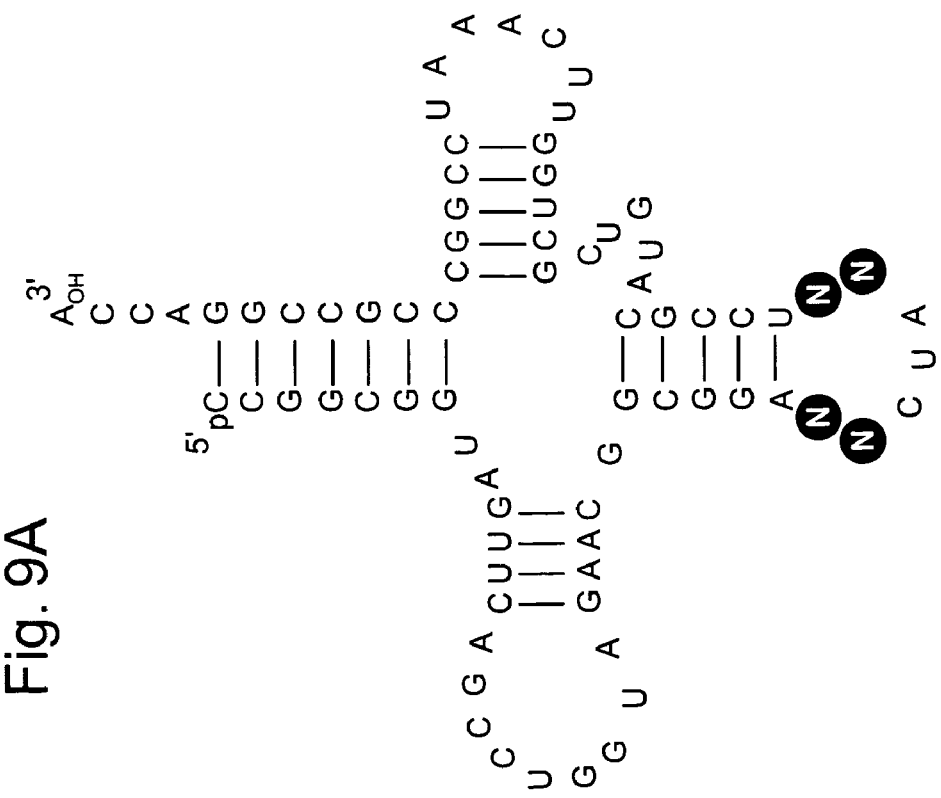

Libraries of mutated tRNA are constructed. See, for example, FIG. 9. Mutations can be introduced at a specific position(s), e.g., at a nonconservative position(s), or at a conservative position, at a randomized position(s), or a combination of both in a desired loop of a tRNA, e.g., an anticodon loop, (D arm, V loop, TψC arm) or a combination of loops or all loops. Chimeric libraries of tRNA are also included in the present invention. It should be noted that libraries of tRNA synthetases from various organism (e.g., microorganisms such as eubacteria or archaebacteria) such as libraries comprising natural diversity (such as libraries that comprise natural diversity (see, e.g., U.S. Pat. No. 6,238,884 to Short et al. and references therein, U.S. Pat. No. 5,756,316 to Schallenberger et al; U.S. Pat. No. 5,783,431 to Petersen et al; U.S. Pat. No. 5,824,485 to Thompson et al; and U.S. Pat. No. 5,958,672 to Short et al), are optionally constructed and screened for orthogonal pairs.

In one embodiment, negatively selecting the library for mutant tRNAs that are aminoacylated by an aminoacyl-tRNA synthetase (step (b) above) includes: introducing a toxic marker gene, wherein the toxic marker gene comprises at least one of the selector codons and the library of mutant tRNAs into a plurality of cells from the second organism; and, selecting surviving cells, wherein the surviving cells contain the pool of mutant tRNAs comprising at least one orthogonal tRNA or nonfunctional tRNA. For example, the toxic marker gene is optionally a ribonuclease barnase gene, wherein the ribonuclease barnase gene comprises at least one amber codon. Optionally, the ribonuclease barnase gene can include two or more amber codons. The surviving cells can be selected, e.g., by using a comparison ratio cell density assay.

In one embodiment, selecting the pool of mutant tRNAs for members that are aminoacylated by an introduced orthogonal RS(O-RS) can include: introducing a positive selection marker gene, wherein the positive selection marker gene comprises a drug resistance gene, e.g., a β-lactamase gene, comprising at least one of the selector codons, e.g., a β-lactamase gene comprising at least one amber stop codon, the O-RS, and the pool of mutant tRNAs into a plurality of cells from the second organism; and, selecting surviving cells grown in the presence of a selection agent, e.g., an antibiotic, thereby providing a pool of cells possessing the at least one recombinant tRNA, wherein the recombinant tRNA is aminoacylated by the O-RS and inserts an amino acid into a translation product encoded by the positive marker gene, in response to the at least one selector codons. In another embodiment, the concentration of the selection agent is varied. Recombinant O-tRNAs produced by the methods are included in the present invention.

As described above for generating O-RS, the stringency of the selection steps can be varied. In addition, other selection/screening procedures, which are described herein, such as FACs, cell and phage display can also be used.

Selector Codons

Selector codons of the present invention expand the genetic codon framework of protein biosynthetic machinery. For example, a selector codon includes, e.g., a unique three base codon, a nonsense codon, such as a stop codon, e.g., an amber codon, or an opal codon, an unnatural codon, a four (or more) base codon or the like. A number of selector codons can be introduced into a desired gene, e.g., one or more, two or more, more than three, etc. Additionally, it will be appreciated that multiple different (or similar or identical) unnatural amino acids can thus be incorporated precisely into amino acids (i.e., thruough use of the multiple selector codons).

The 64 genetic codons code for 20 amino acids and 3 stop codons. Because only one stop codon is needed for translational termination, the other two can in principle be used to encode nonproteinogenic amino acids. The amber stop codon, UAG, has been successfully used in in vitro biosynthetic system and in *Xenopus* oocytes to direct the incorporation of unnatural amino acids. Among the 3 stop codons, UAG is the least used stop codon in *Escherichia coli*. Some *Escherichia coli* strains contain natural suppressor tRNAs, which recognize UAG and insert a natural amino acid in response to UAG. In addition, these amber suppressor tRNAs have been widely used in conventional protein mutagenesis. Different species preferentially use different codons for their natural amino acids, such preferentiallity is optionally utilized in designing/choosing the selector codons herein.

Although discussed with reference to unnatural amino acids herein, it will be appreciated that a similar strategy can be used incorporate a natural amino acid in response to a particular selector codon. That is, a synthetase can be modified to load a natural amino acid onto an orthogonal tRNA that recognizes a selector codon in a manner similar to the loading of an unnatural amino acid as described throughout.

In one embodiment, the methods involve the use of a selector codon that is a stop codon for the incorporation of unnatural amino acids in vivo. For example, an O-tRNA is generated that recognizes the stop codon, e.g., UAG, and is aminoacylated by an O-RS with a desired unnatural amino acid. This O-tRNA is not recognized by the naturally occurring aminoacyl-tRNA synthetases. Conventional site-directed mutagenesis can be used to introduce the stop codon, e.g., TAG, at the site of interest in the protein gene. See, e.g., Sayers, J. R., Schmidt, W. Eckstein, F. 5', 3' Exonuclease in phosphorothioate-based oligonucleotide-directed mutagenesis. *Nucleic Acids Res*, 791-802 (1988). When the O-RS, O-tRNA and the mutant gene are combined in vivo, the unnatural amino acid is incorporated in response to the UAG codon to give a protein containing the unnatural amino acid at the specified position.

The incorporation of unnatural amino acids in vivo can be done without significant perturbation of the host, e.g., *Escherichia coli*. For example, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. Additionally, suppression efficiency and unnatural amino acid uptake by carrying out random mutagenesis on an organism or on a portion of an organism's genome and performing proper selection using, e.g., one of the reporter systems described herein.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., C. H. Ma, W. Kudlicki, O. W. Odom, G. Kramer and B. Hardesty, *Biochemistry*, 32:7939 (1993). In this case, the synthetic tRNA competes with the naturally occurring tRNA$^{Arg}$, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., A. K. Kowal and J. S. Oliver, *Nucl. Acid. Res.*, 25:4685 (1997). Components of the present invention can be generated to use these rare codons in vivo.

Selector codons also comprise four or more base codons, such as, four, five six or more. Examples of four base codons include, e.g., AGGA, CUAG, UAGA, CCCU and the like. Examples of five base codons include, e.g., AGGAC, CCCCU, CCCUC, CUAGA, CUACU, UAGGC and the like. For example, in the presence of mutated O-tRNAs, e.g., a special frameshift suppressor tRNAs, with anticodon loops, e.g., with at least 8-10 nt anticodon loops, the four or more base codon is read as single amino acid. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using the four or more base codon. See also, J. Christopher Anderson et al., Exploring the Limits of Codon and Anticodon Size, *Chemistry and Biology*, Vol. 9, 237-244 (2002); Thomas J. Magliery, Expanding the Genetic Code: Selection of Efficient Suppressors of Four-base Codons and Identification of "Shifty" Four-base Codons with a Library Approach in *Escherichia coli, J. Mol. Biol.* 307: 755-769 (2001).

Methods of the present invention include using extended codons based on frameshift suppression. Four or more base codons can insert, e.g., one or multiple unnatural amino acids into the same protein. For example, four-base codons have been used to incorporate unnatural amino acids into proteins using in vitro biosynthetic methods. See, e.g., C. H. Ma, W. Kudlicki, O. W. Odom, G. Kramer and B. Hardesty, *Biochemistry*, 1993, 32, 7939 (1993); and, T. Hohsaka, D. Kajihara, Y. Ashizuka, H. Murakami and M. Sisido, *J. Am. Chem. Soc.*, 121:34 (1999). CGGG and AGGU were used to simultaneously incorporate 2-naphthylalanine and an NBD derivative of lysine into streptavidin in vitro with two chemically acylated frameshift suppressor tRNAs. See, e.g., T. Hohsaka, Y. Ashizuka, H. Sasaki, H. Murakami and M. Sisido, *J. Am. Chem. Soc.*, 121:12194 (1999). In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with ai efficiency of 13 to 26% with little decoding in the 0 or −1 frame. See, B. Moore, B. C. Persson, C. C. Nelson, R. F. Gesteland and J. F. Atkins, *J. Mol. Biol.*, 298:195 (2000). In one embodiment, extended codons based on rare codons or nonsense codons can be used in present invention, which can reduce missense readthrough and frameshift suppression at unwanted sites.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Alternatively, or in combination with others methods described above to incorporate an unnatural amino acid in a polypeptide, a trans-translation system can be used. This system involves a molecule called tmRNA present in *Escherichia coli*. This RNA molecule is structurally related to an alanyl tRNA and is aminoacylated by the alanyl synthetase. The difference between tmRNA and tRNA is that the anticodon loop is replaced with a special large sequence. This sequence allows the ribosome to resume translation on sequences that have stalled using an open reading frame encoded within the tmRNA as template. In the present invention, an orthogonal tmRNA can be generated that is preferentially aminoacylated with an orthogonal synthetase and loaded with an unnatural amino acid. By transcribing a gene by the system, the ribosome stalls at a specific site; the unnatural amino acid is introduced at that site, and translation resumes using the sequence encoded within the orthogonal tmRNA.

Selector codons also optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., An unnatural base pair for incorporating amino acid analogues into protein, *Nature Biotechnology,* 20:177-182 (2002). Other publications are listed below.

Figure 10:
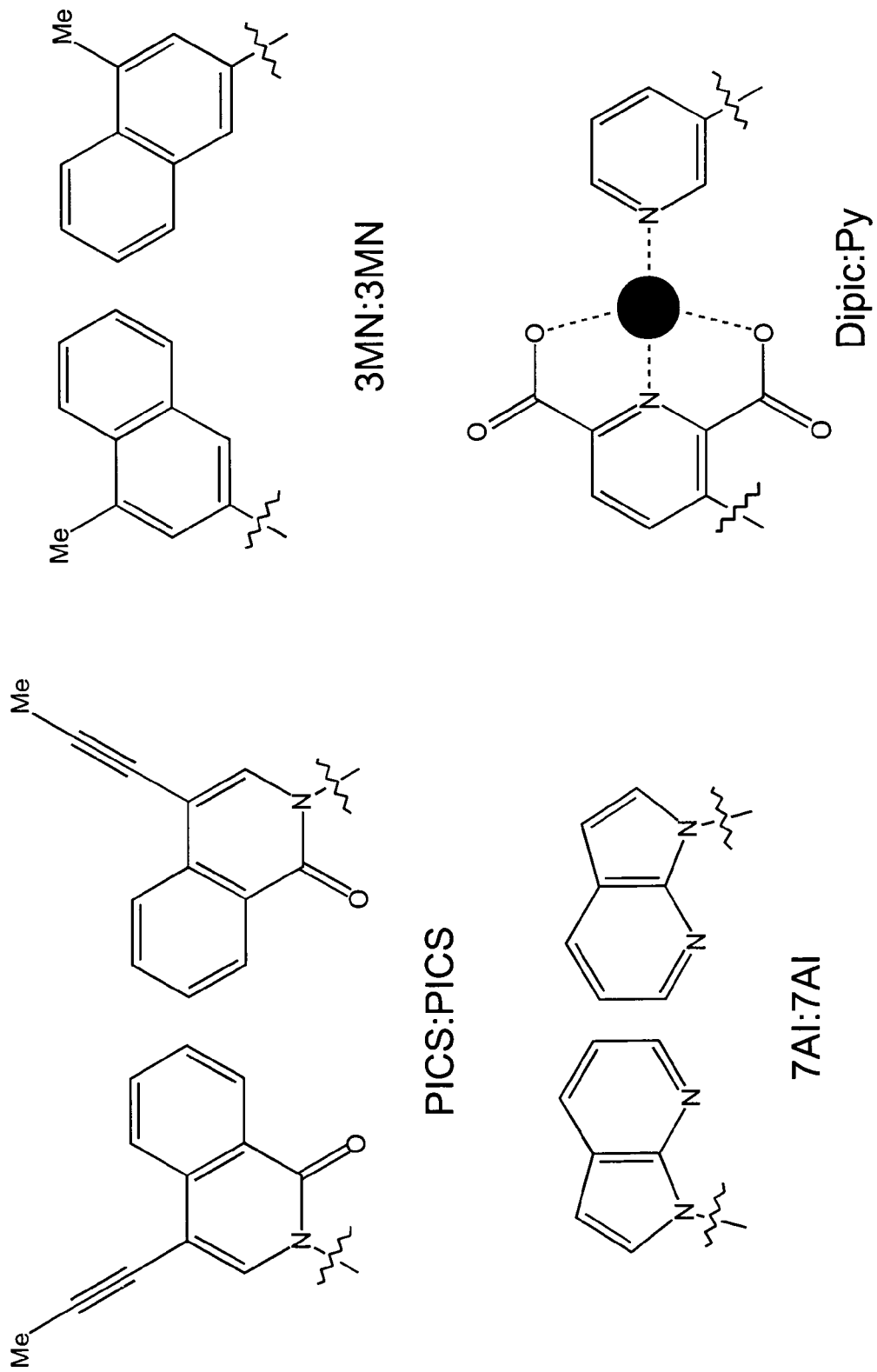
FIG. 10 schematically illustrates examples of structures of unnatural base pairs which pair by forces other than hydrogen bonding (PICS:PICS, 3MN:3MN, 7AI:7AI, Dipic:Py).

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., C. Switzer, S. E. Moroney and S. A. Benner, *J. Am. Chem. Soc.,* 111:8322 (1989); and, J. A. Piccirilli, T. Krauch, S. E. Moroney and S. A. Benner, *Nature,* 1990, 343:33 (1990); and E. T. Kool, *Curr. Opin. Chem. Biol.,* 4:602 (2000). These bases in general mispair to some degree with natural bases and cannot be enzymatically replicated. Kool and co-workers demonstrated that hydrophobic packing interactions between bases can replace hydrogen bonding to drive the formation of base pair. See, E. T. Kool, *Curr. Opin. Chem. Biol.,* 4:602 (2000); and, K. M. Guckian and E. T. Kool, *Angew. Chem. Int. Ed. Engl.,* 36, 2825 (1998). In an effort to develop an unnatural base pair satisfying all the above requirements, Schultz, Romesberg and co-workers have systematically synthesized and studied a series of unnatural hydrophobic bases. The PICS:PICS self-pair, which is shown in FIG. 10, is found to be more stable than natural base pairs, and can be efficiently incorporated into DNA by the Klenow fragment of *Escherichia coli* DNA polymerase I (KF). See, e.g., D. L. McMinn, A. K. Ogawa, Y. Q. Wu, J. Q. Liu, P. G. Schultz and F. E. Romesberg, *J. Am. Chem. Soc.,* 121:11586 (1999); and, A. K. Ogawa, Y. Q. Wu, D. L. McMinn, J. Q. Lu, P. G. Schultz and F. E. Romesberg, *J. Am. Chem. Soc.,* 122:3274 (2000). A 3MN:3MN self-pair can be synthesized by KF with efficiency and selectivity sufficient for biological function. See, e.g., A. K. Ogawa, Y. Q. Wu, M. Berger, P. G. Schultz and F. E. Romesberg, *J. Am. Chem. Soc.,* 122:8803 (2000). However, both bases act as a chain terminator for further replication. A mutant DNA polymerase has been recently evolved that can be used to replicate the PICS self pair. In addition, a 7AI self pair can be replicated using a combination of KF and pol β polymerase. See, e.g., E. J. L. Tae, Y. Q. Wu, G. Xia, P. G. Schultz and F. E. Romesberg, *J. Am. Chem. Soc.,* 123:7439 (2001). A novel metallobase pair, Dipic:Py, has also been developed, which forms a stable pair upon binding Cu(II). See, E. Meggers, P. L. Holland, W. B. Tolman, F. E. Romesberg and P. G. Schultz, *J. Am. Chem. Soc.,* 122:10714 (2000). Because extended codons and unnatural codons are intrinsically orthogonal to natural codons, the methods of the present invention can take advantage of this property to generate orthogonal tRNAs for them.

Orthogonal tRNA and Orthogonal Aminoacyl-tRNA Synthetase Pairs

An orthogonal pair is composed of an O-tRNA, e.g., a suppressor tRNA, a frameshift tRNA, or the like, and an O-RS. The O-tRNA is not acylated by endogenous synthetases and is capable of decoding a selector codon, as described above. The O-RS recognizes the O-tRNA, e.g., with an extended anticodon loop, and preferentially aminoacylates the O-tRNA with an unnatural amino acid. Methods for generating orthogonal pairs along with compositions of orthogonal pairs are included in the present invention. The development of multiple orthogonal tRNA/synthetase pairs can allow the simultaneous incorporation of multiple unnatural amino acids using different codons into the same polypeptide/protein.

In the present invention, methods and related compositions relate to the generation of orthogonal pairs (O-tRNA/O-RS) that can incorporate an unnatural amino acid into a protein in vivo. For example, compositions of O-tRNAs of the present invention can comprise an orthogonal aminoacyl-tRNA synthetase (O-RS). In one embodiment, the O-tRNA and the O-RS can be complementary, e.g., an orthogonal O-tRNA/O-RS pair. Examples of pairs include a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. In one embodiment, an orthogonal pair of the present invention comprises the desired properties of the orthogonal tRNA-aminoacyl-tRNA synthetase pair and is other than a mutRNAGln-mutGlnRS derived from *Escherichia coli,* a mutRNAAsp-mutAspRS derived from yeast or a mutRNAPheCUA-mutphenlalanineRS from yeast, where these pairs do not possess the properties of the pairs of the present invention.

The O-tRNA and the O-RS can be derived by mutation of a naturally occurring tRNA and/or RS from a variety of organisms, which are described under sources and hosts. In one embodiment, the O-tRNA and O-RS are derived from at least one organism. In another embodiment, the O-tRNA is derived by mutation of a naturally occurring or mutated naturally occurring tRNA from a first organism and the O-RS is derived by mutation of a naturally occurring or mutated naturally occurring RS from a second organism.

Methods for generating specific O-tRNA/O-RS pairs are also provided in the present invention. These methods solve the problems discussed below for the other strategies that were attempted to generate orthogonal tRNA/RS pairs. Specifically, methods of the present invention include: (a) generating a library of mutant tRNAs derived from at least one tRNA from a first organism; (b) negatively selecting the library for mutant tRNAs that are aminoacylated by an aminoacyl-tRNA synthetase (RS) from a second organism in the absence of a RS from the first organism, thereby providing a pool of mutant tRNAs; (c) selecting the pool of mutant tRNAs for members that are aminoacylated by an introduced orthogonal RS(O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes: (d) generating a library of mutant RSs derived from at least one aminoacyl-tRNA synthetase (RS) from a third organism; (e) selecting the library of mutant RSs for members that preferentially aminoacylate the at least one recombinant O-tRNA in the presence of an unnatural amino acid and a natural amino acid, thereby providing a pool of active mutant RSs; and, (f) negatively selecting the pool for active mutant RSs that preferentially aminoacylate the at least one recombinant O-tRNA in the absence of the unnatural amino acid, thereby providing the at least one specific O-tRNA/O-RS pair, where the at least one specific O-tRNA/O-RS pair comprises at least one recombinant O-RS that is specific for the unnatural amino acid and the at least one recombinant O-tRNA. Pairs produced by the methods of the present invention are also included.

Previously, generation of an orthogonal tRNA/synthetase pair from an existing *Escherichia coli* tRNA/synthetase pair was attempted. The method involves eliminating the tRNA's affinity toward its cognate synthetase by mutating nucleotides at the tRNA-synthetase interface while preserving its orthogonality to other synthetases and its ability to function in translation. Using the cognate wild-type synthetase as the starting template, a mutant synthetase is then evolved that uniquely recognizes the engineered orthogonal tRNA. Based on an analysis of the X-ray crystal structure of *Escherichia coli* glutaminyl-tRNA synthetase (GlnRS) complexed with tRNAGln2, three sites ("knobs") in tRNAGln2 were identified which make specific contacts with GlnRS. See, e.g., D. R. Liu, T. J. Magliery and P. G. Schultz, *Chem. Biol.*, 4:685 (1997); and, D. R. Liu, T. J. Magliery, M. Pastmak and P. G. Schultz, *Proc. Natl. Acad. Sci. USA,* 94:10092 (1997). These sites were mutated in the tRNA, and mutant suppressor tRNAs containing all possible combinations of knobs 1, 2, and 3 were generated and tested individually by in vitro aminoacylation with GlnRS and in vitro suppression of amber mutants of chorismate mutase. A mutant tRNA (O-tRNA) bearing all three-knob mutations was shown to be orthogonal to all endogenous *Escherichia coli* synthetases and competent in translation. Next, multiple rounds of DNA shuffling together with oligonucleotide-directed mutagenesis were used to generate libraries of mutant GlnRS's. These mutant enzymes were selected for their ability to acylate the O-tRNA in vivo using *Escherichia coli* strain BT235. Only if a mutant GlnRS charges the O-tRNA with glutamine can the genomic amber codon in lacZ be suppressed, enabling BT235 cells to grow on lactose minimal media. Several mutant synthetases surviving each round of selection were purified and assayed in vitro. The ratio of wild-type (wt) tRNAGln acylation to O-tRNA acylation by mutant synthetase decreased significantly upon multiple rounds of selection. However, no mutant *Escherichia coli* GlnRS's have been evolved that charge the O-tRNA more efficiently than wild-type *Escherichia coli* tRNAGln2. The best mutant evolved after seven rounds of DNA shuffling and selection acylates the O-tRNA at only one-ninth the rate of wt tRNAGln. However, these experiments failed to produce a synthetase candidate with the desired properties, e.g., a synthetase that does not acylate any wt tRNA, since misacylation of a wt tRNA with an unnatural amino acid could result in a lethal phenotype. In addition, the mutations within the tRNA interact in complicated, non-additive ways with respect to both aminoacylation and translation. See, D. R. Liu, T. J. Magliery and P. G. Schultz, *Chem. Biol.*, 14:685 (1997). Thus, alternative methods are typically used to provide a functional pair with the desired properties.

A second strategy for generating an orthogonal tRNA/synthetase pair involves importing a tRNA/synthetase pair from another organism into *Escherichia coli*. The properties of the heterologous synthetase candidate include, e.g., that it does not charge any *Escherichia coli* tRNA, and the properties of the heterologous tRNA candidate include, e.g., that it is not acylated by any *Escherichia coli* synthetase. In addition, the suppressor tRNA derived from the heterologous tRNA is orthogonal to all *Escherichia coli* synthetases. Schimmel et al. reported that *Escherichia coli* GlnRS (EcGlnRS) does not acylate *Saccharomyces cerevisiae* tRNAGln (EcGlnRS lacks an N-terminal RNA-binding domain possessed by *Saccharomyces cerevisiae* GlnRS (ScGlnRS)). See, E. F. Whelihan and P. Schimmel, *EMBO J.,* 16:2968 (1997). The *Saccharomyces cerevisiae* amber suppressor tRNAGln (SctRNAGlnCUA) was then analyzed to determine whether it is also not a substrate for EcGlnRS. In vitro aminoacylation assays showed this to be the case; and in vitro suppression studies show that the SctRNAGlnCUA is competent in translation. See, e.g., D. R. Lu and P. G. Schultz, *Proc. Natl. Acad. Sci. USA,* 96:4780 (1999). It was further shown that ScGlnRS does not acylate any *Escherichia coli* tRNA, only the SctRNAGlnCUA in vitro. The degree to which ScGlnRS is able to aminoacylate the SctRNAGlnCUA in *Escherichia coli* was also evaluated using an in vivo complementation assay. An amber nonsense mutation was introduced at a permissive site in the β-lactamase gene. Suppression of the mutation by an amber suppressor tRNA should produce full-length β-lactamase and confer ampicillin resistance to the cell. When only SctRNAGlnCUA is expressed, cells exhibit an $IC_{50}$ of 20 μg/mL ampicillin, indicating virtually no acylation by endogenous *Escherichia coli* synthetases; when SctRNAGlnCUA is coexpressed with ScGlnRS, cells acquire an $IC_{50}$ of about 500 μg/mL ampicillin, demonstrating that ScGlnRS acylates SctRNAGlnCUA efficiently in *Escherichia coli*. See, D. R. Liu and P. G. Schultz, *Proc. Natl. Acad. Sci. USA,* 96:4780 (1999). The *Saccharomyces cerevisiae* tRNAGlnCUA/GlnRS is orthogonal to *Escherichia coli*.

This strategy was later applied to a $tRNA^{Asp}$/AspRS system. *Saccharomyces cerevisiae* tRNAAsp is known to be orthogonal to *Escherichia coli* synthetases. See, e.g., B. P. Doctor and J. A. Mudd, *J. Biol. Chem.*, 238:3677 (1963); and, Y. Kwok and J. T. Wong, *Can. J. Biochem.,* 58:213 (1980). It was demonstrated that an amber suppressor tRNA derived from it (SctRNAAspCUA) is also orthogonal in *Escherichia coli* using the in vivo β-lactamase assay described above. However, the anticodon of $tRNA^{Asp}$ is a critical recognition element of AspRS, see, e.g., R. Giege, C. Florentz, D. Kern, J. Gangloff, G. Eriani and D. Moras, *Biochimie,* 78:605 (1996), and mutation of the anticodon to CUA results in a loss of affinity of the suppressor for AspRS. An *Escherichia coli* AspRS E93K mutant has been shown to recognize *Escherichia coli* amber suppressor tRNAAspCUA about an order of magnitude better than wt AspRS. See, e.g., F. Martin, 'Thesis', Universite Louis Pasteur, Strasbourg, France, 1995. It was speculated that introduction of the related mutation in *Saccharomyces cerevisiae* AspRS (E188K) might restore its affinity for SctRNAAspCUA. It was determined that the *Saccharomyces cerevisiae* AspRS(E188K) mutant does not acylate *Escherichia coli* tRNAs, but charges SctRNAAspCUA with moderate efficiency as shown by in vitro aminoacylation experiments. See, e.g., M. Pastrnak, T. J. Magliery and P. G. Schultz, *Helv. Chim. Acta,* 83:2277 (2000). Although the SctRNAAspCUA/ScAspRS(E188K) can serve as another orthogonal pair in *Escherichia coli*, it possesses weak activity.

A similar approach involves the use of a heterologous synthetase as the orthogonal synthetase but a mutant initiator tRNA of the same organism or a related organism as the orthogonal tRNA. RajBhandary and coworkers found that an amber mutant of human initiator tRNAfMet is acylated by *Escherichia coli* GlnRS and acts as an amber suppressor in yeast cells only when EcGlnRS is coexpressed. See, A. K. Kowal, C. Kohrer and U. L. RajBhandary, *Proc. Natl. Acad. Sci. USA.* 98:2268 (2001). This pair thus represents an orthogonal pair for use in yeast. Also, an *Escherichia coli* initiator tRNAfMet amber mutant was found that is inactive toward any *Escherichia coli* synthetases. A mutant yeast TyrRS was selected that charges this mutant tRNA, resulting in an orthogonal pair in *Escherichia coli*. See, A. K. Kowal, et al, (2001), supra.

The prokaryotic and eukaryotic tRNATyr/TyrRS pairs have significant differences: the identity elements of prokaryotic tRNATyr include a long variable arm in contrast to the short arm of eukaryotic tRNATyr. In addition, eukaryotic tRNATyr contains a $C_1$:G72 positive recognition element whereas prokaryotic tRNATyr has no such consensus base pair. In vitro studies have also shown that tRNATyr of *Saccharomyces cerevisiae* and *H. sapiens* cannot be aminoacylated by bacterial synthetases, nor do their TyrRS aminoacylate bacterial tRNA. See, e.g., K. Wakasugi, C. L. Quinn, N. Tao and P. Schimmel, *EMBO J.*, 17:297 (1998); and, T. A. Kleeman, D. Wei, K. L. Simpson and E. A. First. *J. Biol. Chem.*, 272: 14420 (1997). But, in spite of all these promising features for orthogonality, in vivo β-lactamase complementation assays showed that the amber suppressor tRNATyrCUA derived from both *Saccharomyces cerevisiae* and *H. sapiens* are not orthogonal in *Escherichia coli*. See, e.g., L. Wang, T. J. Magliery, D. R. Liu and P. G. Schultz, *J. Am. Chem. Soc.*, 122:5010 (2000). The susceptibility of the suppressor tRNA to acylation by *Escherichia coli* synthetases is due to the change of one single nucleotide in the anticodon (G34 to C34).

Using the methods of the present invention, the pairs and components of pairs desired above are evolved to generate orthogonal tRNA/synthetase pairs that possess desired characteristic, e.g., that can preferentially aminoacylate an O-tRNA with an unnatural amino acid.

Source and Host Organisms

The orthogonal tRNA-RS pair, e.g., derived from at least a first organism or at least two organisms, which can be the same or different, can be used in a variety of organisms, e.g., a second organism. The first and the second organisms of the methods of the present invention can be the same or different. In one embodiment, the first organism is a prokaryotic organism, e.g., *Methanococcus jannaschii*, *Methanobacterium thermoautotrophicum*, *Halobacterium*, *Escherichia coli*, *A. fulgidus*, *Halobacterium*, *P. furiosus*, *P. horikoshii*, *A. pernix*, *T. thermophilus*, or the like. Alternatively, the first organism is a eukaryotic organism, e.g., plants (e.g., complex plants such as monocots, or dicots), algae, protists, fungi (e.g., yeast, etc), animals (e.g., mammals, insects, arthropods, etc.), or the like. In another embodiment, the second organism is a prokaryotic organism, *Methanococcus jannaschii*, *Methanobacterium thermoautotrophicum*, *Halobacterium*; *Escherichia coli*, *A. fulgidus*, *Halobacterium*, *P. furiosus*, *P. horikoshii*, *A. pernix*, *T. thermophilus*, or the like. Alternatively, the second organism can be a eukaryotic organism, e.g., plants, fungi, animals, or the like.

As described above, the individual components of a pair can be derived from the same organism or different organisms. For example, tRNA can be derived from a prokaryotic organism, e.g., an archaebacterium, such as *Methanococcus jannaschii* and *Halobacterium* NRC-1 or a *eubacterium*, such as *Escherichia coli*, while the synthetase can be derived from same or another prokaryotic organism, such as, *Methanococcus jannaschii*, *Archaeoglobus fulgidus*, *Methanobacterium thermoautotrophicum*, *P. furiosus*, *P. horikoshii*, *A. pernix*, *T. thermophilus*, *Halobacterium*, *Escherichia coli* or the like. Eukaryotic sources can also be used, e.g., plants (e.g., complex plants such as monocots, or dicots), algae, protists, fungi (e.g., yeast, etc.), animals (e.g., mammals, insects, arthropods, etc.), or the like.

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from the second organism; and, selecting for surviving cells in the first set that fail to survive in the duplicate cell set, where the first set and the duplicate cell set are grown in the presence of a selection agent, and where the surviving cells comprise the orthogonal tRNA-tRNA synthetase pair for use in the in the in vivo translation system of the second organism. In one embodiment, comparing and selecting includes an in vivo complementation assay. In another embodiment, the concentration of the selection agent is varied.

For example, a tRNA/synthetase pair can be chosen based on where the identity elements, which are recognition sites of the tRNA for the synthetase, are found. For example, a tRNA/synthetase pair is chosen when the identity elements are outside of the anticodon, e.g., the tRNATyr/TyrRS pair from the archaebacterial *Methanococcus jannaschii*. This TyrRS is missing most of the non-conserved domain binding for the anticodon loop of its tRNATyr, but can discriminate tRNA with C1:G72 from that with G1:C72. Furthermore, the *Methanococcus jannaschii* TyrRS(MjTyrRS) aminoacylates *Saccharomyces cerevisiae* but not *Escherichia coli* crude tRNA. See, e.g., B. A. Steer and P. Schimmel, *J. Biol. Chem.*, 274:35601 (1999). Using an in vivo complementation assay with an expression vector containing a reporter gene, e.g., β-lactamase gene, with at least one selector codon, cells expressing the *Methanococcus jannaschii* tRNATyrCUA (Mj tRNATyrCUA) alone survive to an $IC_{50}$ of 55 µg/mL ampicillin; cells coexpressing Mj tRNATyrCUA with its TyrRS survive to an $IC_{50}$ of 1220 ug/mL ampicillin. Although Mj tRNATyrCUA is less orthogonal in *Escherichia coli* than the SctRNAGlnCUA ($IC_{50}$ 20 µg/mL), the MjTyrRS has higher aminoacylation activity toward its cognate amber suppressor tRNA. See, e.g., L. Wang, T. J. Magliery, D. R. Liu and P. G. Schultz, *J. Am. Chem. Soc.*, 122:5010 (2000). As a result, *Methanococcus jannaschii*/TyrRS is identified as an orthogonal pair in *Escherichia coli* and can be selected for use in an in vivo translation system.

Unnatural Amino Acids

A wide variety of unnatural amino acids can be used in the methods of the invention. The unnatural amino acid can be chosen based on desired characteristics of the unnatural amino acid, e.g., function of the unnatural amino acid, such as modifying protein biological properties such as toxicity, biodistribution, or half life, structural properties, spectroscopic properties, chemical and/or photochemical properties, catalytic properties, ability to react with other molecules (either covalently or noncovalently), or the like.

As used herein an "unnatural amino acid" refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

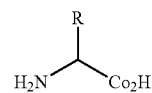

I

An unnatural amino acid is typically any structure having Formula I wherein the R group is any substituent other than one used in the twenty natural amino acids. See, e.g., any biochemistry text such as *Biochemistry* by L. Stryer, 3$^{rd}$ ed. 1988, Freeman and Company, New York, for structures of the twenty natural amino acids. Note that, the unnatural amino acids of the present invention may be naturally occurring compounds other than the twenty alpha-amino acids above. Because the unnatural amino acids of the invention typically differ from the natural amino acids in side chain only, the unnatural amino acids form amide bonds with other amino acids, e.g., natural or unnatural, in the same manner in which they are formed in naturally occurring proteins. However, the unnatural amino acids have side chain groups that distinguish them from the natural amino acids. For example, R in Formula I optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or polyether, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, and amino acids comprising one or more toxic moiety.

In addition to unnatural amino acids that contain novel side chains, unnatural amino acids also optionally comprise modified backbone structures, e.g., as illustrated by the structures of Formula II and III:

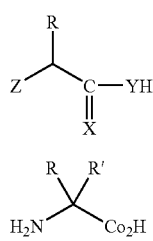

wherein Z typically comprises OH, NH$_2$, SH, NH—R', or S—R'; X and Y, which may be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Figure 29:
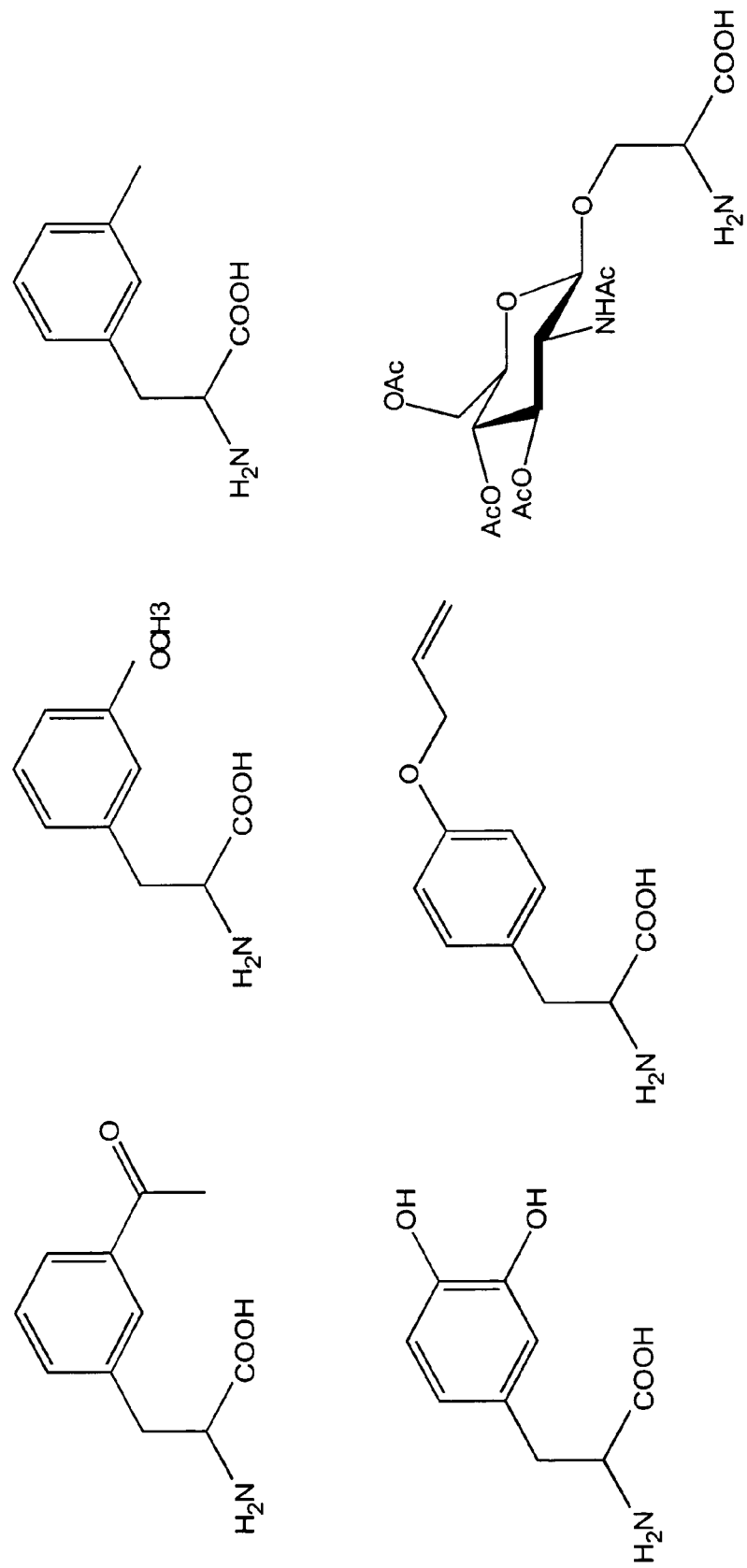
FIG. 29 illustrates exemplary unnatrual amino acids as utilized in the current invention.
Figure 30:
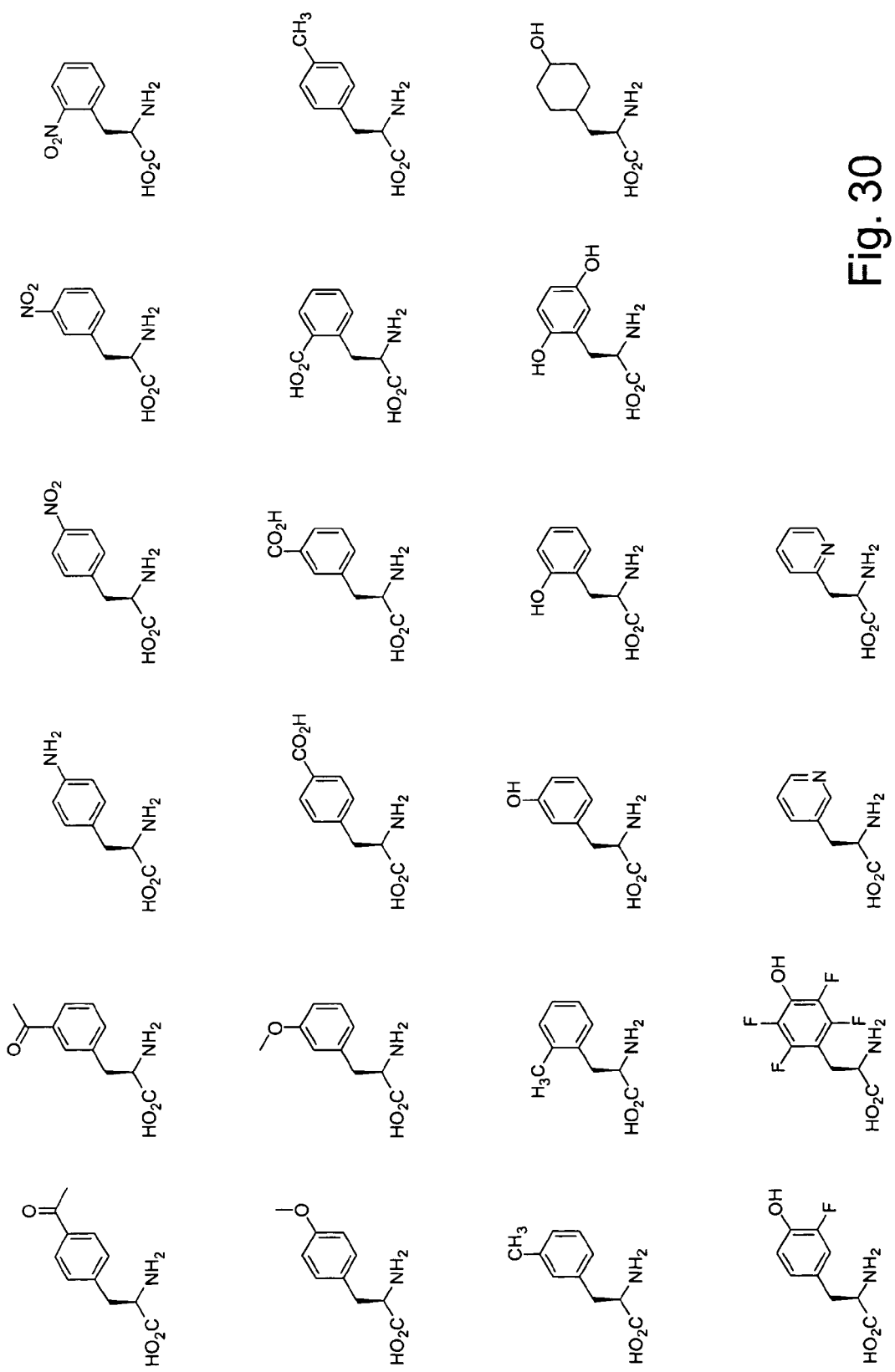
FIG. 30 illustrates exemplary unnatrual amino acids as utilized in the current invention.
Figure 31:
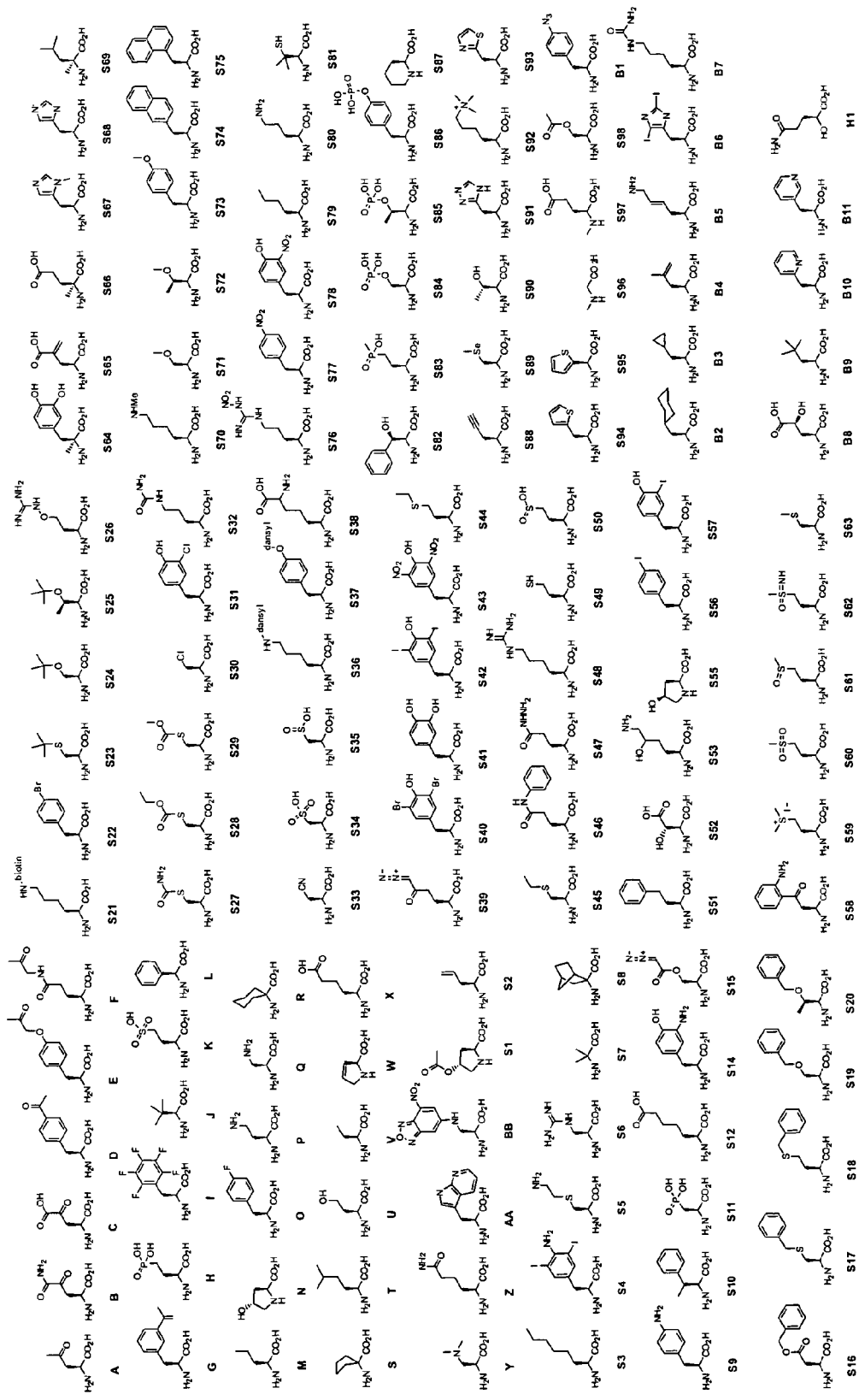
FIG. 31 illustrates exemplary unnatrual amino acids as utilized in the current invention.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like. Specific examples of unnatural amino acids include, but are not limited to, O-methyl-L-tyrosine, an L-3-(2-naphthyl)alanine, a 3-methyl-phenylalanine, an O-4-allyl-L-tyrosine, a 4-propyl-L-tytosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of non-limiting unnatural amino acids are provided in the figures, e.g., FIGS. 29, 30, and 31.

Typically, the unnatural amino acids of the invention are selected or designed to provide additional characteristics unavailable in the twenty natural amino acids. For example, unnatural amino acid are optionally designed or selected to modify the biological properties of a protein, e.g., into which they are incorporated. For example, the following properties are optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Further details regarding unnatural amino acids are described in corresponding application, "In vivo Incorporation of Unnatural Amino Acids", US publication 20030082575, filed Apr. 19, 2002, which is incorporated herein by reference.

Use of Mutant tRNA and O-RS and O-tRNA/O-RS Pairs

The compositions of the present invention and compositions made by the methods of the present invention optionally are in a cell. The O-tRNA/O-RS pairs or individual components of the present invention can then be used in a host system's translation machinery, which results in an unnatural amino acid being incorporated into a protein. The corresponding patent application "In vivo Incorporation of Unnatural Amino Acids", US publication 20030082575 describes this process and is incorporated herein by reference. For example, when an O-tRNA/O-RS pair is introduced into a host, e.g., *Escherichia coli*, the pair leads to the in vivo incorporation of an unnatural amino acid, e.g., a synthetic amino acid, such as O-methyl-L-tyrosine, which can be exogenously added to the growth medium, into a protein, e.g., dihydrofolate reductase or a therapeutic protein such as EPO, in response to a selector codon, e.g., an amber nonsense codon. Optionally, the compositions of the present invention can be in an in vitro translation system, or in an in vivo system(s).

Nucleic Acid and Polypeptide Sequence Variants

As described above and below, the invention provides for nucleic acid polynucleotide sequences and polypeptide amino acid sequences, e.g., O-tRNAs and O-RSs, and, e.g., compositions and methods comprising said sequences. Examples of said sequences, e.g., O-tRNAs and O-RSs are disclosed herein. However, one of skill in the art will appreciate that the invention is not limited to those sequences disclosed herein. One of skill will appreciate that the present invention also provides many related and unrelated sequences with the functions described herein, e.g., encoding an O-tRNA or an O-RS.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences, see, Table 1 below. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 1

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Trytophan (W) | |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to the nucleic acids represented by SEQ ID NO:1-3 or SEQ ID NO:4-34 (see, Table 5) under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at lest ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, infra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, infra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid which comprises a unique subsequence in a nucleic acid selected from the sequences of O-tRNAs and O-RSs disclosed herein, e.g., SEQ ID NO:1-3 or SEQ ID NO:4-34 (see, Table 5). The unique subsequence is unique as compared to a nucleic acid corresponding to any previously known O-tRNA or O-RS nucleic acid sequence, e.g., as found in Genbank. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein, e.g., SEQ ID NO:35-66 (see, Table 5). Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides. Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, preferably 80%, most preferably 90-95% nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the sequences that is at least about 50 residues in length, more preferably over a region of at least about 100 residues, and most preferably the sequences are substantially identical over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Defining Polypeptides by Immunoreactivity

Because the polypeptides of the invention provide a variety of new polypeptide sequences (e.g., comprising unnatural amino acids in the case of proteins synthesized in the translation systems herein, or, e.g., in the case of the novel synthetases herein, novel sequences of standard amino acids), the polypeptides also provide new structural features which can be recognized, e.g., in immunological assays. The generation of antisera which specifically bind the polypeptides of the invention, as well as the polypeptides which are bound by such antisera, are a feature of the invention.

For example, the invention includes synthetase proteins that specifically bind to or that are specifically immunoreactive with an antibody or antisera generated against an immunogen comprising an amino acid sequence selected from one or more SEQ ID NO:35-66 (see, Table 5). To eliminate cross-reactivity with other homologues, the antibody or antisera is subtracted with available synthetases, such as the wild-type *Methanococcus jannaschii* (*M. jannaschii*) tyrosyl synthetase (TyrRS), e.g., the "control" polypeptides. Where the the wild-type *Methanococcus jannaschii* (*M. jannaschii*) tyrosyl synthetase (TyrRS) corresponds to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to one or more of SEQ ID NO:35-66 (see, Table 5) or a substantial subsequence thereof (i.e., at least about 30% of the full length sequence provided). The set of potential polypeptide immunogens derived from SEQ ID NO:35-66 (see, Table 5) are collectively referred to below as "the immunogenic polypeptides." The resulting antisera is optionally selected to have low cross-reactivity against the control synthetase homologues and any such cross-reactivity is removed, e.g., by immunoabsorbtion, with one or more of the control synthetase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional references and discussion of antibodies is also found herein and can be applied here to defining polypeptides by immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control synthetase polypeptides to produce subtracted pooled titered polyclonal antisera.

The subtracted pooled titered polyclonal antisera are tested for cross reactivity against the control homologues in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic synthetase as compared to binding to the control synthetase homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control synthetase homologues under discriminatory binding conditions, and at least about a ½ signal to noise ratio as compared to the immunogenic polypeptide(s), shares substantial structural similarity with the immunogenic polypeptide as compared to known synthetases, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is optionally determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides as compared to the control polypeptides and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

General Techniques

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of orthogonal tRNA, orthogonal synthetases, and pairs thereof.

Various types of mutagenesis are used in the present invention, e.g., to produce novel sythetases or tRNAs. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications and references cited within: Sieber, et al., Nature Biotechnology, 19:456460 (2001); Ling et al., Approaches to DNA mutagenesis: an overview, *Anal Biochem*. 254(2): 157-178 (1997); Dale et al., Oligonucleotide-directed random mutagenesis using the phosphorothioate method, *Methods Mol. Biol.* 57:369-374 (1996); I. A. Lorimer, I. Pastan, *Nucleic Acids Res.* 23, 3067-8 (1995); W. P. C. Stemmer, *Nature* 370, 389-91 (1994); Arnold, Protein engineering for unusual environments, *Current Opinion in Biotechnology* 4:450-455 (1993); Bass et al., Mutant Trp repressors with new DNA-binding specificities, *Science* 242:240-245 (1988); Fritz et al., Oligonucleotide-directed construction of mutations: a gapped duplex DNA procedure without enzymatic reactions in vitro, *Nucl. Acids Res.* 16: 6987-6999 (1988); Kramer et al., Improved enzymatic in vitro reactions in the gapped duplex DNA approach to oligonucleotide-directed construction of mutations, *Nucl. Acids Res.* 16: 7207 (1988); Sakamar and Khorana, Total synthesis and expression of a gene for the α-subunit of bovine rod outer segment guanine nucleotide-binding protein (transducin), *Nucl. Acids Res.* 14: 6361-6372 (1988); Sayers et al., Y-T Exonucleases in phosphorothioate-based oligonucleotide-directed mutagenesis, *Nucl. Acids Res.* 16:791-802 (1988); Sayers et al., Strand specific cleavage of phosphorothioate-containing DNA by reaction with restriction endonucleases in the presence of ethidium bromide, (1988) *Nucl. Acids Res.* 16: 803-814; Carter, Improved oligonucleotide-directed mutagenesis using M13 vectors, *Methods in Enzymol.* 154: 382403 (1987); Kramer & Fritz Oligonucleotide-directed construction of mutations via gapped duplex DNA, *Methods in Enzymol.* 154:350-367 (1987); Kunkel, The efficiency of oligonucleotide directed mutagenesis, in *Nucleic Acids & Molecular Biology* (Eckstein, F. and Lilley, D. M. J. eds., Springer Verlag, Berlin)) (1987); Kunkel et al., Rapid and efficient site-specific mutagenesis without phenotypic selection, *Methods in Enzymol.* 154, 367-382 (1987); Zoller & Smith, Oligonucleotide-directed mutagenesis: a simple method using two oligonucleotide primers and a single-stranded DNA template, *Methods in Enzymol.* 154:329-350 (1987); Carter, Site-directed mutagenesis, *Biochem. J.* 237:1-7 (1986); Eghtedarzadeh & Henikoff, Use of oligonucleotides to generate large deletions, *Nucl. Acids Res.* 14: 5115 (1986); Mandecki, Oligonucleotide-directed double-strand break repair in plasmids of *Escherichia coli*: a method for site-specific mutagenesis, *Proc. Natl. Acad. Sci. USA*, 83:7177-7181 (1986); Nakamaye & Eckstein, Inhibition of restriction endonuclease Nci I cleavage by phosphorothioate groups and its application to oligonucleotide-directed mutagenesis, *Nucl. Acids Res.* 14: 9679-9698 (1986); Wells et al., Importance of hydrogen-bond formation in stabilizing the transition state of subtilisin, *Phil.*

Trans. R. Soc. Lond. A 317: 415423 (1986); Botstein & Shortle, Strategies and applications of in vitro mutagenesis, *Science* 229:1193-1201 (1985); Carter et al., Improved oligonucleotide site-directed mutagenesis using M13 vectors, *Nucl. Acids Res.* 13: 4431-413 (1985); Grundstrom et al., Oligonucleotide-directed mutagenesis by microscale 'shotgun' gene synthesis, *Nucl. Acids Res.* 13: 3305-3316 (1985); Kunkel, Rapid and efficient site-specific mutagenesis without phenotypic selection, *Proc. Natl. Acad. Sci. USA* 82:488492 (1985); Smith, In vitro mutagenesis, *Ann. Rev. Genet.* 19:423462 (1985); Taylor et al., The use of phosphorothioate-modified DNA in restriction enzyme reactions to prepare nicked DNA, *Nucl. Acids Res.* 13: 8749-8764 (1985); Taylor et al., The rapid generation of oligonucleotide-directed mutations at high frequency using phosphorothioate-modified DNA, *Nucl. Acids Res.* 13: 8765-8787 (1985); Wells et al., Cassette mutagenesis: an efficient method for generation of multiple mutations at defined sites, *Gene* 34:315-323 (1985); Kramer et al., The gapped duplex DNA approach to oligonucleotide-directed mutation construction, *Nucl. Acids Res.* 12: 9441-9456 (1984); Kramer et al., Point Mismatch Repair, *Cell* 38:879-887 (1984); Nambiar et al., Total synthesis and cloning of a gene coding for the ribonuclease S protein, *Science* 223: 1299-1301 (1984); Zoller & Smith, Oligonucleotide-directed mutagenesis of DNA fragments cloned into M13 vectors, *Methods in Enzymol.* 100:468-500 (1983); and Zoller & Smith, Oligonucleotide-directed mutagenesis using M13-derived vectors: an efficient and general procedure for the production of point mutations in any DNA fragment, *Nucleic Acids Res.* 10:6487-6500 (1982). Additional details on many of the above methods can be found in *Methods in Enzymology Volume* 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, *Tetrahedron Letts.* 22(20):1859-1862, (1981) e.g., using an automated synthesizer, as described in Needham-VanDevanter et al., *Nucleic Acids Res.*, 12:6159-6168 (1984).

In addition, essentially any nucleic acid can be custom or standard ordered from any of a variety of commercial sources, such as The Midland Certified Reagent Company, The Great American Gene Company, ExpressGen Inc., Operon Technologies Inc. (Alameda, CA) and many others.

The present invention also relates to host cells and organisms for the in vivo incorporation of an unnatural amino acid via orthogonal tRNA/RS pairs. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods.

The engineered host cells can be cultured in conventional nutrient media modified as appropriate for such activities as, for example, screening steps, activating promoters or selecting transformants. These cells can optionally be cultured into transgenic organisms.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, Flex-iPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Ghema et al. (eds.) published by the ATCC. Additional basic procedures for sequencing, cloning and other aspects of molecular biology and underlying theoretical considerations are also found in Watson et al. (1992) *Recombinant DNA Second Edition* Scientific American Books, NY.

EXAMPLES

The following examples are offered to illustrate, but not to limit the claimed invention.

Example 1

Improvement of Orthogonality of a tRNA from *Methanococcus jannaschii*

Because of the complex nature of tRNA-synthetase interactions that are required to achieve a high degree of fidelity in protein translation, the rational design of orthogonal tRNA-synthetase pairs is difficult. This example describes methods that exploit the poor cross recognition of some interspecies tRNA-synthetase pairs, coupled with subsequent in vivo evolution of tRNAs with enhanced orthogonality. See, also, L. Wang and P. G. Schultz, *Chem. Biol.*, 8:883 (2001). Specifically, a library of amber suppressor tRNAs derived from *Methanococcus jannaschii* tRNATyr was generated. tRNATyrCUAs that are substrates for endogenous *Escherichia coli* aminoacyl-tRNA synthetases were deleted from the pool by negative selection based on suppression of amber nonsense mutations in the barnase gene. The remaining tRNATyrCUAs were then selected for their ability to suppress amber nonsense codons in the β-lactamase gene in the presence of the cognate *Methanococcus jannaschii* tyrosyl-tRNA synthetase (TyrRS). Four mutant suppressor tRNAs were selected that are poorer substrates for *Escherichia coli* synthetases than *Methanococcus jannaschii* tRNATyrCUA, but still can be charged efficiently by *Methanococcus jannaschii* TyrRS. The mutant suppressor tRNATyrCUA together with the *Methanococcus jannaschii* TyrRS provide a useful orthogonal tRNA-synthetase pair for the in vivo incorporation of unnatural amino acids into proteins.

The tRNATyr of *Methanococcus jannaschii*, an archaebacterium, has different identity elements from those of *Escherichia coli* tRNATyr. In particular, the *Escherichia coli* tRNATyr has a G1C72 pair in the acceptor stem while the *Methanococcus jannaschii* tRNATyr has a C1G72 pair. An amber suppressor tRNA derived from *Methanococcus jannaschii* tRNATyr was shown not to be efficiently aminoacylated by the *Escherichia coli* synthetases, but functions efficiently in protein translation in *Escherichia coli*. See, e.g., L. Wang, T. J. Magliery, D. R. Liu, P. G. Schultz, A new functional suppressor tRNA/aminoacyl-tRNA synthetase pair for the in vivo incorporation of unnatural amino acids into proteins, *J. Am. Chem. Soc.* 122:5010-5011 (2000). In addition, the *Methanococcus jannaschii* TyrRS, which has only a minimalist anticodon-loop-binding domain, does not aminoacylate *Escherichia coli* tRNAs, but still efficiently aminoacylates its own suppressor tRNATyrCUA. See, e.g., B. A. Steer, P. Schimmel, Major anticodon-binding region missing from an archaebacterial tRNA synthetase, *J. Biol. Chem.* 274 (1999) 35601-35606; and, Wang et al., (2000), supra.

To test the orthogonality of this suppressor tRNA in *Escherichia coli*, an amber codon was introduced at a permissive site (Ala184) in the β-lactamase gene. See, e.g., D. R. Liu, P. G. Schultz, Progress toward the evolution of an organism with an expanded genetic code, *Proc. Natl. Acad. Sci. USA* 96:4780-4785 (1999). Those tRNAs that can be charged by *Escherichia coli* synthetases will suppress the amber codon and allow cells to live in the presence of ampicillin. The *Methanococcus jannaschii* tRNATyrCUA suppresses the amber codon in the β-lactamase gene with an $IC_{50}$ value of 56 µg/ml ampicillin. See Wang et al., (2000), supra. In contrast, the orthogonal tRNAGlnCUA derived from *Saccharomyces cerevisiae* tRNAGln2 has an $IC_{50}$ of 21 µg/ml ampicillin when tested in the same assay. See Liu & Schultz, (1999), supra. The $IC_{50}$ for *Escherichia coli* in the absence of any suppressor tRNA is 10 µg/ml ampicillin. This result shows that the *Methanococcus jannaschii* tRNATyrCUA is a better substrate for *Escherichia coli* synthetases than the tRNAGln-CUA. Consequently, if the *Methanococcus jannaschii* tRNATyrCUA is used in vivo to deliver unnatural amino acids into proteins in *Escherichia coli*, it can also be mischarged with natural amino acids by *Escherichia coli* synthetases, leading to heterogeneous amino acid incorporation.

The improvement of the orthogonality of the *Methanococcus jannaschii* tRNATyrCUA was accomplished by the introduction of 'negative recognition determinants' to prevent recognition by endogenous *Escherichia coli* synthetases. These mutations should not strongly interfere with the tRNA's interaction with its cognate *Methanococcus jannaschii* TyrRS or the ribosome. Since *Methanococcus jannaschii* TyrRS lacks most of the anticodon-binding domain, see, e.g., B. A. Steer, P. Schimmel, Major anticodon-binding region missing from an archaebacterial tRNA synthetase, *J. Biol. Chem.* 274: 35601-35606 (1999), mutations introduced at the anticodon loop of the tRNA are expected to have a minimal effect on TyrRS recognition. An anticodon-loop library with four randomized nucleotides was constructed. See FIG. 9. Given the various combinations and locations of identity elements for various *Escherichia coli* tRNAs, mutations at additional positions can increase the likelihood of finding a mutant tRNA with the desired properties. Thus, a second library containing mutations at nonconserved positions in all of the tRNA loops (all-loop library) was also constructed. See FIG. 9. Conserved nucleotides were not randomized so as to maintain the tertiary interactions that stabilize the 'L'-shaped structure of the tRNA. See, e.g., G. Dirheimer, G. Keith, P. Dumas, E. Westhof, Primary, secondary, and tertiary structures of tRNAs, in: D. Söll, U. L. RajBhandary (eds.), *tRNA Structure, Biosynthesis, and Function*, ASM Press, Washington, D.C., 1995, pp. 93-126; and, R. Giege, M. Sissler, C. Florentz, Universal rules and idiosyncratic features in tRNA identity, *Nucleic Acids Res.* 26:5017-5035 (1998). Stem nucleotides were also not mutated since substitution of one such nucleotide requires a compensatory mutation. The 11 nucleotides (C16, C17, U17a, U20, C32, G37, A38, U45, U47, A59, and U60) were randomized. See, FIG. 9. The theoretical size of this library is about $4.19 \times 10^6$, and a library with a size of about $1.93 \times 10^8$ colony-forming units was constructed to ensure complete coverage of the mutant library.

The methods used an *Escherichia coli* strain, e.g., DH10B, which was obtained from Gibco/BRL. Suppressor tRNA expression plasmids were derived from a plasmid, e.g., pAC123. See, e.g., D. R. Liu, T. J. Magliery, M. Pastrnak, P. G. Schultz, Engineering a tRNA and aminoacyl-tRNA synthetase for the site-specific incorporation of unnatural amino acids into proteins in vivo, *Proc. Natl. Acad. Sci. USA* 94:10091-10097 (1997). Plasmids for negative selections were derived from plasmids, e.g., pBATS, pYsupA38B2 and pYsupA38B3 as described below. See, e.g., K. Gabriel, W. H. McClain, A set of plasmids constitutively producing different RNA levels in *Escherichia coli*, *J. Mol. Biol.* 290 (1999) 385-389; and, Liu & Shultz, (1999), supra.

To select for a member of the *Methanococcus jannaschii* tRNA library with enhanced orthogonality, a combination of negative and positive selections in the absence and presence of the cognate synthetase was used. See FIG. 8. In the negative selection, selector codon(s), e.g., amber nonsense, are introduced in a negative marker gene, e.g., a toxic gene, at e.g., a nonessential position. When a member of the mutated, e.g., suppressor, tRNA library is aminoacylated by endogenous (e.g., *Escherichia coli*) synthetases (i.e. it is not orthogonal to the *Escherichia coli* synthetases), the selector codon is suppressed and the toxic gene product produced leads to cell death. Only cells harboring orthogonal tRNAs or nonfunctional tRNAs can survive. All survivors are then subjected to a positive selection in which a selector codon, e.g., an amber codon, is placed in a positive selection marker, e.g., drug resistance gene at, e.g., a nonessential position. tRNAs are then selected for their ability to be aminoacylated by the coexpressed cognate synthetase and to insert an amino acid in response to this amber codon. Cells harboring nonfunctional tRNAs, or tRNAs that cannot be recognized by the synthetase of interest will be sensitive to antibiotic. Therefore, only tRNAs that (1) are not substrates for endogenous *Escherichia coli* synthetases; (2) can be aminoacylated by the synthetase of interest; (3) are functional in translation will survive both selections.

A negative selection was chosen that takes advantage of the toxicity of barnase when produced in *Escherichia coli* in the absence of its natural inhibitor barstar. See, e.g., R. W. Hartley, Barnase and barstar. Expression of its cloned inhibitor permits expression of a cloned ribonuclease, *J. Mol. Biol.* 202:913-915 (1988). Amber codons were introduced at nonessential positions in the barnase gene based on analysis of the three-dimensional structure of barnase. See, e.g., Liu & Schultz, (1999), supra. Because of barnase's extreme autotoxicity, a low copy number pSC101 origin was placed in the plasmid expressing barnase. In addition, different numbers of amber codons were tested to modulate the stringency of the selection. Plasmid pSCB2 was used to express a barnase mutant with two amber stop codons at Gln2 and Asp44; plasmid pSCB3 contained an additional amber stop codon at Gly65.

For negative selection, a PCR fragment containing the β-lactamase gene and the pSC101 origin was generated from pBATS using the following oligonucleotides: LW115, 5'-ATGCATGCTGCATTAATGAATCGGCCAACG-3' (SEQ ID NO:67); LW116, 5'-TCCCCGCGGAGGTG-GCACTTTTCGGGG-3' (SEQ ID NO:68). DNA encoding barnase containing two (residues Gln2 and Asp44) or three (residues Gln2, Asp44 and Gly65) amber codons were obtained from pYsupA38B2 and pYsupA38B3, respectively, by digestion with SacII and SphI. Ligation of the above fragments afforded plasmids pSCB2 and pSCB3. The expression of barnase was under arabinose induction. Genes encoding different suppressor tRNAs for in vivo expression were constructed from two overlapping synthetic oligonucleotides (Operon, Alameda, CA, USA) by Klenow extension and inserted between the EcoRI and PstI sites of pAC123 to generate pAC-YYG1 and pAC-JY, respectively, placing transcription under control of the lpp promoter and the rrnC terminator. pAC-Cm is the control plasmid without any tRNA. To optimize the negative selection conditions, competent DH10B cells harboring pSCB2 or pSCB3 were transformed by electroporation with pAC-Cm, pAC-YYG1, and pAC-JY, separately. Single colonies were picked and grown in 2×YT with chloramphenicol (Cm, 34 µg/ml) and ampicillin (Amp, 100 µg/ml). Cell cultures grown overnight were washed twice with minimal media containing 1% glycerol and 0.3 mM leucine (GMML), and resuspended in GMML with Cm and Amp to an OD600 of 0.1. After recovering at 30° C. for 10 min, into one culture (set 1) was added 20 mM of arabinose to induce the expression of barnase; no arabinose was added to the second culture (set 2). At different time points, a small amount of cell culture was diluted and plated on 2×YT agar with Cm and Amp to measure cell density. For negative selections of the suppressor tRNA libraries, the pAC plasmids containing the library were transformed into DH10B cells harboring pSCB2. Cells were quenched by addition of SOC medium and recovered at 30° C. for 1 hour, then were washed with phosphate buffer and GMML, and cultured in 1 l GMML. After recovering at 30° C. for 30 min, Cm, Amp, and 20 mM arabinose were added. After 36 hours, cells were pelleted and pAC plasmids were isolated and purified by agarose gel electrophoresis.

Figure 11:
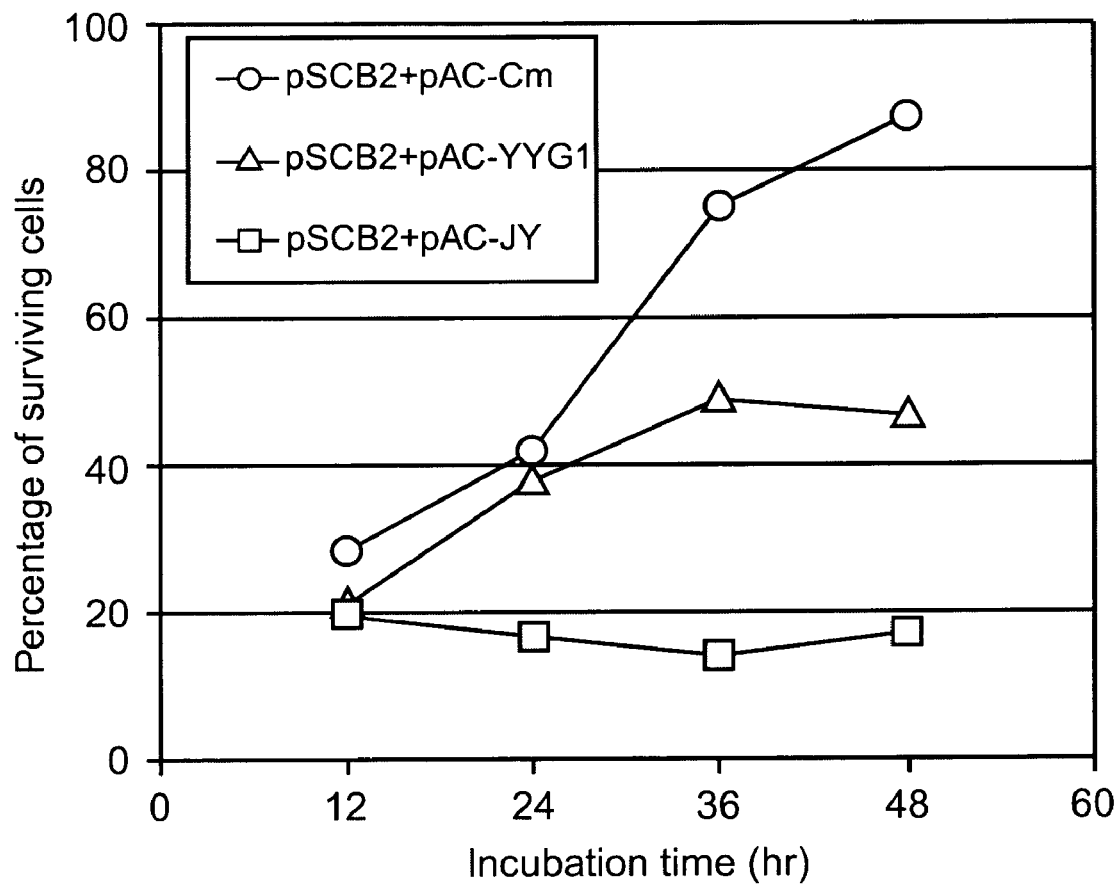
FIG. 11 is a graph of results of a negative selection method for suppressor tRNAs, which shows the percentage of surviving cells containing one of three constructs, for a given amount of time based on the suppression of two amber codons in the barnase gene introduced by a vector, e.g., plasmid pSCB2. This plasmid encodes the barnase gene containing two amber codons. Selections are carried out in GMML liquid medium, and 20 mM of arabinose is used to induce barnase expression. Three constructs are indicated by the following: (1) a circle which represents a control plasmid with no suppressor tRNA; (2) a triangle which represents a suppressor tRNA on plasmid, pAC-YYG1; and, (3) a square which represents a suppressor tRNA on plasmid, pAC-JY.

To optimize the selection conditions, two suppressor tRNAs were used that are known to be poorly recognized by the *Escherichia coli* synthetases. A mutant suppressor tRNATyr derived from *Saccharomyces cerevisiae* (sc-tRNATyrCUA, expressed in pAC-YYG1) suppresses the amber codon (Ala184TAG) in the β-lactamase gene, affording an $IC_{50}$ value of 12 µg/ml ampicillin for *Escherichia coli* cells; and the suppressor tRNATyr derived from *Methanococcus jannaschii* (mj-tRNATyrCUA, expressed in pAC-JY) affords an $IC_{50}$ of 56 µg/ml ampicillin for host cells. See, e.g., Wang et al, (2000), supra. For comparison, the suppressor tRNA-GlnCUA derived from *Saccharomyces cerevisiae* tRNAGln2 has an $IC_{50}$ of 21 µg/1 ml ampicillin when tested in the same assay, and has been demonstrated to be orthogonal to *Escherichia coli* synthetases in vitro and in vivo. See, e.g., Liu & Schultz, (1999), supra. Therefore, a negative selection that eliminates cells expressing mj-tRNATyrCUA, but allows the growth of cells expressing sc-tRNATyrCUA deletes non-orthogonal suppressor tRNAs. Cells were grown in liquid minimal media containing 1% glycerol and 0.3 mM leucine (GMML) with appropriate antibiotics to maintain plasmid pSCB2 and the pAC plasmid. Arabinose was added to one set of cells (set 1) to induce the expression of the barnase, while in set 2 no arabinose was added. The fraction of cells surviving the selection was determined by the ratio of cell densities in set 1 relative to set 2. See FIG. 11: cells harboring the control plasmid pAC-Cm (without suppressor tRNA) and plasmid pAC-YYG1 survived, while cells harboring plasmid pAC-JY largely died. When plasmid pSCB3 was used, cells harboring plasmid pAC-JY started to grow in 24 hours. Therefore, the negative selection was carried out using pSCB2, which encodes the barnase gene containing two amber codons under the above conditions for the library selection.

For positive selection, a plasmid, e.g., pBLAM-JYRS was constructed by inserting the *Methanococcus jannaschii* TyrRS gene from pBSA50 between NdeI and PstI sites of pBLAM-YQRS using oligonucleotides LW 104, 5'-GGAAT-TCCATTAGGACGAATTTGAAATG-3' (SEQ ID NO:69); and LW105, 5'-AAACTGCAGTTATAATCTCTTTCTAAT-TGGCTC-3' (SEQ ID NO:70). See, e.g., Steer, et al., (1999), supra; and, Liu & Schultz, (1999), supra. To optimize the positive selection conditions, competent DH10B cells harboring pBLAM-JYRS were transformed with pAC-Cm, pAC-YYG1, and pAC-JY, separately. Single colonies were picked and grown in 2×YT with Cm and tetracycline (Tet, 40 µg/ml). In liquid selections, overnight cell cultures were diluted into 2 ×YT with Cm and Tet at a starting OD600 of 0.1. Various concentrations of Amp were added, and cell growth was monitored by OD600. In plate selections, approximately 103 to 105 cells were plated on two sets of 2 ×YT agar plates containing Cm and Tet, one set of which contained 500 µg/ml Amp. For selections involving the mutant tRNA library, pAC plasmids isolated from the cells from the negative selection were transformed into competent DH10B cells harboring pBLAM-JYRS. Cells were recovered at 37° C. for 45 minutes, and approximately 105 cells were plated onto each 2 ×YT agar plate containing Cm, Tet and 500 µg/ml of Amp. After 24 hours, colonies were picked and re-grown in 6 ml 2 ×YT containing Cm, Tet and 200 µg/ml of Amp. DNA was isolated and pAC plasmid was purified by agarose gel electrophoresis.

Figure 12A:
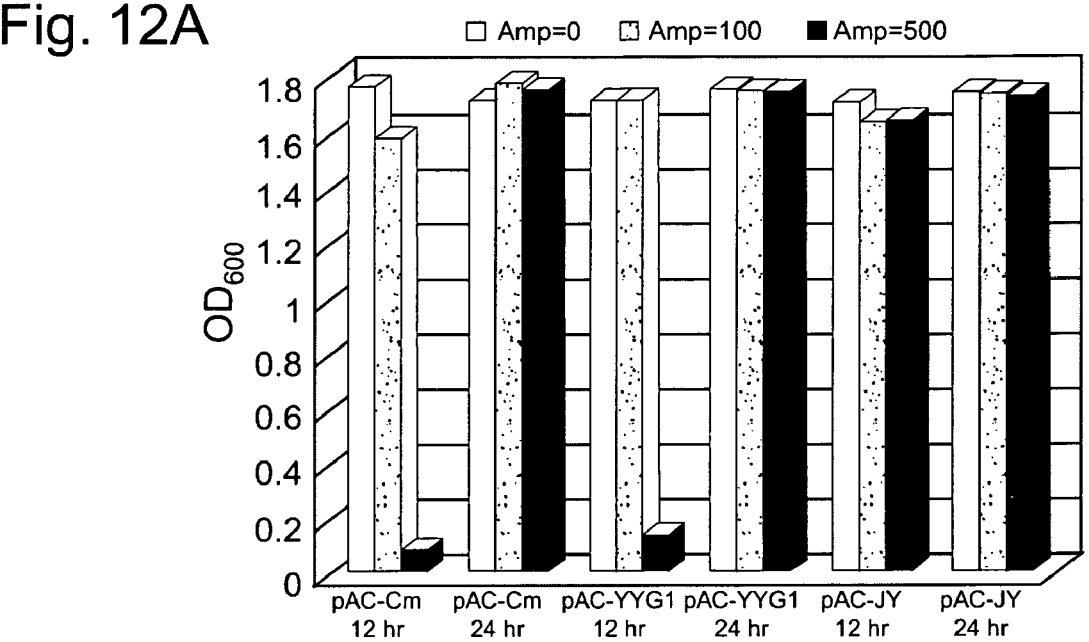
FIG. 12 displays growth histograms, illustrating positive selection based on the suppression of an amber codon in the β-lactamase gene. A vector encoding a suppressor tRNA, e.g., pAC plasmid, is cotransformed with a vector encoding a synthetase, e.g., pBLAM-JYRS, in an organism, e.g., *Escherichia coli* DH10B cells. The growth of cells harboring synthetase and different pAC plasmids in liquid 2×YT medium with various concentrations of ampicillin, e.g., 0, 100 and 500 μg/ml, is shown in Panel A, where pAC is a control plasmid with no suppressor tRNA, where pAC-YYG1 is a plasmid with a suppressor tRNA, and where pAC-JY is a plasmid with a suppressor tRNA. Panel B shows positive selection of the same constructs using 2×YT agar plates with 500 μg/ml ampicillin. Three constructs are indicated by the following: (1) a circle which represents a control plasmid with no suppressor tRNA; (2) a triangle which represents a suppressor tRNA on plasmid, pAC-YYG1; and, (3) a square which represents a suppressor tRNA on plasmid, pAC-JY.
Figure 12B:
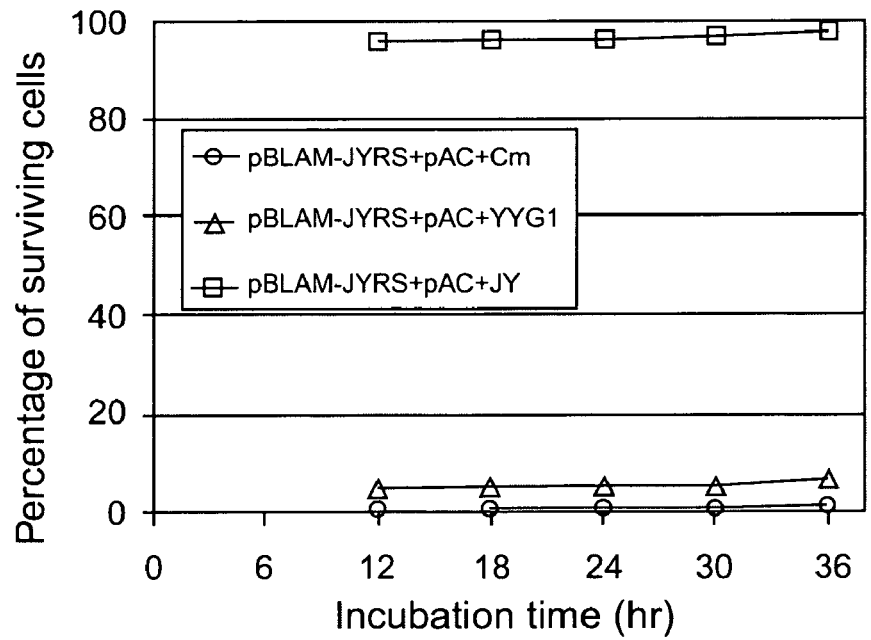

The positive selection is based on suppression of an amber stop codon introduced at position Ala184 in the TEM-1 β-lactamase gene. Plasmid pBLAM-JYRS encodes the gene for the *Methanococcus jannaschii* tyrosyl-tRNA synthetase and a lactamase with an amber mutation at Ala184. pAC plasmids isolated from cells surviving the negative selection were cotransformed with pBLAM-JYRS into *Escherichia coli* DH10B cells. Cells harboring nonfunctional tRNAs or tRNAs that are poor substrates for the *Methanococcus jannaschii* synthetase die; those with tRNAs that can be charged by the synthetase survive. To test the feasibility of the positive selection, two model suppressor tRNAs were tested in the presence of *Methanococcus jannaschii* TyrRS. The sc-tRNATyrCUA has a G1:C72 base pair and is not charged efficiently by *Methanococcus jannaschii* TyrRS. When they were coexpressed in cells with the Ala184amber β-lactamase mutant, cells survived to an $IC_{50}$ of 18 µg/ml ampicillin. In contrast, cells containing the *Methanococcus jannaschii* tRNATyrCUA and the cognate TyrRS survive to an $IC_{50}$ of 1220 µg/ml ampicillin. See, e.g., Wang, et al., (2000), supra. The model positive selection was first tried in liquid 2×YT medium. The growth of cells harboring pBLAM-JYRS and different pAC plasmids in liquid 2×YT medium with various concentrations of ampicillin are shown in FIG. 12, Panel A. Cells transformed with the mj-tRNATyrCUA grew at a faster rate and at higher concentrations of ampicillin. If cells were grown longer than 24 hours, cells transformed with either pAC-Cm or pAC-YYG1 also grew to saturation. Therefore, the positive selection was carried out on plates with initial cell densities between 103 and 105 per plate. See FIG. 12, Panel B. The survival ratio (number of colonies on plates with ampicillin relative to plates without ampicillin) did not change significantly with different initial cell densities, and was stable over the growth time. The positive selection on ampicillin plates resulted in preferential growth of cells with mj-tRNATyrCUA expressed. Therefore, for the library selection the positive selection was carried out on plates instead of in liquid medium.

The library of mutant tRNAs was generated by using the sequences of the two overlapping oligonucleotides used to construct the anticodon-loop library are (the tRNA sequence underlined): LW125, 5'-GGAATTC-3'; LW126, 5'-AAAACTGCAG-3' (SEQ ID NO:71) (where N is equimolar of A, C, T or G). The sequences of oligonucleotides for the all-loop library are: LW145, 5'-GGAATTC-3' and LW146, 5'-AAAACTGCAG-3' (SEQ ID NO:72). These genes were inserted into pAC123 similarly as described above to afford the tRNA libraries.

The negative and positive selections were carried out in tandem as described above on both the anticodon-loop and all-loop libraries. The selected suppressor tRNAs were isolated and retransformed into *Escherichia coli* DH10B harboring pBLAM to test the tRNA's orthogonality to *Escherichia coli* synthetases. The tRNAs were then retransformed into *Escherichia coli* harboring pBLAM-JYRS to test how efficiently the tRNA was charged by *Methanococcus jannaschii* TyrRS. Sequencing of the clones resulting from one round of negative and positive selection of anticodon-loop library revealed that three independent tRNAs were isolated. See FIG. 13. When cotransformed with pBLAM, all had lower $IC_{50}$ values than the parent *Methanococcus jannaschii* tRNATyrCUA, indicating they are poorer substrates for *Escherichia coli* synthetases.

Mutant AA2 also had very high affinity for *Methanococcus jannaschii* TyrRS. Although this mutant tRNA could be stably maintained in *Escherichia coli*, it slowed the growth rate of cells for unknown reasons. This effect likely led to the emergence of mutants AA3 and AA4, which both had a mutation outside of the randomization region. Cells harboring AA3 or AA4 grew normally. Nevertheless, AA3 and AA4 were relatively poor substrates for the *Methanococcus jannaschii* TyrRS.

Four independent tRNAs were selected from two rounds of negative and positive selections using the all-loop library. See FIG. 13. All were poorer substrates for the *Escherichia coli* synthetase than the parent *Methanococcus jannaschii* tRNATyrCUA, yet were still efficiently charged by the *Methanococcus jannaschii* TyrRS as shown by the in vivo β-lactamase assay. See Table 2. The $IC_{50}$ value for cells expressing the best mutant, J17, was 12 µg/ml ampicillin, which is even lower than that of cells with the orthogonal tRNAGlnCUA derived from *Saccharomyces cerevisiae* expressed (21 µg/ml ampicillin). When J17 was coexpressed with the *Methanococcus jannaschii* TyrRS, cells survived to an $IC_{50}$ value of 436 µg/ml ampicillin, providing a selection window (ratio of $IC_{50}$ value with TyrRS to IC50 value without TyrRS) of 35-fold. In addition, the expression of all these mutant tRNAs did not affect the growth of *Escherichia coli* cells.

TABLE 2

In vivo β-lactamase assay of selected suppressor tRNAs

| | $IC_{50}$ (µg/ml of ampicillin) | |
|---|---|---|
| | Coexpressed with pBLAM | Coexpressed with pBLAM-JYRS |
| Suppressor tRNA | | |
| mj-tRNATyrCUA | 56 | 1220 |
| No tRNATyrCUA | 10 | 10 |
| Mutant tRNAs selected from anticodon-loop library | | |
| AA2 | 22 | 1420 |
| AA3 | 10 | 110 |
| AA4 | 12 | 135 |
| Mutant tRNAs selected from all-loop library | | |
| Mutant tRNAs surviving both selections | | |
| J15 | 30 | 845 |
| J17 | 12 | 436 |
| J18 | 20 | 632 |
| J22 | 14 | 459 |
| Mutant tRNAs surviving negative selection only | | |
| N11 | 11 | 16 |
| N12 | 9 | 18 |
| N13 | 10 | 12 |
| N16 | 9 | 9 |

Plasmid pBLAM was used to express the β-lactamase gene with an amber codon at Ala184; plasmid pBLAM-JYRS expressed the amber mutant and the TyrRS of *Methanococcus jannaschii*. Suppressor tRNAs were encoded on pAC plasmid and cotransformed with pBLAM or pBLAM-JYRS in the assay.

To confirm the properties of the selected suppressor tRNAs, they were tested in another in vivo assay based on the suppression of an amber codon in the chloramphenicol acetyltransferase (CAT) gene. In contrast to β-lactamase which is secreted into the periplasm, CAT localizes in the cytoplasm. Moreover, ampicillin is bacteriocidal while chloramphenicol is bacteriostatic. As shown in Table 3 below, the selected suppressor tRNAs also were orthogonal in the CAT assay, indicating their suitability for CAT selections.

TABLE 3

In vivo chloramphenicol acetyltransferase assay of selected suppressor tRNAs

| | $IC_{50}$ (µg/ml of chloramphenicol) | |
|---|---|---|
| Suppressor tRNA | pYC only | pYC + pBK – JYRS |
| mj-tRNATyrCUA | 27 | 308 |
| No tRNATyrCUA | 3 | 3 |
| J15 | 11 | 297 |
| J17 | 4 | 240 |

TABLE 3-continued

In vivo chloramphenicol acetyltransferase assay of selected suppressor tRNAs

| Suppressor tRNA | IC$_{50}$ (µg/ml of chloramphenicol) | |
|---|---|---|
| | pYC only | pYC + pBK - JYRS |
| J18 | 6 | 284 |
| J22 | 5 | 271 | pYC plasmids encoded the chloramphenicol acetyltransferase gene with an amber codon at Asp112 and different suppressor tRNAs listed in the left column of the table. pBK-JYRS was used to express the TyrRS of *Methanococcus jannaschii*.

The in vivo complementation assay which is based on suppression of an amber codon in the β-lactamase gene was carried out as described. See, e.g., Liu & Schultz, (1999), supra; and, Wang, et al., (2000), supra. In the chloramphenicol acetyltransferase (CAT) assay, an amber codon was substituted for Asp112 in the CAT gene of pACYC184 to afford pACMD112TAG. See, e.g., M. Pastrnak, T. J. Magliery, P. G. Schultz, A new orthogonal suppressor tRNA/aminoacyl-tRNA synthetase pair for evolving an organism with an expanded genetic code, *Helv. Chim. Acta* 83:2277-2286 (2000). The genes encoding the suppressor tRNAs under the control of the lpp promoter and rrnC terminator were excised from pAC plasmids with NcoI and AvaI, and inserted into the pre-digested pACMD112TAG to afford plasmids pYC-JY, pYC-J15, pYC-J17, pYC-J18, and pYC-J22, respectively. Plasmid pBK-JYRS, a derivative of pBR322, was used to express the *Methanococcus jannaschii* TyrRS under the control of the *Escherichia coli* GlnRS promoter and terminator. The survival of *Escherichia coli* DH10B cells transformed with pYC plasmid alone or cotransformed with pYC and pBK-JYRS was titrated against a wide range of chloramphenicol concentrations added to the growth media, and IC50 values were interpolated from the curves.

For comparison, four colonies were randomly picked that passed the negative selection only, and tested the tRNAs using the in vivo complementation assay. All of them had very low IC$_{50}$ values when transformed with pBLAM, indicating the negative selection worked well. See Table 2. The IC$_{50}$ values were also low when cotransformed with pBLAM-JYRS, revealing that the positive selection functions to delete tRNAs that cannot be charged by the *Methanococcus jannaschii* TyrRS.

Analysis of the DNA sequences of the selected tRNAs yielded a characteristic pattern of nucleotide substitutions. See FIG. 13. tRNAs that passed both negative and positive selections all had C32 and T60 unchanged, while G37 was mutated to A, and T17a was mutated to either A or G. Some semi-conserved changes included mutation of A38 to either C or A; mutation of T45 to either T or A; mutation of T47 to either G or T. Other mutations had no obvious common pattern. Twenty (20) tRNAs that passed the negative selection only were also sequenced, four of which are shown in FIG. 13, and found they all lacked at least one of the common mutations listed above.

The preferred nucleotides in the selected mutant suppressor tRNAs can play the following roles: (i) they can function as negative determinants for recognition by the *Escherichia coli* synthetases; (ii) they can be identity elements for aminoacylation by *Methanococcus jannaschii* TyrRS; or (iii) they can also optimize the tRNA's interaction with *Escherichia coli*'s translational machinery so as to increase the suppression efficiency of the tRNA. It is noteworthy that the G37A mutation was found in tRNAs selected from both the anticodon-loop and all-loop library. This mutation is consistent with previous studies that showing that adenine at position 37 enhances amber suppression efficiency. See, e.g., M. Yarus, Translational efficiency of transfer RNA's: Use of an expanded anticodon, *Science* 218:646-652 (1982); D. Bradley, J. V. Park, L. Soll, *tRNA*2Gln Su+2 mutants that increase amber suppression, *J. Bacteriol.* 145:704-712 (1981); and, L. G. Kleina, J. Masson, J. Normanly, J. Abelson, J. H. Miller, Construction of *Escherichia coli* amber suppressor tRNA genes. II. Synthesis of additional tRNA genes and improvement of suppressor efficiency, *J. Mol. Biol.* 213:705-717 (1990). Fechter et al. recently reported that the complete identity set for *Methanococcus jannaschii* tRNATyr is six nucleotides (C1G72, A73, and anticodon G34U35A36). See P. Fechter, J. Rudinger-Thirion, M. Tukalo, R. Giegé, Major tyrosine identity determinants in *Methanococcus jannaschii* and *Saccharomyces cerevisiae* tRNATyr are conserved but expressed differently, *Eur. J. Biochem.* 268:761-767 (2001). The presence of C32 and T60 in all selected mutant suppressors therefore is not required for recognition by *Methanococcus jannaschii* TyrRS. All *Escherichia coli* tRNAs have T at position 60 except four tRNAs which have C. See, M. Sprinzl, C. Horn, M. Brown, A. Loudovitch, S. Steinberg, Compilation of tRNA sequences and sequences of tRNA genes, *Nucleic Acids Res.* 26:148-153 (1998). Based on the crystal structure of yeast tRNAPhe, nucleotide 60 does not interact with other nucleotides. See J. L. Sussman, S. R. Holbrook, R. W. Warrant, G. M. Church, S. H. Kim, Crystal structure of yeast phenylalanine transfer RNA. I. Crystallographic refinement, *J. Mol. Biol.* 123:607-630 (1978). Thus, T60 may maintain the shape of the TC loop for productive interaction with the *Escherichia coli* translational machinery. The change of the TC loop structure may affect translational fidelity, as the insertion of a nucleotide between T60 and the conserved C61 enables a glycine tRNA to shift reading frame. See, D. J. O'Mahony, B. H. Hims, S. Thompson, E. J. Murgola, J. F. Atkins, Glycine tRNA mutants with normal anticodon loop size cause 1 frameshifting, *Proc. Natl. Acad. Sci. USA* 86:7979-7983 (1989). The role of C32 is not obvious—position 32 in *Escherichia coli* tRNAs includes T, C, and A, and two *Escherichia coli* tRNATyrs do have C32. As for position 17a, only tRNAThr has an A at this position.

All of the selected suppressor tRNAs are poorer substrates for *Escherichia coli* synthetases relative to the *Methanococcus jannaschii* tRNATyrCUA, resulting in less mischarging when introduced into *Escherichia coli*. These tRNAs can also be stably maintained in *Escherichia coli* without adverse effects on the growth of host cells. Moreover, they can still be charged efficiently by *Methanococcus jannaschii* TyrRS. All these properties make the mutant suppressor tRNA together with the *Methanococcus jannaschii* TyrRS a robust orthogonal tRNA-synthetase pair for the selective incorporation of unnatural amino acids into proteins in vivo. The J17 mutant suppressor tRNA and an engineered mutant TyrRS has been used to deliver O-methyl-L-tyrosine in response to a TAG codon with a fidelity rivaling that of the common 20 amino acids. See, L. Wang, A. Brock, B. Herberich, P. G. Schultz, Expanding the genetic code of *Escherichia coli, Science,* 292:498-500 (2001).

Example 2

Mutating TyrRS so that it Charges the mutRNA Tyr/CUA with an Unnatural Amino Acid, O-methyl-L-tyrosine A unique transfer RNA (tRNA)-aminoacyl tRNA synthetase pair has been generated that expands the number of genetically encoded amino acids in *Escherichia coli*. When introduced into *Escherichia coli*, this pair leads to the in vivo incorporation of the synthetic amino acid O-methyl-L-tyrosine, added exogenously to the growth medium, into protein in response to an amber nonsense codon. The fidelity of translation is greater than 99%, as determined by analysis of dihydrofolate reductase containing the unnatural amino acid. This approach provides a general method for increasing the genetic repertoire of living cells to include a variety of amino acids with novel structural, chemical and physical properties not found in the common twenty amino acids.

An orthogonal tRNA/synthetase pair in *Escherichia coli* can be generated by importing a pair from a different organism, if cross-species aminoacylation is inefficient, and, optionally, the anticodon loop is not a key determinant of synthetase recognition. One such candidate pair is the tyrosyl tRNA/synthetase pair of *Methanococcus jannaschii* (*Methanococcus jannaschii*), an archaebacterium whose tRNATyr identity elements differ from those of *Escherichia coli* tRNA$^{Tyr}$ (in particular, the first base pair of the acceptor stem is GC in *Escherichia coli* and CG in *Methanococcus jannaschii*), and whose tyrosyl synthetase (TyrRS) has only a minimalist anticodon loop binding domain. See, e.g., B. A. Steer, & P. Schimmel, *J. Biol. Chem.* 274:35601-6 (1999). In addition, the *Methanococcus jannaschii* TyrRS does not have an editing mechanism, see, e.g., Jakubowski & Goldman, *Microbiol. Rev.*, 56:412 (1992), and therefore should not proofread an unnatural amino acid ligated to the tRNA. The *Methanococcus jannaschii* TyrRS efficiently aminoacylates an amber suppressor tRNA derived from its cognate tRNATyr, see, e.g., Wang, et al., (2000 *J. Am. Chem. Soc.*, supra., but does not aminoacylate *Escherichia coli* tRNAs, see, e.g., Steer & Schimmel, (1999), supra. Moreover, the *Methanococcus jannaschii* tRNA$_{CUA}^{Tyr}$ is a poor substrate for the *Escherichia coli* synthetases but functions efficiently in protein translation in *Escherichia coli*. See, e.g., Wang, et al., (2000 *J. Am. Chem. Soc.*, supra.

To further reduce recognition of the orthogonal tRNA, *Methanococcus jannaschii* tRNA$_{CUA}^{Tyr}$, by *Escherichia coli* synthetases, eleven nucleotides of the tRNA that do not interact directly with the *Methanococcus jannaschii* TyrRS(C16, C17, U17a, U20, C32, G37, A38, U45, U47, A59 and U60) were randomly mutated to generate a suppressor tRNA library. This tRNA library was passed through a negative selection (e.g., suppression of amber mutations in a toxic reporter gene, e.g., barnase gene), which removes tRNAs that are aminoacylated by *Escherichia coli* synthetases, and then a positive selection for tRNAs that are efficiently aminoacylated by *Methanococcus jannaschii* TyrRS (e.g., suppression of amber mutations in a reporter gene, e.g., β-lactamase gene).

The orthogonal nature of the resulting suppressor tRNAs was tested by an in vivo complementation assay, which is based on suppression of an amber stop codon at a nonessential position (e.g., Ala184) of a reporter gene on a vector, e.g., the TEM-1 β-lactamase gene carried on plasmid pBLAM. Aminoacylation of a transformed suppressor tRNA by any endogenous *Escherichia coli* synthetase results in cell growth in the presence of ampicillin. *Escherichia coli* transformed with *Methanococcus jannaschii* tRNA$_{CUA}^{Tyr}$ and the reporter construct, pBLAM, survive at 55 μg/mL ampicillin. When the best mutant suppressor tRNA (mtRNA$_{CUA}^{Tyr}$) selected from the library was expressed, cells survived at only 12 μg/mL ampicillin; similar values are obtained in the absence of any suppressor tRNA. The mutant suppressor tRNA contained the following nucleotide substitutions: C17A, U17aG, U20C, G37A, and U47G. When the *Methanococcus jannaschii* TyrRS is coexpressed with this mtRNA$_{CUA}^{Tyr}$, cells survive at 440 μg/mL ampicillin. Thus, the mtRNA$_{CUA}^{Tyr}$ is a poorer substrate for the endogenous synthetases than the *Methanococcus jannaschii* tRNA$_{CUA}^{Tyr}$ but is still aminoacylated efficiently by the *Methanococcus jannaschii* TyrRS.

Figure 14:
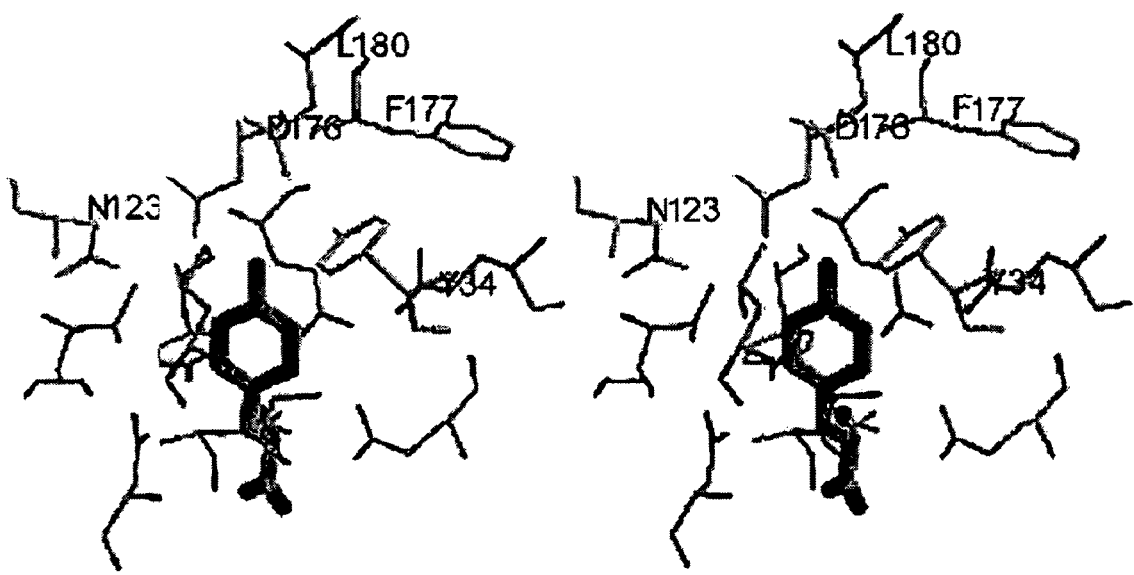
FIG. 14 schematically illustrates a stereo view of the active site of TyrRS. Residues from *B. stearothermophilus* TyrRS are illustrated in the figure. Corresponding residues from *Methanococcus jannaschii* TyrRS are $Tyr^{32}(Tyr^{34})$, $Glu^{107}$ ($Asn^{123}$), $Asp^{158}(Asp^{176})$, $Ile^{159}(Phe^{177})$, and $Leu^{162}$ ($Leu^{180}$) with residues from *B. stearothermophilus* TyrRS in parentheses.

To alter the amino acid specificity of the orthogonal TyrRS so that it charges the mtRNA$_{CUA}^{Tyr}$ with a desired unnatural amino acid, a library of TyrRS mutants was generated and screened. Based on the crystal structure of the homologous TyrRS from *Bacillus stearothermophilus*, see, e.g., P. Brick, T. N. Bhat, D. M. Blow, *J. Mol. Biol.*, 208:83 (1988), five residues (Tyr$^{32}$, Glu$^{107}$, Asp$^{158}$, Ile$^{159}$ and Leu$^{162}$) in the active site of *Methanococcus jannaschii* TyrRS which are within 6.5 Å of the para position of the aryl ring of bound tyrosine were mutated. See, FIG. 14. These residues were all initially mutated to alanine, and the resulting inactive Ala5 TyrRS was used as a template for polymerase chain reaction (PCR) random mutagenesis with doped oligonucleotides.

For example, the TyrRS gene was expressed under the control of *Escherichia coli* GlnRS promoter and terminator in plasmid pBK-JYRS, a pBR322 derived plasmid with kanamycin resistance. Residues Tyr$^{32}$, Glu$^{107}$, Asp$^{158}$, Ile$^{159}$ and Leu$^{162}$ were substituted with Ala by site-directed mutagenesis to provide plasmid pBK-JYA5. Eight (8) oligonucleotides with NNK (N=A+T+G+C and K=G+T, and M=C+A), e.g., oligonucleotides LW157 5'-GGAATTCCATATGGAC-GAATTTGAAATG-3' (SEQ ID NO:73), LW164 5'-GTATTT TACCACTTGGTTCAAAACCTATMNNAG-CAGATTTTTCATCTTTTTTTCATCTTTTT TTAAAAC-3' (SEQ ID NO:74), LW159 5'-TAGGTTTTGAACCAAGTG-GTAAAATAC -3' (SEQ ID NO:75), LW 165 5'-CATTCAGT-GTATAATCCTTATCAAGCTGGAAMNNACTTCCATAA ACATATTTTGCCTTTAAC-3' (SEQ ID NO:76), LW161 5'-TCCAGCTTGATAAGGATTATACA CTGAATG-3' (SEQ ID NO:77), LW167 5'-CATCCCTCCAACTGCAA-CATCAACGCCMNNATA ATGMNNMNNATTAACCTG-CATTATTGGATAGATAAC-3' (SEQ ID NO:78), LW163 5'-GCGT TGATGTTGCAGTTGGAGGGATG-3' (SEQ ID NO:79), and LW105 5'-AAACTGCAGTTATAAT CTCTTTCTAATTGGCTC-3' (SEQ ID NO:70) (Operon, CA) at the mutation sites were used for PCR amplification of the Ala$_5$ TyrRS mutant (pBK-JYA5) and ligated back into the NdeI-PstI-digested pBK-JYA5 to afford the TyrRS library. The ligated vectors were transformed into Escherichia coli DH10B competent cells to yield a library of 1.6×10$^9$ colony forming unit (cfu). The TyrRS genes from 40 randomly picked colonies were sequenced to confirm that there was no base bias at the randomized NNK positions and no other unexpected mutations. The library was amplified by maxiprep, and supercoiled DNA was used to transform the selection strain pYC-J17.

A positive selection was then applied to the library of mutated orthogonal-TyrRS that is based on suppression of an amber stop codon at a nonessential position (e.g., Asp112) in the chloramphenicol acetyltransferase (CAT) gene. See, e.g., M. Pastrnak, T. J. Magliery, P. G. Schultz, *Helv. Chim. Acta,* 83:2277 (2000). Cells transformed with the mutant TyrRS library and mtRNA$_{CUA}^{Tyr}$ gene were grown in media containing the unnatural amino acid and selected for their survival in the presence of various concentrations of chloramphenicol. If a mutant TyrRS charges the orthogonal mtRNA$_{CUA}^{Tyr}$ with any amino acid, either natural or unnatural, the cell produces CAT and survives. The surviving cells were then grown in the presence of chloramphenicol and in the absence of the unnatural amino acid. Those cells that did not survive, e.g., which encode mutant TyrRS's that charge the orthogonal mtRNA$_{CUA}^{Tyr}$ with an unnatural amino acid, were isolated from a replica plate supplemented with the unnatural amino acid. The mutant TyrRS genes were isolated from these cells, recombined in vitro by DNA shuffling, and transformed back into *Escherichia coli* for further rounds of selection with increasing concentrations of chloramphenicol.

A tyrosine analogue with the para hydroxyl group substituted with the methoxy group was used in the selection. Optionally, other tyrosine analogues can also be used in selection, e.g., tyrosine analogues with different functional groups at the para position of the aryl ring (acetyl, amino, carboxyl, isopropyl, methyl, O-methyl and nitro, etc.). For example, the gene encoding mtRNA$_{CUA}^{Tyr}$ was expressed in *Escherichia coli* DH10B cells under the control of the lpp promoter and rrnC terminator in plasmid pYC-J17, a pACYC184 derivative that also encodes the Asp$_{112}$ TAG CAT mutant. Supercoiled DNA encoding the TyrRS library was transformed into *Escherichia coli* DH10B competent cells containing pYC-J17 to yield a library of size greater than 3×10$^9$ cfu, ensuring complete coverage of the original library. Cells were then plated on minimal media plates containing 1% glycerol and 0.3 mM leucine (GMML) with 17 μg/mL tetracycline (Tet), 25 μg/mL kanamycin (Kan), 50 μg/mL of chloramphenicol (Cm), and 1 mM unnatural amino acid. After incubation at 37° C. for 44 hours, colonies on plates supplied with O-methyl-L-tyrosine were pooled, plasmids were isolated and retransformed into *Escherichia coli* DH10B competent cells containing pYC-J17, and the transformed cells were positively selected on 50 μg/mL of Cm. Colonies (96) were individually picked from the plate, diluted into 100 μL of liquid GMML media, and streaked onto two sets of Kan/Tet GMML plates with various concentration of Cm. No O-methyl-L-tyrosine was added to plate set 1 and the concentration of Cm was varied from 10-25 μg/mL; plate set 2 contained 1 mM O-methyl-L-tyrosine and 50 μg/mL of Cm. Replicates of colonies that did not grow on 15 μg/mL of Cm in plate set 1 were picked from plate set 2. Plasmids containing the TyrRS gene were purified and recombined in vitro by DNA shuffling using Stemmer's protocol with the exception of 10 mM Mn2+ instead of Mg2+ in the fragmentation reaction. See, W. P. C. Stemmer, Nature 370, 389-91 (1994); and, I. A. Lorimer, I. Pastan, *Nucleic Acids Res.* 23, 3067-8 (1995). The library was then religated into predigested pBK-JYA5 vector to afford a second generation TyrRS library with a typical size of 8×10$^8$ to 3×10$^9$ cfu. Thirty randomly selected members from the library were sequenced. The mutagenic rate introduced by DNA shuffling was 0.35%. This library was transformed into the selection strain for the next round of selection followed by shuffling. The concentration of Cm in the positive selection and in plate set 2 was raised to 80 μg/mL for the second round and 120 μg/mL for the third round; the concentration of Cm in plate set 1 was unchanged. After three rounds of DNA shuffling, colonies began to grow on 20-25 μg/mL Cm in plate set 1, indicating that the TyrRS mutants were accepting natural amino acids as substrates. Therefore, the best clone selected after two rounds of DNA shuffling was characterized in detail.

Two rounds of selection and DNA shuffling were carried out and a clone was evolved whose survival in chloramphenicol was dependent on the addition of 1 mM O-methyl-L-tyrosine to the growth media. In the absence of O-methyl-L-tyrosine, cells harboring the mutant TyrRS were not viable on minimal media plates containing 1% glycerol, 0.3 mM leucine (GMML), and 15 μg/mL of chloramphenicol. Cells were able to grow on GMML plates with 125 μg/mL chloramphenicol in the presence of 1 mM O-methyl-L-tyrosine. Similar results were obtained in liquid GMML. As a control, cells with the mtRNA$_{CUA}^{Tyr}$ and the inactive Ala$_5$ TyrRS did not survive at the lowest concentration of chloramphenicol used, either in the presence or absence of 1 mM O-methyl-L-tyrosine. See FIG. 14. Addition of 1 mM O-methyl-L-tyrosine itself does not significantly affect the growth rate of *Escherichia coli*.

Analysis of the sequence of the mutant TyrRS that charges the mtRNA$_{CUA}^{Tyr}$ with O-methyl-L-tyrosine revealed the following mutations: Tyr$^{32}$→Gln$^{32}$, Asp$^{158}$→Ala$^{158}$, Glu$^{107}$→Thr$^{107}$, and Leu$^{162}$→Pro$^{162}$. See FIG. 14. Based on the x-ray crystal structure of the homologous *B. stearothermophilus* TyrRS, the loss of the hydrogen-bonding network between Tyr$^{32}$, Asp$^{158}$ and substrate tyrosine can disfavor binding of tyrosine to the mutant TyrRS. Indeed, mutation of Asp$^{176}$ (which corresponds to Asp$^{158}$ in *Methanococcus jannaschii*) of B. stearothernophilus TyrRS yields inactive enzyme. See, e.g., G. D. P. Gray, H. W. Duckworth, A. R. Fernst, *FEBS Lett.* 318:167 (1993). At the same time, the Asp$^{158}$→Ala$^{158}$ and Leu$^{162}$→Pro$^{162}$ mutations create a hydrophobic pocket that allows the methyl group of O-methyl-L-tyrosine to extend further into the substrate-binding cavity. Other important catalytic residues in the active site, which bind to the ribose or the phosphate group of the adenylate, were unchanged after two rounds of DNA shuffling.

Kinetics of adenylate formation of O-methyl-L-tyrosine and tyrosine with adenosine triphosphate (ATP) catalyzed by the mutant TyrRS were analyzed in vitro using a pyrophosphate-exchange assay at 37° C. For example, the mutant TyrRS gene with six histidines at its C-terminus was cloned into plasmid pQE-60 (Qiagen, CA) to generate plasmid pQE-mJYRS. Protein was purified by immobilized metal affinity chromatography according to manufacture's protocol (Qiagen, CA). Pyrophosphate (PPi) exchange was carried out at 37° C. in a reaction mixture containing 100 mM Tris HCl (pH7.5), 10 mM KF, 5 mM MgCl2, 2 mM ATP, 2 mM NaPPi, 0.1 mg/mL bovine serum albumin, approximately 0.01 μCi/μL [$^{32}$P]NaPPi, and various concentrations of tyrosine or O-methyl-L-tyrosine. Reactions were initiated with the addition of the purified mutant TyrRS, and aliquots were periodically taken and quenched with 0.2 M NaPPi, 7% perchloric acid, and 2% activated charcoal. The charcoal was filtered and washed with 10 mM NaPPi (pH2), then measured by scintillation counting to determine the $^{32}$P levels in charcoal-adsorbed ATP. Values of k$_{cat}$ and K$_m$ were calculated by direct fitting of the Michaelis-Menten equation using nonlinear regression analysis.

The Michaelis constant (K$_m$) for tyrosine (5833+/−902 μM) is approximately 13-fold higher than that for O-methyl-L-tyrosine (443+/−93 μM), and the catalytic rate constant (k$_{cat}$) for tyrosine (1.8+/−0.2×10$^{-3}$ s$^{-1}$) is eightfold less than that for O-methyl-L-tyrosine (14+/−1×10$^{-3}$ s$^{-1}$). Thus, the value of k$_{cat}$/K$_m$ of the mutant TyrRS for O-methyl-L-tyrosine is about 100-fold higher than that of tyrosine. The physiological concentration of tyrosine in *Escherichia coli* is about 80 μM, which is far below K$_m$ value (5833 μM) of the mutant TyrRS for tyrosine. Presumably, the concentration of O-methyl-L-tyrosine in cells is comparable or greater than the K$_m$ (443 μM).

This example shows that it is possible to augment the protein biosynthetic machinery of *Escherichia coli* to accommodate additional genetically encoded amino acids. The ability to introduce novel amino acids into proteins directly in living cells will provide new tools for studies of protein and cellular function and can lead to generation of proteins with enhanced properties compared to a naturally occurring protein. The methods described here can be applied to other amino acids with novel spectroscopic, chemical, structural or the like properties. The *Escherichia coli* ribosome has been shown to be able to incorporate amino acids with a wide array of side chains into proteins using in vitro protein synthesis. See, e.g., C. J. Noren, S. J. Anthony-Cahill, M. C. Griffith, P. G. Schultz, *Science* 244, 182-8 (1989). Additional orthogonal tRNA/synthetase pairs, see, e.g., D. R. Liu, P. G. Schultz, *Proc. Natl. Acad. Sci. USA* 96,4780-5 (1999); and, A. K. Kowal, C. Kohrer, U. L., RajBhandary, *Proc. Natl. Acad. Sci, U.S.A.,* 98:2268 (2001), as well as four base codons, see, e.g., T. J. Magliery, J. C. Anderson, P. G. Schultz, *J. Mol. Biol.* 307:755 (2001); and, B. Moore, B. C. Persson, C. C. Nelson, R. F. Gesteland, J. F. Atkins, *J. Mol. Biol.,* 298:195 (2000), and other selector codons described herein, can further expand the number and scope of amino acids that can be incorporated. Orthogonal pairs for eukaryotic cells can also be generated by the methods provided herein.

See also corresponding patent application "In vivo Incorporation of Unnatural Amino Acids" US publication 20030082575 which is incorporated herein by reference. This application describes an example of the generation of an O-methyl-L-tyrosine mutant of dihydrofolate reductase (DHFR) using the above-described system.

Example 3

Mutating TyrRS so that it Charges the mutRNA Tyr/CUA with an Unnatural Amino Acid, L-3-(2-Napthyl)alanine This example provides another orthogonal pair that can be used to incorporate a second unnatural amino acid, L-3-(2-Napthyl)alanine into proteins in an organism, e.g., *Escherichia coli*. An example of the methods used to generate the orthogonal pair that incorporates the unnatural amino acid into proteins is described below. More details describing the incorporation of the unnatural amino acid into a protein can be found in corresponding patent application "In vivo incorporation of unnatural amino acid" US publication 20030082575 incorporated herein by reference.

Figure 15:
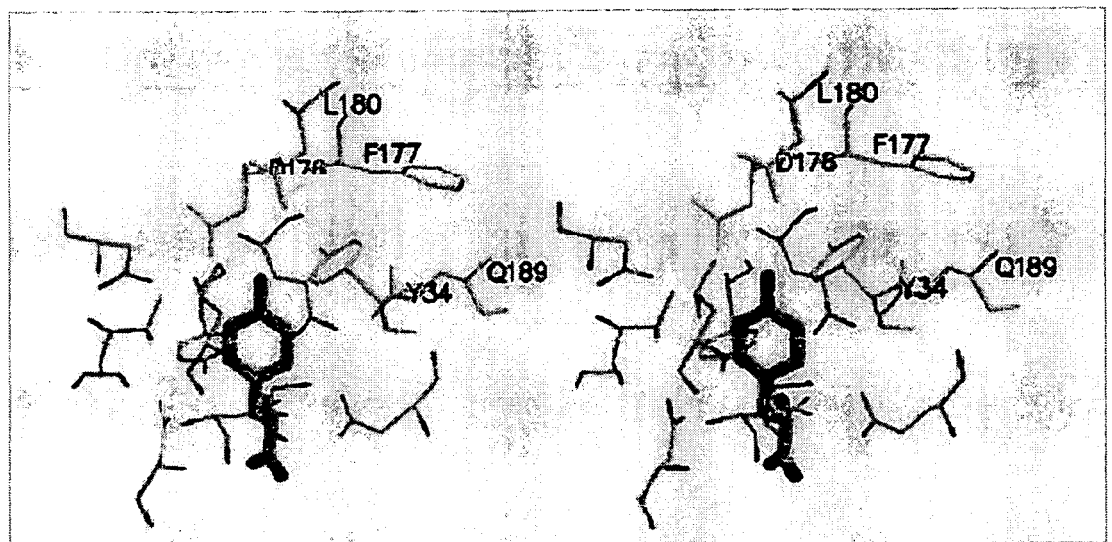
FIG. 15 schematically illustrates a view of the active site of TyrRS. Residues from *B. stearothermophilus* TyrRS are illustrated in the figure. Corresponding residues from *Methanococcus jannaschii* TyrRS are $Tyr^{32}(Tyr^{34})$, $Asp^{158}(Asp^{176})$, $Ile^{159}(Phe^{177})$, $Leu^{162}(Leu^{180})$ and $Ala^{167}(Gln^{189})$ with residues from *B. stearothermophilus* TyrRS in parentheses.

An amber stop codon and its corresponding orthogonal amber suppressor tRNA, mu $tRNA_{CUA}^{Tyr}$, were selected to encode an unnatural amino acid. As described above, and see Wang & Schultz, *Chem. Biol.* 8:883-890 (2001). The *Methanococcus jannaschii* tyrosyl-tRNA synthetase (TyrRS) was used as the starting point for the generation of an orthogonal synthetase with unnatural amino acid specificity. This TyrRS does not aminoacylate any endogenous *Escherichia coli* tRNAs, see, e.g., Steer & Schimmel, *J. Biol. Chem.,* 274: 35601-35606 (1999), but aminoacylates the mu $tRNA_{CUA}^{Tyr}$ with tyrosine. See, e.g., Wang, Magliery, Liu, Schultz, *J. Am. Chem. Soc.,* 122:5010-5011 (2000). L-3-(2-naphthyl)-alanine was chosen for this study since it represents a significant structural perturbation from tyrosine and may have novel packing properties. To change the amino acid specificity of the TyrRS so that it charges the mu $tRNA_{CUA}^{Tyr}$ with L-3-(2-naphthyl)-alanine and not any common 20 amino acids, a library of *Methanococcus jannaschii* TyrRS mutants was generated and screened. On the basis of an analysis of the crystal structure of the homologous TyrRS from *Bacillus stearothermophilus*, see, Brick, Bhat, Blow, *J. Mol. Biol.,* 208:83-98 (1989), five residues ($Tyr^{32}$, $Asp^{158}$, $Ile^{159}$, $Lue^{162}$, and $Ala^{167}$) in the active site of *Methanococcus jannaschii* TyrRS that are within 7 Å of the para position of the aryl ring of tyrosine were mutated. See FIG. 15. No synthetases specific for L-3-(2-naphthyl)alanine were selected from the mutant TyrRS library reported in Wang, Brock, Herberich, Schultz, *Science,* 292:498-500 (2001). To reduce the wild-type synthetase contamination in the following selection, these residues (except $Ala^{167}$) were first all mutated to alanine. The resulting inactive $Ala_5$ TyrRS gene was used as a template for polymerase chain reaction (PCR) random mutagenesis with oligonucleotides bearing random mutations at the corresponding sites.

The mutant TyrRS library was first passed through a positive selection based on suppression of an amber stop codon at a nonessential position ($Asp^{112}$) in the chloramphenicol acetyltransferase (CAT) gene. Cells transformed with the mutant TyrRS library and the mu $tRNA_{CUA}^{Tyr}$ gene were grown in minimal media containing 1 mM L-3-(2-naphthyl)-alanine and 80 µg/mL chloramphenicol. Cells can survive only if a mutant TyrRS aminoacylates the mu $tRNA_{CUA}^{Tyr}$ with either natural amino acids or L-3-(2-naphthyl)-alanine. The surviving cells were then grown in the presence of chloramphenicol and the absence of the unnatural amino acid. Those cells that did not survive must encode a mutant TyrRS that charges the mu $tRNA_{CUA}^{Tyr}$ with L-3-(2-naphthyl)-alanine, and were picked from a replica plate supplied with the unnatural amino acid. After three rounds of positive selection followed by a negative screen, four TyrRS's were characterized using an in vivo assay based on the suppression of the $Asp^{112}$TAG codon in the CAT gene.

TABLE 4

In vivo chloramphenicol acetyltransferase assay of mutant TyrRS.[a]

| | $IC_{50}$ (µg/mL of chloramphenicol) | |
|---|---|---|
| | No L-3-(2-naphthyl)-Ala | Add L-3-(2-naphthyl)-Ala |
| Mutant TyrRS | | |
| no TyrRS | 4 | 4 |
| wt TyrRS | 240 | 240 |
| After selection | | |
| S1-TyrRS | 30 | 120 |
| S2-TyrRS | 30 | 120 |
| S3-TyrRS | 25 | 110 |
| S4-TyrRS | 35 | 100 |
| After DNA shuffling | | |
| SS12-TyrRS | 9 | 150 |

[a]A pYC-J17 plasmid was used to express the mu $tRNAS_{CUA}^{Tyr}$ gene and the chloramphenicol acetyltransferase gene with an amber stop codon at Asp112. A pBK plasmid was used to express TyrRS, and was cotransformed with pYC-J17 into *Escherichia coli* DH10B. Cell survival on GMML plates was titrated in the presence of different concentrations of chloramphenicol.

In the absence of L-3-(2-naphthyl)-alanine, cells expressing the selected TyrRS and the mu $tRNA_{CUA}^{Tyr}$ survived in 25 to 35 µg/mL chloramphenicol on minimal media plates containing 1% glycerol and 0.3 mM leucine (GMML plate); in the presence of L-3-(2-naphthyl)-alanine, cells survived in 100 to 120 µg/mL chloramphenicol on GMML plates. Compared to the $IC_{50}$ value in the absence of any TyrRS (4 µg/1 mL chloramphenicol), these results indicate that the selected TyrRS's accept L-3-(2-naphthyl)-alanine, but also still charge natural amino acids to some degree. See Table 4 above.

To further reduce the activity of the mutant TyrRS toward natural amino acids, one round of DNA shuffling was carried out using the above four mutant genes as templates. The resulting mutant TyrRS library was passed through two additional rounds of positive selections and negative screens. One mutant TyrRS(SS12-TyrRS) was evolved, whose activity for natural amino acids was greatly reduced ($IC_{50}$=9 µg/mL chloramphenicol) while its activity toward L-3-(2-naphthyl)-alanine was enhanced ($IC_{50}$=150 µg/mL chloramphenicol). See Table 4.

The evolved SS12-TyrRS has the following mutations: Tyr$^{32}$→Leu$^{32}$, Asp$^{158}$→Pro$^{158}$, Ile$^{159}$→Ala$^{159}$, Leu$^{162}$→Gln$^{162}$, and Ala$^{167}$→Val$^{167}$. See FIG. 15. Based on the crystal structure of the homologous *B. stearothermophilus* TyrRS, the mutations of Tyr$^{32}$→Leu$^{32}$ and Asp$^{158}$→Pro$^{158}$ can result in the loss of hydrogen bonds between Tyr$^{32}$, Asp$^{158}$, and the native substrate tyrosine, thus disfavoring the binding of tyrosine to SS12-TyrRS. Most residues are mutated to amino acids with hydrophobic side chains, which are expected to favor binding of L-3-(2-naphthyl)-alanine. The crystal structure of the wild-type *Methanococcus jannaschii* TyrRS and the evolved SS12-TyrRS can be determined by available methods.

The mu tRNA$_{CUA}^{Tyr}$/SS12-TyrRS pair was capable of selectively inserting L-3-(2-naphthyl)-alanine into proteins in response to the amber codon with fidelity rivaling that of the natural amino acids based on cell growth, protein expression and mass spectrometry examples described herein and in corresponding application "In vivo incorporation of unnatural amino acids" US publication 20030082575. See also, Wang, Brock, and Schultz, Adding L-3-(2-Naphthyl)alanine to the genetic code of *E. coli*, J. Am. Chem Soc., (2002) 124(9):1836-7. This result, which involves an amino acid that is structurally distinct from tyrosine, confirms that the methods described herein are generalizable to a variety of unnatural amino acids.

Example 4

Mutating TyrRS so that it Charges the mutRNA Tyr/CUA and Screening for the Mutated TyrRS with the Desired Properties by Other Methods, e.g., FACs and Phage Display and Panning Orthogonal pairs can also be selected by using reporter genes and proteins as described above, along with in vivo FACS screening, antibody detection, in vitro phage display and panning, or the like. See, Wang & Schultz, Expanding the genetic code, *Chem. Commun.*, 1:1-11 (2002).

Figure 16B:
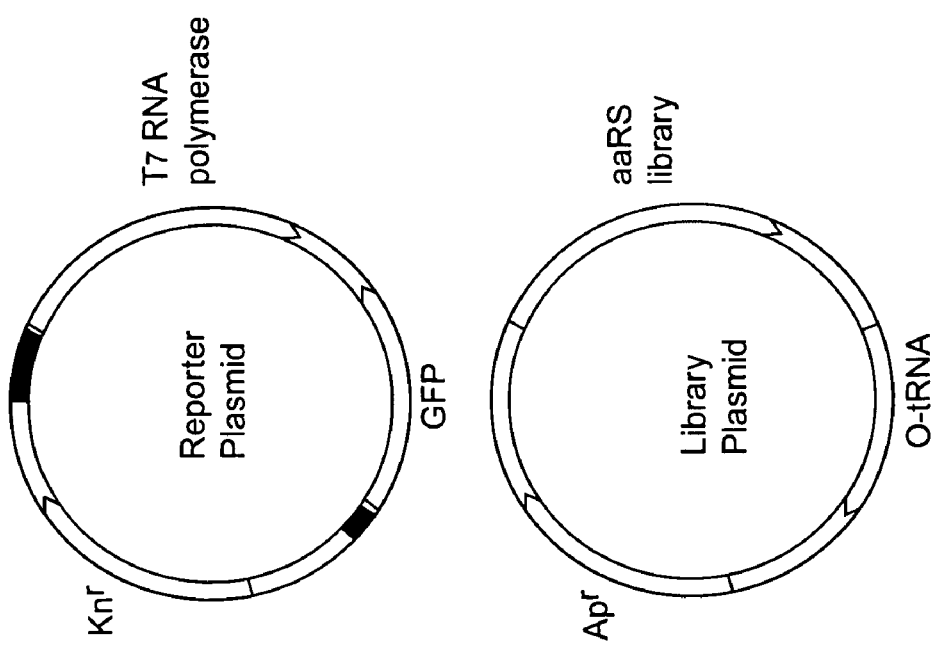
FIG. 16, Panel A and Panel B schematically illustrate an example of FACS-based selection and screening methods used to generate a component of the present invention, e.g., orthogonal synthetase. Panel A schematically illustrates vectors, e.g., plasmids, for expression of orthogonal synthetase library and O-tRNA (library plasmid) and for the T7 RNA polymerase/GFP reporter system (reporter plasmid), with one or more selector codons, e.g., TAG. Panel B schematically illustrates positive selection/negative screen scheme, where the cells are grown the presence and absence of the unnatural amino acid, the presence and absence of a selection agent, and screened for fluorescing cells and non-fluorescing cells in the screening process, where the "+" and empty circles correspond to fluorescing and non-fluorescing cells, respectively.
Figure 16A:
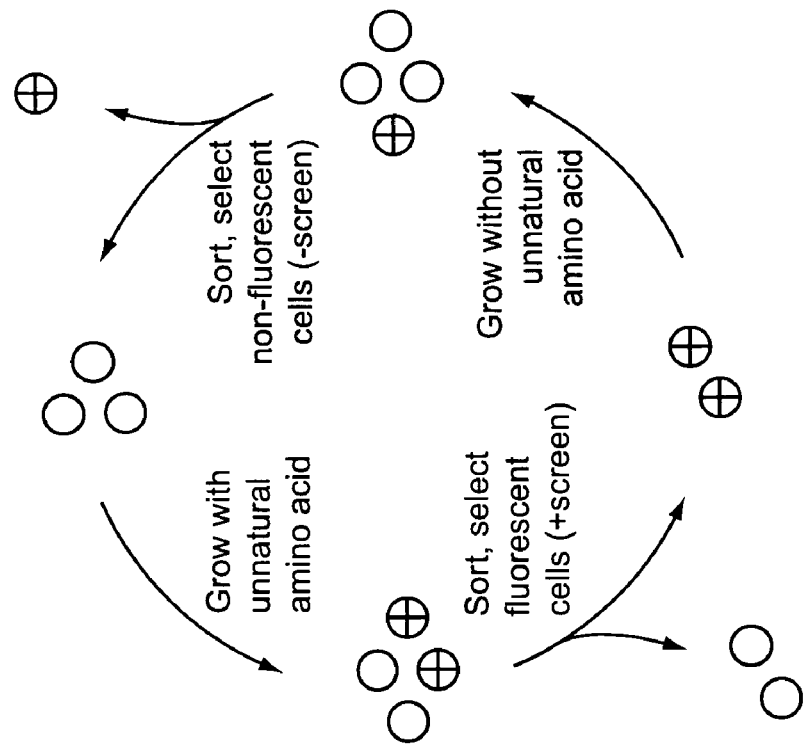
Figure 26:
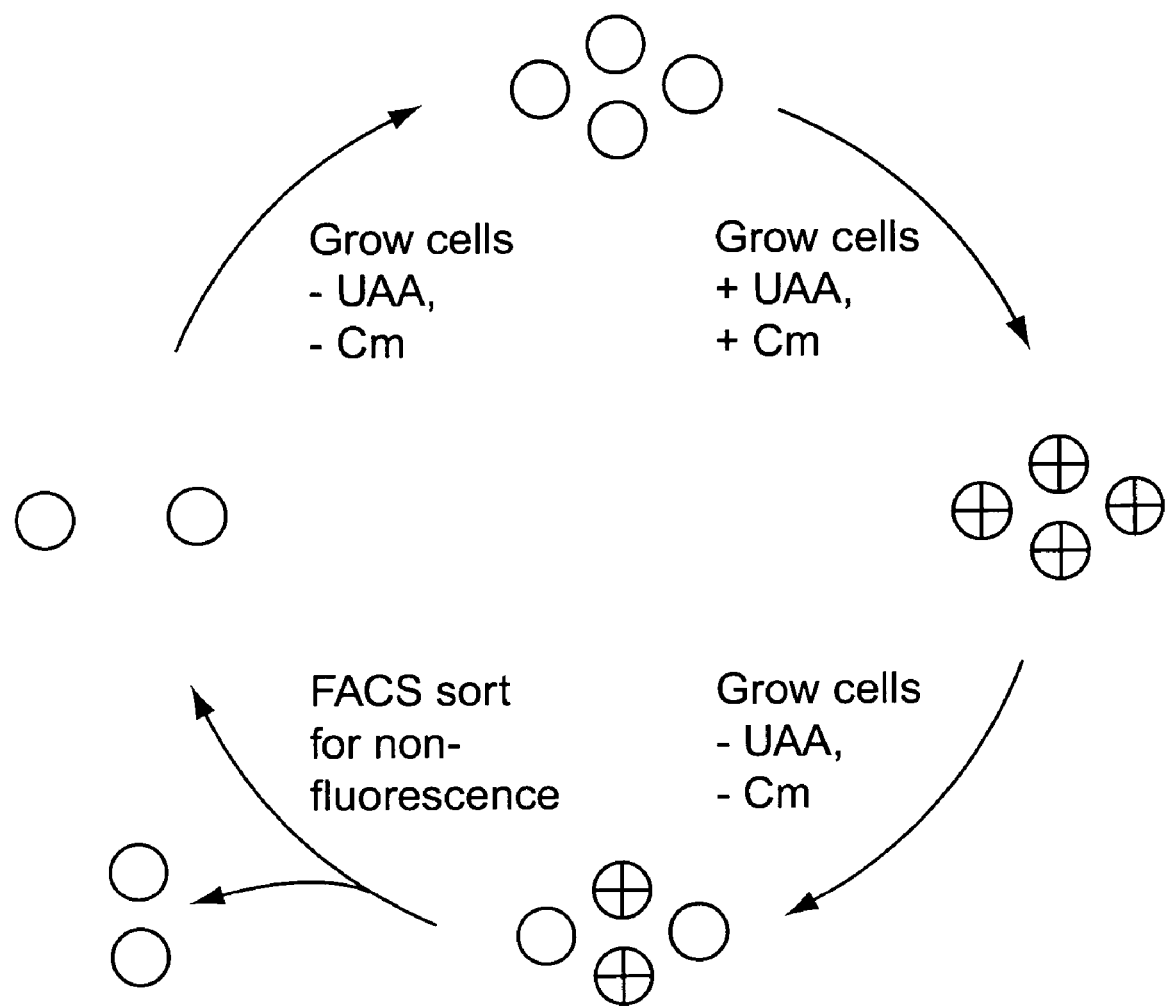
FIG. 26 illustrates the strategy for the evolution of an aminoacyl-tRNA synthetase using plasmid pREP/YC-JY-CUA. Fluorescent and non-fluorescent cells are shown in black and white, respectively.

For example, a general fluorescence-activated cell sorting (FACS) based screen has been developed with, e.g., green fluorescent protein (GFP) as the reporter, to screen for synthetases. See FIG. 16, Panel A, and Panel B Synthetase activity is reported by suppression of the selector codon, e.g., an amber stop codon (TAG) within T7 RNA polymerase, which drives the expression of GFP. See, e.g., FIG. 26 for another example of selection/screening methods of the invention. Only when the amber codons are suppressed can cells produce functional T7 RNA polymerase and express GFP, rendering cells fluorescent. In the positive screen, fluorescent cells are collected which encode active synthetases charging the orthogonal tRNA with either natural or unnatural amino acids. The selected cells are then diluted and grown in the absence of the unnatural amino acid, and then sorted by FACS for cells without fluorescence, e.g., that express synthetases with specificities for unnatural amino acids only. FIG. 17, Panel A, Panel B Panel C and Panel D illustrates suppression of a selector codon, e.g., an amber codon, using glutamine synthetase. By setting the collection threshold of the fluorescence intensity, the stringency of both positive and negative screen can be conveniently controlled.

Figure 18:
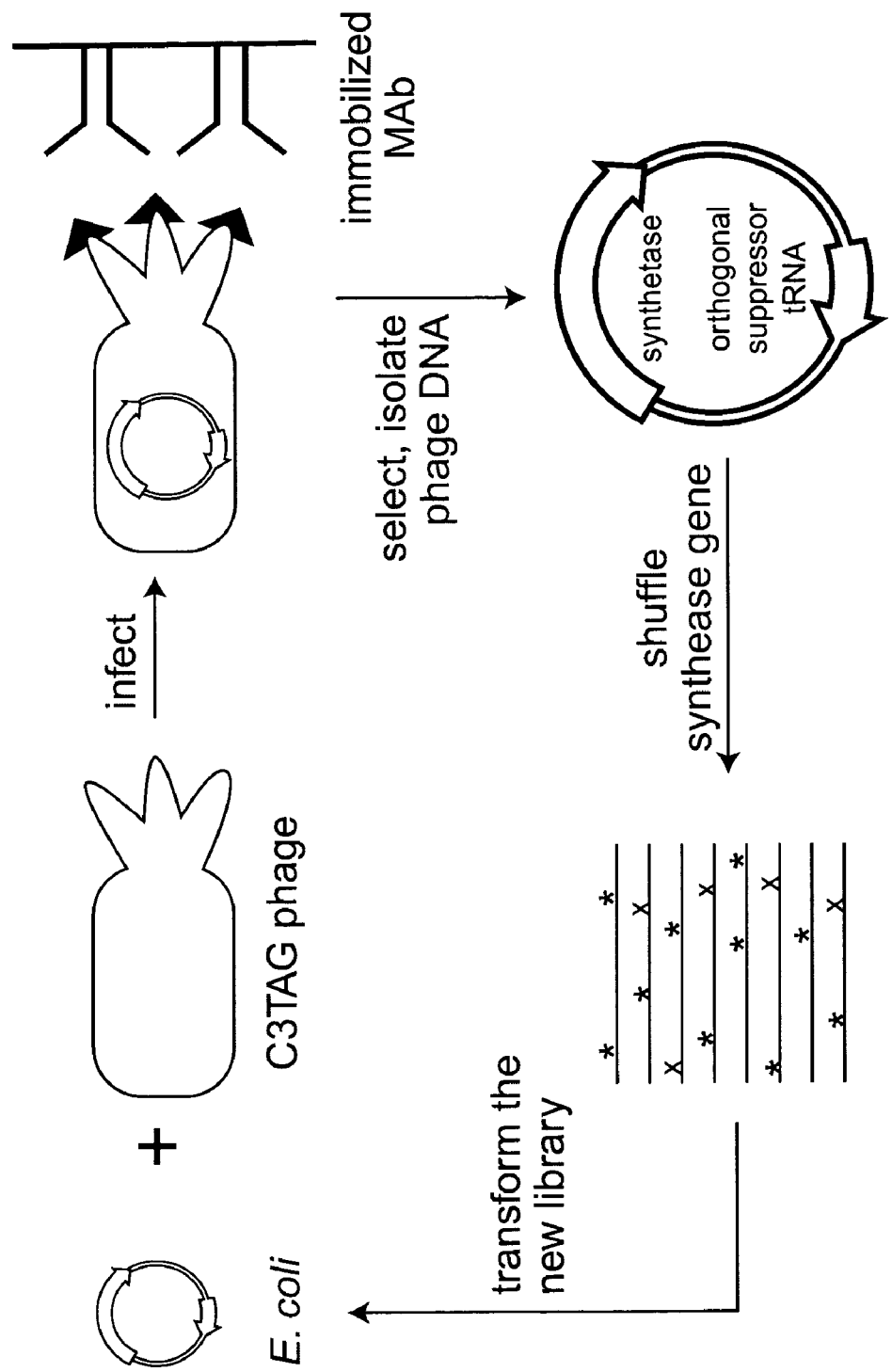
FIG. 18 schematically illustrates phage-based selection for the incorporation of unnatural amino acids into a surface epitope. For example, *Escherichia coli* carrying the mutant synthetase library are infected by phage with a stop codon in a gene encoding a surface protein. Phage containing an active synthetase display the unnatural amino acid on the phage surface and are selected with immobilized monoclonal antibodies.

A direct positive selection specific for a particular unnatural amino acid has also been developed which exploits the high affinity of a monoclonal antibody for an unnatural amino acid displayed on a phage surface. See FIG. 18. See, M. Pastrnak and P. G. Schultz, *Bioorg. Med. Chem.*, 9:2373 (2001). For example, a C3 peptide with an amber mutation is fused to the N-terminus of VSCM13 phage coat protein pIII, such that phage production requires suppression of the amber stop codon. Cells harboring a phagemid that expresses an orthogonal suppressor tRNA and a synthetase library are infected with the C3TAG phage. An active synthetase results in suppression of C3TAG and display of its cognate amino acid on the phage surface. The phage pool is then incubated with immobilized monoclonal antibodies directed against the unnatural amino acid to isolate only those phage carrying the synthetase specific for the unnatural amino acid. In a simulated selection, phage displaying Asp were enriched over 300-fold from a pool of phage displaying Asn using antibodies raised against the Asp-containing epitope.

Figure 19:
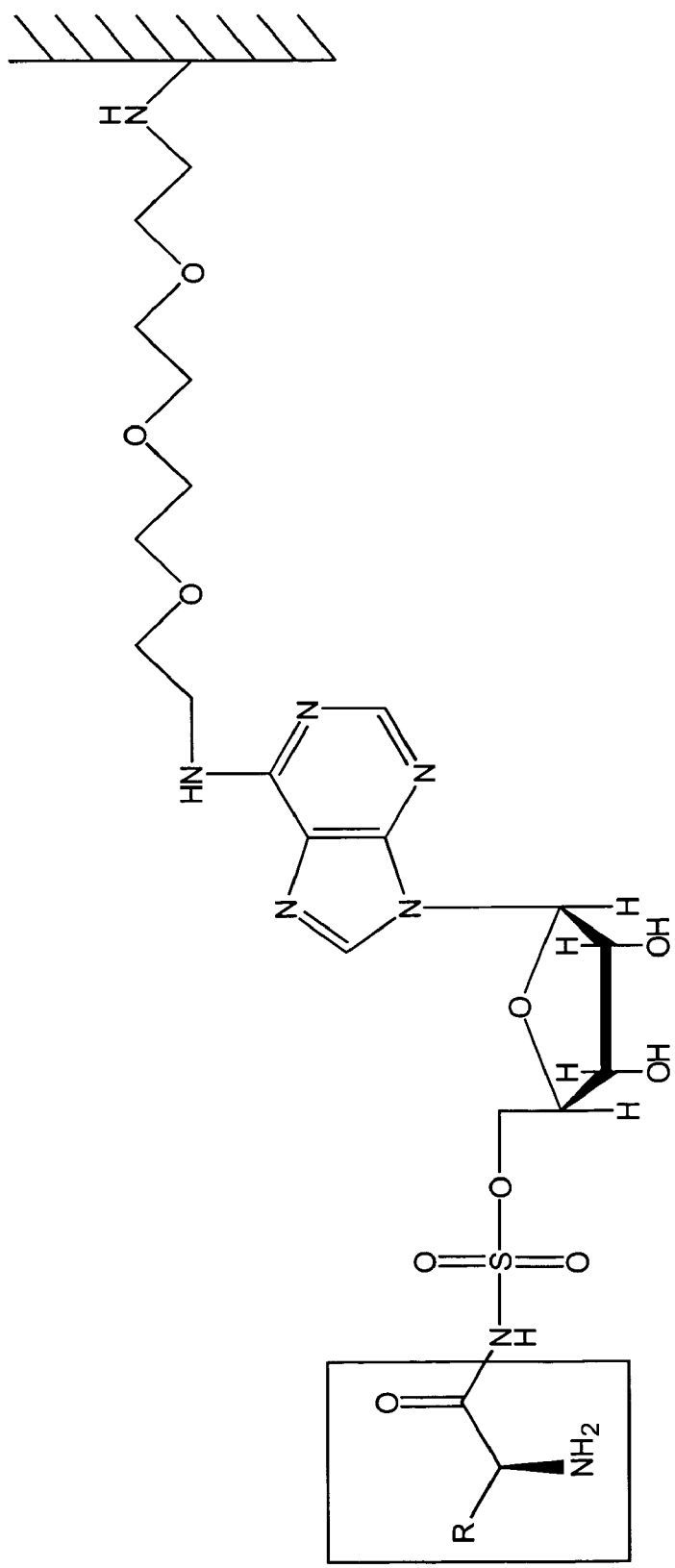
FIG. 19 schematically illustrates an example of a molecule, e.g., immobilized aminoalkyl adenylate analog of the aminoacyl adenylate intermediate, used to screen displayed synthetases, e.g., phage-displayed synthetases, with unnatural amino acid specificity.

Several in vitro screen methods can also be used. In one such method, a library of mutant synthetases is displayed on the phage, and the phage particles are panned against immobilized aminoalkyl adenylate analogs of the aminoacyl adenylate intermediate. See FIG. 19. For example, *Methanococcus jannaschii* TyrRS was fused to the pIII coat protein of M13 phage. This phage was enriched 1000-fold over a control phage displaying an unrelated antibody after panning against the aminoalkyl adenylate analog of tyrosyl adenylate. Given that only 0.1 to 1% of the starting TyrRS phage population displays the TyrRS protein, the actual enrichment factor can be as high as $10^5$ to $10^6$.

Example 5

Generating an Archaeal leucyl-tRNA Synthetase Pair

Figure 20:
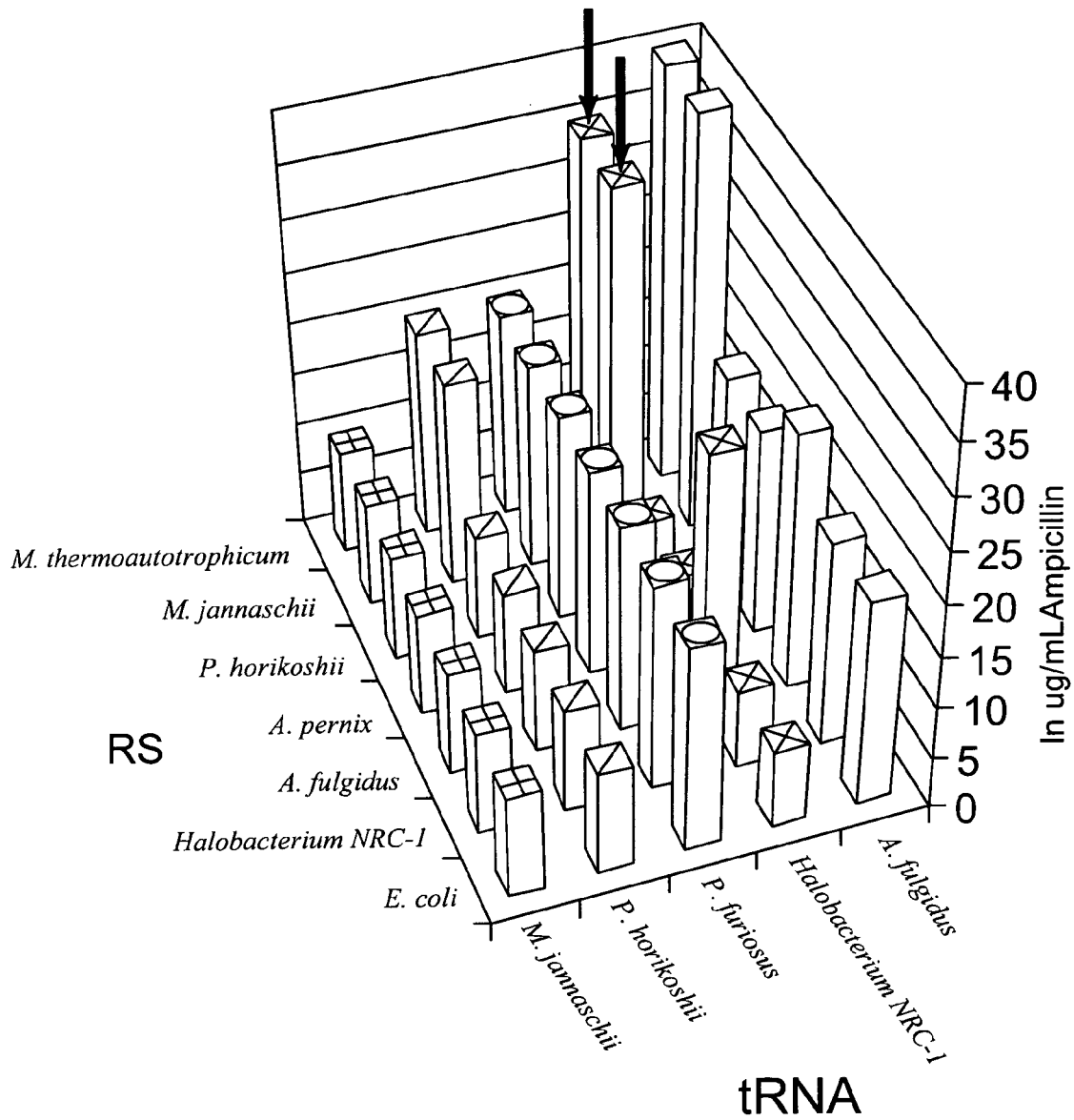
FIG. 20 is a graph illustrating ampicillin resistance of various orthogonal pairs from a variety of organisms. The figure illustrates an example of finding an orthogonal pair using a reporter constructs, each containing a reporter gene, e.g., a β-lactamase gene, with a selector codon, e.g., an amber codon, and a suppressor tRNA (with a selector anticodon), where the suppressor tRNA can be from a variety of organisms, e.g., *A. fulgidus*, Halobacterium NRC-1, *P. furiosus*, *P. horikoshii*, and *Methanococcus jannaschii*. The reporter constructs and cloned synthetases from different organisms, e.g., *M. thermoautotrophicum*, *Methanococcus jannaschii*, *P. horikoshii*, *A. pernix*, *A. fulgidus*, Halobacterium NRC-1, and *Escherichia coli* are transformed into a cell. Cells are grown in various concentrations of a selector agent, e.g., ampicillin. Cells possessing an orthogonal tRNA/RS pair are selected, e.g., using an in vivo complementation assay. As shown, two systems showed suppression levels significant higher than was observed with *Escherichia coli* synthetase. They are *M. thermoautotrophicum* and *Methanococcus jannaschii*.

A leucyl-tRNA synthetase from an archaebacterium, *Methanobacterium thermoautotrophicum*, was identified that can aminoacylate amber and frameshift suppressor tRNAs derived from archaeal leucyl tRNAs, but does not aminoacylate any tRNAs native to *Escherichia coli*. Using a selection strategy described in the present invention, highly active tRNA substrates were identified that are selectively charged by the synthetase. Mutant libraries of synthetases can be generated and selected for that are capable of selectively charging unnatural amino acids.

β-lactamase reporter genes were constructed with amber codons and suppressor tRNAs derived from five different archael leucyl tRNAs for which the anticodon was replaced with a CUA anticodon to make amber suppressor tRNAs. Seven different leucyl tRNA synthetases were cloned and were cotransformed with reporter constructs. Three synthetases gave higher levels of survival on ampicillin in the presence of the synthetase than controls lacking synthetase, and these systems were examined further. See, FIG. 20.

The next step involved determination of a synthetase that charges the suppressor tRNA without interacting with host tRNA. The two chosen systems, *Methanobacterium thermoautotrophicum* and *Methanococcus jannaschii* were expressed, and aminoacylation was performed in vitro on purified tRNA from *Halobacterium* as a positive control, and for *Escherichia coli* total tRNA. It was found that the *Methanococcus jannaschii* synthetase was able to effectively charge *Escherichia coli* tRNA, but the *Methanobacterium thermoautotrophicum* synthetase was specific towards the *Halobacterium* tRNA.

Further improvements were made to increase the efficiency of the suppression system. The A$^{37}$ site of the anticodon loop was a G$^{37}$ in the leucyl tRNA synthetases. This mutation has been shown to be a negative determinant against aminoacylation by non-cognate synthetases in various eukaryotic cells and *Halobacterium*, and also a positive determinate for aminoacylation in yeast, but not in *Halobacterium*. A$^{37}$ was also shown to be a key requirement for efficient suppression. The anticodon loop was randomly mutagenized and selected for more efficient suppression. Mutating $G^{37}$ to A, resulted in a more efficient suppressor, which could suppress 20 fold higher concentrations of ampicillin compared to the un-mutated version. See, FIG. 21.

To improve the tRNA so that is not preferentially charged by other synthetases in *Escherichia coli*, the acceptor stem of the tRNA was randomly mutagenized. A positive/negative selection was used to identify tRNAs that would not be charged in the absence of *Methanobacterium thermoautotrophicum* RS.

Amongst the selected mutated tRNAs observed, all conserved the discriminator base, $A^{73}$, which has been shown in all previous systems to be a critical positive determinate for leucyl aminoacylation. Also conserved was a $C^3:G^{70}$ base pair amongst all hits that had improved orthogonality. The best mutant tRNA observed gave about a 3-fold decrease in aminoacylation without synthetase and actually an increase in suppression in the presence of *Methanobacterium thermoautotrophicum* RS.

Figure 22:
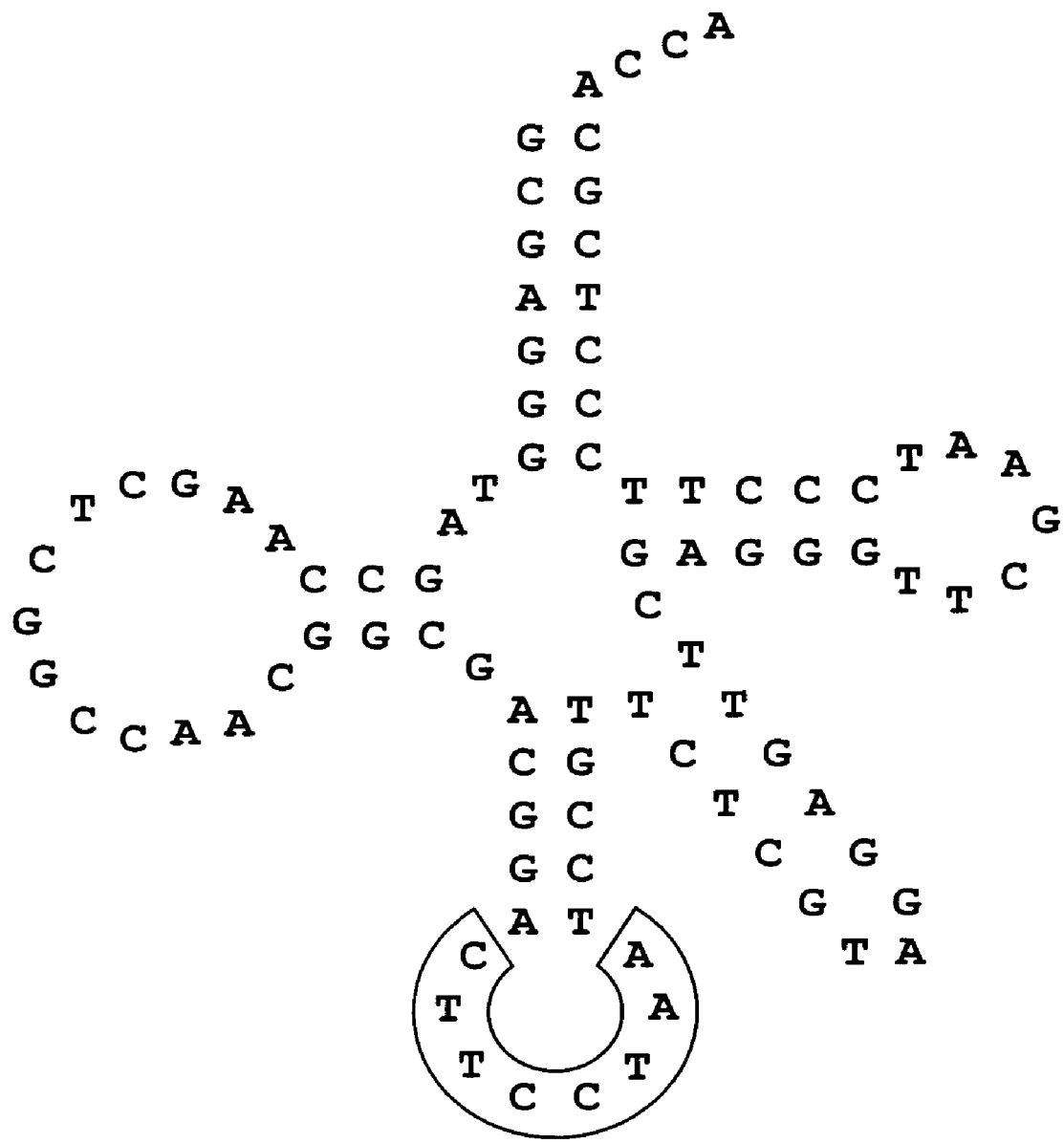
FIG. 22 illustrates a tRNA suppressor for a base codon (SEQ ID NO:105). The tRNA suppressor illustrated in this figure was isolated from a library derived from the Halobacterium NRC-1 TTG tRNA, where the anticodon loop was randomized with 8 nucleotides and subjected to ampicillin selection with a reporter construct containing a β-lactamase gene with an AGGA codon at the A184 site.
Figure 24:
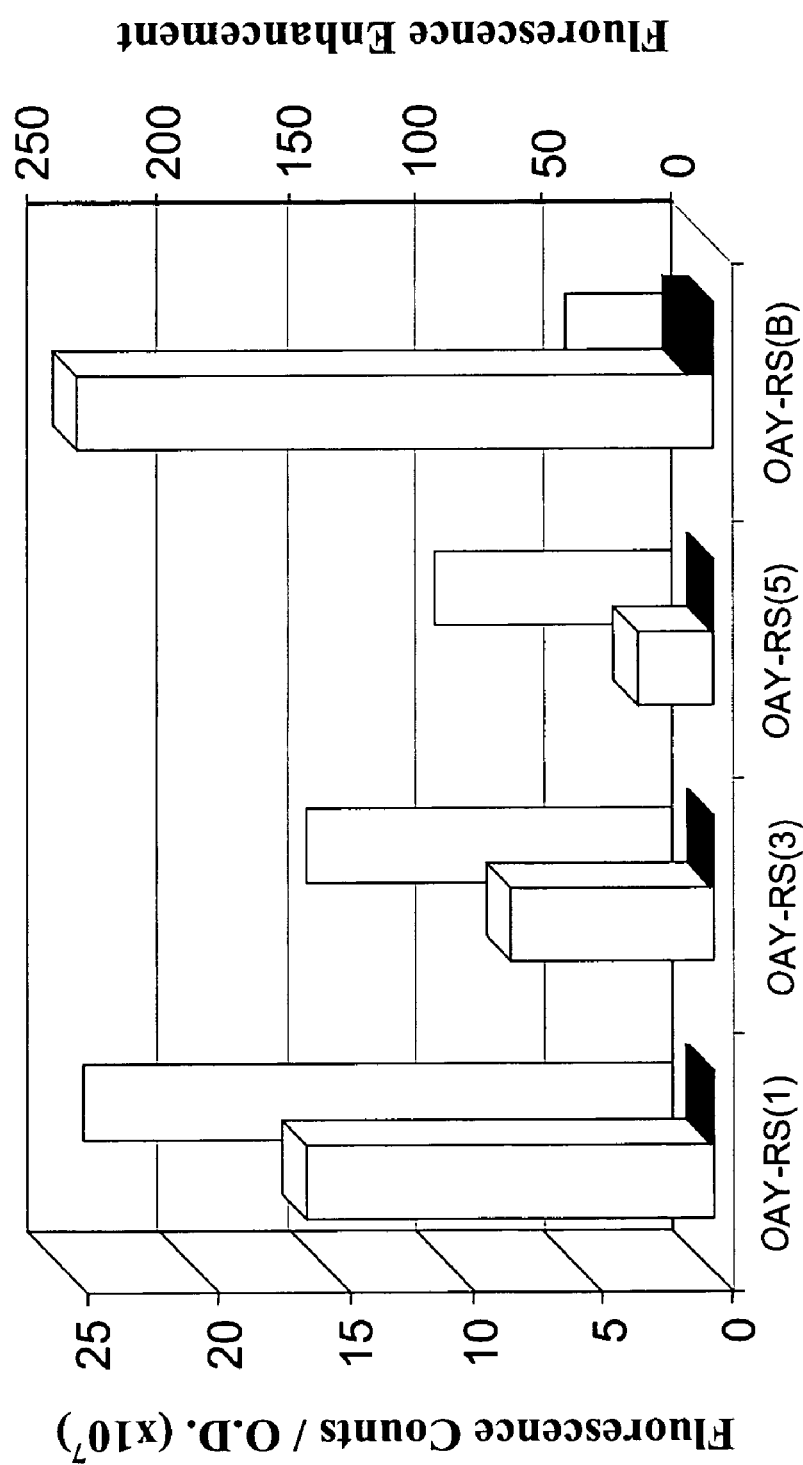
FIG. 24, illustrates activity comparisons of OAY-RS variants derived using a negative FACS-based screen (OAY-RS (1,3,5)) or negative barnase-based selection (OAY-RS(B)). Cells containing pREP/YC-JYCUA and the indicated synthetase variant were grown in either the presence (solid block, left) or absence (solid block, right) of the corresponding unnatural amino acid and analyzed fluorimetrically. Fluorescence enhancement (bar, back) is calculated as the cell concentration-corrected ratio of fluorescence of cells grown in the presence versus the absence of unnatural amino acid.

Variants were also made that could suppress four-base codons instead of, e.g., three base codons. Four base codons offer the possibility of decoding the genetic code four bases at a time, for which 256 things could be encoded rather than 3 at a time, where only 64 amino acids can be encoded. The difficulty with using four-base codons is that they require expansion of the anticodon loop for the tRNA, a perturbation which most systems are unlikely to accept. However, a first generation AGGA suppressor for the leucyl system was identified. This was generated by randomly mutagenizing the anticodon loop with 8 bases and performing selection with an AGGA-β-lactamase reporter system. See FIG. 22.

The editing mechanism of the synthetase was also mutated to eliminate the editing function. The leucyl system, like several other synthetases has (at least) two active sites. One site performs activation of the amino acid with ATP to form an enzyme bound aminoacyl adenylate in complex with the synthetase, and then transfer of the amino acid onto the 3' terminus of the tRNA. A second site, however, is able to hydrolyze the amino acid from the tRNA if it is not leucine. The leucine system is known to perform this post-transfer editing function for methionine and isoleucine, and it optionally does this to unnatural amino acids as well.

Initially, the editing domain was deleted. The editing domain was replaced with a library of 6 tandem random amino acids. A positive selection was used, which was based on suppression of a stop codon in β-lactamase. Many functional synthetases were obtained, but upon trying to purify the synthetases, no material in any cases could be detected, and all of these synthetases displayed a temperature sensitive phenotype suggesting that the deletion of the editing domain resulted in a less stable protein.

Next, point mutations were made in the editing domain. The catalytic core of the editing domain is well conserved across species and even for different amino acids, at least for the family of branched chain amino acids. Several of these conserved sites have previously been mutated, for example a T→P mutation, and found to knock out editing function. Mutants of *Methanobacterium thermoautotrophicum* RS were constructed that were similar to several known mutants, and also a 20 member NNK library derived from T214 was made. Proteins were expressed and examined in vitro for aminoacylation with leucine and methionine. None of the previously identified mutations were transferable to our system, but a desirable mutation was identified from the T214 library. Two mutants were identified that were capable of charging with leucine, T214S and T214Q. Of these mutations, only T214Q was capable of charging methionine. The T214S mutant apparently retains the ability to edit out methionine whereas the Gln mutant has lost this function.

A library was then designed based on the crystal structure that has been solved for the *Thermus thermophilus* leucyl synthetase. The leucine side chain of the leucine aminoalkyl adenylate analog adenosine inhibitor was bound in the active site. Six sites surrounding the leucine side chain-binding pocket were replaced with randomized amino acids to create a larger library. The synthetases from this library can then be screened, e.g., by performing positive/negative double sieve selections, to identify synthetases capable of charging unnatural amino acids selectively.

Example 6

Identification of tRNAs that Efficiently Suppress Four-Base Codons

A combinatorial approach was used to identify mutated tRNAs that efficiently suppress four-base codons. See, T. J. Magliery, J. C. Anderson and P. G. Schultz, *J. Mol. Biol.*, 307:755 (2001). A reporter library was constructed in which a serine codon in the β-lactamase gene was replaced by four random nucleotides. A mutated tRNA, e.g., suppressor tRNA, suppressor library was then generated that consists of derivatives of *Escherichia coli* with the anticodon loop (7 nt) replaced with eight or nine random nucleotides. When these two libraries are crossed, an appropriate frameshift suppressor tRNA that decodes the four-base sequence as a single codon results in translation of full-length β-lactamase, rendering the cells resistant to ampicillin. Survival at higher concentrations of ampicillin indicates that the corresponding tRNA has higher suppression efficiency for the four-base codon. Using this selection, four quadruplet codons AGGA, CUAG, UAGA, and CCCU and their cognate suppressor tRNAs were identified that decode only the canonical four-base codon with efficiencies close to that of natural triplet codon suppressors. Novel five- and six-base codon suppressors have also been selected using this strategy. See, Anderson, Magliery, Schultz, Exploring the Limits of Codon and Anticodon Size, *Chemistry & Biology*, 9:237-244 (2002). These extended codons, some of which are newly identified, can be useful for the incorporation of multiple unnatural amino acids in vitro and for in vivo protein mutagenesis.

Example 7

Generation of an Orthogonal tRNA-Synthetase for p-aminophenylalanine

To generate an orthogonal synthetase pair for p-aminophenylalanine (pAF), the *Methanococcus jannaschii* tyrosyl-tRNA synthetase (TyrRS) and mutant tyrosine amber suppressor tRNA (TyrCUA mutRNA) pair were used as a starting point. See, Wang, L., Magliery, T. J., Liu, D. R. & Schultz, P. G. A new functional suppressor tRNA/aminoacyl-tRNA synthetase pair for the in vivo incorporation of unnatural amino acids into proteins. *J. Am. Chem. Soc.* 122:5010-5011 (2000); and, Wang, L. & Schultz, P. G. *Chem. and Biol.* 8:883 (2001). The pAF specific synthetase (pAFRS) was generated by modifying the amino acid specificity of the *Methanococcus jannaschii* TyrRS to accept pAF and not any of the common twenty amino acids. A combination of positive selections and negative screens was used to identify the pAFRS enzyme from a library of TyrRS variants 12 containing random amino acids at five positions (Tyr$^{32}$, Glu$^{107}$, Asp$^{158}$, Ile$^{159}$, and Leu$^{162}$). See, Wang, L., Brock, A., Herberich, B. & Schultz, P. G. Expanding the genetic code of *Escherichia coli. Science* 292:498-500 (2001). A single reporter plasmid was used for both selection and screening. For example, the reporter plasmid is pREP(2)/YC-JYCUA, which contains the genes for CAT, T7 RNA polymerase, GFP, and TyCUA mutRNA, and a selectable marker for Tet resistance. The CAT gene contains a TAG codon substitution at position D112. The T7 RNA polymerase gene contains a seven-amino acid N-terminal leader peptide and TAG substitutions at M1 and Q107.

The positive selection is based on suppression of a TAG codon at a permissive position within the chloramphenicol acetyltransferase (CAT) gene by either pAF or an endogenous amino acid. See, e.g., Wang et al. (2001), supra; and, Pastrnak, M., Magliery, T. J. & Schultz, P. G. A new orthogonal suppressor tRNA/aminoacyl-tRNA synthetase pair for evolving an organism with an expanded genetic code. *Helvetica Chemica Acta* 83:2277 (2000). Cells containing the TyrRS library and reporter plasmid were grown in liquid culture containing pAF and selected for survival in the presence of chloramphenicol (Cm). For example, for the positive selection, cells were grown in GMML minimal media containing 35 µg/ml Kn, 25 µg/ml Tet, 75 µg/ml Cm, and 1 mM pAF (Sigma).

The negative screen is based on the inability to suppress in the absence of pAF two TAG stop codons at permissive positions within the T7 RNA polymerase gene. Expression of full length T7 RNA polymerase drives expression of green fluorescent protein (GFP). Cells from the positive selection were grown in the absence of pAF and Cm, and then screened using fluorescence activated cell sorting (FACS) for a lack of fluorescence. For example, for the negative screen, cells were grown in GMML media containing 35 µg/ml Kn, 25 µg/ml Tet, and 0.002% arabinose. FACS was carried out using a BDIS FACVantage TSO cell sorter with a Coherent Enterprise II ion laser. The excitation wavelength was 351 nm and emission was detected using a 575/25 nm bandpass filter. Collected cells were diluted into at least 10 volumes of LB, containing Tet and Kn, and grown to saturation.

The desired pAFRS was identified following two rounds of positive selection in liquid media, one round of negative screening, another round of positive selection in liquid media, and one round of positive selection on plates. The pAFRS enzyme contains five mutations relative to the wild type TyrRS(Y32T, E107T, D158P, I159L, and L162A). In the absence of pAF, the IC$_{50}$ of cells expressing the selected pAFRS and reporter plasmid was 10 µg/ml Cm on GMML minimal media plates. The Icso was 120 µg/ml Cm with 1 mMpAF. Thus, pAF is selectively suppressing the UAG codon.

Example 8

Evolution of an Aminoacyl-tRNA Synthetase Using Fluorescence-Activated Cell Sorting A FACs based screening system was used to rapidly evolve three highly selective synthetase variants that accept amino-, isopropyl-, or allyl-containing tyrosine analogues. The system included a multipurpose reporter plasmid used for application of both positive and negative selection pressure and for the facile and quantitative evaluation of synthetase activity. A chloramphenicol acetyl transferase (CAT) marker allowed positive selection for activity of the *M. jannaschii* tyrosyl-tRNA synthetase (TyrRS). A T7 polymerase/GFP reporter system allowed assessment of synthetase activity within cells grown in both the presence and absence of an unnatural amino acid. Fluorescence activated cell sorting (FACS) was used to screen against synthetase variants that accept natural amino acids, while visual and fluorimetric analyses were to assess synthetase activity qualitatively and quantitatively, respectively.

Design of an amplifiable fluorescence reporter system. Efforts to develop a versatile screening system for the assessment of synthetase activity in living cells initially arose out of a desire for a greater degree of control over the selective pressure applied to populations of synthetase variants, especially negative selective pressure. As the system was to be used to assess the activities of large numbers of synthetase variants, a reporter was sought that would be amenable to high-throughput screening. In addition, a reporter that would allow for facile qualitative and quantitative evaluation of synthetase activity was desired. To meet these requirements, a fluorescence-based screen was designed. The system was based on the synthetase-dependent production of GFPuv, a variant of the green fluorescent protein that has been optimized for expression in *E. coli* (see, Crameri, A., Whitehorn, E. A., Tate, E. & Stemmer, W. P., *Nature Biotechnol*. 1996, 14, 315-319). This fluorophore is amenable to use in FACS and fluorimetry, as well as visual inspection on plates and in liquid culture. The system was designed such that synthetase-dependent suppression of selector, e.g., amber nonsense codons would result in the production of a fluorescence signal. In order to maximize the sensitivity of the reporter, it was made amplifiable by placement of the amber codons within the gene for T7 RNA polymerase, which was designed to drive expression of the GFPuv reporter gene in analogy to other amplifiable intracellular reporter systems (see, Lorincz, M., Roederer, M., Diwu, Z., Herzenberg, L. A., Nolan, G. P. *Cytometry,* 1996, 24, 321-329; and Zlokarnik, G., Negulescu, P. A., Knapp, T. E., Mere, L., Burres, N., Feng, L., Whitney, M., Roemer, K. & Tsien, R. Y., *Science,* 1998, 279, 84-88). The T7 RNA polymerase gene was placed under control of the arabinose promoter in order to allow facile optimization of the production of the RNA transcript for amber codon-containing T7 RNA polymerase.

Figure 17A:
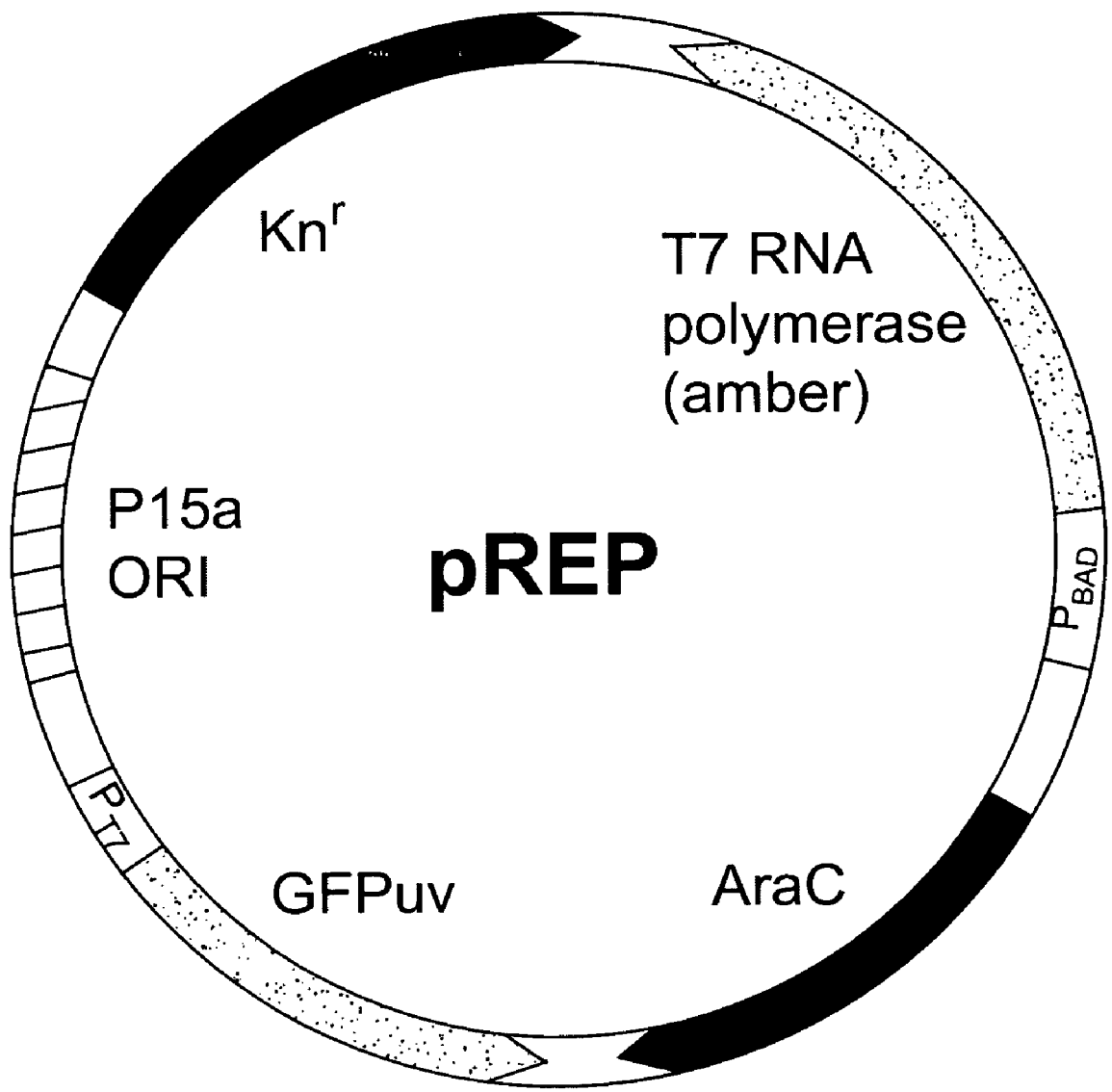
FIG. 17, Panel A, Panel B, Panel C and Panel D illustrates an amplifiable fluorescence reporter system. Panel A schematically illustrates vectors that can be used in the screen, e.g., plasmids, such as pREP, where T7 RNA polymerase transcription is controlled by the ara promoter; protein expression depends on suppression of amber codons at varying locations in the gene. Reporter expression, e.g., GFPuv expression is controlled by T7 RNA polymerase. The reporter vector, e.g., plasmid pREP, is compatible for use with a vector for expressing an orthogonal synthetase/tRNA pair, e.g., a ColE1 plasmid. Panel B illustrates compositions and fluorescence enhancement of T7 RNA polymerase gene constructs within pREP (1-12). The construct number is indicated to the left of each. Fluorescence enhancements, indicated to the right of each construct, are calculated as the cell concentration-corrected ratio of fluorescence, as measured fluorimetrically, of cells containing pREP(1-12) and pQ or pQD. The position of the amber mutations within a gene are indicated. Panel C illustrates cytometric analysis of cells containing pREP (10) and either pQD (top) or pQ (bottom). Panel D illustrates fluorimetric analyses of cells containing pREP (10) and expressing various *Escherichia coli* suppressor tRNAs. "None" indicates that the cells contain no suppressor tRNA.
Figure 17C:
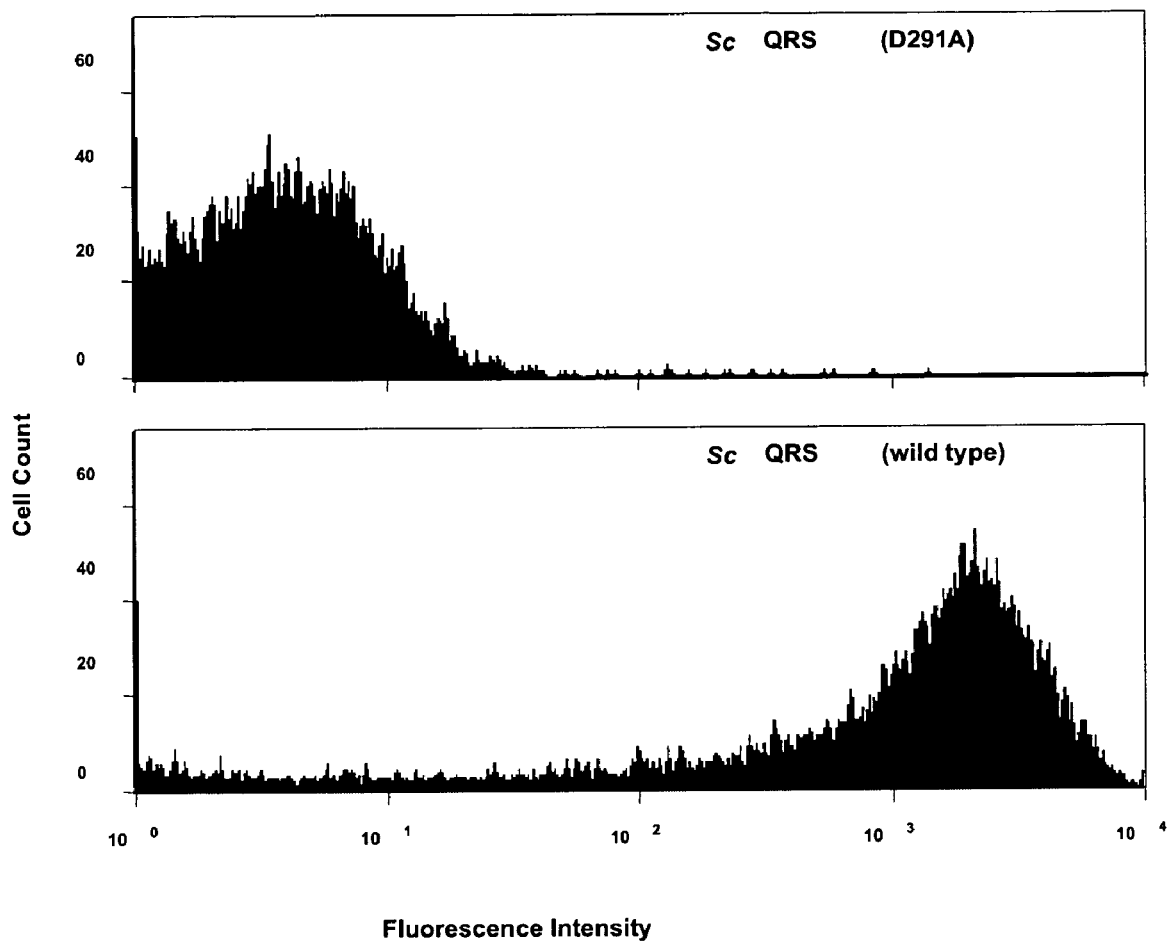
Figure 17D:
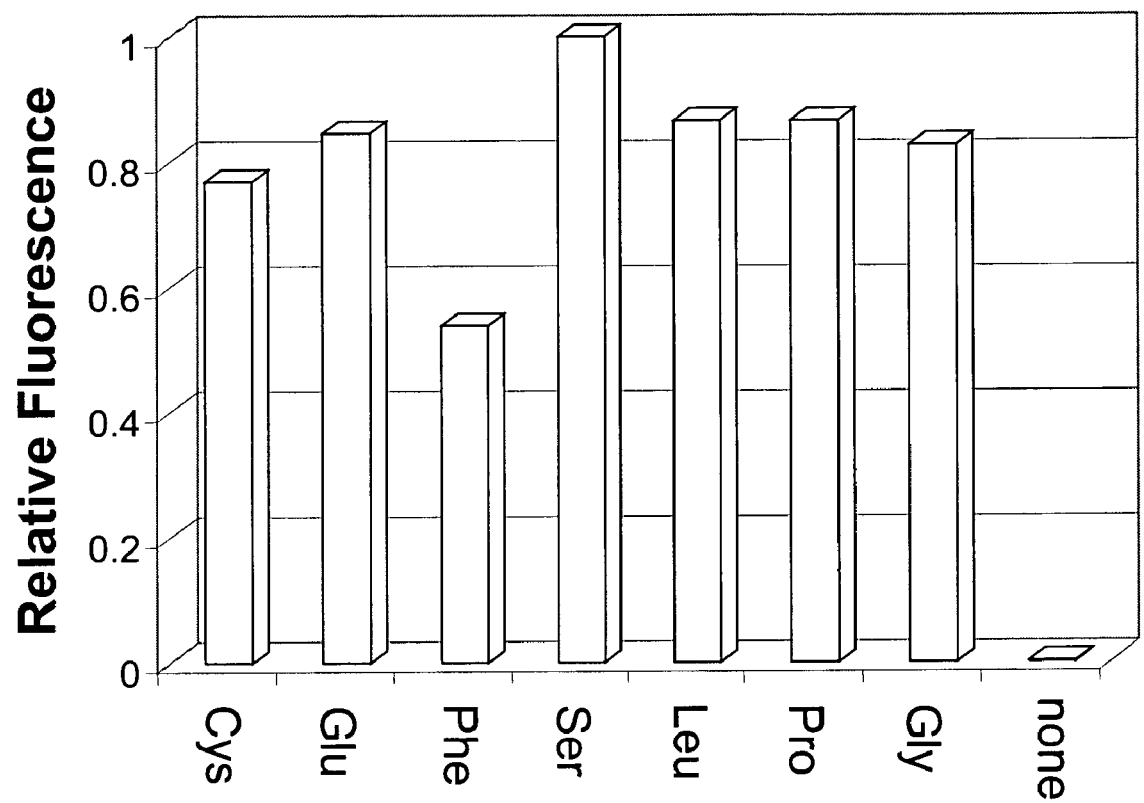

Optimization of the T7 RNA polymerase/GFPuv reporter system. A medium-copy reporter plasmid, pREP, was designed to express amber-containing T7 RNA polymerase variants under control of the arabinose promoter and the GFPuv gene under control of the T7 promoter (FIG. 17*a*). A series of twelve T7 RNA polymerase variants, designed to optimize synthetase-dependent fluorescence enhancement (FIG. 17*b*), were inserted into pREP to create plasmids pREP (1-12). All variants contained an N-terminal leader sequence of seven amino acids (MTMITVH) and 1-3 amber stop codons (TAG). Variants 1-3 contained one, two, and three amber stop codons, respectively, substituted for the original methionine at position one (M1), just downstream of the leader sequence. Variants 4-9 contained an amber codon substituted for D10, R96, Q107, A159, Q169, or Q232, respectively, which were predicted to be located in loop regions of the structure (see, Jeruzalmi, D. & Steitz, T. A., *EMBO J.,* 1998, 17, 41014113). Variants 10-12 contained amber stop codons substituted at positions M1 and either Q107, A159, or Q232, respectively. Plasmid constructs were evaluated by fluorimetry and flow cytometry of live cells for fluorescence enhancement using a compatible plasmid containing the orthogonal glutaminyl-tRNA synthetase and Glutamine tRNA$_{CUA}$ from *S. cerevisiae*. Plasmids pREP(1-12) were found to provide varying levels of synthetase-dependent fluorescence enhancement, with the best construct, pREP(10) exhibiting 220-fold greater fluorescence by fluorimetry (FIG.

17c) and ~400-fold greater median fluorescence by cytometry (FIG. 17d) in cells containing the wild type synthetase versus an inactive mutant. Substitution of a variety of functional groups at positions corresponding to the amber codons within pREP(10) demonstrate that position 107 within T7 RNA polymerase is highly permissive.

Figure 25A:
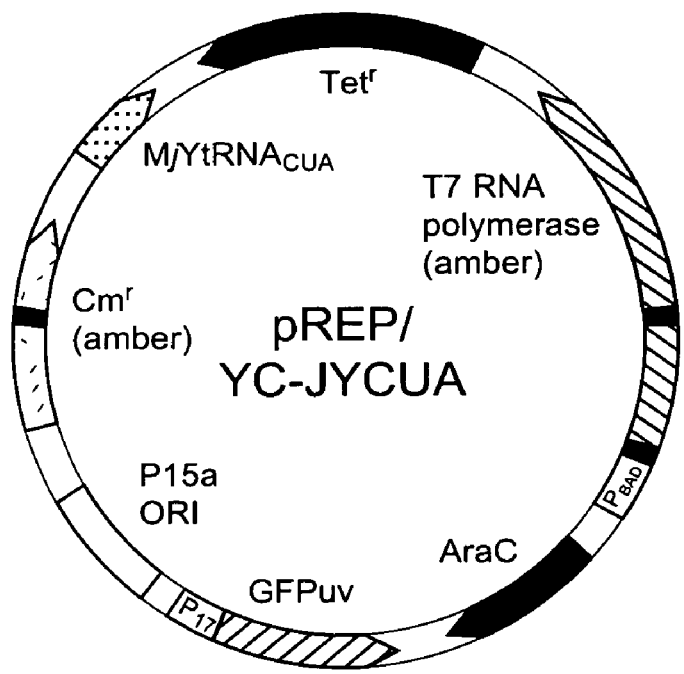
FIG. 25A illustrates plasmid pREP/YC-JYCUA. Plasmid pREP/YC-JYCUA is compatible for use with plasmid pBK and variants.

Construction of a multipurpose reporter plasmid. In order to construct a multipurpose plasmid to be used both for selecting and screening variants of a M. jannaschii TyrRS, plasmid pREP(10) was combined with plasmid pYC-J17 (see, Wang, L, Brock, A., Herberich, B. & Schultz, P. G., Science, 2001, 292,498-500) to obtain pREP/YC-JYCUA (FIG. 25a). Plasmid pREP/YC-JYCUA was assayed for function with a compatible plasmid expressing a variant of M. jannaschii TyrRS (pBK-mJYRS; Wang, L, Brock, A., Herberich, B. & Schultz, P. G., Science, 2001, 292, 498-500) selective for incorporating O-Methyl-Tyrosine (OMY). Cells containing pREP/YC-JYCUA and pBK-mJYRS, grown in the presence of OMY, exhibited a chloramphenicol (Cm) $IC_{50}$ value of 120 μg/μl, identical to that obtained using plasmid pYC-J17, and a fluorescence enhancement of 330-fold for cells grown in the presence versus the absence of OMY, as measured by fluorimetry.

Figure 25B:
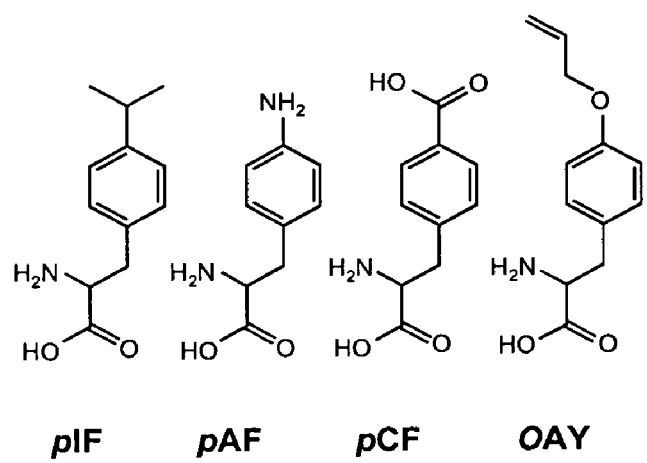
FIG. 25B illustrates structures of unnatural amino acids used as targets for the evolution of *M. jannaschii* TyrRS.

Evolution of the substrate specificity of the M. jannaschii tyrosyl-tRNA synthetase. Results have shown that the amino acid side chain binding pocket of the M. jannaschii TyrRS can be evolved to selectively accommodate chemical groups other than the phenol side chain of tyrosine (see, Wang, L, Brock, A., Herberich, B. & Schultz, P. G., Science, 2001, 292,498-500; Wang, L., Brock, A. & Schultz, P. G. J. Am. Chem. Soc. 2002, 124, 1836-1837). We sought to further explore the generality of unnatural amino acid accommodation by M. jannaschii TyrRS by challenging the enzyme to accept four new functionalities: p-Isopropyl-Phenylalanine (pIF), p-Amino-Phenylalanine (pAF), p-Carboxyl-Phenylalanine (pCF), or O-Allyl-Tyrosine (OAT) (FIG. 25b). A library of M. jannaschii TyrRS variants containing randomizations at positions Y32, E107, D158, 1159, and L162 (Wang, L, Brock, A., Herberich, B. & Schultz, P. G., Science, 2001, 292, 498-500), residues thought to form the binding pocket for the para position of the tyrosyl ring, was introduced into cells containing plasmid pREP/YC-JYCUA. These cells, encompassing a library diversity of $\sim 10^9$, were used to begin four evolution experiments to identify synthetase variants selective for pIF, pAF, pCF, or OAT (FIG. 25b). Two cycles of positive selection were carried out by allowing the cell cultures to grow to saturation in the presence of Cm and one of the four unnatural amino acids. Cell aliquots were removed following the second cycle of positive selection and used to inoculate a new culture containing no added amino acid or Cm, and the culture was again allowed to grow to saturation. At this point, cells that fluoresce are likely to contain synthetase variants that can accept one of the 20 natural amino acids. Approximately $10^8$ cells from each line were subjected to negative screening using FACS in order to eliminate natural amino acid-accepting synthetase variants. The non-fluorescent cells were collected and amplified through growth to saturation. These amplified cells were used to inoculate a new culture for a final cycle of positive selection in liquid culture containing unnatural amino acid and Cm. Following growth to saturation, each population of cells was plated on media containing 0, 30, 60, or 100 μg/mL Cm and either 0 or 1 mM of the appropriate unnatural amino acid.

Identification and characterization of evolved synthetase variants. Cm plates supplemented with pIF, pAF, and OAT produced 10-100-fold greater numbers of fluorescent colonies than plates containing no added amino acid. In contrast, plates for the pCF population produced the same number of fluorescent colonies with or without addition of pCF. The ten largest fluorescent colonies were picked for each of the pIF, pAF, and OAT populations from unnatural amino acid-containing plates and grown to saturation in liquid media with or without added unnatural amino acid. A qualitative assessment of fluorescence production was made visually with the use of a hand-held long-wavelength ultraviolet lamp (FIG. 23a).

Synthetase variants corresponding to clones producing significant differences in fluorescence were sequenced. All ten clones from the pIF and pAF populations had identical sequences, while three different clones were identified from the OAT population. Amino acid changes occurred within the five randomized sites in all clones, with the exception of two additional substitutions within the pIF-tRNA synthetase (pIF-RS) variant. The activities of the different clones were quantitatively assessed. Fluorescence was measured fluorimetrically for cells grown in liquid culture in the presence or absence of unnatural amino acid (FIG. 23b). The Cm $IC_{50}$s were determined by plating the cells on varying concentrations of Cm in the presence or absence of unnatural amino acid (FIG. 23c).

A myoglobin gene containing an amber codon in the fourth position was used to assess the production of unnatural amino acid-containing protein. The gene was expressed in cells, using the pIF-RS, pAF-RS, or OMY-RS variant, respectively, in either the presence or absence of pIF, pAF, or OAT (FIG. 23d). Protein yields were comparable for all three variants, ranging from 1-2 milligrams of protein per liter of unnatural amino acid-containing cell culture. In contrast, protein production was virtually undetectable in cultures grown in the absence of unnatural amino acid. Proteins were analyzed by electrospray mass spectrometry, giving masses of 18457.40±0.81 (18457.28 expected) for the pIF-containing protein, and 18430.30±0.27 (18430.21 expected) for the pAF-containing protein. Activity measurements obtained using the Cm $IC_{50}$, fluorimetry, and protein expression analyses correlated well, however the activity of the pIF-RS appears to be somewhat underestimated by fluorimetry. As compared to other assays, the disproportionately low fluorimetry measurement for the pIF-RS variant, suggests that T7 RNA polymerase may be partially destabilized upon incorporation of the pIF analogue, despite the apparent permissivity of the amber positions within the reporter (see, FIG. 17c).

Utility of the multipurpose reporter system. The reporter system described here allows the use of a single multipurpose plasmid for both positive selection and negative screening, obviating the need to shuttle plasmids between alternating rounds of positive and negative selection. A total of only three rounds of positive selection and one round of negative screening were required to enable the identification of synthetase variants that selectively accept desired unnatural amino acids. These features allow evolution experiments to be carried out in a matter of days. The screening system can be used to readily identify active synthetase variants using agar plates containing unnatural amino acid and to individually assay the amino acid specificity of the variants.

As described above, the T7 RNA polymerase/GFP system can be used to quantitatively compare the activities of synthetase variants. The availability of the three OAT-RS clones described here and a different OAT-RS clone derived independently from the same library using a positive/negative selection based on CAT and barnase allows the possibility of comparing the two different evolution systems in terms of the synthetase variants resulting from each. This analysis reveals that the three clones derived from positive selection and negative screening exhibit slightly lower levels of fluorescence in the presence of OAT, but ~10-fold lower background levels in the absence of the unnatural amino acid. The fluorescence enhancement for cells grown in the presence versus the absence of the unnatural amino acid is thus about 6-fold higher for cells expressing OAT-RS(1) from selection and screening than for cells expressing the OAT-RS clone derived from positive/negative selection using barnase. Although it is not clear whether this example is representative, these data suggest that the T7 RNA polymerase/GFP system may allow more stringency in selecting against synthetase variants that are promiscuous towards natural amino acid substrates. However, the fluorescence enhancement for cells grown in the presence versus the absence of an unnatural amino acid is expected to represent a lower limit for the fidelity of unnatural amino acid incorporation, as competition of unnatural amino acids for being bound by an evolved synthetase variant would reduce binding of natural amino acids. Moreover, although high fidelity is clearly desirable, there is likely to be a trade-off between fidelity and overall synthetase activity, which may depend on the desired application.

Generality of aminoacyl tRNA synthetase evolution. Previous results and those presented here demonstrate that the amino acid side chain binding pocket of the M. jannaschii TyrRS is quite malleable. The enzyme can be evolved to accommodate a variety of functionalities in place of the phenol side chain of tyrosine and can do so with high selectivity. In this application it was demonstrated that enzyme can be evolved to accommodate an amine, isopropyl, or allyl ether functionality at the para position of the tyrosine ring, instead of hydroxyl. It was not possible to identify an enzyme variant that could accept the pCF unnatural amino acid. A second attempt to evolve a synthetase to accept the pCF amino acid was also unsuccessful. Using LC/MS analysis, pCF could not be detected upon toluenization of E. coli cells grown in the presence of the unnatural amino acid, suggesting that pCF is not transported into cells or that it is metabolized upon entry.

Of the three successful evolution experiments described here, only the evolution of the OAT-RS resulted in the identification of more than one active clone. The OAT-RS evolution was also the experiment that produced the most active synthetase variant. These results suggest that some amino acid specificities may be easier to select for than others. This could be due, in part, to the relative difficulty of selectively recognizing different unnatural amino acids in the context of the 20 natural amino acids. It may be, for example, that pAF, due to its structural and electronic similarities to tyrosine, is more difficult to selectively recognize than OAT. This would explain why a greater number of OAT-RS clones were identified than pAF-RS clones and why the pAF-RS clone is less active than the best OAT-RS clone.

Plasmid Construction. Plasmid pREP (FIG. 17a) was constructed by insertion of a BamHI/ApaLI overlap PCR fragment containing the T7 RNA polymerase gene upstream of an mmB transcription termination region, followed by an ApaLI/AhdI overlap PCR fragment containing the araC gene and ara promoter region from the pBAD/Myc-His A plasmid (Invitrogen; for transcriptional control of the T7 RNA polymerase gene) and the GFPuv gene (Clontech; upstream of the T7 terminator region and downstream of the T7 promoter) between the AhdI/BamHI sites of plasmid pACYC177 (New England Biolabs). Plasmids pREP(1-12) were constructed by replacement of an HpaI/ApaLI fragment of T7 RNA polymerase with overlap PCR fragments containing amber mutations at the positions described. Plasmid pREP/YC-JYCUA was constructed by ligation of an AfeI/SacII fragment from pREP(10) and an EarI(blunted)/SacII fragment from pYC-J17 (Wang, L, Brock, A., Herberich, B. & Schultz, P. G., Science, 2001, 292, 498-500). The desired construct was identified following transformation into cells containing plasmid pQ screening for fluorescence.

Plasmid pQ was constructed by triple ligation of a AatII/SalI overlap PCR fragment containing the SCQRS downstream of the lac promoter region and upstream of the E. coli QRS termination region, a SalI/AvaI overlap PCR fragment containing the S. cerevisiae tRNA(CUA)$^{Gln}$ downstream of the lpp promoter region and upstream of an rrnC termination region, and the AvaI/AatII fragment of pBR322 (New England Biolabs). Plasmid pQD was constructed by replacement of pQ fragment between BamHI and BglII with a BamHI/BglII fragment of the SCQRS(D291A) mutant.

Plasmid pBAD/JYAMB-4TAG was constructed by insertion of a PCR fragment of the S4Amber mutant of myoglobin, containing a C-terminal 6His-tag, into the pBAD/YC-JY-CUA plasmid, a hybrid of plasmid pYC-J17 (Wang, L, Brock, A., Herberich, B. & Schultz, P. G., Science, 2001, 292, 498-500) and pBAD/Myc-His A (Invitrogen) containing the gene for MjYtRNA$_{CUA}$, and the pBAD promoter and cloning regions for heterologous expression of an inserted gene.

Fluorimetric and cytometric analyses. Single colonies containing desired plasmids were used to inoculate 2-mL GMML cultures containing the appropriate antibiotics, 0.002% Arabinose, and an appropriate unnatural amino acid, if desired. Cultures were grown to saturation and cells (200 μL) were pelleted and resuspended in 1 mL phosphate-buffered saline (PBS). Cell concentrations were analyzed by absorbance at 600 nm and fluorescence levels were measured at 505 nm with excitation at 396 nm using a FluoroMax-2 fluorimeter. Cells suspended in PBS were analyzed cytometrically. To evaluate the permissivity of the amber positions within the T7 polymerase gene of pREP(10), the reporter plasmid was transformed into a panel of suppressor strains, which were subsequently analyzed fluorimetrically.

Evolution of aminoacyl-tRNA synthetase variants. M. jannaschii TyrRS variants randomized at positions Y32, E107, D158, I159, and L162 (Wang, L, Brock, A., Herberich, B. & Schultz, P. G., Science, 2001, 292, 498-500) were transformed into DH10B E. coli cells (Life Technologies) containing pREP/YC-JYCUA to generate a library with a diversity of ~10$^9$. Transformants were allowed to recover in SOC medium for 60 min at 37° C., and were grown to saturation in LB medium. To begin an initial positive selection, 2 mL of library culture, pelleted and resuspended in GM medium, was used to inoculate 500 mL of GMML containing 25 μg/mL Tetracycline (Tet), 35 μg/mL Kanamycin (Kn), and 1 mMpIF, pAF, pCF, or OAY. After incubation for 3 hours at 37° C., Cm was added to a final concentration of 75 μg/mL and cells were grown to saturation (~48 hours). For the second positive selection, a 100-mL GMML culture containing Tet, Kn, 75 μg/mL Cm, and 1 mMpIF, pAF, pCF, or OAY was inoculated with cells from the initial positive selection (500 μL) and grown to saturation at 37° C. (~24-36 hours). In preparation for negative screening, a 25-mL GMML culture containing Tet, Kn, and 0.02% arabinose (Ara) was inoculated with cells from the second positive selection (100 μL, pelleted and resuspended in GMML) and grown to saturation at 37° C. (~24 hours). Ara-induced cells grown in the absence of unnatural amino acids (1 mL) were pelleted and resuspended in 3 mL of phosphate-buffered saline (PBS). Cells were sorted for lack of expression of GFPuv using a BDIS FAC-Vantage TSO cell sorter with a Coherent Enterprise II ion laser with excitation at 351 nm and emissions detected using a 575/25 nm bandpass filter. Collected cells were diluted in at least 10 volumes of LB, containing Tet and Kn, and grown to saturation. To begin the third round of positive selection, 100

μL of cells from the negative screen were pelleted, resuspended in GMML, and used to inoculate 25 mL of GMML containing Tet, Kn, and 1 mM pIF, pAF, pCF, or OAY. After incubation for 3 hours at 37° C., Cm was added to a final concentration of 75 μg/mL and cells were grown to saturation (~24 hours). Following the third positive selection, cells were plated on GMM agar containing Tet, Kn, 0.002% Ara, 0, 75, or 100 μg/mL Cm, and 0 or 1 mM pIF, pAF, pCF, or OAY, and grown for 48 hours at 37° C.

Expression and characterization of unnatural amino acid-containing proteins. DH10B cells co-transformed with pBAD/JYAMB4TAG and the appropriate pBK plasmid were used to inoculate a 100-mL GMML starter culture containing Kn and Tet, which was grown to saturation. A 500-mL culture containing Kn, Tet, 0.002% Ara, 5 μM $FeCl_3$, and the desired unnatural amino acid (or none) was inoculated with 50 mL of the starter culture and grown to saturation (~18 hours). Cultures were pelleted, sonicated, and the myoglobin protein isolated according to the protocol of the QiaExpressionist (Qiagen) His-tag purification kit. Proteins were analyzed electrophoretically on a 12-20% gradient SDS polyacrylamide gel and by electrospray mass spectrometry.

Example 9

Orthogonal tRNA/Threonyl-tRNA Synthetase Pair

Figure 27:
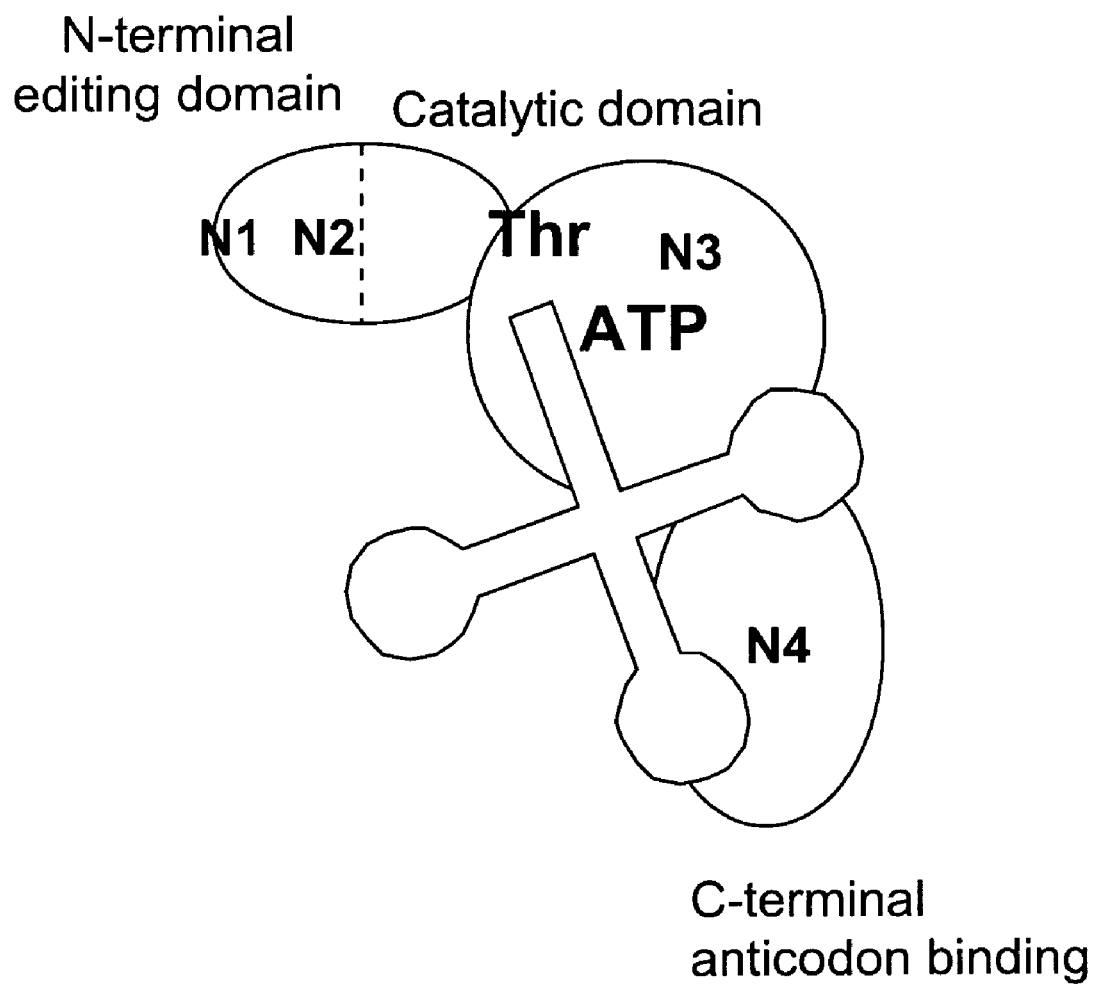
FIG. 27 illustrates a threonyl-tRNA synthetase from *Thermus thermophilus*.

This example illustrates the generation of an orthogonal tRNA/Threonyl-tRNA synthetase pair. FIG. 27 illustrates a threonyl-tRNA synthetase from *Thermus thermophilus*. This synthetase has two N-terminal editing domains, a catalytic domain and a C-terminal anticodon binding domain (659 amino acids). To generate the orthogonal synthetase based on the *T. thermophilus* synthetase, the editing domain(s), N1 or N1 and N2 was deleted from the synthetase to generate an N-truncated *T. thermophilus* ThrRS (475 amino acids). This synthetase has the same catalytic activity but lacks the proofreading activity. The N-truncated synthetase was screened for activity. The N-truncated synthetase did not aminoacylate *Escherichia coli* tRNA.

Figure 28:
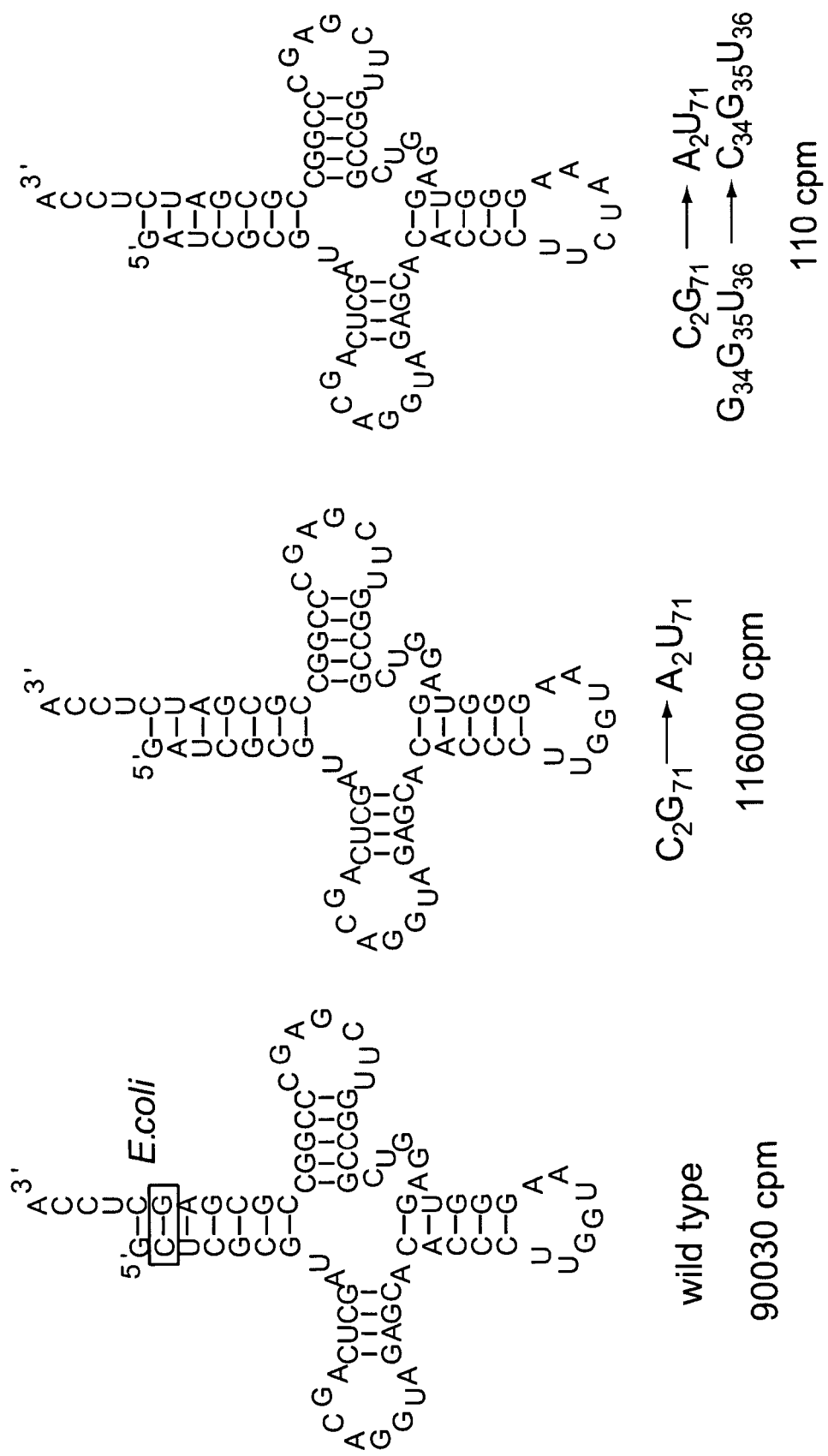
FIG. 28 illustrates the generation of an orthogonal tRNA for a *T. thermophilus* orthogonal threonyl-tRNA/RS. Wild type (SEQ ID NO:106) and two mutant ($C_2G_{71} \rightarrow A_2U_{71}$ (SEQ ID NO. 107) and $C_2G_{71} \rightarrow A_2U_{71}G_{34}G_{35}U_{36} \rightarrow C_{34}G_{35}U_{36}$ (SEQ ID NO. 108)) tRNAs are illustrated.

Because, the *T. thermophilus* tRNAThr was found to be a substrate for *Escherichia coli* Threonyl-tRNA synthetase, the *T. thermophilus* tRNAThr was mutated in order to generate an orthogonal pair. FIG. 28 illustrates the mutations made in the tRNA. Specifically, C2G71 was mutated to A2U71. In vitro charging experiments demonstrate that this mutant is not a substrate for the *E. coli* Threonyl-tRNA synthetase but is a good substrate for the *T. thermophilus* Threonyl-tRNA synthetase. Another mutant was also constructed, which included the following mutations:—C2G71→A2U71 and G34G35U36→C34G35U36 in order to generate an amber suppressor tRNA. Other mutant tRNAs with modified anticodon loops in addition to C2G71→A2U71 were also generated to suppress three and four base codons such as TGA, ACCA, ACAA, AGGA, CCCT, TAGA, and CTAG. All these tRNAs were not as good as substrate as the wild type tRNAThr (with A2U71) but can be improved by mutating the anticodon binding site of the *T. thermophilus* Threonyl-tRNA synthetase.

Example 10

Sequences of Exemplary O-tRNAs and O-RSs

Exemplary O-tRNAs comprise a nucleic acid comprising a polynucleotide sequence selected from the group consisting of: SEQ ID NO:1-3 and/or a complementary polynucleotide sequence thereof. See, Table 5, Appendix 1. Similarly, example O-RS include polypeptides selected from the group consisting of: a polypeptide comprising an amino acid sequence selected from the group consisting of SEQ ID NO: 35-66 and a polypeptide encoded by a nucleic acid comprising a polynucleotide sequence selected from the group consisting of: SEQ ID NO:4-34 and a complementary polynucleotide sequence thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising an aminoacyl-tRNA synthetase (RS), wherein the RS preferentially aminoacylates a tRNA with an unnatural amino acid; wherein the RS displays a lower $K_m$ for the unnatural amino acid than for any of the 20 common naturally occurring amino acids; wherein the RS also displays a higher $K_{cat}$ for the unnatural amino acid than for any of the 20 common naturally occurring amino acids; wherein the unnatural amino acid comprises a tyrosine analogue or derivative, a phenylalanine analogue or derivative, or a leucine analogue or derivative; wherein the RS is derived from a TyrRS or a LeuRS; wherein the RS comprises an amino acid sequence selected from the group consisting of SEQ ID NO: 35-64 and conservative variants thereof; and wherein the tRNA is derived from a tRNATyr or a tRNALeu.

2. The composition of claim 1, wherein the RS aminoacylates the tRNA with the unnatural amino acid in vivo.

3. The composition of claim 1, wherein the unnatural amino acid is selected from the group consisting of: an O-methyl-L-tyrosine, an L-3-(2-naphthyl)alanine, a 3-methyl-phenylalanine, an O-4-allyl-L-tyrosine, a 4-propyl-L-tyrosine, an L-Dopa, a fluorinated phenylalanine, an isopropyl-L-phenylalanine, a p-azido-L-phenylalanine, a p-acyl-L-phenylalanine, a p-benzoyl-L-phenylalanine, a phosphonotyrosine, a p-iodo-phenylalanine, a p-bromophenylalanine, a p-amino-L-phenylalanine, and an isopropyl-L-phenylalanine.

4. The composition of claim 1, wherein the unnatural amino acid is selected from the group consisting of: an unnatural analogue of a tyrosine amino acid; an unnatural analogue of a phenylalanine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid, a photoisomerizable amino acid; a biotin or biotin-analogue containing amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a redox-active amino acid; an α-hydroxy containing acid; an amino thio acid containing amino acid; an α,α disubstituted amino acid; a β-amino acid; and a cyclic amino acid other than proline.

5. The composition of claim 1, wherein the RS displays a higher $k_{cat}$/Km for the unnatural amino acid as compared to any of the 20 common naturally occurring amino acids.

6. A polypeptide comprising an amino acid sequence encoded by a coding polynucleotide sequence, the coding polynucleotide sequence selected from the group consisting of:
  a) a coding polynucleotide sequence that encodes a polypeptide selected from SEQ ID NO:35-64; and,
  b) the complementary sequence of any one of the sequences of (a).

7. The polypeptide of claim 6, wherein the encoded polypeptide is an orthogonal aminoacyl tRNA sythetase.

8. A polypeptide comprising the amino acid sequence of SEQ ID NO: 46.

9. A composition comprising an orthogonal tRNA (O-tRNA), wherein the O-tRNA recognizes a selector codon and wherein the O-tRNA is preferentially aminoacylated with an unnatural amino acid by an orthogonal aminoacyl-tRNA synthetase, the composition comprising the orthogonal aminoacyl-tRNA synthetase (O-RS) wherein the O-RS displays a lower $K_m$ for the unnatural amino acid than for any of the 20 common naturally occurring amino acids, and also displays a higher $K_{cat}$ for the unnatural amino acid than for any of the 20 common naturally occurring amino acids, wherein the unnatural amino acid comprises a tyrosine analogue or derivative, a phenylalanine analogue or derivative, or a leucine analogue or derivative, wherein the RS is derived from a TyrRS, or a LeuRS, wherein the RS comprises an amino acid sequence selected from the group consisting of SEQ ID NO: 35-64 and conservative variants thereof, and wherein the tRNA is derived from a tRNATyr, or a tRNALeu.

10. The composition of claim 9, wherein the O-tRNA and the O-RS are complementary.

11. The composition of claim 9, wherein the composition comprises a mutant tRNATyr-mutant TyrRS pair.

12. The composition of claim 11, wherein the composition comprises a mutant tRNATyr-SS12TyrRS pair.

13. The composition of claim 9, wherein the composition comprises a mutant tRNALeu-mutant LeuRS pair.

14. The composition of claim 9, wherein the O-tRNA and the O-RS are derived by mutation of a naturally occurring tRNA and an RS from at least one organism, wherein the at least one organism is a prokaryotic organism.

15. The composition of claim 14, wherein the at least one organism is selected from the group consisting of: *Methanococcus jannaschii*, *Methanobacterium thermoautotrophicum*, and *Halobacterium*.

16. The composition of claim 9, wherein the O-tRNA and the O-RS are derived by mutation of a naturally occurring tRNA and RS from at least one organism, wherein the at least one organism is a eukaryotic organism.

17. The composition of claim 16, wherein the at least one organism is selected from the group consisting of: yeasts, mammals, fungi, insects, plants and protists.

18. The composition of claim 9, wherein the O-tRNA is derived by mutation of a naturally occurring tRNA from a first organism and the O-RS is derived by mutation of a naturally occurring RS from a second organism.

19. The composition of claim 9, wherein the O-tRNA and the O-RS are isolated from at least one organism, wherein the at least one organism is a prokaryotic organism.

20. The composition of claim 19, wherein the at least one organism is selected from the group consisting of: *Methanococcus jannaschii*, *Methanobacterium thermoautotrophicum*, and *Halobacterium*.

21. The composition of claim 9, wherein the O-tRNA and the O-RS are isolated from at least one organism, wherein the at least one organism is a eukaryotic organism.

22. The composition of claim 21, wherein the at least one organism is selected from the group consisting of: yeasts, mammals, fungi, insects, plants and protists.

23. The composition of claim 9, wherein the O-tRNA is isolated from a first organism and the O-RS is isolated from a second organism.

24. The composition of claim 9, wherein one or more of the O-tRNA and the O-RS is isolated from one or more library, which one or more library comprises an O-tRNA or an O-RS from one or more organism.

25. The composition of claim 24, wherein the one or more organism comprises a prokaryote or a eukaryote.

26. The composition of claim 9, wherein the composition comprises a cell that comprises the O-RS and the O-tRNA.

27. The composition of claim 9, wherein the composition comprises an in vitro translation system.

28. A recombinant O-RS produced by a method, the method comprising:
  (a) generating a library of variant RS molecules derived from at least one aminoacyl-tRNA synthetase (RS) from a first organism;
  (b) selecting or screening the library of variant RSs for members that aminoacylate an orthogonal tRNA (O-tRNA) in the presence of an unnatural amino acid or a natural amino acid, thereby providing a pool of active RSs; and,
  (c) selecting or screening the pool of active RS to identify active RSs that preferentially aminoacylate the O-tRNA in the absence of the unnatural amino acid, thereby identifying at least one member of the pool that is specific for the unnatural amino acid, providing the at least one recombinant O-RS; wherein the at least one recombinant O-RS preferentially aminoacylates the O-tRNA with the unnatural amino acid and wherein the RS comprises an amino acid sequence selected from the group consisting of SEQ ID NO: 35-64 and conservative variants thereof.

29. The recombinant O-RS of claim 28, wherein the method comprises negatively selecting members of the pool that preferentially aminoacylate the O-tRNA in the absence of the unnatural amino acid.

30. The recombinant O-RS of claim 28, wherein the method comprises positively selecting those members of the pool that do not aminoacylate the O-tRNA in the absence of the unnatural amino acid.

31. The composition of claim 1, wherein the unnatural amino acid is selected from the group consisting of: O-allyl-L-tyrosine, para-substituted L-tyrosine wherein the substitution comprises a saturated or unsaturated hydrocarbon, p-iodo-L-phenylalanine, p-bromo-L-phenylalanine, 3,4-dihydroxy-L-phenylalanine, p-acetyl-L-phenylalanine, m-acetyl-L-phenylalanine, and 4-(2-oxo-propoxy)-L-phenylalanine.

* * * * *

UNITED STATES PATENT AND TRADEMARK OFFICE
CERTIFICATE OF CORRECTION

Page 1 of 1

PATENT NO. : 8,183,012 B2
APPLICATION NO. : 11/009635
DATED : May 22, 2012
INVENTOR(S) : Schultz et al.

It is certified that error appears in the above-identified patent and that said Letters Patent is hereby corrected as shown below:

In the Specification

Column 1, Lines 16-26, the paragraph STATEMENT AS TO RIGHTS OF INVENTIONS MADE UNDER FEDERALLY SPONSORED RESEARCH AND DEVELOPMENT should be changed to:
-- STATEMENT OF GOVERNMENT LICENSE RIGHTS
This invention was made with government support under grant number GM062159 awarded by the National Institutes of Health, under grant numbers DE-FG03-00ER45812 and DE-AC03-76SF00098 awarded by the United States Department of Energy, and grant number N00014-98-F-0402 awarded by the Office of Naval Research. The government has certain rights in the invention. --

Signed and Sealed this
Thirty-first Day of March, 2020

Andrei Iancu
*Director of the United States Patent and Trademark Office*